(12) United States Patent
Jackson et al.

(10) Patent No.: US 7,521,044 B2
(45) Date of Patent: Apr. 21, 2009

(54) HUMAN HISTONE DEACETYLASE, HDAC9C

(75) Inventors: Donald G. Jackson, Lawrenceville, NJ (US); Matthew V. Lorenzi, Philadelphia, PA (US); Liana M. Lee, San Francisco, CA (US); John N. Feder, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 121 days.

(21) Appl. No.: 11/497,205

(22) Filed: Aug. 1, 2006

(65) Prior Publication Data

US 2006/0269559 A1 Nov. 30, 2006

Related U.S. Application Data

(62) Division of application No. 10/172,094, filed on Jun. 14, 2002, now Pat. No. 7,199,227.

(60) Provisional application No. 60/298,296, filed on Jun. 14, 2001.

(51) Int. Cl.
*A61K 38/43* (2006.01)
*C12N 9/00* (2006.01)
*C07K 14/00* (2006.01)

(52) U.S. Cl. .................. 424/94.1; 435/183; 530/350

(58) Field of Classification Search ................. None
See application file for complete search history.

(56) References Cited

U.S. PATENT DOCUMENTS

| 4,218,478 | A | 8/1980 | Omura et al. |
| 6,068,987 | A | 5/2000 | Dulski et al. |
| 6,110,697 | A | 8/2000 | Dulski et al. |
| 6,600,351 | B2 | 7/2003 | Bisanti et al. |
| 7,063,973 | B2 | 6/2006 | Richon et al. |
| 2003/0129724 | A1 | 7/2003 | Grozinger et al. |

FOREIGN PATENT DOCUMENTS

| EP | 1394274 A2 | 3/2004 |
| WO | WO95/11994 | 5/1995 |
| WO | WO95/25116 | 9/1995 |
| WO | WO02/102984 A2 | 12/2002 |
| WO | WO03/029451 A2 | 4/2003 |
| WO | WO03/065006 A2 | 8/2003 |
| WO | WO03/068268 A2 | 8/2003 |
| WO | WO03/087768 A2 | 10/2003 |
| WO | WO2004/005513 A2 | 1/2004 |
| WO | WO2004/094591 A2 | 11/2004 |

OTHER PUBLICATIONS

Zhou et al (PNAS, 2001, 98:10572-10577, IDS).*
Ruijter et al (Biochem J, 2003, 370:737-749).*
Wang et al (Molecular and Cellular Biology, 1999, 19:7816-7827, IDS).*
NCBI Entrez Accession No. AF124924 (gi:6119845), Wang, et al., Oct. 27, 1999.
The Sanger Center, "Toward a Complete Human Genome Sequence", Genome Res., vol. 8, pp. 1097-1108 (1998).
Altschul, Stephen F., "A Protein Alignment Scoring System Sensitive at All Evolutionary Distances", J. Mol. Evol., vol. 36, pp. 290-300 (1993).
Altschul, et al., "Gapped Blast and PSI-Blast: a new generation of protein database search programs", Nucleic Acids Res., vol. 25(17), pp. 3389-3402 (1997).
Bateman, et al., "The Pfam Protein Families Database", Nucleic Acids Res., vol. 30(1), pp. 276-280 (2002).
Bateman, et al., "Pfam 3.1: 1313 multiple alignments and profile HMMs match the majority of proteins", Nucleic Acids Res., vol. 27(1), pp. 260-262 (1999).
Birney, et al., "Using GeneWise in the *Drosophila* Annotation Experiment", Genome Res., vol. 10, pp. 547-548 (2000).
Bolton, et al., "The Labelling of Proteins to High Specific Radioactivities by Conjugation to a $^{125}$I-Containing Acylating Agent", Biochem. J., vol. 133, pp. 529-539 (1973).
Burge, et al., "Prediction of Complete Gene Structures in Human Genomic DNA", J. Mol. Biol., vol. 268, pp. 78-94 (1997).
Butler, et al., "Inhibition of Transformed Cell Growth and Induction of Cellular Differentiation by Pyroxamide, an Inhibitor of Histone Deacetylase", Clin. Cancer Res., vol. 7, pp. 962-970 (2001).
Coffey, et al., "The Histone Deacetylase Inhibitor, CBHA, Inhibits Growth of Human Neuroblastoma Xenografts in Vivo, Alone and Synergistically with *All-Trans* Retinoic Acid", Cancer Res., vol. 61, pp. 3591-3594 (2001).
Cress, et al., "Histone Deacetylases, Transcriptional Control, and Cancer", J. Cell. Physiol., vol. 184, pp. 1-16 (2000).
David, et al., "Molecular characterization of a familial translocation implicates disruption of *HDAC9* and possible position effect on *TGFβ2* in the pathogenesis of Peters' anomaly", Genomics, vol. 81, pp. 489-503 (2003).

(Continued)

*Primary Examiner*—Laura B Goddard
(74) *Attorney, Agent, or Firm*—Stephen C. D'Amico

(57) ABSTRACT

The present invention relates to newly discovered human histone deacetylases (HDACs), also referred to as histone deacetylase-like polypeptides. The polynucleotide sequences and encoded polypeptides of the novel HDACs are encompassed by the invention, as well as vectors comprising these polynucleotides and host cells comprising these vectors. The invention also relates to antibodies that bind to the disclosed HDAC polypeptides, and methods employing these antibodies. Also related are methods of screening for modulators, such as inhibitors or antagonists, or agonists. The invention also relates to diagnostic and therapeutic applications which employ the disclosed HDAC polynucleotides, polypeptides, and antibodies, and HDAC modulators. Such applications can be used with diseases and disorders associated with abnormal cell growth or proliferation, cell differentiation, and cell survival, e.g., neoplastic cell growth, and especially breast and prostate cancers or tumors.

9 Claims, 66 Drawing Sheets

OTHER PUBLICATIONS

Finnin, et al., "Structures of a histone deacetylase homologue bound to the TSA and SAHA inhibitors", Nature, vol. 401, pp. 188-193 (1999).

Florea, et al., "A Computer Program for Aligning a cDNA Sequence with a Genomic DNA Sequence", Genome Res., vol. 8, pp. 967-974 (1998).

Gray, et al., "The Human Histone Deacetylase Family", Experimental Cell Res., vol. 262, pp. 75-83 (2001).

Grozinger, et al., "Three proteins define a class of human histone deacetylases related to yeast Hdalp", PNAS, vol. 96, pp. 4868-4873 (1999).

Han, et al., "Mechanism of Recruitment of Class II Histone Deacetylases by Myocyte Enhancer Factor-2", J. Mol. Biol., vol. 345, pp. 91-102 (2005).

Henderson, et al., "Lymphoid Enhancer Factor-1 Blocks Adenomatous Polyposis Coli-mediated Nuclear Export and Degregation of β-Catenin", J. Biol. Chem., vol. 277 (27), pp. 24258-24264 (2002).

Higgins, et al., "Using Clustal for Multiple Sequence Alignments", Methods Enzymol., vol. 266, pp. 383-402 (1996).

Hillier, et al., "The DNA sequence of human chromosome 7", Nature, vol. 424, pp. 157-164 (2003).

Hofmann, et al., The Prosite database, its status in 1999, Nucleic Acids Res., vol. 27 (1), pp. 215-219 (1999).

Huang, et al., "Suberoylanilide Hydroxamic Acid as a Potential Therapeutic Agent for Human Breast Cancer Treatment", Mol. Medicine, vol. 6 (10), pp. 849-866 (2000).

Khochbin, et al., "Functional significance of histone deacetylase diversity", Curr. Opin. Genetics Develop., vol. 11, pp. 162-166 (2001).

King, et al., "Amplification of a Novel v-erbB-Related Gene in a Human Mammary Carcinoma", Science, vol. 229, pp. 974-976 (1985).

Komatsu, et al., "Cyclic Hydroxamic-acid-containing Peptide 31, a Potent Synthetic Histone Deacetylase Inhibitor with Antitumor Activity", Cancer Res., vol. 61, pp. 4459-4466 (2001).

Lomonte, et al., "Functional Interaction between Class II Histone Deacetylases and ICP0 of Herpes Simplex Virus Type 1", J. Virol., vol. 78 (13), pp. 6744-6757 (2004).

Lorenzi, et al., "Distinct expression patterns and transforming properties of multiple isoforms of Ost, an exchange factor for RhoA and Cdc-42", Oncogene, vol. 18, pp. 4742-4755 (1999).

Lorenzi, et al., "Expression cloning, developmental expression and chromosomal localization of fibroblast growth factor-8", Oncogene, vol. 10, pp. 2051-2055 (1995).

LoRusso, et al., "Preclinical antitumor activity of CI-994", Invest. New Drugs, vol. 14, pp. 349-356 (1996).

Mahlknecht, et al., Chromosomal organization and localization of the human histone deacetylase 9 gene (HDAC9), Biochem. Biophys. Res. Comm., vol. 293, pp. 182-191 (2002).

Marks, et al., "Histone Deacetylase Inhibitors: Inducers of Differentiation or Apoptosis of Transformed Cells", J. National Cancer Institute, vol. 92 (15), pp. 1210-1216 (2000).

Marks, et al., "Histone deacetylase inhibitors as new cancer drugs", Curr. Opin. Oncology, vol. 13, pp. 477-483 (2001).

McInerney, et al., "Long-term silencing of retroviral vectors is resistant to reversal by trichostatin A and 5-azacytidine", Gene Ther., vol. 7, pp. 653-663 (2000).

Nagase, et al., "Prediction of the Coding Sequences of Unidentified Human Genes. XI. The Complete Sequences of 100 New cDNA Clones from Brain Which Code for Large Proteins in vitro", DNA Res., vol. 5, pp. 277-286 (1998).

Petrie, et al., "The Histone Deacetylase 9 Gene Encodes Multiple Protein Isoforms", J. Biol. Chem., vol. 278 (18), pp. 16059-16072 (2003).

Petrie, et al., "Role of a Novel Class II Histone Deacetylase in Normal and Leukemia-Associated Transcriptional Repression", Blood, vol. 98 (11) (part 1), pp. 568A (2001).

Prakash, et al., "Chronic oral administration of CI-994: a Phase 1 study", Investigational New Drugs, vol. 19, pp. 1-11 (2001).

Saito, et al., "A synthetic inhibitor of histone deacetylase, MS-27-275, with marked in vivo antitumor activity against human tumors" PNAS, vol. 96, pp. 4592-4597 (1999).

Sanchez Del Pino, et al., "Properties of the yeast nuclear histone deacetylase", Biochem. J., vol. 303, pp. 723-729 (1994).

Sandor, et al., "Phase I Trial of the Histone Deacetylase Inhibitor, Depsipeptide (FR901228, NSC 630176), in Patients with Refractory Neoplasms", Clinical Cancer Res., vol. 8, pp. 718-728 (2002).

Sonnhammer, et al., "Pfam:A Comprehensive Database of Protein Domain Families Based on Seed Alignments", Proteins, vol. 28, pp. 405-420 (1997).

Sowa, et al., "Sp3, but not Sp1, Mediates the Transcriptional Activation of the p21/WAF1/Cip1 Gene Promoter by Histone Deacetylase Inhibitor", Cancer Res., vol. 59, pp. 4266-4270 (1999).

Sparrow, et al., "MEF-2 function is modified by a novel co-repressor, MITR", EMBO J., vol. 18 (18), pp. 5085-5098 (1999).

Sun, et al., "Gelsolin, a Multifunctional Actin Regulatory Protein", J. Biol. Chem., vol. 274 (47), pp. 33179-33182 (1999).

Verdin, et al., "Class II histone deacetylases: versatile regulators", Trends Genetics, vol. 19 (5), pp. 286-293 (2003).

Vigushin, et al., "Histone deacetylase inhibitors in cancer treatment", Anti-Cancer Drugs, vol. 13, pp. 1-13 (2002).

Weidle, et al., "Inhibition of Histone Deacetylases: a New Strategy to Tartet Epigenetic Modifications for Anticancer Treatment", Anticancer Res., vol. 20, pp. 1471-1486 (2000).

Wharton, et al., "Inhibition of Mitogenesis in Balb/c-3T3 Cells by Trichostatin A", J. Biol. Chem., vol. 275 (43), pp. 33981-33987 (2000).

Wang, et al., "HDAC4, a Human Histone Deacetylase Related to Yeast HDA1, Is a Transcriptional Corepressor", Molec. Cell. Biol., vol. 19 (11), p. 7816-7827 (1999).

Yan, et al., "Role of DNA Methylation and Histone Acetylation in Steroid Receptor Expression in Breast Cancer", J. Mammary Gland Biol. Neoplasia, vol. 6 (2), pp. 183-192 (2001).

Yoshida, et al., "A Novel Tetracyclic Peptide, Trapoxin, Induces Phenotypic Change from Transformed to Normal in sis-Oncogene-transforded NIH3T3 Cells", Jpn. J. Cancer Res., vol. 83, pp. 324-328 (1992).

Yoshida, et al., "Histone deacetylase as a new target for cancer chemotherapy", Cancer Chemother. Pharmacol., vol. 48 (Suppl 1), pp. S20-S26 (2001).

Youn, et al., "Calcium Regulates Transcriptional Repression of Myocyte Enhancer Factor 2 by Histone Deacetylase 4", J. Biol. Chem., vol. 275 (29), pp. 22563-22567 (2000).

Zhang, et al., "Association of COOH-terminal-binding Protein (CtBP) and MEF2-interacting Transcription Repressor (MITR) Contributes to Transcriptional Repression of the MEF2 Transcription Factor", J. Biol. Chem., vol. 276 (1), pp. 35-39 (2001).

Zhang, et al., "Association of Class II Histone Deacetylases with Heterochromatin Protein 1: Potential Role for Histone Methylation in Control of Muscle Differentiation", Molec. Cell. Biol., vol. 22 (20), pp. 7302-7312 (2002).

Zhou, et al., "Identification of a transcriptional repressor related to the noncatalytic domain of histone deacetylases 4 and 5", PNAS, vol. 97 (3), pp. 1056-1061 (2000).

Zhou, et al., "Cloning and characterization of a histone deacetylase, HDAC9", vol. 98 (19), pp. 10572-10577 (2001).

NCBI Entrez Accession No. AA287983 (gi:1933807), NCI-CGAP, Aug. 14, 1997.

NCBI Entrez Accession No. AAC78618 (gi:30142019), Hillier, et al., Jan. 30, 2004.

NCBI Entrez Accession No. AAD15364 (gi:30142008), Sulston, et al., Oct. 8, 2003.

NCBI Entrez Accession No. AAK66821 (gi:15590680), Zhou, et al., Sep. 12, 2001.

NCBI Entrez Accession No. AAO27363 (gi:28629389), Petrie, et al., Apr. 28, 2003.

NCBI Entrez Accession No. AAQ54273 (gi:33770475), Bisanti, et al., Aug. 17, 2003.

NCBI Entrez Accession No. AAQ54275 (gi:33770477), Bisanti, et al., Aug. 17, 2003.

NCBI Entrez Accession No. AB018287 (gi:3882208), Nagase, et al., Jan. 10, 2004.

NCBI Entrez Accession No. AC002088 (gi:21322174), Sulston, et al., Jun. 4, 2002.
NCBI Entrez Accession No. AC002410 (gi:21322222), Hillier, et al., Jan. 31, 2004.
NCBI Entrez Accession No. AC004994 (gi:3900849), Hillier, et al., Jan. 30, 2004.
NCBI Entrez Accession No. AC016186 (gi:7230177), Birren, et al., Mar. 12, 2000.
NCBI Entrez Accession No. AF132608 (gi:4754908), Grozinger, et al., May 6, 1999.
NCBI Entrez Accession No. AY032737 (gi:15590679), Zhou, et al., Sep. 12, 2001.
NCBI Entrez Accession No. AY032738 (gi:15590681), Zhou, et al., Sep. 12, 2001.
NCBI Entrez Accession No. BAA34464 (gi:40788348), Nagase, et al., Jan. 10, 2004.
NCBI Entrez Accession No. CAD30851 (gi:30089124), David, et al., Apr. 22, 2003.
NCBI Entrez Accession No. CAD91072 (gi:30577168), Zelent, et al., May 12, 2003.
NCBI Entrez Accession No. NM_014707 (gi:7662279), Han, et al., Oct. 16, 2005.
NCBI Entrez Accession No. NM_058176 (gi:17158038), Han, et al., Oct. 17, 2005.
NCBI Entrez Accession No. NM_058177 (gi:17158040), Han, et al., Oct. 17, 2005.
NCBI Entrez Accession No. NM_178423 (gi:30795201), Han, et al., Oct. 18, 2005.
NCBI Entrez Accession No. NP_055522 (gi:7662280), Han, et al., Oct. 16, 2005.
NCBI Entrez Accession No. NP_478056 (gi:17158039), Han, et al., Oct. 17, 2005.
NCBI Entrez Accession No. NP_478057 (gi:17158041), Han, et al., Oct. 17, 2005.
NCBI Entrez Accession No. NP_848510 (gi:30795202), Han, et al., Oct. 18, 2005.
NCBI Entrez Accession No. NP_848512 (gi:30795204), Han, et al., Oct. 18, 2005.
NCBI Entrez Accession No. XP_518986 (gi:55628200), NCBI's Annotation Project, Nov. 9, 2004.
NCBI Entrez Accession No. XP_004963 (gi:12733405), NCBI's Annotation Project, Oct. 16, 2001.
NCBI Entrez Accession No. CAH18349 (gi:51476771), Koehrer, et al., Apr. 17, 2005.
NCBI Entrez Accession No. gi|12733405, NCBI Annotation Project, Oct. 16, 2001.
NCBI Entrez Accession No. gi|13183017, Zhou, X. et al., Mar. 2, 2001.
NCBI Entrez Accession No. gi|15590680, Zhou, X. et al., Sep. 12, 2001.
NCBI Entrez Accession No. gi|15590682, Zhou, X. et al., Sep. 12, 2001.
NCBI Entrez Accession No. gi|16162463, NCBI Annotation Project, Oct. 16, 2001.
NCBI Entrez Accession No. gi|16162465, NCBI Annotation Project, Oct. 16, 2001.
NCBI Entrez Accession No. gi|17158039, Sparrow, D.B. et al., Nov. 5, 2002.
NCBI Entrez Accession No. gi|17158041, Sparrow, D.B. et al., Nov. 5, 2002.
NCBI Entrez Accession No. gi|18202676, Zhou, X. et al., Oct. 16, 2001.
NCBI Entrez Accession No. gi|19865267, Zhou, X. et al., Jun. 15, 2002.
NCBI Entrez Accession No. gi|21756856, Tanigami, A. et al., Jul. 15, 2002.
NCBI Entrez Accession No. gi|3882209, Nagase, T. et al., Jun. 16, 1999.
NCBI Entrez Accession No. gi|7662280, Sparrow, D.B. et al., Nov. 5, 2002.
Mahlknecht, U. et al., "Chromosomal organization and localization of the human histone deacetylase 9 gene (*HDAC9*)", Biochemical and Biophysical Research Communications 293, pp. 182-191 (2002).
Marks, P.A. et al., "Histone Deacetylase Inhibitors: Inducers of Differentation or Apoptosis of Transformed Cells", Journal of the National Cancer Institute, vol. 92, No. 15, pp. 1210-1216 (2000).
Nagase, T. et al., "Prediction of the Coding Sequences of Unidentified Human Genes. XI. The Complete Sequences of 100 New cDNA Clones from Brain Which Code for Large Proteins in vitro", DNA Research 5, pp. 277-286 (1998).
Sparrow, D.B. et al., "MEF-2 function is modified by a novel co-repressor, MITR", The EMBO Journal, vol. 18, No. 18, pp. 5085-5098 (1999).
Wang, A.H. et al., "HDAC4, a Human Histone Deacetylase Related to Yeast HDA1, is a Transcriptional Corepressor", Molecular and Cellular Biology, vol. 19, No. 11, pp. 7816-7827 (1999).
Zhang, C.L. et al., "Association of COOH-terminal-binding Protein (CtBP) and MEF2-interacting Transcription Repressor (MITR) Contributes to Transcriptional Repression of the MEF2 Transcription Factor", The Journal of Biological Chemistry, vol. 276, No. 1, pp. 35-39 (2001).
Zhou, X. et al., "Cloning and characterization of a histone deacetylase, HDAC9", Proc. Natl. Acad. Sci. U.S.A., vol. 98, No. 19, pp. 10572-10577 (2001).

\* cited by examiner

FIG. 1

```
     GlyIleAlaTyrAspProLeuMetLeuLysHisGlnCysValCysGly
  1  ggaattgcctatgaccccttgatgctgaaacaccagtgcgtttgtggc
     ccttaacggatactggggaactacgactttgtggtcacgcaaacaccg AsnSerThrThrHisProGluHisAlaGlyArgIleGlnSerIleTrp
 49  aattccaccacccaccctgagcatgctggacgaatacagagtatctgg
     ttaaggtggtgggtgggactcgtacgacctgcttatgtctcatagacc SerArgLeuGlnGluThrGlyLeuLeuAsnLysCysGluArgIleGln
 97  tcacgactgcaagaaactgggctgctaaataaatgtgagcgaattcaa
     agtgctgacgttctttgacccgacgatttatttacactcgcttaagtt GlyArgLysAlaSerLeuGluGluIleGlnLeuValHisSerGluHis
145  ggtcgaaaagccagcctggaggaaatacagcttgttcattctgaacat
     ccagcttttcggtcggacctcctttatgtcgaacaagtaagacttgta HisSerLeuLeuTyrGlyThrAsnProLeuAspGlyGlnLysLeuAsp
193  cactcactgttgtatggcaccaaccccctggacggacagaagctggac
     gtgagtgacaacataccgtggttgggggacctgcctgtcttcgacctg ProArgIleLeuLeuGlyAspAspSerGlnLysPhePheSerSerLeu
241  cccaggatactcctaggtgatgactctcaaaagttttttcctcatta
     gggtcctatgaggatccactactgagagttttcaaaaaaggagtaat ProCysGlyGlyLeuGlyValSerThr
289  ccttgtggtggacttggggtaagtaca
     ggaacaccacctgaaccccattcatgt
```

FIG. 2A

```
                    701                                              750
AQUIFEX_HDAL  (12)  YGKYRYPKNHPLKIPRVSLLLRFKDAMNLIDEKELIKSRPATKEELLLFH
   BMY_HDAL1  (16)  G----NSTTHPEHAGRIQSIWSRLQETGLLNKCERIQGRKASLEEIQLVH
   BMY_HDAL2   (1)  --------------------------------------------------
   BMY_HDAL3   (1)  --------------------------------------------------
        HDA4 (670)  G----SSSSHPEHAGRIQSIWSRLQETGLRGKCECIRGRKATLEELQTVH
        HDA5 (699)  G----NTHVHPEHAGRIQSIWSRLQETGLLSKCERIRGRKATLDEIQTVH
        HDA7 (496)  G----DNSRHPEHAGRIQSIWSRLQERGLRSQCECLRGRKASLEELQSVH
      SC_HDA1 (74)  TSYFEYIDPHPEDPRRIYRIYKILAENGLIN-----DPTLSGVDDLGDLM 751                                              800
AQUIFEX_HDAL  (62)  TEDYINTLMEAERCQCVPKG-------------------AREKYNIGGY
   BMY_HDAL1  (62)  SEHHSLLYGTNPLDGQKLDPRILLGDDSQKFFSSLPCGGLGVST------
   BMY_HDAL2   (1)  ---------------------------------------VDSDTIWNE
   BMY_HDAL3   (1)  --------------------------------------------------
        HDA4 (716)  SEAHTLLYGTNPLNRQKLDSKKLLG-SLASVFVRLPCGGVGVDSDTIWNE
        HDA5 (745)  SEYHTLLYGTSPLNRQKLDSKKLLGPISQKMYAVLPCGGIGVDSDTVWNE
        HDA7 (542)  SERHVLLYGTNPLSRLKLDNGKLAGLLAQRMFEMLPCGGVGVDTDTIWNE
     SC_HDA1 (119)  LKIPVRAATSEEILEVHTKEHLEFIESTEKMSRE-ELLKETEKGDSVYFN 801                                              850
AQUIFEX_HDAL  (92)  ENPVSYAMFTGSSLATGSTVQAIEEFLKGNVAFNPAGGMHHAFKSRANGF
   BMY_HDAL1 (106)  --------------------------------------------------
   BMY_HDAL2  (10)  LHSSGAARMAVGCVIELASKVASGELKNGFAVVRPPG--HHAEESTAMGF
   BMY_HDAL3   (1)  --------------------------------------------------
        HDA4 (765)  VHSAGAARLAVGCVVELVFKVATGELKNGFAVVRPPG--HHAEESTPMGF
        HDA5 (795)  MHSSSAVRMAVGCLLELAFKVAAGELKNGFAIIRPPG--HHAEESTAMGF
        HDA7 (592)  LHSSNAARWAAGSVTDLAFKVASRELKNGFAVVRPPG--HHADHSTAMGF
     SC_HDA1 (168)  NDSYASARLPCGGAIEACKAVVEGRVKNSLAVVRPPG--HHAEPQAAGGF 851                                              900
AQUIFEX_HDAL (142)  CYINNPAVGIEYLRKK----GFKRILYIDLDAHHCDGVQEAFYDTDQVFV
   BMY_HDAL1 (106)  --------------------------------------------------
   BMY_HDAL2  (58)  CFFNSVAITAKYLRDQ---LNISKILIVDLDVHHGNTQQAFYADPSILY
   BMY_HDAL3   (1)  --------------------------------------------------
        HDA4 (813)  CYFNSVAVAAKLLQQR---LSVSKILIVDWDVHHGNGTQQAFYSDPSVLY
        HDA5 (843)  CFFNSVAITAKLLQQK---LNVGKVLIVDWDIHHGNGTQQAFYNDPSVLY
        HDA7 (640)  CFFNSVAIACRQLQQQSKASKASKILIVDWDVHHGNGTQQTFYQDPSVLY
     SC_HDA1 (216)  CLESNVAVAAKNILKN-YPESVRRIMILDWDIHHGNGTQKSFYQDDQVLY 901                                              950
AQUIFEX_HDAL (188)  LSLHQ-SPEYAFPFE-KGFLEEIGEGKGKGYNLNIPLPKG----LNDNEF
   BMY_HDAL1 (106)  --------------------------------------------------
   BMY_HDAL2 (105)  ISLHRYDEGNFFPG--SGAPNEVGTGLGEGYNINIAWTGGLDPPMGDVEY
   BMY_HDAL3   (1)  --------------------------------------------------
        HDA4 (860)  MSLHRYDDGNFFPG--SGAPDEVGTGPGVGFNVNMAFTGGLDPPMGDAEY
        HDA5 (890)  ISLHRYDNGNFFPG--SGAPEEVGGGPGVGYNVNVAWTGGVDPPIGDVEY
        HDA7 (690)  ISLHRHDDGNFFPG--SGAVDEVGAGSGEGFNVNVAWAGGLDPPMGDPEY
     SC_HDA1 (265)  VSLHRFEMGKYYPGTIQGQYDQTGEGKGEGFNCNITWPVG---GVGDAEY
```

FIG. 2B

```
                         951                                              1000
AQUIFEX_HDAL   (232)  LFALEKSLEIVKEVFEPEVYLLQLGTDP--LLEDYLSKFNLSNVAFLKAF
   BMY_HDAL1   (106)  --------------------------------------------------
   BMY_HDAL2   (153)  LEAFRLVLLSL---------------------------------------
   BMY_HDAL3     (1)  ----RTIVKPVAKEFDPDMVLVSAGFDALEGHTPPLGGYKVTAKCFGHLT
        HDA4   (908)  LAAFRTVVMPIASEFAPDVVLVSSGFDAVEGHPTPLGGYNLSARCFGYLT
        HDA5   (938)  LTAFRTVVMPIAHEFSPDVVLVSAGFDAVEGHLSPLGGYSVTARCFGHLT
        HDA7   (738)  LAAFRIVVMPIAREFSPDLVLVSAGFDAAEGHPAPLGGYHVSAKCFGYMT
     SC_HDA1   (312)  MWAFEQVVMPMGREFKPDLVIISSGFDAADG--DTIGQCHVTPSCYGHMT 1001                                              1050
AQUIFEX_HDAL   (280)  NIVREVFGEGVYLG-GGGYHPYALARAWTLIWCELSGR---EVPEKLNNK
   BMY_HDAL1   (106)  --------------------------------------------------
   BMY_HDAL2   (164)  --------------------------------------------------
   BMY_HDAL3    (47)  KQLMTLADGRVVLALEGGHDLTAICDASEACVNALLGNELEPLAEDILHQ
        HDA4   (958)  KQLMGLAGGRIVLALEGGHDLTAICDASEACVSALLGNELDPLPEKVLQQ
        HDA5   (988)  RQLMTLAGGRVVLALEGGHDLTAICDASEACVSALLSVELQPLDEAVLQQ
        HDA7   (788)  QQLMNLAGGAVVLALEGGHDLTAICDASEACVAALLGNRVDPLSEEGWKQ
     SC_HDA1   (360)  HMLKSLARGNLCVVLEGGYNLDAIARSALSVAKVLIGEPPDELPDPLSDP 1051                                              1100
AQUIFEX_HDAL   (326)  AKELLKSIDFEEFDDEVDRSYMLETLKDPWRGGEVRKEVKDTLEKAKASS
   BMY_HDAL1   (106)  --------------------------------------------------
   BMY_HDAL2   (164)  --------------------------------------------------
   BMY_HDAL3    (97)  SPNMNAVISLQKIIEIQSKYWKSVRMVAVPRGCALAGAQL--QEETETVS
        HDA4  (1008)  RPNANAVRSMEKVMEIHSKYWRCLQRTTSTAGRSLIEAQTCENEEAETVT
        HDA5  (1038)  KPNINAVATLEKVIEIQSKHWSCVQKFAAGLGRSLREAQAGETEEAETVS
        HDA7   (838)  KPQPQCHPLSGGRDPGAQ--------------------------------
     SC_HDA1   (410)  KPE--VIEMIDKVIRLQSKYWNCFRRRHANSGCNFNEPINDSIISKNFPL 1101                                              1150
AQUIFEX_HDAL   (376)  --------------------------------------------------
   BMY_HDAL1   (106)  --------------------------------------------------
   BMY_HDAL2   (164)  --------------------------------------------------
   BMY_HDAL3   (145)  ALASLTVDVEQPFAQEDSRTAG----EPMEEEPAL---------------
        HDA4  (1058)  AMASLSVGVKPAEKRPDEEPME--------EEPPL---------------
        HDA5  (1088)  AMALLSVGAEQAQAAAAREHSPRPAEEPMEQEPAL---------------
        HDA7   (856)  --------------------------------------------------
     SC_HDA1   (458)  QKAIRQQQQHYLSDEFNFVTLPLVSMDLPDNTVLCTPNISESNTIIIVVH
```

FIG. 3A

```
Genewise results from HDA5_HUMAN_run2 applied to AC002088
Hit 1: bits = 149
      BAC start:56543
      BAC end:74703
      Protein start:684
      Protein end:788

>Results for GCGPROT:HDA5_HUMAN vs AC002088 (forward) [0]

genewisedb output
Score 149.09 bits over entire alignment.
This will be different from per-alignment scores. See manual for details
For computer parsable output, try genewisedb -help or read the manual
Scores as bits over a synchronous coding model Alignment 1 Score 148.82 (Bits)

HDA5         684 G  V  V  Y  D  T  F  M  L  K  H  Q  C  M  C  G  N  T  H  V
                 G  +     Y  D     +  M  L  K  H  Q  C  +  C  G  N  +
                 G  I  A  Y  D  P  L  M  L  K  H  Q  C  V  C  G  N  S  T  T
AC002088 56543 ggaattgcctatgaccccttgatgctgaaacaccagtgcgtttgtggcaattccaccacc H  P  E  H  A  G  R  I  Q  S  I  W  S  R  L  Q  E  T  G
                 H  P  E  H  A  G  R  I  Q  S  I  W  S  R  L  Q  E  T  G
                 H  P  E  H  A  G  R  I  Q  S  I  W  S  R  L  Q  E  T  G
                cacccctgagcatgctggacgaatacagagtatctggtcacgactgcaagaaactggg HDA5         723 L  L  S  K  C  E                       R  I  R  G  R  K
                 L  L  +  K  C  E                       R  I  +  G  R  K
                 L  L  N  K  C  E                       R  I  Q  G  R  K
AC002088 56660 ctgctaaataaatgtgagGTAATCC   Intron 1    CAGcgaattcaaggtcgaaaa
                                         <0-----[56678:69695]-0>

A  T  L  D
                 A  +  L  +
                 A  S  L  E
                gccagcctggag HDA5         739 E  I  Q  T  V  H  S  E  Y  H  T  L  L  Y  G  T  S  P  L  N
                 E  I  Q     V  H  S  E  +  H  +  L  L  Y  G  T  +  P  L  +
                 E  I  Q  L  V  H  S  E  H  H  S  L  L  Y  G  T  N  P  L  D
AC002088 69726 gaaatacagcttgttcattctgaacatcactcactgttgtatggcaccaaccccctggac R  Q  K  L  D  S  K  K  L  L
                    Q  K  L  D     +     L  L
                 G  Q  K  L  D  P  R  I  L  L
                ggacagaagctggaccccaggatactccta HDA5     769                               P  I  S  Q  K  M  Y  A  V  L  P
                                           S  Q  K  +  +     +        L  P
                              G:G[ggt]     D  D  S  Q  K  F  F  S  S  L  P
AC002088 69816 GGTCTGTA   Intron 2     TAGGTgatgactctcaaaagttttttttcctcattacct
                        <1-----[69817:74644]-1>
```

```
                    C  G  G  I  G  V  D  S
                    C  G  G  +  G  V     +
                    C  G  G  L  G  V  S  T
                    tgtggtggacttggggtaagtaca HDA5          783   G  I  G  V  D  S
                    G  +  G  V     +
                    G  L  G  V  S  T
AC002088    74686   ggacttggggtaagtaca
```

```
MOTIFS FROM: BMY_HDAL1.AA.FASTA

MISMATCHES: 0

BMY_HDAL1.AA.FASTA   CHECK: 4620   LENGTH: 105    !

AMIDATION             XG(R,K)(R,K)
                      XG(R)(K)
         48: KCERI       QGRK       ASLEE (ABSTRACT FILE: 0009.PDOC)

ASN_GLYCOSYLATION    N-(P)(S,T)-(P)
                     N-P(T)-P
         17: QCVCG       NSTT       HPEHA (ABSTRACT FILE: 0001.PDOC)

CAMP_PHOSPHO_SITE     (R,K)2X(S,T)
                      (R,K){2}X(S)
         50: ERIQG       RKAS       LEEIQ (ABSTRACT FILE: 0004.PDOC)

CK2_PHOSPHO_SITE      (S,T)X2(D,E)
                      (T)X{2}(E)
         20: CGNST       THPE       HAGRI (S)X{2}(E)
         53: QGRKA       SLEE       IQLVH (ABSTRACT FILE: 0006.PDOC)

MYRISTYL              G-(E,D,R,K,H,P,F,Y,W)X2(S,T,A,G,C,N)-(P)
                      G-(E,D,R,K,H,P,F,Y,W)X{2}(T)-P
         16: HQCVC                 GNSTTH                  PEHAG

G-(E,D,R,K,H,P,F,Y,W)X{2}(S)-P
        100: SLPCG                 GLGVST (ABSTRACT FILE: 0008.PDOC)

PKC_PHOSPHO_SITE      (S,T)X(R,K)
                      (S)X(K)
         89: LLGDD       SQK        FFSSL (ABSTRACT FILE: 0005.PDOC)
```

FIG. 5

```
      ValAspSerAspThrIleTrpAsnGluLeuHisSerSerGlyAlaAlaArgMetAlaVal
  1   GTGGACAGTGACACCATTTGGAATGAGCTACACTCGTCCGGTGCTGCACGCATGGCTGTT
      CACCTGTCACTGTGGTAAACCTTACTCGATGTGAGCAGGCCACGACGTGCGTACCGACAA

GlyCysValIleGluLeuAlaSerLysValAlaSerGlyGluLeuLysAsnGlyPheAla
 61   GGCTGTGTCATCGAGCTGGCTTCCAAAGTGGCCTCAGGAGAGCTGAAGAATGGGTTTGCT
      CCGACACAGTAGCTCGACCGAAGGTTTCACCGGAGTCCTCTCGACTTCTTACCCAAACGA

ValValArgProProGlyHisHisAlaGluGluSerThrAlaMetGlyPheCysPhePhe
121   GTTGTGAGGCCCCCTGGCCATCACGCTGAAGAATCCACAGCCATGGGGTTCTGCTTTTTT
      CAACACTCCGGGGGACCGGTAGTGCGACTTCTTAGGTGTCGGTACCCCAAGACGAAAAAA

AsnSerValAlaIleThrAlaLysTyrLeuArgAspGlnLeuAsnIleSerLysIleLeu
181   AATTCAGTTGCAATTACCGCCAAATACTTGAGAGACCAACTAAATATAAGCAAGATATTG
      TTAAGTCAACGTTAATGGCGGTTTATGAACTCTCTGGTTGATTTATATTCGTTCTATAAC

IleValAspLeuAspValHisHisGlyAsnGlyThrGlnGlnAlaPheTyrAlaAspPro
241   ATTGTAGATCTGGATGTTCACCATGGAAACGGTACCCAGCAGGCCTTTTATGCTGACCCC
      TAACATCTAGACCTACAAGTGGTACCTTTGCCATGGGTCGTCCGGAAAATACGACTGGGG

SerIleLeuTyrIleSerLeuHisArgTyrAspGluGlyAsnPhePheProGlySerGly
301   AGCATCCTGTACATTTCACTCCATCGCTATGATGAAGGGAACTTTTTCCCTGGCAGTGGA
      TCGTAGGACATGTAAAGTGAGGTAGCGATACTACTTCCCTTGAAAAAGGGACCGTCACCT

AlaProAsnGluValGlyThrGlyLeuGlyGluGlyTyrAsnIleAsnIleAlaTrpThr
361   GCCCCAAATGAGGTTGGAACAGGCCTTGGAGAAGGGTACAATATAAATATTGCCTGGACA
      CGGGGTTTACTCCAACCTTGTCCGGAACCTCTTCCCATGTTATATTTATAACGGACCTGT

GlyGlyLeuAspProProMetGlyAspValGluTyrLeuGluAlaPheArgLeuValLeu
421   GGTGGCCTTGATCCTCCCATGGGAGATGTTGAGTACCTTGAAGCATTCAGGTTGGTACTT
      CCACCGGAACTAGGAGGGTACCCTCTACAACTCATGGAACTTCGTAAGTCCAACCATGAA

LeuSerLeu
481   CTTTCTCTC
      GAAAGAGAG
```

FIG. 6A

```
GENEWISE RESULTS FROM HDA5_HUMAN_RUN3 APPLIED TO AC002410
HIT 1: BITS = 262
      BAC START:15451
      BAC END:58122
      PROTEIN START:786
      PROTEIN END:948

>RESULTS FOR GCGPROT:HDA5_HUMAN VS AC002410 (FORWARD) [0]

GENEWISEDB OUTPUT
SCORE 262.30 BITS OVER ENTIRE ALIGNMENT.
THIS WILL BE DIFFERENT FROM PER-ALIGNMENT SCORES. SEE MANUAL FOR DETAILS
FOR COMPUTER PARSABLE OUTPUT, TRY GENEWISEDB -HELP OR READ THE MANUAL
SCORES AS BITS OVER A SYNCHRONOUS CODING MODEL

ALIGNMENT 1 SCORE 261.25 (BITS)

HDA5       786 V  D  S  D  T  V  W  N  E  M  H  S  S  S  A  V  R  M  A  V  G  C  L
               V  D  S  D  T  +  W  N  E  +  H  S  S     A     R  M  A  V  G  C  +
               V  D  S  D  T  I  W  N  E  L  H  S  S  G  A  A  R  M  A  V  G  C  V
AC002410 15451 GTGGACAGTGACACCATTTGGAATGAGCTACACTCGTCCGGTGCTGCACGCATGGCTGTTGGCTGTGTC

L  E  L  A  F  K  V  A  A  G  E  L  K
               +  E  L  A     K  V  A     G  E  L  K
               I  E  L  A  S  K  V  A  S  G  E  L  K
               ATCGAGCTGGCTTCCAAAGTGGCCTCAGGAGAGCTGAAG

HDA5       822                                            N  G  F  A  I  I  R  P  P  G  H  H  A  E  E  S
                                                          N  G  F  A  +  +  R  P  P  G  H  H  A  E  E  S
                                                          N  G  F  A  V  V  R  P  P  G  H  H  A  E  E  S
AC002410 15559 GTGAGGT    INTRON 1       CAGAATGGGTTTGCTGTTGTGAGGCCCCCTGGCCATCACGCTGAAGAATCC
                       <0-----[15559:51266]-0>

HDA5       838 T  A                             G  F  C  F  F  N  S  V  A  I  T
               T  A                             G  F  C  F  F  N  S  V  A  I  T
               T  A            M:M[ATG]         G  F  C  F  F  N  S  V  A  I  T
AC002410 51315 ACAGCCATGTAAGTA   INTRON 2   CAGGGGGTTCTGCTTTTTTAATTCAGTTGCAATTACC
                              <2-----[51323:51566]-2>

HDA5       852 A  K  L  L  Q  Q  K  L  N  V  G  K  V  L  I  V  D  W
               A  K     L  +        +  L  N  +     K  +  L  I  V  D
               A  K  Y  L  R  D  Q  L  N  I  S  K  I  L  I  V  D  L
AC002410 51601 GCCAAATACTTGAGAGACCAACTAAATATAAGCAAGATATTGATTGTAGATCTGGTATGTA     INTRON 3
                                                                          <0---[51655:57572]

HDA5       870    D  I  H  H  G  N  T  Q  Q  A  F  Y  N  D  P  S  V  L  Y  I  S  L
                  D  +  H  H  G  N  T  Q  Q  A  F  Y     D  P  S  +  L  Y  I  S  L
                  D  V  H  H  G  N  T  Q  Q  A  F  Y  A  D  P  S  I  L  Y  I  S  L
AC002410   57570 TAGGATGTTCACCATGGAAACGGTACCCAGCAGGCCTTTTATGCTGACCCCAGCATCCTGTACATTTCACTC
                  -0>
                  H  R  Y  D  N  G  N  F  F  P  G  S  G
                  H  R  Y  D     G  N  F  F  P  G  S  G
                  H  R  Y  D  E  G  N  F  F  P  G  S  G
                  CATCGCTATGATGAAGGGAACTTTTTCCCTGGCAGTGGA

HDA5       906 A  P  E  E                          V  G  G  C  P  G  V  G  Y  N  V  N
               A  P     E                          V  G     C     G        Y  N  +  N
               A  P  N  E                          V  G  T  G  L  G  E  G  Y  N  I  N
AC002410 57681 GCCCCAAATGAGGTTCGGT   INTRON 4   CAGGTTGGAACAGGCCTTGGAGAAGGGTACAATATAAAT
                                 <0-----[57693:58005]-0>
```

FIG. 6B

```
HDA5      922 V A W T G G V D P P I G D V E Y L T A F R T V V
              + A W T G G + D P P + G D V E Y L   A F R   V +
              I A W T G G L D P P M G D V E Y L E A F R L V L
AC002410 58042 ATTGCCTGGACAGGTGGCCTTGATCCTCCCATGGGAGATGTTGAGTACCTTGAAGCATTCAGGTTGGTACTT

M P I
              + +
              L S L
              CTTTCTCTC
```

FIG. 7

PROSITE motifs identified in the partial predicted amino acid sequence of BMY_HDAL2.
MOTIFS FROM: BMY_HDAL2.AA.FASTA

MISMATCHES: 0

BMY_HDAL2.AA.FASTA   CHECK: 2381   LENGTH: 163   !

ASN_GLYCOSYLATION        N-(P)(S,T)-(P)
                         N-P(S)-P
            75: LRDQL        NISK        ILIVD

N-P(T)-P
            90: DVHHG        NGTQ        QAFYA (ABSTRACT FILE: 0001.PDOC)

MYRISTYL                 G-(E,D,R,K,H,P,F,Y,W)X2(S,T,A,G,C,N)-(P)
                         G-(E,D,R,K,H,P,F,Y,W)X{2}(A)-P
            91: VHHGN                GTQQAF              YADPS

G-(E,D,R,K,H,P,F,Y,W)X{2}(G)-P
           126: APNEV                GTGLGE              GYNIN

G-(E,D,R,K,H,P,F,Y,W)X{2}(G)-P
           128: NEVGT                GLGEGY              NINIA (ABSTRACT FILE: 0008.PDOC)

PKC_PHOSPHO_SITE         (S,T)X(R,K)
                         (T)X(K)
            66: NSVAI        TAK        YLRDQ (ABSTRACT FILE: 0005.PDOC)

FIG. 8A

```
GENEWISE RESULTS FROM HDA5_HUMAN_RUN3 APPLIED TO AC004994
HIT 1: BITS = 176
     BAC START:79767
     BAC END:11
     PROTEIN START:942
     PROTEIN END:1055

>RESULTS FOR GCGPROT:HDA5_HUMAN VS AC004994 (REVERSE) [0]

GENEWISEDB OUTPUT
SCORE 176.62 BITS OVER ENTIRE ALIGNMENT.
THIS WILL BE DIFFERENT FROM PER-ALIGNMENT SCORES. SEE MANUAL FOR DETAILS
FOR COMPUTER PARSABLE OUTPUT, TRY GENEWISEDB -HELP OR READ THE MANUAL
SCORES AS BITS OVER A SYNCHRONOUS CODING MODEL

ALIGNMENT 1 SCORE 174.85 (BITS)

HDA5_HUMAN  942 R  T  V  V  M  P  I  A  H  E  F  S  P  D  V  V  L  V  S  A  G  F  D  A
                R  T  +  V     P  +  A     E  F     P  D  +  V  L  V  S  A  G  F  D  A
                R  T  I  V  K  P  V  A  K  E  F  D  P  D  M  V  L  V  S  A  G  F  D  A
AC004994 -79767 AGGACCATCGTGAAGCCTGTGGCCAAAGAGTTTGATCCAGACATGGTCTTAGTATCTGCTGGATTTGATGCA
                V  E  G  H  L  S  P  L  G  G  Y  S  V  T  A
                +  E  G  H        P  L  G  G  Y     V  T  A
                L  E  G  H  T  P  P  L  G  G  Y  K  V  T  A
                TTGGAAGGCCACACCCCTCCTCTAGGAGGGTACAAAGTGACGGCA

HDA5_HUMAN  981 R                          F  G  H  L  T  R  Q  L  M  T  L  A
                +                          F  G  H  L  T  +  Q  L  M  T  L  A
                K           C:C[TGT]       F  G  H  L  T  K  Q  L  M  T  L  A
AC004994 -79650 AAATGTAAGTA   INTRON 1      TAGGTTTTGGTCATTTGACGAAGCAATTGATGACATTGGCT
                          <1-----[79646:18435]-1>

HDA5_HUMAN  995 G  G  R  V  V  L  A  L  E  G  G  H  D  L  T  A  I  C  D  A  S  E  A  C
                   G  R  V  V  L  A  L  E  G  G  H  D  L  T  A  I  C  D  A  S  E  A  C
                   D  G  R  V  V  L  A  L  E  G  G  H  D  L  T  A  I  C  D  A  S  E  A  C
AC004994 -18396 GATGGACGTGTGGTGTTGGCTCTAGAAGGAGGACATGATCTCACAGCCATCTGTGATGCATCAGAAGCCTGT
                V  S  A  L  L  S  V  E
                V  +  A  L  L     E
                V  N  A  L  L  G  N  E
                GTAAATGCCCTTCTAGGAAATGAG

HDA5_HUMAN 1027                      L  Q  P  L  D  E  A  V  L  Q  Q  K  P  N  I  N
                                     L  +  P  L     E     +  L     Q        P  N  +  N
                                     L  E  P  L  A  E  D  I  L  H  Q  S  P  N  M  N
AC004994 -18300 GTAAAAA   INTRON 2    CAGCTGGAGCCACTTGCAGAAGATATTCTCCACCAAAGCCCGAATATGAAT
                       <0-----[18300:   98]-0>

HDA5_HUMAN 1043 A  V  A  T  L  E  K  V  I  E  I  Q  S
                A  V     +  L  +  K  +  I  E  I  Q  S
                A  V  I  S  L  Q  K  I  I  E  I  Q  S
AC004994    -49 GCTGTTATTTCTTTACAGAAGATCATTGAAATTCAAAGT
```

FIG. 8B

```
GENEWISE RESULTS FROM HDA5_HUMAN_RUN3 APPLIED TO AC004744
HIT 1: BITS = 57
      BAC START:85491
      BAC END:43563
      PROTEIN START:1022
      PROTEIN END:1122

>RESULTS FOR GCGPROT:HDA5_HUMAN VS AC004744 (REVERSE) [0]

GENEWISEDB OUTPUT
SCORE 57.38 BITS OVER ENTIRE ALIGNMENT.
THIS WILL BE DIFFERENT FROM PER-ALIGNMENT SCORES. SEE MANUAL FOR DETAILS
FOR COMPUTER PARSABLE OUTPUT, TRY GENEWISEDB -HELP OR READ THE MANUAL
SCORES AS BITS OVER A SYNCHRONOUS CODING MODEL

ALIGNMENT 1 SCORE 55.39 (BITS)

HDA5 1022       L  L  S  V  E  L  Q  P  L  D  E  A  V  L  Q  Q  K  P  N
                L  L  +  +  L  +  P  L     E     +  L     Q     P  N
                L  L  F  L  Q  L  E  P  L  A  E  D  I  L  H  Q  S  P  N
AC004744 -85491 CTACTATTCTTGCAGCTGGAGCCACTTGCAGAAGATATTCTCCACCAAAGCCCGAAT

I  N  A  V     T  L  E  K  V  I  E  I  Q
                +  N  A  V     +  L  +  K  +  I  E  I  Q
                M  N  A  V  I  S  L  Q  K  I  I  E  I  Q
                ATGAATGCTGTTATTTCTTTACAGAAGATCATTGAAATTCAA

HDA5 1055                                  K  H  W  S  C  V  Q  K  F  A  A  G  L
                                           K  +  W        V  +           A
                         S:S[AGC]          K  Y  W  K  S  V  R  M  V  A  V  P  R
AC004744 85392 AGTATGTC    INTRON 1     TAGGCAAGTATTGGAAGTCAGTAAGGATGGTGGCTGTGCCAAGG
                         <1-----[85391:63817]-1>

HDA5 1069       G  R  S  L  R  E  A  Q  A    GET  E  E  A  E  T  V  S  A  M
                G     +  L        A  Q            E  E     E  T  V  S  A  +
                G  C  A  L  A  G  A  Q  L    --Q  E  E  T  E  T  V  S  A  L
AC004744 -63775 GGCTGTGCTCTGGCTGGTGCTCAGTTG    CAAGAGGAGACAGAGACCGTTTCTGCCCTG

A  L  L  S  V  G  A  E  Q  A  Q  A     AAARE  H
                A     L  +  V        E  Q     A
                A  S  L  T  V  D  V  E  Q  P  F  A     ----Q  E
                GCCTCCCTAACAGTGGATGTGGAACAGCCCTTTGCT        CAGGAA

HDA5 1108       S  P                             P  A  E  E  P  M  E  Q  E  P  A  L
                                                 A        E  P  M  E  +  E  P  A  L
                D  S        R:R[AGA]             T  A  G  E  P  M  E  E  E  P  A  L
AC004744 -63676 GACAGCAGGTATGAA  INTRON 2      CAGAACTGCTGGTGAGCCTATGGAAGAGGAGCCAGCCTTG
                         <2-----[63668:43600]-2>
```

FIG. 9

```
                              1                                              50
»    AC004744   (1)
»    AC004994   (1)     aggaccatcgtgaagcctgtggccaaagagtttgatccagacatggtct
     BMY_HDAL3  (1)     aggaccatcgtgaagcctgtggccaaagagtttgatccagacatggtct 51                                            100
»    AC004744   (1)
»    AC004994   (50)    tagtatctgctggatttgatgcattggaaggccacacccctcctctagga
     BMY_HDAL3  (50)    tagtatctgctggatttgatgcattggaaggccacacccctcctctagga 101                                           150
»    AC004744   (1)
»    AC004994   (100)   gggtacaaagtgacggcaaaatgttttggtcatttgacgaagcaattgat
     BMY_HDAL3  (100)   gggtacaaagtgacggcaaaatgttttggtcatttgacgaagcaattgat 151                                           200
»    AC004744   (1)
»    AC004994   (150)   gacattggctgatggacgtgtggtgttggctctagaaggaggacatgatc
     BMY_HDAL3  (150)   gacattggctgatggacgtgtggtgttggctctagaaggaggacatgatc 201                                           250
»    AC004744   (1)
»    AC004994   (200)   tcacagccatctgtgatgcatcagaagcctgtgtaaatgcccttctagga
     BMY_HDAL3  (200)   tcacagccatctgtgatgcatcagaagcctgtgtaaatgcccttctagga 251                                           300
»    AC004744   (1)         agctggagccacttgcagaagatattctccaccaaagcccgaatat
»    AC004994   (250)   aatgagctggagccacttgcagaagatattctccaccaaagcccgaatat
     BMY_HDAL3  (250)   aatgagctggagccacttgcagaagatattctccaccaaagcccgaatat 301                                           350
»    AC004744   (50)    gaatgctgttatttctttacagaagatcattgaaattcaaagcaagtatt
»    AC004994   (300)   gaatgctgttatttctttacagaagatcattgaaattcaaa
     BMY_HDAL3  (300)   gaatgctgttatttctttacagaagatcattgaaattcaaagcaagtatt 351                                           400
»    AC004744   (100)   ggaagtcagtaaggatggtggctgtgccaaggggctgtgctctggctggt
»    AC004994   (•340)
     BMY_HDAL3  (350)   ggaagtcagtaaggatggtggctgtgccaaggggctgtgctctggctggt 401                                           450
»    AC004744   (150)   gctcagttgcaagaggagacagagaccgtttctgccctggcctccctaac
»    AC004994   (•340)
     BMY_HDAL3  (400)   gctcagttgcaagaggagacagagaccgtttctgccctggcctccctaac 451                                           500
»    AC004744   (200)   agtggatgtggaacagcccttgctcaggaagacagcagaactgctggtg
»    AC004994   (•340)
     BMY_HDAL3  (450)   agtggatgtggaacagcccttgctcaggaagacagcagaactgctggtg 501              525
»    AC004744   (250)   agcctatggaagaggagccagcctt
»    AC004994   (•340)
     BMY_HDAL3  (500)   agcctatggaagaggagccagcctt
```

FIG. 10

```
         ArgThrIleValLysProValAlaLysGluPheAspProAspMetValLeuValSerAla
  1      AGGACCATCGTGAAGCCTGTGGCCAAAGAGTTTGATCCAGACATGGTCTTAGTATCTGCT
         TCCTGGTAGCACTTCGGACACCGGTTTCTCAAACTAGGTCTGTACCAGAATCATAGACGA

GlyPheAspAlaLeuGluGlyHisThrProProLeuGlyGlyTyrLysValThrAlaLys
 61      GGATTTGATGCATTGGAAGGCCACACCCCTCCTCTAGGAGGGTACAAAGTGACGGCAAAA
         CCTAAACTACGTAACCTTCCGGTGTGGGGAGGAGATCCTCCCATGTTTCACTGCCGTTTT

CysPheGlyHisLeuThrLysGlnLeuMetThrLeuAlaAspGlyArgValValLeuAla
121      TGTTTTGGTCATTTGACGAAGCAATTGATGACATTGGCTGATGGACGTGTGGTGTTGGCT
         ACAAAACCAGTAAACTGCTTCGTTAACTACTGTAACCGACTACCTGCACACCACAACCGA

LeuGluGlyGlyHisAspLeuThrAlaIleCysAspAlaSerGluAlaCysValAsnAla
181      CTAGAAGGAGGACATGATCTCACAGCCATCTGTGATGCATCAGAAGCCTGTGTAAATGCC
         GATCTTCCTCCTGTACTAGAGTGTCGGTAGACACTACGTAGTCTTCGGACACATTTACGG

LeuLeuGlyAsnGluLeuGluProLeuAlaGluAspIleLeuHisGlnSerProAsnMet
241      CTTCTAGGAAATGAGCTGGAGCCACTTGCAGAAGATATTCTCCACCAAAGCCCGAATATG
         GAAGATCCTTTACTCGACCTCGGTGAACGTCTTCTATAAGAGGTGGTTTCGGGCTTATAC

AsnAlaValIleSerLeuGlnLysIleIleGluIleGlnSerLysTyrTrpLysSerVal
301      AATGCTGTTATTTCTTTACAGAAGATCATTGAAATTCAAAGCAAGTATTGGAAGTCAGTA
         TTACGACAATAAAGAAATGTCTTCTAGTAACTTTAAGTTTCGTTCATAACCTTCAGTCAT

ArgMetValAlaValProArgGlyCysAlaLeuAlaGlyAlaGlnLeuGlnGluGluThr
361      AGGATGGTGGCTGTGCCAAGGGGCTGTGCTCTGGCTGGTGCTCAGTTGCAAGAGGAGACA
         TCCTACCACCGACACGGTTCCCCGACACGAGACCGACCACGAGTCAACGTTCTCCTCTGT

GluThrValSerAlaLeuAlaSerLeuThrValAspValGluGlnProPheAlaGlnGlu
421      GAGACCGTTTCTGCCCTGGCCTCCCTAACAGTGGATGTGGAACAGCCCTTTGCTCAGGAA
         CTCTGGCAAAGACGGGACCGGAGGGATTGTCACCTACACCTTGTCGGGAAACGAGTCCTT

AspSerArgThrAlaGlyGluProMetGluGluGluProAlaLeu
481      GACAGCAGAACTGCTGGTGAGCCTATGGAAGAGGAGCCAGCCTTG
         CTGTCGTCTTGACGACCACTCGGATACCTTCTCCTCGGTCGGAAC
```

FIG. 11

```
PROSITE MOTIFS FROM: BMY_HDAL3.AA.FASTA

MISMATCHES:0

BMY_HDAL3.AA.FASTA   CHECK: 3930   LENGTH: 175    !

CK2_PHOSPHO_SITE       (S,T)X2(D,E)
                       (T)X{2}(D)
            51: TKQLM      TLAD      GRVVL (T)X{2}(E)
           164: QEDSR      TAGE      PMEEE (ABSTRACT FILE: 0006.PDOC)

MYRISTYL               G-(E,D,R,K,H,P,F,Y,W)X2(S,T,A,G,C,N)-(P)
                       G-(E,D,R,K,H,P,F,Y,W)X{2}(A)-P
           128: VAVPR            GCALAG                AQLQE (ABSTRACT FILE: 0008.PDOC)

PKC_PHOSPHO_SITE       (S,T)X(R,K)
                       (T)X(K)
            38: GGYKV     TAK       CFGHL (S)X(R)
           119: SKYWK     SVR       MVAVP (ABSTRACT FILE: 0005.PDOC)
```

FIG. 12

Multiple sequence alignment of BMY_HDAL3, AAC78618 and AAD15364

```
                    1                                                   50
AAC78618    (1)   -TIVKPVAKEFDPDMVLVSAGFDALEGHTPPLGGYKVTAKCFGHLTKQLM
AAD15364    (1)   --------------------------------------------------
BMY_HDAL3   (1)   RTIVKPVAKEFDPDMVLVSAGFDALEGHTPPLGGYKVTAKCFGHLTKQLM 51                                                  100
AAC78618    (50)  TLADGRVVLALEGGHDLTAICDASEACVNALLGNELEPLAEDILHQSPNM
AAD15364    (1)   ---------------------------------LEPLAEDILHQSPNM
BMY_HDAL3   (51)  TLADGRVVLALEGGHDLTAICDASEACVNALLGNELEPLAEDILHQSPNM 101                                                 150
AAC78618    (100) NAVISLQKIIEIQ------------------------------------
AAD15364    (16)  NAVISLQKIIEIQKLLVSLWKRSQPCEVPSPPLIFPVCDIIVYPPTPVPS
BMY_HDAL3   (101) NAVISLQKIIEIQSKYWKSVRMVAVPRGCALAGAQLQEETETVSALASLT 151             175
AAC78618    (113) -------------------------
AAD15364    (66)  DMSCLLPGWHRFNGT----------
BMY_HDAL3   (151) VDVEQPFAQEDSRTAGEPMEEEPAL
```

FIG. 13

BLASTN alignment of AA287983 and BMY_HDAL3

```
SCORE =   224 BITS (113), EXPECT = 4E-57
  IDENTITIES = 120/121 (99%), GAPS = 1/121 (0%)
  STRAND = PLUS / MINUS

BMY_HDAL3:  405 ATTTTGCCGTCACTTTGTACCCTCCTAGAGGAGGGGTGTGGCCTTCCAATGCATCAAATC
464
                ||||||||||||||||||||||||||||||||||||||||||||||||||||||||||||
AA287983:   207 ATTTTGCCGTCACTTTGTACCCTCCTAGAGGAGGGGTGTGGCCTTCCAATGCATCAAATC
148

BMY_HDAL3:  465 CAGCAGATACTAAGACCATGTCTGGATCAAACTCTTTGGCCACAGGCTTCACGATGGTCC
524
                |||||||||||||||||||||||||||||||||||||| |||||||||||||||||||||
AA287983:   147 CAGCAGATACTAAGACCATGTCTGGATCAAACTCTTT-GCCACAGGCTTCACGATGGTCC  89

BMY_HDAL3:  525 T 525
                |
AA287983:   88  T 88
```

FIG. 14A

Aquifex ACUC Protein

```
  1 MKKVKLIGTL DYGKYRYPKN HPLKIPRVSL LLRFKDAMNL IDEKELIKSR
 51 PATKEELLLF HTEDYINTLM EAERCQCVPK GAREKYNIGG YENPVSYAMF
101 TGSSLATGST VQAIEEFLKG NVAFNPAGGM HHAFKSRANG FCYINNPAVG
151 IEYLRKKGFK RILYIDLDAH HCDGVQEAFY DTDQVFVLSL HQSPEYAFPF
201 EKGFLEEIGE GKGKGYNLNI PLPKGLNDNE FLFALEKSLE IVKEVFEPEV
251 YLLQLGTDPL LEDYLSKFNL SNVAFLKAFN IVREVFGEGV YLGGGGYHPY
301 ALARAWTLIW CELSGREVPE KLNNKAKELL KSIDFEEFDD EVDRSYMLET
351 LKDPWRGGEV RKEVKDTLEK AKASS
```

FIG. 14B

Saccharomyces Cerevisiae Histone Deacetylase 1

```
  1 MDSVMVKKEV LENPDHDLKR KLEENKEEEN SLSTTSKSKR QVIVPVCMPK
 51 IHYSPLKTGL CYDVRMRYHA KIFTSYFEYI DPHPEDPRRI YRIYKILAEN
101 GLINDPTLSG VDDLGDLMLK IPVRAATSEE ILEVHTKEHL EFIESTEKMS
151 REELLKETEK GDSVYFNNDS YASARLPCGG AIEACKAVVE GRVKNSLAVV
201 RPPGHHAEPQ AAGGFCLFSN VAVAAKNILK NYPESVRRIM ILDWDIHHGN
251 GTQKSFYQDD QVLYVSLHRF EMGKYYPGTI QGQYDQTGEG KGEGFNCNIT
301 WPVGGVGDAE YMWAFEQVVM PMGREFKPDL VIISSGFDAA DGDTIGQCHV
351 TPSCYGHMTH MLKSLARGNL CVVLEGGYNL DAIARSALSV AKVLIGEPPD
401 ELPDPLSDPK PEVIEMIDKV IRLQSKYWNC FRRRHANSGC NFNEPINDSI
451 ISKNFPLQKA IRQQQQHYLS DEFNFVTLPL VSMDLPDNTV LCTPNISESN
501 TIIIVVHDTS DIWAKRNVIS GTIDLSSSVI IDNSLDFIKW GLDRKYGIID
551 VNIPLTLFEP DNYSGMITSQ EVLIYLWDNY IKYFPSVAKI AFIGIGDSYS
601 GIVHLLGHRD TRAVTKTVIN FLGDKQLKPL VPLVDETLSE WYFKNSLIFS
651 NNSHQCWKEN ESRKPRKKFG RVLRCDTDGL NNIIEERFEE ATDFILDSFE
701 EWSDEE
```

FIG. 14C

Homo Sapiens Histone Deacetylase 4

```
   1 MSSQSHPDGL SGRDQPVELL NPARVNHMPS TVDVATALPL QVAPSAVPMD
  51 LRLDHQFSLP VAEPALREQQ LQQELLALKQ KQQIQRQILI AEFQRQHEQL
 101 SRQHEAQLHE HIKQQQEMLA MKHQQELLEH QRKLERHRQE QELEKQHREQ
 151 KLQQLKNKEK GKESAVASTE VKMKLQEFVL NKKKALAHRN LNHCISSDPR
 201 YWYGKTQHSS LDQSSPPQSG VSTSYNHPVL GMYDAKDDFP LRKTASEPNL
 251 KLRSRLKQKV AERRSSPLLR RKDGPVVTAL KKRPLDVTDS ACSSAPGSGP
 301 SSPNNSSGSV SAENGIAPAV PSIPAETSLA HRLVAREGSA APLPLYTSPS
 351 LPNITLGLPA TGPSAGTAGQ QDTERLTLPA LQQRLSLFPG THLTPYLSTS
 401 PLERDGGAAH SPLLQHMVLL EQPPAQAPLV TGLGALPLHA QSLVGADRVS
 451 PSIHKLRQHR PLGRTQSAPL PQNAQALQHL VIQQQHQQFL EKHKQQFQQQ
 501 QLQMNKIIPK PSEPARQPES HPEETEEELR EHQALLDEPY LDRLPGQKEA
 551 HAQAGVQVKQ EPIESDEEEA EPPREVEPGQ RQPSEQELLF RQQALLLEQQ
 601 RIHQLRNYQA SMEAAGIPVS FGGHRPLSRA QSSPASATFP VSVQEPPTKP
 651 RFTTGLVYDT LMLKHQCTCG SSSSHPEHAG RIQSIWSRLQ ETGLRGKCEC
 701 IRGRKATLEE LQTVHSEAHT LLYGTNPLNR QKLDSKKLLG SLASVFVRLP
 751 CGGVGVDSDT IWNEVHSAGA ARLAVGCVVE LVFKVATGEL KNGFAVVRPP
 801 GHHAEESTPM GFCYFNSVAV AAKLLQQRLS VSKILIVDWD VHHGNGTQQA
 851 FYSDPSVLYM SLHRYDDGNF FPGSGAPDEV GTGPGVGFNV NMAFTGGLDP
 901 PMGDAEYLAA FRTVVMPIAS EFAPDVVLVS SGFDAVEGHP TPLGGYNLSA
 951 RCFGYLTKQL MGLAGGRIVL ALEGGHDLTA ICDASEACVS ALLGNELDPL
1001 PEKVLQQRPN ANAVRSMEKV MEIHSKYWRC LQRTTSTAGR SLIEAQTCEN
1051 EEAETVTAMA SLSVGVKPAE KRPDEEPMEE EPPL
```

FIG. 14D

Homo Sapiens Histone Deacetylase 5

```
   1 MNSPNESDGM SGREPSLEIL PRTSLHSIPV TVEVKPVLPR AMPSSMGGGG
  51 GGSPSPVELR GALVGSVDPT LREQQLQQEL LALKQQQQLQ KQLLFAEFQK
 101 QHDHLTRQHE VQLQKHLKQQ QEMLAAKQQQ EMLAAKRQQE LEQQRQREQQ
 151 RQEELEKQRL EQQLLILRNK EKSKESAIAS TEVKLRLQEF LLSKSKEPTP
 201 GGLNHSLPQH PKCWGAHHAS LDQSSPPQSG PPGTPPSYKL PLPGPYDSRD
 251 DFPLRKTASE PNLKVRSRLK QKVAERRSSP LLRRKDGTVI STFKKRAVEI
 301 TGAGPGASSV CNSAPGSGPS SPNSSHSTIA ENGFTGSVPN IPTEMLPQHR
 351 ALPLDSSPNQ FSLYTSPSLP NISLGLQATV TVTNSHLTAS PKLSTQQEAE
 401 RQALQSLRQG GTLTGKFMST SSIPGCLLGV ALEGDGSPHG HASLLQHVLL
 451 LEQARQQSTL IAVPLHGQSP LVTGERVATS MRTVGKLPRH RPLSRTQSSP
 501 LPQSPQALQQ LVMQQQHQQF LEKQKQQQLQ LGKILTKTGE LPRQPTTHPE
 551 ETEEELTEQQ EVLLGEGALT MPREGSTESE STQEDLEEED EEEDGEEEED
 601 CIQVKDEEGE SGAEEGPDLE EPGAGYKKLF SDAQPLQPLQ VYQAPLSLAT
 651 VPHQALGRTQ SSPAAPGGMK SPPDQPVKHL FTTGVVYDTF MLKHQCMCGN
 701 THVHPEHAGR IQSIWSRLQE TGLLSKCERI RGRKATLDEI QTVHSEYHTL
 751 LYGTSPLNRQ KLDSKKLLGP ISQKMYAVLP CGGIGVDSDT VWNEMHSSSA
 801 VRMAVGCLLE LAFKVAAGEL KNGFAIIRPP GHHAEESTAM GFCFFNSVAI
 851 TAKLLQQKLN VGKVLIVDWD IHHGNGTQQA FYNDPSVLYI SLHRYDNGNF
 901 FPGSGAPEEV GGGPGVGYNV NVAWTGGVDP PIGDVEYLTA FRTVVMPIAH
 951 EFSPDVVLVS AGFDAVEGHL SPLGGYSVTA RCFGHLTRQL MTLAGGRVVL
1001 ALEGGHDLTA ICDASEACVS ALLSVELQPL DEAVLQQKPN INAVATLEKV
1051 IEIQSKHWSC VQKFAAGLGR SLREAQAGET EEAETVSAMA LLSVGAEQAQ
1101 AAAAREHSPR PAEEPMEQEP AL
```

FIG. 14E

Homo Sapiens Histone Deacetylase 7

```
  1 MDLRVGQRPP VEPPPEPTLL ALQRPQRLHH HLFLAGLQQQ RSVEPMRLSM
 51 DTPMPELQVG PQEQELRQLL HKDKSKRSAV ASSVVKQKLA EVILKKQQAA
101 LERTVHPNSP GIPYRTLEPL ETEGATRSML SSFLPPVPSL PSDPPEHFPL
151 RKTVSEPNLK LRYKPKKSLE RRKNPLLRKE SAPPSLRRRP AETLGDSSPS
201 SSTPASGCS  SPNDSEHGPN PILGDSDRRT HPTLGPRGPI LGSPHTPLFL
251 PHGLEPEAGG TLPSRLQPIL LLDPSGSHAP LLTVPGLGPL PFHFAQSLMT
301 TERLSGSGLH WPLSRTRSEP LPPSATAPPP PGPMQPRLEQ LKTHVQVIKR
351 SAKPSEKPRL RQIPSAEDLE TDGGGPGQVV DDGLEHRELG HGQPEARGPA
401 PLQQHPQVLL WEQQRLAGRL PRGSTGDTVL LPLAQGGHRP LSRAQSSPAA
451 PASLSAPEPA SQARVLSSSE TPARTLPFTT GLIYDSVMLK HQCSCGDNSR
501 HPEHAGRIQS IWSRLQERGL RSQCECLRGR KASLEELQSV HSERHVLLYG
551 TNPLSRLKLD NGKLAGLLAQ RMFEMLPCGG VGVDTDTIWN ELHSSNAARW
601 AAGSVTDLAF KVASRELKNG FAVVRPPGHH ADHSTAMGFC FFNSVAIACR
651 QLQQQSKASK ASKILIVDWD VHHGNGTQQT FYQDPSVLYI SLHRHDDGNF
701 FPGSGAVDEV GAGSGEGFNV NVAWAGGLDP PMGDPEYLAA FRIVVMPIAR
751 EFSPDLVLVS AGFDAAEGHP APLGGYHVSA KCFGYMTQQL MNLAGGAVVL
801 ALEGGHDLTA ICDASEACVA ALLGNRVDPL SEEGWKQKPQ PQCHPLSGGR
851 DPGAQ
```

FIG. 14F

Human EST AA287983

```
  1 ggccttggagaagggtacaatataaatattgcctggacaggtggcctt
 49 gatcctcccatgggagatgttgagtaccttgaagcattcaggaccatc
 97 gtgaagcctgtggcaaagagtttgatccagacatggtcttagtatctg
145 ctggatttgatgcattggaaggccacacccctcctctaggagggtaca
193 aagtgacggcaaaataaactcctgtgctggaggtacaacagtttggaa
241 gtatacttggggaaagagaaaacacaagatggaaggaagatctctctt
289 ttcacatcgggagcac
```

FIG. 14G

Human predicted protein AAD15364

```
  1 LEPLAEDILH QSPNMNAVIS LQKIIEIQKL LVSLWKRSQP CEVPSPPLIF
 51 PVCDIIVYPP TPVPSDMSCL LPGWHRFNGT
```

FIG. 14H

Human predicted protein AAC78618

```
  1 TIVKPVAKEF DPDMVLVSAG FDALEGHTPP LGGYKVTAKC FGHLTKQLMT
 51 LADGRVVLAL EGGHDLTAIC DASEACVNAL LGNELEPLAE DILHQSPNMN
101 AVISLQKIIE IQ
```

FIG. 15A

```
   1 ATGCACAGTATGATCAGCTCAGTGGATGTGAAGTCAGAAGTTCCTGTGGGCCTGGAGCCC   60
   1  M  H  S  M  I  S  S  V  D  V  K  S  E  V  P  V  G  L  E  P    20

61 ATCTCACCTTTAGACCTAAGGACAGACCTCAGGATGATGATGCCCGTGGTGGACCCTGTT  120
  21  I  S  P  L  D  L  R  T  D  L  R  M  M  M  P  V  V  D  P  V    40

121 GTCCGTGAGAAGCAATTGCAGCAGGAATTACTTCTTATCCAGCAGCAGCAACAAATCCAG  180
  41  V  R  E  K  Q  L  Q  Q  E  L  L  L  I  Q  Q  Q  Q  Q  I  Q    60

181 AAGCAGCTTCTGATAGCAGAGTTTCAGAAACAGCATGAGAACTTGACACGGCAGCACCAG  240
  61  K  Q  L  L  I  A  E  F  Q  K  Q  H  E  N  L  T  R  Q  H  Q    80

241 GCTCAGCTTCAGGAGCATATCAAGTTGCAACAGGAACTTCTAGCCATAAAACAGCAACAA  300
  81  A  Q  L  Q  E  H  I  K  L  Q  Q  E  L  L  A  I  K  Q  Q  Q   100

301 GAACTCCTAGAAAAGGAGCAGAAACTGGAGCAGCAGAGGCAAGAACAGGAAGTAGAGAGG  360
 101  E  L  L  E  K  E  Q  K  L  E  Q  Q  R  Q  E  Q  E  V  E  R   120

361 CATCGCAGAGAACAGCAGCTTCCTCCTCTCAGAGGCAAAGATAGAGGACGAGAAAGGGCA  420
 121  H  R  R  E  Q  Q  L  P  P  L  R  G  K  D  R  G  R  E  R  A   140

421 GTGGCAAGTACAGAAGTAAAGCAGAAGCTTCAAGAGTTCCTACTGAGTAAATCAGCAACG  480
 141  V  A  S  T  E  V  K  Q  K  L  Q  E  F  L  L  S  K  S  A  T   160

481 AAAGACACTCCAACTAATGGAAAAAATCATTCCGTGAGCCGCCATCCCAAGCTCTGGTAC  540
 161  K  D  T  P  T  N  G  K  N  H  S  V  S  R  H  P  K  L  W  Y   180

541 ACGGCTGCCCACCACACATCATTGGATCAAAGCTCTCCACCCCTTAGTGGAACATCTCCA  600
 181  T  A  A  H  H  T  S  L  D  Q  S  S  P  P  L  S  G  T  S  P   200

601 TCCTACAAGTACACATTACCAGGAGCACAAGATGCAAAGGATGATTTCCCCCTTCGAAAA  660
 201  S  Y  K  Y  T  L  P  G  A  Q  D  A  K  D  D  F  P  L  R  K   220

661 ACTGCCTCTGAGCCCAACTTGAAGGTGCGGTCCAGGTTAAAACAGAAAGTGGCAGAGAGG  720
 221  T  A  S  E  P  N  L  K  V  R  S  R  L  K  Q  K  V  A  E  R   240

721 AGAAGCAGCCCCTTACTCAGGCGGAAGGATGGAAATGTTGTCACTTCATTCAAGAAGCGA  780
 241  R  S  S  P  L  L  R  R  K  D  G  N  V  V  T  S  F  K  K  R   260

781 ATGTTTGAGGTGACAGAATCCTCAGTCAGTAGCAGTTCTCCAGGCTCTGGTCCCAGTTCA  840
 261  M  F  E  V  T  E  S  S  V  S  S  S  S  P  G  S  G  P  S  S   280

841 CCAAACAATGGGCCAACTGGAAGTGTTACTGAAAATGAGACTTCGGTTTTGCCCCCTACC  900
 281  P  N  N  G  P  T  G  S  V  T  E  N  E  T  S  V  L  P  P  T   300

901 CCTCATGCCGAGCAAATGGTTTCACAGCAACGCATTCTAATTCATGAAGATTCCATGAAC  960
 301  P  H  A  E  Q  M  V  S  Q  Q  R  I  L  I  H  E  D  S  M  N   320

961 CTGCTAAGTCTTTATACCTCTCCTTCTTTGCCCAACATTACCTTGGGGCTTCCCGCAGTG 1020
 321  L  L  S  L  Y  T  S  P  S  L  P  N  I  T  L  G  L  P  A  V   340

1021 CCATCCCAGCTCAATGCTTCGAATTCACTCAAAGAAAAGCAGAAGTGTGAGACGCAGACG 1080
 341  P  S  Q  L  N  A  S  N  S  L  K  E  K  Q  K  C  E  T  Q  T   360

1081 CTTAGGCAAGGTGTTCCTCTGCCTGGGCAGTATGGAGGCAGCATCCCGGCATCTTCCAGC 1140
 361  L  R  Q  G  V  P  L  P  G  Q  Y  G  G  S  I  P  A  S  S  S   380

1141 CACCCTCATGTTACTTTAGAGGGAAAGCCACCCAACAGCAGCCACCAGGCTCTCCTGCAG 1200
 381  H  P  H  V  T  L  E  G  K  P  P  N  S  S  H  Q  A  L  L  Q   400

1201 CATTTATTATTGAAAGAACAAATGCGACAGCAAAAGCTTCTTGTAGCTGGTGGAGTTCCC 1260
 401  H  L  L  L  K  E  Q  M  R  Q  Q  K  L  L  V  A  G  V  P   420

1261 TTACATCCTCAGTCTCCCTTGGCAACAAAAGAGAGAATTTCACCTGGCATTAGAGGTACC 1320
 421  L  H  P  Q  S  P  L  A  T  K  E  R  I  S  P  G  I  R  G  T   440

1321 CACAAATTGCCCCGTCACAGACCCCTGAACCGAACCCAGTCTGCACCTTTGCCTCAGAGC 1380
 441  H  K  L  P  R  H  R  P  L  N  R  T  Q  S  A  P  L  P  Q  S   460

1381 ACGTTGGCTCAGCTGGTCATTCAACAGCAACACCAGCAATTCTTGGAGAAGCAGAAGCAA 1440
 461  T  L  A  Q  L  V  I  Q  Q  Q  H  Q  Q  F  L  E  K  Q  K  Q   480
```

FIG. 15B

```
1441  TACCAGCAGCAGATCCACATGAACAAACTGCTTTCGAAATCTATTGAACAACTGAAGCAA  1500
 481   Y  Q  Q  Q  I  H  M  N  K  L  L  S  K  S  I  E  Q  L  K  Q   500

1501  CCAGGCAGTCACCTTGAGGAAGCAGAGGAAGAGCTTCAGGGGGACCAGGCGATGCAGGAA  1560
 501   P  G  S  H  L  E  E  A  E  E  E  L  Q  G  D  Q  A  M  Q  E   520

1561  GACAGAGCGCCCTCTAGTGGCAACAGCACTAGGAGCGACAGCAGTGCTTGTGTGGATGAC  1620
 521   D  R  A  P  S  S  G  N  S  T  R  S  D  S  S  A  C  V  D  D   540

1621  ACACTGGGACAAGTTGGGGCTGTGAAGGTCAAGGAGGAACCAGTGGACAGTGATGAAGAT  1680
 541   T  L  G  Q  V  G  A  V  K  V  K  E  E  P  V  D  S  D  E  D   560

1681  GCTCAGATCCAGGAAATGGAATCTGGGGAGCAGGCTGCTTTTATGCAACAGCCTTTCCTG  1740
 561   A  Q  I  Q  E  M  E  S  G  E  Q  A  A  F  M  Q  Q  P  F  L   580

1741  GAACCCACGCACACGTGCGCTCTCTGTGCGCCAAGCTCCGCTGGCTGCGGTTGGCATG    1800
 581   E  P  T  H  T  R  A  L  S  V  R  Q  A  P  L  A  A  V  G  M   600

1801  GATGGATTAGAGAAACACCGTCTCGTCTCCAGGACTCACTCTTCCCCTGCTGCCTCTGTT  1860
 601   D  G  L  E  K  H  R  L  V  S  R  T  H  S  S  P  A  A  S  V   620

1861  TTACCTCACCCGGCAATGGACCGCCCCCTCCAGCCTGGCTCTGCAACTGGAATTGCCTAT  1920
 621   L  P  H  P  A  M  D  R  P  L  Q  P  G  S  A  T  G  I  A  Y   640

1921  GACCCCTTGATGCTGAAACACCAGTGCGTTTGTGGCAATTCCACCACCCACCCTGAGCAT  1980
 641   D  P  L  M  L  K  H  Q  C  V  C  G  N  S  T  T  H  P  E  H   660

1981  GCTGGACGAATACAGAGTATCTGGTCACGACTGCAAGAAACTGGGCTGCTAAATAAATGT  2040
 661   A  G  R  I  Q  S  I  W  S  R  L  Q  E  T  G  L  L  N  K  C   680

2041  GAGCGAATTCAAGGTCGAAAAGCCAGCCTGGAGGAAATACAGCTTGTTCATTCTGAACAT  2100
 681   E  R  I  Q  G  R  K  A  S  L  E  E  I  Q  L  V  H  S  E  H   700

2101  CACTCACTGTTGTATGGCACCAACCCCCTGGACGGACAGAAGCTGGACCCCAGGATACTC  2160
 701   H  S  L  L  Y  G  T  N  P  L  D  G  Q  K  L  D  P  R  I  L   720

2161  CTAGGTGATGACTCTCAAAAGTTTTTTTCCTCATTACCTTGTGGTGGACTTGGGGTGGAC  2220
 721   L  G  D  D  S  Q  K  F  F  S  S  L  P  C  G  G  L  G  V  D   740

2221  AGTGACACCATTTGGAATGAGCTACACTCGTCCGGTGCTGCACGCATGGCTGTTGGCTGT  2280
 741   S  D  T  I  W  N  E  L  H  S  S  G  A  A  R  M  A  V  G  C   760

2281  GTCATCGAGCTGGCTTCCAAAGTGGCCTCAGGAGAGCTGAAGAATGGGTTTGCTGTTGTG  2340
 761   V  I  E  L  A  S  K  V  A  S  G  E  L  K  N  G  F  A  V  V   780

2341  AGGCCCCCTGGCCATCACGCTGAAGAATCCACAGCCATGGGGTTCTGCTTTTTTAATTCA  2400
 781   R  P  P  G  H  H  A  E  E  S  T  A  M  G  F  C  F  F  N  S   800

2401  GTTGCAATTACCGCCAAATACTTGAGAGACCAACTAAATATAAGCAAGATATTGATTGTA  2460
 801   V  A  I  T  A  K  Y  L  R  D  Q  L  N  I  S  K  I  L  I  V   820

2461  GATCTGGATGTTCACCATGGAAACGGTACCCAGCAGGCCTTTTATGCTGACCCCAGCATC  2520
 821   D  L  D  V  H  H  G  N  G  T  Q  Q  A  F  Y  A  D  P  S  I   840

2521  CTGTACATTTCACTCCATCGCTATGATGAAGGGAACTTTTTCCCTGGCAGTGGAGCCCCA  2580
 841   L  Y  I  S  L  H  R  Y  D  E  G  N  F  F  P  G  S  G  A  P   860

2581  AATGAGGTTGGAACAGGCCTTGGAGAAGGGTACAATATAAATATTGCCTGGACAGGTGGC  2640
 861   N  E  V  G  T  G  L  G  E  G  Y  N  I  N  I  A  W  T  G  G   880

2641  CTTGATCCTCCCATGGGAGATGTTGAGTACCTTGAAGCATTCAGGACCATCGTGAAGCCT  2700
 881   L  D  P  P  M  G  D  V  E  Y  L  E  A  F  R  T  I  V  K  P   900

2701  GTGGCCAAAGAGTTTGATCCAGACATGGTCTTAGTATCTGCTGGATTTGATGCATTGGAA  2760
 901   V  A  K  E  F  D  P  D  M  V  L  V  S  A  G  F  D  A  L  E   920

2761  GGCCACACCCCTCCTCTAGGAGGGTACAAAGTGACGGCAAAATGTTTTGGTCATTTGACG  2820
 921   G  H  T  P  P  L  G  G  Y  K  V  T  A  K  C  F  G  H  L  T   940

2821  AAGCAATTGATGACATTGGCTGATGGACGTGTGGTGTTGGCTCTAGAAGGAGGACATGAT  2880
 941   K  Q  L  M  T  L  A  D  G  R  V  V  L  A  L  E  G  G  H  D   960
```

FIG. 15C

```
2881 CTCACAGCCATCTGTGATGCATCAGAAGCCTGTGTAAATGCCCTTCTAGGAAATGAGCTG 2940
 961  L  T  A  I  C  D  A  S  E  A  C  V  N  A  L  L  G  N  E  L   980
2941 GAGCCACTTGCAGAAGATATTCTCCACCAAAGCCCGAATATGAATGCTGTTATTTCTTTA 3000
 981  E  P  L  A  E  D  I  L  H  Q  S  P  N  M  N  A  V  I  S  L  1000
3001 CAGAAGATCATTGAAATTCAAAGCAAGTATTGGAAGTCAGTAAGGATGGTGGCTGTGCCA 3060
1001  Q  K  I  I  E  I  Q  S  K  Y  W  K  S  V  R  M  V  A  V  P  1020
3061 AGGGGCTGTGCTCTGGCTGGTGCTCAGTTGCAAGAGGAGACAGAGACCGTTTCTGCCCTG 3120
1021  R  G  C  A  L  A  G  A  Q  L  Q  E  E  T  E  T  V  S  A  L  1040
3121 GCCTCCCTAACAGTGGATGTGGAACAGCCCTTTGCTCAGGAAGACAGCAGAACTGCTGGT 3180
1041  A  S  L  T  V  D  V  E  Q  P  F  A  Q  E  D  S  R  T  A  G  1060
3181 GAGCCTATGGAAGAGGAGCCAGCCTTGTGAAGTGCCAAGTCCCCCTCTGATATTTCCTGT 3240
1061  E  P  M  E  E  E  P  A  L                                   1069
3241 GTGTGACATCATTGTGTATCCCCCCACCCCAGTACCCTCAGACATGTCTTGTCTGCTGCC 3300
3301 TGGGTGGCACAGATTCAATGGAACATAAACACTGGGCACAAAATTCTGAACAGCAGCTTC 3360
3361 ACTTGTTCTTTGGATGGACTTGAAAGGGCATTAAAGATTCCTTAAACGTAACCGCTGTGA 3420
3421 TTCTAGAGTTACAGTAAACCACGATTGGAAGAAACTGCTTCCAGCATGCTTTTAATATGC 3480
3481 TGGGTGACCCACTCCTAGACACCAAGTTTGAACTAGAAACATTCAGTACAGCACTAGATA 3540
3541 TTGTTAATTTCAGAAGCTATGACAGCCAGTGAAATTTTGGGCAAAACCTGAGACATAGTC 3600
3601 ATTCCTGACATTCTGATCAGCTTTTTTTGGGGTAATTTGTTTTTCAAACAGTCTTAACTT 3660
3661 GTTTACAAGATTTGCTTTTAGCTATGAACGGATCGTAATTCCACCCAGAATGTAATGTTT 3720
3721 CTTGTTTGTTTGTTTTGTTTTGTTAGGGTTTTTTTCTCAACTTTAACACACAGTTCAACT 3780
3781 GTTCCTAGTAAAAGTTCAAGATGGAGGAACTAGCATGAGGCTTTTTTCAGTATCTCGAAG 3840
3841 TCCAAATGCCAAAGGAACCTCACACACTGTTTGTAATGGTGCAATATTTTATATCACTTT 3900
3901 TTTTTAAACATCCCCAACATCTTTGTGTTCTCACACACAGGCAATTTGCAATGTTGCAAT 3960
3961 TGTGTTGGAGAATGAAGTCCCCCCACCTCCCAGCCACACACACATCCTTTGTTCTCATGA 4020
4021 CAGTAGGTCTGAGCAAATGTTCCACCAAGCATTTTCAGTGTCTTTGAAAAGCACGTAACT 4080
4081 TTTCAAAGGTGGTCTTAATTTGCTGCATATCTATCAAGGACTTATTCACTCACCTTTCCT 4140
4141 TTTCTGCCCTCTATCAATTGATTTCTTCTTACCTTTCATCATTCATTCCTTCCTTTAGAA 4200
4201 AAACTGAAGATTACCCATAATCTCCTCTTATTACTTGAGGGCCTTGACTATTTAGTTTAT 4260
4261 TTTGTTTACTTTACAGGTTAACACAGTTGTTTTGTCTGATTGCATTTTATTAACTGTGAA 4320
4321 GCCGTTGAAATGAATATCACTTAAGCAACGTTGCTAAATTTCTATGTGTTTGAAATGTGT 4380
4381 TAATGAAGGCACTGCTTATTTGTAGTCACCTTGAACTGACTTAACCTAGAAGCTGTGCCT 4440
4441 TCTTGTGAAAAAAAAAAAAAAAAAAA 4467
```

FIG. 15D

```
              1                                                    50
HDAC9c    (1) ------------------------MHSMISSVDVKSEVPVGLEPISPLDL
AY032737  (1) ------------------------MHSMISSVDVKSEVPVGLEPISPLDL
AY032738  (1) ------------------------MHSMISSVDVKSEVPVGLEPISPLDL
AF132608  (1) MNSPNESDGMSGREPSLEILPRTSLHSIPVTVEVKPVLPRAMPSSMGGGG 51                                                  100
HDAC9c   (27) RTDLR------MMMPVVDPVVREKQLQQELLLIQQQQQIQKQLLIAEFQK
AY032737 (27) RTDLR------MMMPVVDPVVREKQLQQELLLIQQQQQIQKQLLIAEFQK
AY032738 (27) RTDLR------MMMPVVDPVVREKQLQQELLLIQQQQQIQKQLLIAEFQK
AF132608 (51) GGSPSPVELRGALVGSVDPTLREQQLQQELLALKQQQQLQKQLLFAEFQK 101                                                 150
HDAC9c   (71) QHENLTRQHQAQLQEHIKLQQELLAIKQQQELLEK--EQKLEQQRQ----
AY032737 (71) QHENLTRQHQAQLQEHIK---ELLAIKQQQELLEK--EQKLEQQRQ----
AY032738 (71) QHENLTRQHQAQLQEHIK---ELLAIKQQQELLEK--EQKLEQQRQ----
AF132608(101) QHDHLTRQHEVQLQKHLKQQQEMLAAKQQQEMLAAKRQQELEQQRQREQQ 151                                                 200
HDAC9c  (115) -EQEVERHRREQQLPPLRGKDRGRERAVASTEVKQKLQEFLLSKSATKDT
AY032737(112) -EQEVERHRREQQLPPLRGKDRGRERAVASTEVKQKLQEFLLSKSATKDT
AY032738(112) -EQEVERHRREQQLPPLRGKDRGRERAVASTEVKQKLQEFLLSKSATKDT
AF132608(151) RQEELEKQRLEQQLLILRNKEKSKESAIASTEVKLRLQEFLLSK--SKEP 201                                                 250
HDAC9c  (164) PTNGKNHSVSRHPKLWYTAAHHTSLDQSSPP---LSGTSPSYKYTLPGAQ
AY032737(161) PTNGKNHSVSRHPKLWYTAAHHTSLDQSSPP---LSGTSPSYKYTLPGAQ
AY032738(161) PTNGKNHSVSRHPKLWYTAAHHTSLDQSSPP---LSGTSPSYKYTLPGAQ
AF132608(199) TPGGLNHSLPQHPKCWG--AHHASLDQSSPPQSGPPGTPPSYKLPLPGPY 251                                                 300
HDAC9c  (211) DAKDDFPLRKTASEPNLKVRSRLKQKVAERRSSPLLRRKDGNVVTSFKKR
AY032737(208) DAKDDFPLRKTASEPNLKVRSRLKQKVAERRSSPLLRRKDGNVVTSFKKR
AY032738(208) DAKDDFPLRKTASEPNLKVRSRLKQKVAERRSSPLLRRKDGNVVTSFKKR
AF132608(247) DSRDDFPLRKTASEPNLKVRSRLKQKVAERRSSPLLRRKDGTVISTFKKR 301                                                 350
HDAC9c  (261) MFEVT-----ESSVSSSSPGSGPSSPNNGPTGSVTENETSVLPPTPHAEQ
AY032737(258) MFEVT-----ESSVSSSSPGSGPSSPNNGPTGSVTENETSVLPPTPHAEQ
AY032738(258) MFEVT-----ESSVSSSSPGSGPSSPNNGPTGSVTENETSVLPPTPHAEQ
AF132608(297) AVEITGAGPGASSVCNSAPGSGPSSPNS--SHSTIAENGFTGSVPNIPTE 351                                                 400
HDAC9c  (306) MVSQQRILIHEDSMNLLSLYTSPSLPNITLGLPAVPSQLNASNSLK----
AY032737(303) MVSQQRILIHEDSMNLLSLYTSPSLPNITLGLPAVPSQLNASNSLK----
AY032738(303) MVSQQRILIHEDSMNLLSLYTSPSLPNITLGLPAVPSQLNASNSLK----
AF132608(345) MLPQHRALPLDSSPNQFSLYTSPSLPNISLGLQATVTVTNSHLTASPKLS
```

FIG. 15E

```
                    401                                                   450
HDAC9c    (352)  ---EKQKCETQTLRQGVPLPGQYGGSIPASSSHPHVTLEGKPPNSSHQAL
AY032737  (349)  ---EKQKCETQTLRQGVPLPGQYGGSIPASSSHPHVTLEGKPPNSSHQAL
AY032738  (349)  ---EKQKCETQTLRQGVPLPGQYGGSIPASSSHPHVTLEGKPPNSSHQAL
AF132608  (395)  TQQEAERQALQSLRQGGTLTGKFMSTSSIPGCLLGVALEGDGSPHGHASL 451                                                   500
HDAC9c    (399)  LQHLLLKEQMRQQKLLVAGGVPLHPQSPLATKERISPGIRGTHKLPRHRP
AY032737  (396)  LQHLLLKEQMRQQKLLVAGGVPLHPQSPLATKERISPGIRGTHKLPRHRP
AY032738  (396)  LQHLLLKEQMRQQKLLVAGGVPLHPQSPLATKERISPGIRGTHKLPRHRP
AF132608  (445)  LQHVLLLEQARQQ--STLIAVPLHGQSPLVTGERVATSMRTVGKLPRHRP 501                                                   550
HDAC9c    (449)  LNRTQSAPLPQS--TLAQLVIQQQHQQFLEKQKQYQQQIHMNKLLSKSIE
AY032737  (446)  LNRTQSAPLPQS--TLAQLVIQQQHQQFLEKQKQYQQQIHMNKLLSKSIE
AY032738  (446)  LNRTQSAPLPQS--TLAQLVIQQQHQQFLEKQKQYQQQIHMNKLLSKSIE
AF132608  (493)  LSRTQSSPLPQSPQALQQLVMQQQHQQFLEKQK--QQQLQLGKILTKTGE 551                                                   600
HDAC9c    (497)  QLKQPGSHLEEAEEELQGDQAMQEDRAPSSGNSTRSDSSACVDDTLGQVG
AY032737  (494)  QLKQPGSHLEEAEEELQGDQAMQEDRAPSSGNSTRSDSSACVDDTLGQVG
AY032738  (494)  QLKQPGSHLEEAEEELQGDQAMQEDRAPSSGNSTRSDSSACVDDTLGQVG
AF132608  (541)  LPRQPTTHPEETEEELTEQQEVLLGEGALTMPREGSTESESTQEDLEEED 601                                                   650
HDAC9c    (547)  AVKVKEEPVDSDEDAQIQEMESGEQAAFMQQP-------FLEPTHTRALS
AY032737  (544)  AVKVKEEPVDSDEDAQIQEMESGEQAAFMQQP-------FLEPTHTRALS
AY032738  (544)  AVKVKEEPVDSDEDAQIQEMESGEQAAFMQQP-------FLEPTHTRALS
AF132608  (591)  EEEDGEEEDCIQVKDEEGESGAEEGPDLEEPGAGYKKLFSDAQPLQPLQ 651                                                   700
HDAC9c    (590)  VRQAPLAAVGMDGLEKHRLVSRTHSSPAASVLPHPAMDRPLQPGSATGIA
AY032737  (587)  VRQAPLAAVGMDGLEKHRLVSRTHSSPAASVLPHPAMDRPLQPGSATGIA
AY032738  (587)  VRQAPLAAVGMDGLEKHRLVSRTHSSPAASVLPHPAMDRPLQPGSATGIA
AF132608  (641)  VYQAPLSLATVP----HQALGRTQSSPAAPGGMKSPPDQPVKHLFTTGVV 701                                                   750
HDAC9c    (640)  YDPLMLKHQCVCGNSTTHPEHAGRIQSIWSRLQETGLLNKCERIQGRKAS
AY032737  (637)  YDPLMLKHQCVCGNSTTHPEHAGRIQSIWSRLQETGLLNKCERIQGRKAS
AY032738  (637)  YDPLMLKHQCVCGNSTTHPEHAGRIQSIWSRLQETGLLNKCERIQGRKAS
AF132608  (687)  YDTFMLKHQCMCGNTHVHPEHAGRIQSIWSRLQETGLLSKCERIRGRKAT 751                                                   800
HDAC9c    (690)  LEEIQLVHSEHHSLLYGTNPLDGQKLDPRILLGDDSQKFFSSLPCGGLGV
AY032737  (687)  LEEIQLVHSEHHSLLYGTNPLDGQKLDPRILLGDDSQKFFSSLPCGGLGV
AY032738  (687)  LEEIQLVHSEHHSLLYGTNPLDGQKLDPRILLGDDSQKFFSSLPCGGLGV
AF132608  (737)  LDEIQTVHSEYHTLLYGTSPLNRQKLDSKKLLGPISQKMYAVLPCGGIGV 801                                                   850
HDAC9c    (740)  DSDTIWNELHSSGAARMAVGCVIELASKVASGELKNGFAVVRPPGHHAEE
AY032737  (737)  DSDTIWNELHSSGAARMAVGCVIELASKVASGELKNGFAVVRPPGHHAEE
AY032738  (737)  DSDTIWNELHSSGAARMAVGCVIELASKVASGELKNGFAVVRPPGHHAEE
AF132608  (787)  DSDTVWNEMHSSSAVRMAVGCLLELAFKVAAGELKNGFAIIRPPGHHAEE
```

FIG. 15F

```
                     851                                                900
    HDAC9c  (790)    STAMGFCFFNSVAITAKYLRDQLNISKILIVDLDVHHGNGTQQAFYADPS
    AY032737 (787)   STAMGFCFFNSVAITAKYLRDQLNISKILIVDLDVHHGNGTQQAFYADPS
    AY032738 (787)   STAMGFCFFNSVAITAKYLRDQLNISKILIVDLDVHHGNGTQQAFYADPS
    AF132608 (837)   STAMGFCFFNSVAITAKLLQQKLNVGKVLIVDWDIHHGNGTQQAFYNDPS 901                                                950
    HDAC9c  (840)    ILYISLHRYDEGNFFPGSGAPNEVGTGLGEGYNINIAWTGGLDPPMGDVE
    AY032737 (837)   ILYISLHRYDEGNFFPGSGAPNEVGTGLGEGYNINIAWTGGLDPPMGDVE
    AY032738 (837)   ILYISLHRYDEGNFFPGSGAPNEVRFISLEPHFYLYLSGNCIA-------
    AF132608 (887)   VLYISLHRYDNGNFFPGSGAPEEVGGGPGVGYNVNVAWTGGVDPPIGDVE 951                                                1000
    HDAC9c  (890)    YLEAFRTIVKPVAKEFDPDMVLVSAGFDALEGHTPPLGGYKVTAKCFGHL
    AY032737 (887)   YLEAFRTIVKPVAKEFDPDMVLVSAGFDALEGHTPPLGGYKVTAKCFGHL
    AY032738 (880)   --------------------------------------------------
    AF132608 (937)   YLTAFRTVVMPIAHEFSPDVVLVSAGFDAVEGHLSPLGGYSVTARCFGHL 1001                                               1050
    HDAC9c  (940)    TKQLMTLADGRVVLALEGGHDLTAICDASEACVNALLGNELEPLAEDILH
    AY032737 (937)   TKQLMTLADGRVVLALEGGHDLTAICDASEACVNALLGNELEPLAEDILH
    AY032738 (880)   --------------------------------------------------
    AF132608 (987)   TRQLMTLAGGRVVLALEGGHDLTAICDASEACVSALLSVELQPLDEAVLQ 1051                                               1100
    HDAC9c  (990)    QSPNMNAVISLQKIIEIQSKYWKSVRMVAVPRGCALAGAQLQEETETVSA
    AY032737 (987)   QSPNMNAVISLQKIIEIQSMSLKFS-------------------------
    AY032738 (880)   --------------------------------------------------
    AF132608 (1037)  QKPNINAVATLEKVIEIQSKHWSCVQKFAAGLGRSLREAQAGETEEAETV 1101                              1136
    HDAC9c  (1040)   LASLTVDVEQPFAQEDSRTAGEPMEEEPAL------
    AY032737 (1012)  ------------------------------------
    AY032738 (880)   ------------------------------------
    AF132608 (1087)  SAMALLSVGAEQAQAAAAREHSPRPAEEPMEQEPAL
```

FIG. 16A
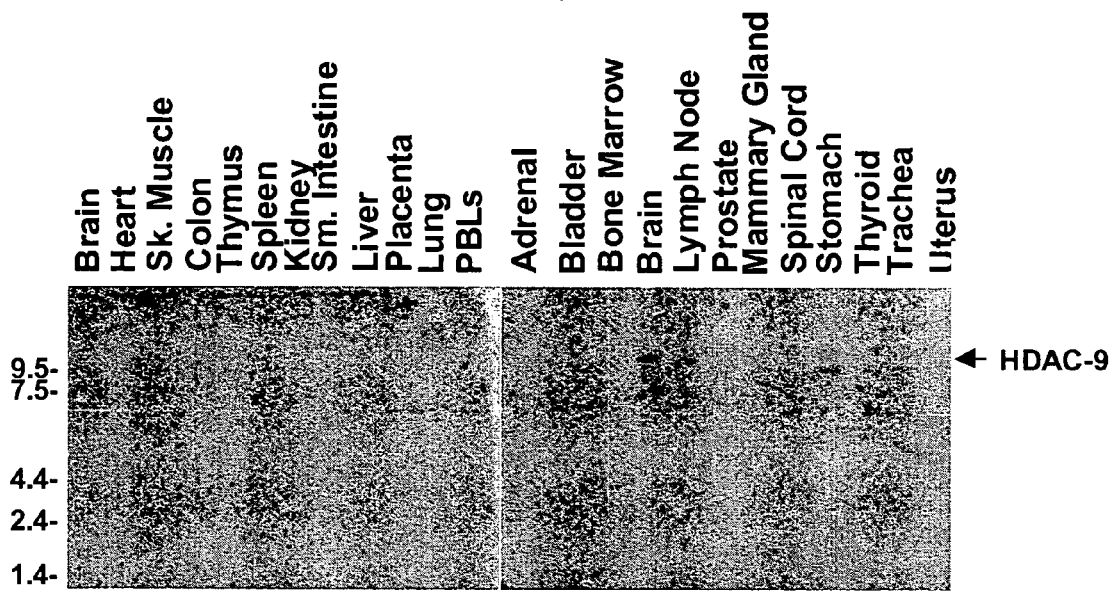
FIG. 16B
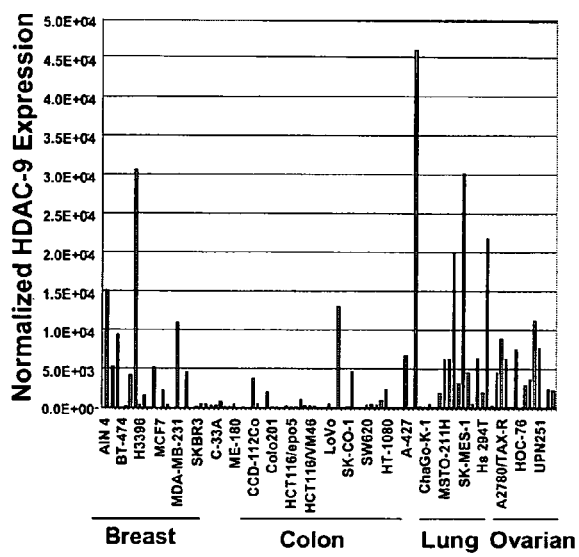
FIG. 16C
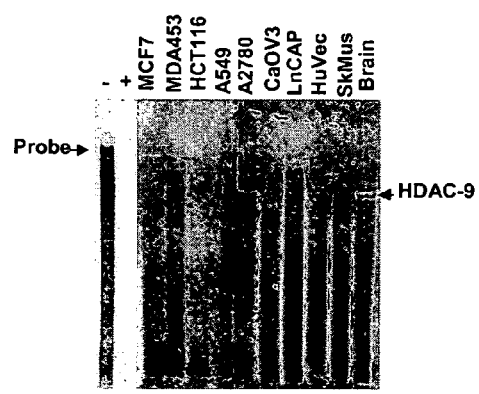
FIG. 16D
```
2901                                    GG AAATGAGCTG GAGCCACTTG
2951 CAGAAGATAT TCTCCACCAA AGCCCGAATA TGAATGCTGT TATTTCTTTA
3001 CAGAAGATCA TTGAAATTCA AAGCAAGTAT TGGAAGTCAG TAAGGATGGT
3051 GGCTGTGCCA AGGGGCTGTG CTCTGGCTGG TGCTCAGTTG CAAGAGGAGA
3101 CAGAGACCGT TTCTGCCCTG GCCTCCCTAA CAGTGGATGT GGAACAGCCC
3151 TTTGCTCAGG AAGACAGCAG AACTGCTGGT GAGCCTATGG AAGAGGAGCC
3201 AGCCTTGTGA
```

FIG. 17A

| Tissue Type | Age | Sex | Histology | Surgery | Resected Margin | Stage | HDAC-9/X | b-Actin |
|---|---|---|---|---|---|---|---|---|
| Breast | Unk | F | Infiltrating ductal adenocarcinoma | Mastectomy | Positive | 2 | +4 | 0 |
| Breast | 72 | F | Infiltrating ductal adenocarcinoma | Mastectomy | Negative | 3 | +2 | +1 |
| Breast | 81 | F | Infiltrating ductal adenocarcinoma | Mastectomy | Negative | 3 | NA | +1 |
| Breast | 43 | F | Infiltrating ductal adenocarcinoma | Mastectomy | | 0 | +2 | +1 |
| Breast | 61 | F | Infiltrating ductal adenocarcinoma | Mastectomy | Negative | 2 | +2 | +1 |
| Breast | 77 | F | Infiltrating ductal adenocarcinoma | Mastectomy | | 3 | +2 | +1 |
| Breast | 69 | F | Infiltrating ductal adenocarcinoma | Mastectomy | Positive | 3 | +3 | +1 |
| Breast | 76 | F | Infiltrating ductal adenocarcinoma | Mastectomy | Negative | 2 | +2 | +1 |
| Breast | Unk | F | Infiltrating ductal adenocarcinoma | Mastectomy | Negative | 2 | +4 | +1 |
| Breast | 44 | F | Infiltrating ductal adenocarcinoma | Mastectomy | | 3 | +2 | 0 |
| Breast | 61 | F | Infiltrating ductal adenocarcinoma | Mastectomy | Negative | 2 | +2 | +1 |
| Breast | 46 | F | Infiltrating ductal adenocarcinoma | Mastectomy | | 3 | +2 | 0 |
| Breast | 86 | F | Infiltrating ductal adenocarcinoma | Biopsy | | 3 | +2 | +1 |
| Breast | 65 | F | Lobular adenocarcinoma | Mastectomy | | 3 | +2 | +1 |
| Breast | 88 | F | Infiltrating ductal adenocarcinoma | Mastectomy | | 3 | +1 | 0 |
| Breast | 47 | F | Infiltrating ductal adenocarcinoma | Biopsy | | 1 | +1 | +1 |
| Prostate | 77 | M | Adenocarcinoma | TUR | | 1 | 0 | +1 |
| Prostate | 74 | M | Adenocarcinoma | TUR | | 1 | +1 | +1 |
| Prostate | 55 | M | Adenocarcinoma | TUR | | 1 | +1 | +1 |
| Prostate | 68 | M | Adenocarcinoma | TUR | | 1 | +1 | +1 |
| Prostate | 71 | M | Adenocarcinoma | TUR | | 1 | +1 | +1 |
| Prostate | 66 | M | Adenocarcinoma | TUR | | 1 | +2 | +1 |
| Prostate | 69 | M | Adenocarcinoma | TUR | | 1 | +2 | +1 |
| Prostate | 73 | M | Adenocarcinoma | TUR | | 1 | +2 | +1 |
| Prostate | 72 | M | Adenocarcinoma | TUR | | 1 | +1 | +1 |
| Prostate | 77 | M | Adenocarcinoma | TUR | | 1 | +4 | +1 |
| Prostate | 77 | M | Adenocarcinoma | TUR | | 1 | +2 | +1 |
| Prostate | 73 | M | Adenocarcinoma | TUR | | 1 | +2 | +1 |
| Prostate | 84 | M | Adenocarcinoma | TUR | | 1 | +1 | +1 |
| Prostate | 93 | M | Adenocarcinoma | TUR | | 1 | +1 | 0 |
| Prostate | 78 | M | Adenocarcinoma | TUR | | 1 | +1 | +1 |
| Prostate | 78 | M | Matched benign specimen | TUR | | | +1 | 0 |

FIG. 17B

| Tissue Type | Age | Sex | Histology | Surgery | Resected Margin | Stage | HDAC-9/X | b-Actin |
|---|---|---|---|---|---|---|---|---|
| Breast | Unk | F | No pathological diagnosis | Biopsy | | | 0 | +1 |
| Breast | Unk | F | No pathological diagnosis | Biopsy | | | 0 | +1 |
| Breast | 43 | F | No pathological diagnosis | Mastectomy | | | 0 | 0 |
| Breast | 88 | F | No pathological diagnosis | Mastectomy | | | 0 | +1 |
| Breast | 55 | F | No pathological diagnosis | Mastectomy | | | 0 | +1 |
| Breast | 74 | F | No pathological diagnosis | Mastectomy | | | +1 | +1 |
| Breast | 51 | F | No pathological diagnosis | Mastectomy | | | +1 | +1 |
| Prostate | 69 | M | No pathological diagnosis | TUR | | | 0 | +1 |
| Prostate | 69 | M | No pathological diagnosis | TUR | | | 0 | +1 |
| Prostate | 66 | M | No pathological diagnosis | TUR | | | 0 | +1 |
| Prostate | 69 | M | No pathological diagnosis | TUR | | | 0 | +1 |
| Prostate | 76 | M | No pathological diagnosis | TUR | | | 0 | +1 |
| Prostate | 64 | M | No pathological diagnosis | TUR | | | 0 | +1 |
| Prostate | 66 | M | No pathological diagnosis | TUR | | | 0 | +1 |

FIG. 18
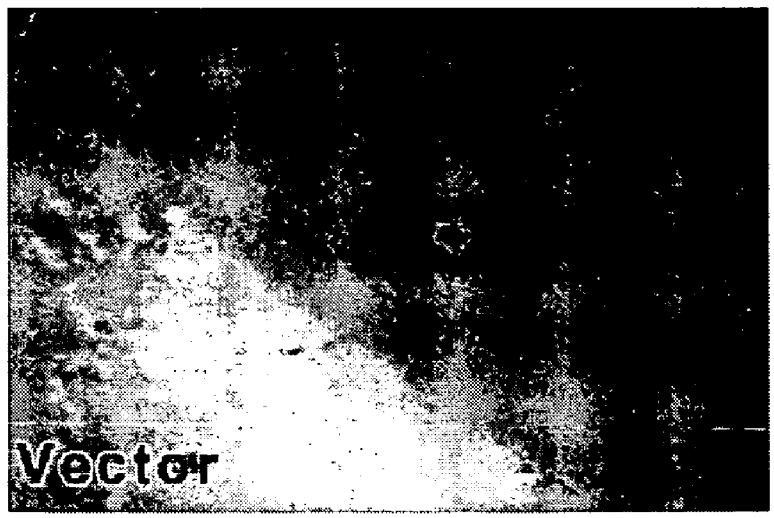
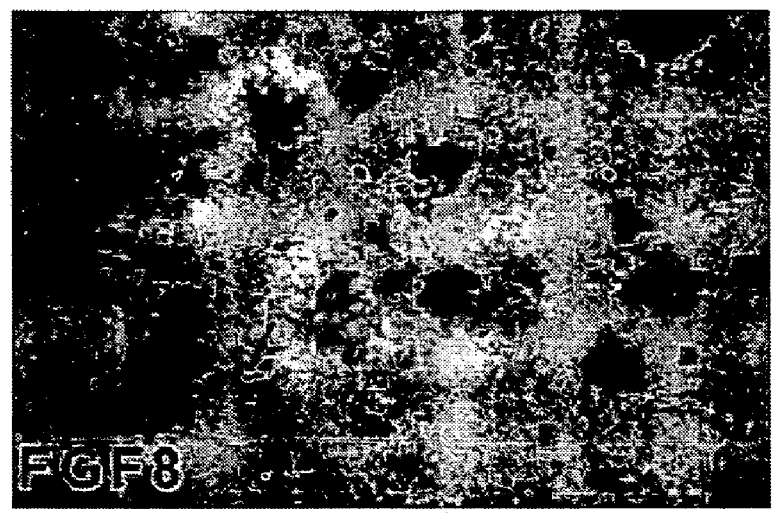

FIG. 20A

```
       AlaGluAsnGluThrSerValLeuProProThrProHisAlaGluGlnMetValSerGln
  1    GCTGAAAATGAGACTTCGGTTTTGCCCCCTACCCCTCATGCCGAGCAAATGGTTTCACAG

GlnArgIleLeuIleHisGluAspSerMetAsnLeuLeuSerLeuTyrThrSerProSer
 61    CAACGCATTCTAATTCATGAAGATTCCATGAACCTGCTAAGTCTTTATACCTCTCCTTCT

LeuProAsnIleThrLeuGlyLeuProAlaValProSerGlnLeuAsnAlaSerAsnSer
121    TTGCCCAACATTACCTTGGGGCTTCCCGCAGTGCCATCCCAGCTCAATGCTTCGAATTCA

LeuLysGluLysGlnLysCysGluThrGlnThrLeuArgGlnGlyValProLeuProGly
181    CTCAAAGAAAAGCAGAAGTGTGAGACGCAGACGCTTAGGCAAGGTGTTCCTCTGCCTGGG

GlnTyrGlyGlySerIleProAlaSerSerSerHisProHisValThrLeuGluGlyLys
241    CAGTATGGAGGCAGCATCCCGGCATCTTCCAGCCACCCTCATGTTACTTTAGAGGGAAAG

ProProAsnSerSerHisGlnAlaLeuLeuGlnHisLeuLeuLeuLysGluGlnMetArg
301    CCACCCAACAGCAGCCACCAGGCTCTCCTGCAGCATTTATTATTGAAAGAACAAATGCGA

GlnGlnLysLeuLeuValAlaGlyGlyValProLeuHisProGlnSerProLeuAlaThr
361    CAGCAAAAGCTTCTTGTAGCTGGTGGAGTTCCCTTACATCCTCAGTCTCCCTTGGCAACA

LysGluArgIleSerProGlyIleArgGlyThrHisLysLeuProArgHisArgProLeu
421    AAAGAGAGAATTTCACCTGGCATTAGAGGTACCCACAAATTGCCCCGTCACAGACCCCTG

AsnArgThrGlnSerAlaProLeuProGlnSerThrLeuAlaGlnLeuValIleGlnGln
481    AACCGAACCCAGTCTGCACCTTTGCCTCAGAGCACGTTGGCTCAGCTGGTCATTCAACAG

GlnHisGlnGlnPheLeuGluLysGlnLysGlnTyrGlnGlnGlnIleHisMetAsnLys
541    CAACACCAGCAATTCTTGGAGAAGCAGAAGCAATACCAGCAGCAGATCCACATGAACAAA

LeuLeuSerLysSerIleGluGlnLeuLysGlnProGlySerHisLeuGluGluAlaGlu
601    CTGCTTTCGAAATCTATTGAACAACTGAAGCAACCAGGCAGTCACCTTGAGGAAGCAGAG

GluGluLeuGlnGlyAspGlnAlaMetGlnGluAspArgAlaProSerSerGlyAsnSer
661    GAAGAGCTTCAGGGGACCAGGCGATGCAGGAAGACAGAGCGCCCTCTAGTGGCAACAGC

ThrArgSerAspSerSerAlaCysValAspAspThrLeuGlyGlnValGlyAlaValLys
721    ACTAGGAGCGACAGCAGTGCTTGTGTGGATGACACACTGGGACAAGTTGGGGCTGTGAAG

ValLysGluGluProValAspSerAspGluAspAlaGlnIleGlnGluMetGluSerGly
781    GTCAAGGAGGAACCAGTGGACAGTGATGAAGATGCTCAGATCCAGGAAATGGAATCTGGG

GluGlnAlaAlaPheMetGlnGlnProPheLeuGluProThrHisThrArgAlaLeuSer
841    GAGCAGGCTGCTTTTATGCAACAGCCTTTCCTGGAACCCACGCACACACGTGCGCTCTCT

ValArgGlnAlaProLeuAlaAlaValGlyMetAspGlyLeuGluLysHisArgLeuVal
901    GTGCGCCAAGCTCCGCTGGCTGCGGTTGGCATGGATGGATTAGAGAAACACCGTCTCGTC

SerArgThrHisSerSerProAlaAlaSerValLeuProHisProAlaMetAspArgPro
961    TCCAGGACTCACTCTTCCCCTGCTGCCTCTGTTTTACCTCACCCGGCAATGGACCGCCCC

LeuGlnProGlySerAlaThrGlyIleAlaTyrAspProLeuMetLeuLysHisGlnCys
1021   CTCCAGCCTGGCTCTGCAACTGGAATTGCCTATGACCCCTTGATGCTGAAACACCAGTGC

ValCysGlyAsnSerThrThrHisProGluHisAlaGlyArgIleGlnSerIleTrpSer
1081   GTTTGTGGCAATTCCACCACCCACCCTGAGCATGCTGGACGAATACAGAGTATCTGGTCA
```

FIG. 20B

```
                ArgLeuGlnGluThrGlyLeuLeuAsnLysCysGluArgIleGlnGlyArgLysAlaSer
1141            CGACTGCAAGAAACTGGGCTGCTAAATAAATGTGAGCGAATTCAAGGTCGAAAAGCCAGC

LeuGluGluIleGlnLeuValHisSerGluHisHisSerLeuLeuTyrGlyThrAsnPro
1201            CTGGAGGAAATACAGCTTGTTCATTCTGAACATCACTCACTGTTGTATGGCACCAACCCC

LeuAspGlyGlnLysLeuAspProArgIleLeuLeuGlyAspAspSerGlnLysPhePhe
1261            CTGGACGGACAGAAGCTGGACCCCAGGATACTCCTAGGTGATGACTCTCAAAAGTTTTTT

SerSerLeuProCysGlyGlyLeuGlyValAspSerAspThrIleTrpAsnGluLeuHis
1321            TCCTCATTACCTTGTGGTGGACTTGGGGTGGACAGTGACACCATTTGGAATGAGCTACAC

SerSerGlyAlaAlaArgMetAlaValGlyCysValIleGluLeuAlaSerLysValAla
1381            TCGTCCGGTGCTGCACGCATGGCTGTTGGCTGTGTCATCGAGCTGGCTTCCAAAGTGGCC

SerGlyGluLeuLysAsnGlyPheAlaValValArgProProGlyHisHisAlaGluGlu
1441            TCAGGAGAGCTGAAGAATGGGTTTGCTGTTGTGAGGCCCCCTGGCCATCACGCTGAAGAA

SerThrAlaMetGlyPheCysPhePheAsnSerValAlaIleThrAlaLysTyrLeuArg
1501            TCCACAGCCATGGGGTTCTGCTTTTTTAATTCAGTTGCAATTACCGCCAAATACTTGAGA

AspGlnLeuAsnIleSerLysIleLeuIleValAspLeuAspValHisHisGlyAsnGly
1561            GACCAACTAAATATAAGCAAGATATTGATTGTAGATCTGGATGTTCACCATGGAAACGGT

ThrGlnGlnAlaPheTyrAlaAspProSerIleLeuTyrIleSerLeuHisArgTyrAsp
1621            ACCCAGCAGGCCTTTTATGCTGACCCCAGCATCCTGTACATTTCACTCCATCGCTATGAT

GluGlyAsnPhePheProGlySerGlyAlaProAsnGluValGlyThrGlyLeuGlyGlu
1681            GAAGGGAACTTTTTCCCTGGCAGTGGAGCCCCAAATGAGGTTGGAACAGGCCTTGGAGAA

GlyTyrAsnIleAsnIleAlaTrpThrGlyGlyLeuAspProProMetGlyAspValGlu
1741            GGGTACAATATAAATATTGCCTGGACAGGTGGCCTTGATCCTCCCATGGGAGATGTTGAG

TyrLeuGluAlaPheArgThrIleValLysProValAlaLysGluPheAspProAspMet
1801            TACCTTGAAGCATTCAGGACCATCGTGAAGCCTGTGGCCAAAGAGTTTGATCCAGACATG

ValLeuValSerAlaGlyPheAspAlaLeuGluGlyHisThrProProLeuGlyGlyTyr
1861            GTCTTAGTATCTGCTGGATTTGATGCATTGGAAGGCCACACCCCTCCTCTAGGAGGGTAC

LysValThrAlaLysCysPheGlyHisLeuThrLysGlnLeuMetThrLeuAlaAspGly
1921            AAAGTGACGGCAAAATGTTTTGGTCATTTGACGAAGCAATTGATGACATTGGCTGATGGA

ArgValValLeuAlaLeuGluGlyGlyHisAspLeuThrAlaIleCysAspAlaSerGlu
1981            CGTGTGGTGTTGGCTCTAGAAGGAGGACATGATCTCACAGCCATCTGTGATGCATCAGAA

AlaCysValAsnAlaLeuLeuGlyAsnGluLeuGluProLeuAlaGluAspIleLeuHis
2041            GCCTGTGTAAATGCCCTTCTAGGAAATGAGCTGGAGCCACTTGCAGAAGATATTCTCCAC

GlnSerProAsnMetAsnAlaValIleSerLeuGlnLysIleIleGluIleGlnSerLys
2101            CAAAGCCCGAATATGAATGCTGTTATTTCTTTACAGAAGATCATTGAAATTCAAAGCAAG

TyrTrpLysSerValArgMetValAlaValProArgGlyCysAlaLeuAlaGlyAlaGln
2161            TATTGGAAGTCAGTAAGGATGGTGGCTGTGCCAAGGGGCTGTGCTCTGGCTGGTGCTCAG

LeuGlnGluGluThrGluThrValSerAlaLeuAlaSerLeuThrValAspValGluGln
2221            TTGCAAGAGGAGACAGAGACCGTTTCTGCCCTGGCCTCCCTAACAGTGGATGTGGAACAG
```

FIG. 20C

```
      ProPheAlaGlnGluAspSerArgThrAlaGlyGluProMetGluGluGluProAlaLeu
2281  CCCTTTGCTCAGGAAGACAGCAGAACTGCTGGTGAGCCTATGGAAGAGGAGCCAGCCTTG

***
2341  TGAAGTGCCAAGTCCCCCTCTGATATTTCCTGTGTGTGACATCATTGTGTATCCCCCCAC
2401  CCCAGTACCCTCAGACATGTCTTGTCTGCTGCCTGGGTGGCACAGATTCAATGGAACATA
2461  AACACTGGGCACAAAATTCTGAACAGCAGCTTCACTTGTTCTTTGGATGGACTTGAAAGG
2521  GCATTAAAGATTCCTTAAACGTAACCGCTGTGATTCTAGAGTTACAGTAAACCACGATTG
2581  GAAGAAACTGCTTCCAGCATGCTTTTAATATGCTGGGTGACCCACTCCTAGACACCAAGT
2641  TTGAACTAGAAACATTCAGTACAGCACTAGATATTGTTAATTTCAGAAGCTATGACAGCC
2701  AGTGAAATTTTGGGCAAAACCTGAGACATAGTCATTCCTGACATTCTGATCAGCTTTTTT
2761  TGGGGTAATTTGTTTTTCAAACAGTCTTAACTTGTTTACAAGATTTGCTTTTAGCTATGA
2821  ACGGATCGTAATTCCACCCAGAATGTAATGTTTCTTGTTTGTTTGTTTTGTTTTGTTAGG
2881  GTTTTTTTCTCAACTTTAACACACAGTTCAACTGTTCCTAGTAAAAGTTCAAGATGGAGG
2941  AACTAGCATGAGGCTTTTTTCAGTATCTCGAAGTCCAAATGCCAAAGGAACCTCACACAC
3001  TGTTTGTAATGGTGCAATATTTTATATCACTTTTTTTTAAACATCCCCAACATCTTTGTG
3061  TTCTCACACACAGGCAATTTGCAATGTTGCAATTGTGTTGGAGAATGAAGTCCCCCCACC
3121  TCCCAGCCACACACACATCCTTTGTTCTCATGACAGTAGGTCTGAGCAAATGTTCCACCA
3181  AGCATTTTCAGTGTCTTTGAAAAGCACGTAACTTTTCAAAGGTGGTCTTAATTTGCTGCA
3241  TATCTATCAAGGACTTATTCACTCACCTTTCCTTTTCTGCCCTCTATCAATTGATTTCTT
3301  CTTACCTTTCATCATTCATTCCTTCCTTTAGAAAAACTGAAGATTACCCATAATCTCCTC
3361  TTATTACTTGAGGGCCTTGACTATTTAGTTTATTTTGTTTACTTTACAGGTTAACACAGT
3421  TGTTTTGTCTGATTGCATTTTATTAACTGTGAAGCCGTTGAAATGAATATCACTTAAGCA
3481  ACGTTGCTAAATTTCTATGTGTTTGAAATGTGTTAATGAAGGCACTGCTTATTTGTAGTC
3541  ACCTTGAACTGACTTAACCTAGAAGCTGTGCCTTCTTGTGAAAAAAAAAAAAAAAAAAAA
3601  AAAAAAAAAAAAAAAAAAAAAAAAAAAAAAAAAAAAAAAAAAA
```

FIG. 21A

```
   1  CCACGCGTCCGTAGGAGAAGGGCACCGGCTGGAGCCACTTGCAGGACTGAGGGTTTTTGC
  61  AACAAAACCCTAGCAGCCTGAAGAACTCTAAGCCAGGTTTAATTGGTTTCTTTTTCTCGT
 121  GGGTAGACTTAATAATTTTCTACGTATTCTGACAAAGAAATAACCCCGAAGCACGTTCCT
 181  ATTTCCCACCTGCTTGTAGTTTCCGGGATAACCTAAACTCCAGAGAGCTATAGCATCCAC
 241  TCTGTCCTTTCTGCTTTGCACACAGATGGGGTGGCTGGACGAGAGCAGCTCTTGGCTCAG

MetHisSerMetIleSerSerValAspValLysSerGluValProValGlyLeu
 301  CAAAGAATGCACAGTATGATCAGCTCAGTGGATGTGAAGTCAGAAGTTCCTGTGGGCCTG

GluProIleSerProLeuAspLeuArgThrAspLeuArgMetMetMetProValValAsp
 361  GAGCCCATCTCACCTTTAGACCTAAGGACAGACCTCAGGATGATGATGCCCGTGGTGGAC

ProValValArgGluLysGlnLeuGlnGlnGluLeuLeuLeuIleGlnGlnGlnGlnGln
 421  CCTGTTGTCCGTGAGAAGCAATTGCAGCAGGAATTACTTCTTATCCAGCAGCAGCAACAA

IleGlnLysGlnLeuLeuIleAlaGluPheGlnLysGlnHisGluAsnLeuThrArgGln
 481  ATCCAGAAGCAGCTTCTGATAGCAGAGTTTCAGAAACAGCATGAGAACTTGACACGGCAG

HisGlnAlaGlnLeuGlnGluHisIleLysLeuGlnGlnGluLeuLeuAlaIleLysGln
 541  CACCAGGCTCAGCTTCAGGAGCATATCAAGTTGCAACAGGAACTTCTAGCCATAAAACAG

GlnGlnGluLeuLeuGluLysGluGlnLysLeuGluGlnGlnArgGlnGluGlnGluVal
 601  CAACAAGAACTCCTAGAAAAGGAGCAGAAACTGGAGCAGCAGAGGCAAGAACAGGAAGTA

GluArgHisArgArgGluGlnGlnLeuProProLeuArgGlyLysAspArgGlyArgGlu
 661  GAGAGGCATCGCAGAGAACAGCAGCTTCCTCCTCTCAGAGGCAAAGATAGAGGACGAGAA

ArgAlaValAlaSerThrGluValLysGlnLysLeuGlnGluPheLeuLeuSerLysSer
 721  AGGGCAGTGGCAAGTACAGAAGTAAAGCAGAAGCTTCAAGAGTTCCTACTGAGTAAATCA

AlaThrLysAspThrProThrAsnGlyLysAsnHisSerValSerArgHisProLysLeu
 781  GCAACGAAAGACACTCCAACTAATGGAAAAAATCATTCCGTGAGCCGCCATCCCAAGCTC

TrpTyrThrAlaAlaHisHisThrSerLeuAspGlnSerSerProProLeuSerGlyThr
 841  TGGTACACGGCTGCCCACCACACATCATTGGATCAAAGCTCTCCACCCCTTAGTGGAACA

SerProSerTyrLysTyrThrLeuProGlyAlaGlnAspAlaLysAspAspPheProLeu
 901  TCTCCATCCTACAAGTACACATTACCAGGAGCACAAGATGCAAAGGATGATTTCCCCCTT

ArgLysThrAlaSerGluProAsnLeuLysValArgSerArgLeuLysGlnLysValAla
 961  CGAAAAACTGCCTCTGAGCCCAACTTGAAGGTGCGGTCCAGGTTAAAACAGAAAGTGGCA

GluArgArgSerSerProLeuLeuArgArgLysAspGlyAsnValValThrSerPheLys
1021  GAGAGGAGAAGCAGCCCCTTACTCAGGCGGAAGGATGGAAATGTTGTCACTTCATTCAAG

LysArgMetPheGluValThrGluSerSerValSerSerSerSerProGlySerGlyPro
1081  AAGCGAATGTTTGAGGTGACAGAATCCTCAGTCAGTAGCAGTTCTCCAGGCTCTGGTCCC

SerSerProAsnAsnGlyProThrGlySerValThrGluAsnGluThrSerValLeuPro
1141  AGTTCACCAAACAATGGGCCAACTGGAAGTGTTACTGAAAATGAGACTTCGGTTTTGCCC

ProThrProHisAlaGluGlnMetValSerGlnGlnArgIleLeuIleHisGluAspSer
1201  CCTACCCCTCATGCCGAGCAAATGGTTTCACAGCAACGCATTCTAATTCATGAAGATTCC

MetAsnLeuLeuSerLeuTyrThrSerProSerLeuProAsnIleThrLeuGlyLeuPro
1261  ATGAACCTGCTAAGTCTTTATACCTCTCCTTCTTTGCCCAACATTACCTTGGGGCTTCCC

AlaValProSerGlnLeuAsnAlaSerAsnSerLeuLysGluLysGlnLysCysGluThr
```

FIG. 21B

```
1321    GCAGTGCCATCCCAGCTCAATGCTTCGAATTCACTCAAAGAAAAGCAGAAGTGTGAGACG

GlnThrLeuArgGlnGlyValProLeuProGlyGlnTyrGlyGlySerIleProAlaSer
1381    CAGACGCTTAGGCAAGGTGTTCCTCTGCCTGGGCAGTATGGAGGCAGCATCCCGGCATCT

SerSerHisProHisValThrLeuGluGlyLysProProAsnSerSerHisGlnAlaLeu
1441    TCCAGCCACCCTCATGTTACTTTAGAGGGAAAGCCACCCAACAGCAGCCACCAGGCTCTC

LeuGlnHisLeuLeuLeuLysGluGlnMetArgGlnGlnLysLeuLeuValAlaGlyGly
1501    CTGCAGCATTTATTATTGAAAGAACAAATGCGACAGCAAAAGCTTCTTGTAGCTGGTGGA

ValProLeuHisProGlnSerProLeuAlaThrLysGluArgIleSerProGlyIleArg
1561    GTTCCCTTACATCCTCAGTCTCCCTTGGCAACAAAAGAGAGAATTTCACCTGGCATTAGA

GlyThrHisLysLeuProArgHisArgProLeuAsnArgThrGlnSerAlaProLeuPro
1621    GGTACCCACAAATTGCCCCGTCACAGACCCCTGAACCGAACCCAGTCTGCACCTTTGCCT

GlnSerThrLeuAlaGlnLeuValIleGlnGlnGlnHisGlnGlnPheLeuGluLysGln
1681    CAGAGCACGTTGGCTCAGCTGGTCATTCAACAGCAACACCAGCAATTCTTGGAGAAGCAG

LysGlnTyrGlnGlnGlnIleHisMetAsnLysGluLeuProMetThrPro***
1741    AAGCAATACCAGCAGCAGATCCACATGAACAAAGAATTGCCTATGACCCCTTGATGCTGA

1801    AACACCAGTGCGTTTGTGGCAATTCCACCACCCACCCTGAGCATGCTGGACGAATACAGA
1861    GTATCTGGTCACGACTGCAAGAAACTGGGCTGCTAAATAAATGTGAGCGAATTCAAGGTC
1921    GAAAAGCCAGCCTGGAGGAAATACAGCTTGTTCATTCTGAACATCACTCACTGTTGTATG
1981    GCACCAACCCCCTGGACGGACAGAAGCTGGACCCCAGGATACTCCTAGGTGATGACTCTC
2041    AAAAGTTTTTTTTCCTCATTACCTTGTGGTGGACTTGGGGTGGACAGTGACACCATTTGA
2101    ATGAGCTACACTCGTCCGGTGCTGCACGCATGGCTGTTGGCTGTGTCATCGAGCTGGCTT
2161    CCAAAGTGGCCTCAGGAGAGCTGAAGGTGAGGTCCGGGTTGCATTAAGTGTGGGAAATCC
2221    AGAGAAGAAACTGAAACAGAGATGTTGTTATGTGGGAATTGCGGGGAGTGTGGCGTGGTA
2281    ATAAAAGGAAGGGCAGAAGGAAGAGGGTAGAGATGGCCACTAAGGTGTGATAATAACTCA
2341    TCTGTAGGCAGGGAGCAGCTCATCCTGCTCTCAGGGCCTTCTTCTGCCTGAGAACACTCT
2401    GCAGTCAGGGCCCACCGGTGTGCATGTAAGAGCACAGAGATAATAAGCAAAGCTATGGTT
2461    CAGGTTAAAAATACCTTTAGTATATACATGTCTGTCATGCCATCCTGAGATTCTCTTTTG
2521    AGGCAATTTTAAAAATATGATTACTGAGAAGTGTGTATAAGCTCAGAATACCACCCAGAG
2581    AGAGGGAGGCAGAGAAAGGTAAATACCAGACGGGAAGGATTGGGAGGAGGAAGGAAATTG
2641    TTGATTAGAAGGGTAATGATCCAGAGTGTGTTTTTCCATGAAAGAACTTAAAAAATGAGC
2701    TATGCTTTATTGTTCTTTTCTTTTTATGGTCTCTTCTTTTCTACATCGTATGAAAAGAAC
2761    AATGTCCAAACCCCAGCGTTTCCCAGTCTAAACAATTTATAAAAGCTAGAGACCTGACAG
2821    ACGTTGACATTTTATTTGGTATTTTAACAGTGCTATTTAAAGGTACGCCATGTGCGTCTT
2881    GAATGCAGTTACCCCAATAAACTTTGTTGGTGCTAACACGGCCTTTTAATGCACTAGTTC
2941    ACACACTTCATGACGCAATCTGGGTCGTGATTGATTCGGTATTTTAGCAATTGCGGGGC
3001    TTAGGGAAATATATTATGACCAATAACATATGCACTGTGAGTTTTGTGAAACCAAGATAA
3061    AATAATTAGGATTACTTTTCTTTATGTCTAGTGAATTTTTATTCAATTACATGGGACTCT
3121    TCCAGTTGTGATTAAAAATGTGGAGTAGGAATGTGCACTTCACAATGCAACGTTTGTCCA
3181    AGAAGTCTTTACTCTTAACTCTTTAAAGAGTCAGAGCCTACGGAAATATAATTTTGATAG
3241    GGTGAGCTCTATTTAAAAGTAGATGTGCCTGTATATATTTGACATAAGTAGTATTAGGA
3301    CATTGCTCATCTCAGGGGATATATGGGTCATTAATGTGGTGCTTACTCTTCAGTCTTTA
3361    CCTTTGAAAATGAGCAAAAAAAAAAAAAAAA
```

FIG. 22A

```
   1 GGGGAAGAGAGGCACAGACACAGATAGGAGAAGGGCACCGGCTGGAGCCACTTGCAGGAC
  61 TGAGGGTTTTTGCAACAAAACCCTAGCAGCCTGAAGAACTCTAAGCCAGATGGGGTGGCT

MetHisSerMetIleSerSerValAspVal
 121 GGACGAGAGCAGCTCTTGGCTCAGCAAAGAATGCACAGTATGATCAGCTCAGTGGATGTG

LysSerGluValProValGlyLeuGluProIleSerProLeuAspLeuArgThrAspLeu
 181 AAGTCAGAAGTTCCTGTGGGCCTGGAGCCCATCTCACCTTTAGACCTAAGGACAGACCTC

ArgMetMetMetProValValAspProValValArgGluLysGlnLeuGlnGlnGluLeu
 241 AGGATGATGATGCCCGTGGTGGACCCTGTTGTCCGTGAGAAGCAATTGCAGCAGGAATTA

LeuLeuIleGlnGlnGlnGlnIleGlnLysGlnLeuLeuIleAlaGluPheGlnLys
 301 CTTCTTATCCAGCAGCAGCAACAAATCCAGAAGCAGCTTCTGATAGCAGAGTTTCAGAAA

GlnHisGluAsnLeuThrArgGlnHisGlnAlaGlnLeuGlnGluHisIleLysGluLeu
 361 CAGCATGAGAACTTGACACGGCAGCACCAGGCTCAGCTTCAGGAGCATATCAAGGAACTT

LeuAlaIleLysGlnGlnGlnGluLeuLeuGluLysGluGlnLysLeuGluGlnGlnArg
 421 CTAGCCATAAAACAGCAACAAGAACTCCTAGAAAAGGAGCAGAAACTGGAGCAGCAGAGG

GlnGluGlnGluValGluArgHisArgArgGluGlnGlnLeuProProLeuArgGlyLys
 481 CAAGAACAGGAAGTAGAGAGGCATCGCAGAGAACAGCAGCTTCCTCCTCTCAGAGGCAAA

AspArgGlyArgGluArgAlaValAlaSerThrGluValLysGlnLysLeuGlnGluPhe
 541 GATAGAGGACGAGAAAGGGCAGTGGCAAGTACAGAAGTAAAGCAGAAGCTTCAAGAGTTC

LeuLeuSerLysSerAlaThrLysAspThrProThrAsnGlyLysAsnHisSerValSer
 601 CTACTGAGTAAATCAGCAACGAAAGACACTCCAACTAATGGAAAAAATCATTCCGTGAGC

ArgHisProLysLeuTrpTyrThrAlaAlaHisHisThrSerLeuAspGlnSerSerPro
 661 CGCCATCCCAAGCTCTGGTACACGGCTGCCCACCACACATCATTGGATCAAAGCTCTCCA

ProLeuSerGlyThrSerProSerTyrLysTyrThrLeuProGlyAlaGlnAspAlaLys
 721 CCCCTTAGTGGAACATCTCCATCCTACAAGTACACATTACCAGGAGCACAAGATGCAAAG

AspAspPheProLeuArgLysThrAlaSerGluProAsnLeuLysValArgSerArgLeu
 781 GATGATTTCCCCCTTCGAAAAACTGCCTCTGAGCCCAACTTGAAGGTGCGGTCCAGGTTA

LysGlnLysValAlaGluArgArgSerSerProLeuLeuArgArgLysAspGlyAsnVal
 841 AAACAGAAAGTGGCAGAGAGGAGAAGCAGCCCCTTACTCAGGCGGAAGGATGGAAATGTT

ValThrSerPheLysLysArgMetPheGluValThrGluSerSerValSerSerSerSer
 901 GTCACTTCATTCAAGAAGCGAATGTTTGAGGTGACAGAATCCTCAGTCAGTAGCAGTTCT

ProGlySerGlyProSerSerProAsnAsnGlyProThrGlySerValThrGluAsnGlu
 961 CCAGGCTCTGGTCCCAGTTCACCAAACAATGGGCCAACTGGAAGTGTTACTGAAAATGAG

ThrSerValLeuProProThrProHisAlaGluGlnMetValSerGlnGlnArgIleLeu
1021 ACTTCGGTTTTGCCCCCTACCCCTCATGCCGAGCAAATGGTTTCACAGCAACGCATTCTA

IleHisGluAspSerMetAsnLeuLeuSerLeuTyrThrSerProSerLeuProAsnIle
1081 ATTCATGAAGATTCCATGAACCTGCTAAGTCTTTATACCTCTCCTTCTTTGCCCAACATT

ThrLeuGlyLeuProAlaValProSerGlnLeuAsnAlaSerAsnSerLeuLysGluLys
1141 ACCTTGGGGCTTCCCGCAGTGCCATCCCAGCTCAATGCTTCGAATTCACTCAAAGAAAAG
```

FIG. 22B

```
                GlnLysCysGluThrGlnThrLeuArgGlnGlyValProLeuProGlyGlnTyrGlyGly
         1201   CAGAAGTGTGAGACGCAGACGCTTAGGCAAGGTGTTCCTCTGCCTGGGCAGTATGGAGGC

SerIleProAlaSerSerSerHisProHisValThrLeuGluGlyLysProProAsnSer
         1261   AGCATCCCGGCATCTTCCAGCCACCCTCATGTTACTTTAGAGGGAAAGCCACCCAACAGC

SerHisGlnAlaLeuLeuGlnHisLeuLeuLeuLysGluGlnMetArgGlnGlnLysLeu
         1321   AGCCACCAGGCTCTCCTGCAGCATTTATTATTGAAAGAACAAATGCGACAGCAAAAGCTT

LeuValAlaGlyGlyValProLeuHisProGlnSerProLeuAlaThrLysGluArgIle
         1381   CTTGTAGCTGGTGGAGTTCCCTTACATCCTCAGTCTCCCTTGGCAACAAAAGAGAGAATT

SerProGlyIleArgGlyThrHisLysLeuProArgHisArgProLeuAsnArgThrGln
         1441   TCACCTGGCATTAGAGGTACCCACAAATTGCCCCGTCACAGACCCCTGAACCGAACCCAG

SerAlaProLeuProGlnSerThrLeuAlaGlnLeuValIleGlnGlnGlnHisGlnGln
         1501   TCTGCACCTTTGCCTCAGAGCACGTTGGCTCAGCTGGTCATTCAACAGCAACACCAGCAA

PheLeuGluLysGlnLysGlnTyrGlnGlnGlnIleHisMetAsnLysLeuLeuSerLys
         1561   TTCTTGGAGAAGCAGAAGCAATACCAGCAGCAGATCCACATGAACAAACTGCTTTCGAAA

SerIleGluGlnLeuLysGlnProGlySerHisLeuGluGluAlaGluGluGluLeuGln
         1621   TCTATTGAACAACTGAAGCAACCAGGCAGTCACCTTGAGGAAGCAGAGGAAGAGCTTCAG

GlyAspGlnAlaMetGlnGluAspArgAlaProSerSerGlyAsnSerThrArgSerAsp
         1681   GGGGACCAGGCGATGCAGGAAGACAGAGCGCCCTCTAGTGGCAACAGCACTAGGAGCGAC

SerSerAlaCysValAspAspThrLeuGlyGlnValGlyAlaValLysValLysGluGlu
         1741   AGCAGTGCTTGTGTGGATGACACACTGGGACAAGTTGGGGCTGTGAAGGTCAAGGAGGAA

ProValAspSerAspGluAspAlaGlnIleGlnGluMetGluSerGlyGluGlnAlaAla
         1801   CCAGTGGACAGTGATGAAGATGCTCAGATCCAGGAAATGGAATCTGGGGAGCAGGCTGCT

PheMetGlnGlnProPheLeuGluProThrHisThrArgAlaLeuSerValArgGlnAla
         1861   TTTATGCAACAGCCTTTCCTGGAACCCACGCACACACGTGCGCTCTCTGTGCGCCAAGCT

ProLeuAlaAlaValGlyMetAspGlyLeuGluLysHisArgLeuValSerArgThrHis
         1921   CCGCTGGCTGCGGTTGGCATGGATGGATTAGAGAAACACCGTCTCGTCTCCAGGACTCAC

SerSerProAlaAlaSerValLeuProHisProAlaMetAspArgProLeuGlnProGly
         1981   TCTTCCCCTGCTGCCTCTGTTTTACCTCACCCAGCAATGGACCGCCCCCTCCAGCCTGGC

SerAlaThrGlyIleAlaTyrAspProLeuMetLeuLysHisGlnCysValCysGlyAsn
         2041   TCTGCAACTGGAATTGCCTATGACCCCTTGATGCTGAAACACCAGTGCGTTTGTGGCAAT

SerThrThrHisProGluHisAlaGlyArgIleGlnSerIleTrpSerArgLeuGlnGlu
         2101   TCCACCACCCACCCTGAGCATGCTGGACGAATACAGAGTATCTGGTCACGACTGCAAGAA

ThrGlyLeuLeuAsnLysCysGluArgIleGlnGlyArgLysAlaSerLeuGluGluIle
         2161   ACTGGGCTGCTAAATAAATGTGAGCGAATTCAAGGTCGAAAAGCCAGCCTGGAGGAAATA

GlnLeuValHisSerGluHisHisSerLeuLeuTyrGlyThrAsnProLeuAspGlyGln
         2221   CAGCTTGTTCATTCTGAACATCACTCACTGTTGTATGGCACCAACCCCCTGGACGGACAG

LysLeuAspProArgIleLeuLeuGlyAspAspSerGlnLysPhePheSerSerLeuPro
         2281   AAGCTGGACCCCAGGATACTCCTAGGTGATGACTCTCAAAAGTTTTTTTCCTCATTACCT
```

FIG. 22C

```
             CysGlyGlyLeuGlyValAspSerAspThrIleTrpAsnGluLeuHisSerSerGlyAla
2341         TGTGGTGGACTTGGGGTGGACAGTGACACCATTTGGAATGAGCTACACTCGTCCGGTGCT

AlaArgMetAlaValGlyCysValIleGluLeuAlaSerLysValAlaSerGlyGluLeu
2401         GCACGCATGGCTGTTGGCTGTGTCATCGAGCTGGCTTCCAAAGTGGCCTCAGGAGAGCTG

LysAsnGlyPheAlaValValArgProProGlyHisHisAlaGluGluSerThrAlaMet
2461         AAGAATGGGTTTGCTGTTGTGAGGCCCCCTGGCCATCACGCTGAAGAATCCACAGCCATG

GlyPheCysPhePheAsnSerValAlaIleThrAlaLysTyrLeuArgAspGlnLeuAsn
2521         GGGTTCTGCTTTTTTAATTCAGTTGCAATTACCGCCAAATACTTGAGAGACCAACTAAAT

IleSerLysIleLeuIleValAspLeuAspValHisHisGlyAsnGlyThrGlnGlnAla
2581         ATAAGCAAGATATTGATTGTAGATCTGGATGTTCACCATGGAAACGGTACCCAGCAGGCC

PheTyrAlaAspProSerIleLeuTyrIleSerLeuHisArgTyrAspGluGlyAsnPhe
2641         TTTTATGCTGACCCCAGCATCCTGTACATTTCACTCCATCGCTATGATGAAGGGAACTTT

~~~~~~~~~~~~~~~~~~~~~~~~~~~~~~~~~~~~~~~~~~~~~~~~~~~~~~~~~~~
             PheProGlySerGlyAlaProAsnGluValGlyThrGlyLeuGlyGluGlyTyrAsnIle
2701         TTCCCTGGCAGTGGAGCCCCAAATGAGGTTGGAACAGGCCTTGGAGAAGGGTACAATATA

AsnIleAlaTrpThrGlyGlyLeuAspProProMetGlyAspValGluTyrLeuGluAla
2761         AATATTGCCTGGACAGGTGGCCTTGATCCTCCCATGGGAGATGTTGAGTACCTTGAAGCA

PheArgThrIleValLysProValAlaLysGluPheAspProAspMetValLeuValSer
2821         TTCAGGACCATCGTGAAGCCTGTGGCCAAAGAGTTTGATCCAGACATGGTCTTAGTATCT

AlaGlyPheAspAlaLeuGluGlyHisThrProProLeuGlyGlyTyrLysValThrAla
2881         GCTGGATTTGATGCATTGGAAGGCCACACCCCTCCTCTAGGAGGGTACAAAGTGACGGCA

LysCysPheGlyHisLeuThrLysGlnLeuMetThrLeuAlaAspGlyArgValValLeu
2941         AAATGTTTTGGTCATTTGACGAAGCAATTGATGACATTGGCTGATGGACGTGTGGTGTTG

AlaLeuGluGlyGlyHisAspLeuThrAlaIleCysAspAlaSerGluAlaCysValAsn
3001         GCTCTAGAAGGAGGACATGATCTCACAGCCATCTGTGATGCATCAGAAGCCTGTGTAAAT

AlaLeuLeuGlyAsnGluLeuGluProLeuAlaGluAspIleLeuHisGlnSerProAsn
3061         GCCCTTCTAGGAAATGAGCTGGAGCCACTTGCAGAAGATATTCTCCACCAAAGCCCGAAT

MetAsnAlaValIleSerLeuGlnLysIleIleGluIleGlnSerMetSerLeuLysPhe
3121         ATGAATGCTGTTATTTCTTTACAGAAGATCATTGAAATTCAAAGTATGTCTTTAAAGTTC

Ser***
3181         TCTTAA
```

FIG. 22D

```
   1  GGGGAAGAGAGGCACAGACACAGATAGGAGAAGGGCACCGGCTGGAGCCACTTGCAGGAC
  61  TGAGGGTTTTTGCAACAAAACCCTAGCAGCCTGAAGAACTCTAAGCCAGATGGGGTGGCT

MetHisSerMetIleSerSerValAspVal
 121  GGACGAGAGCAGCTCTTGGCTCAGCAAAGAATGCACAGTATGATCAGCTCAGTGGATGTG

LysSerGluValProValGlyLeuGluProIleSerProLeuAspLeuArgThrAspLeu
 181  AAGTCAGAAGTTCCTGTGGGCCTGGAGCCCATCTCACCTTTAGACCTAAGGACAGACCTC

ArgMetMetMetProValValAspProValValArgGluLysGlnLeuGlnGlnGluLeu
 241  AGGATGATGATGCCCGTGGTGGACCCTGTTGTCCGTGAGAAGCAATTGCAGCAGGAATTA

LeuLeuIleGlnGlnGlnGlnIleGlnLysGlnLeuLeuIleAlaGluPheGlnLys
 301  CTTCTTATCCAGCAGCAGCAACAAATCCAGAAGCAGCTTCTGATAGCAGAGTTTCAGAAA

GlnHisGluAsnLeuThrArgGlnHisGlnAlaGlnLeuGlnGluHisIleLysGluLeu
 361  CAGCATGAGAACTTGACACGGCAGCACCAGGCTCAGCTTCAGGAGCATATCAAGGAACTT

LeuAlaIleLysGlnGlnGlnGluLeuLeuGluLysGluGlnLysLeuGluGlnGlnArg
 421  CTAGCCATAAAACAGCAACAAGAACTCCTAGAAAAGGAGCAGAAACTGGAGCAGCAGAGG

GlnGluGlnGluValGluArgHisArgArgGluGlnGlnLeuProProLeuArgGlyLys
 481  CAAGAACAGGAAGTAGAGAGGCATCGCAGAGAACAGCAGCTTCCTCCTCTCAGAGGCAAA

AspArgGlyArgGluArgAlaValAlaSerThrGluValLysGlnLysLeuGlnGluPhe
 541  GATAGAGGACGAGAAAGGGCAGTGGCAAGTACAGAAGTAAAGCAGAAGCTTCAAGAGTTC

LeuLeuSerLysSerAlaThrLysAspThrProThrAsnGlyLysAsnHisSerValSer
 601  CTACTGAGTAAATCAGCAACGAAAGACACTCCAACTAATGGAAAAAATCATTCCGTGAGC

ArgHisProLysLeuTrpTyrThrAlaAlaHisHisThrSerLeuAspGlnSerSerPro
 661  CGCCATCCCAAGCTCTGGTACACGGCTGCCCACCACACATCATTGGATCAAAGCTCTCCA

ProLeuSerGlyThrSerProSerTyrLysTyrThrLeuProGlyAlaGlnAspAlaLys
 721  CCCCTTAGTGGAACATCTCCATCCTACAAGTACACATTACCAGGAGCACAAGATGCAAAG

AspAspPheProLeuArgLysThrAlaSerGluProAsnLeuLysValArgSerArgLeu
 781  GATGATTTCCCCCTTCGAAAAACTGCCTCTGAGCCCAACTTGAAGGTGCGGTCCAGGTTA

LysGlnLysValAlaGluArgArgSerSerProLeuLeuArgArgLysAspGlyAsnVal
 841  AAACAGAAAGTGGCAGAGAGGAGAAGCAGCCCCTTACTCAGGCGGAAGGATGGAAATGTT

ValThrSerPheLysLysArgMetPheGluValThrGluSerSerValSerSerSerSer
 901  GTCACTTCATTCAAGAAGCGAATGTTTGAGGTGACAGAATCCTCAGTCAGTAGCAGTTCT

ProGlySerGlyProSerSerProAsnAsnGlyProThrGlySerValThrGluAsnGlu
 961  CCAGGCTCTGGTCCCAGTTCACCAAACAATGGGCCAACTGGAAGTGTTACTGAAAATGAG

ThrSerValLeuProProThrProHisAlaGluGlnMetValSerGlnGlnArgIleLeu
1021  ACTTCGGTTTTGCCCCCTACCCCTCATGCCGAGCAAATGGTTTCACAGCAACGCATTCTA

IleHisGluAspSerMetAsnLeuLeuSerLeuTyrThrSerProSerLeuProAsnIle
1081  ATTCATGAAGATTCCATGAACCTGCTAAGTCTTTATACCTCTCCTTCTTTGCCCAACATT

ThrLeuGlyLeuProAlaValProSerGlnLeuAsnAlaSerAsnSerLeuLysGluLys
1141  ACCTTGGGGCTTCCCGCAGTGCCATCCCAGCTCAATGCTTCGAATTCACTCAAAGAAAAG
```

FIG. 22E

```
     GlnLysCysGluThrGlnThrLeuArgGlnGlyValProLeuProGlyGlnTyrGlyGly
1201 CAGAAGTGTGAGACGCAGACGCTTAGGCAAGGTGTTCCTCTGCCTGGGCAGTATGGAGGC

SerIleProAlaSerSerSerHisProHisValThrLeuGluGlyLysProProAsnSer
1261 AGCATCCCGGCATCTTCCAGCCACCCTCATGTTACTTTAGAGGGAAAGCCACCCAACAGC

SerHisGlnAlaLeuLeuGlnHisLeuLeuLeuLysGluGlnMetArgGlnGlnLysLeu
1321 AGCCACCAGGCTCTCCTGCAGCATTTATTATTGAAAGAACAAATGCGACAGCAAAAGCTT

LeuValAlaGlyGlyValProLeuHisProGlnSerProLeuAlaThrLysGluArgIle
1381 CTTGTAGCTGGTGGAGTTCCCTTACATCCTCAGTCTCCCTTGGCAACAAAAGAGAGAATT

SerProGlyIleArgGlyThrHisLysLeuProArgHisArgProLeuAsnArgThrGln
1441 TCACCTGGCATTAGAGGTACCCACAAATTGCCCCGTCACAGACCCCTGAACCGAACCCAG

SerAlaProLeuProGlnSerThrLeuAlaGlnLeuValIleGlnGlnGlnHisGlnGln
1501 TCTGCACCTTTGCCTCAGAGCACGTTGGCTCAGCTGGTCATTCAACAGCAACACCAGCAA

PheLeuGluLysGlnLysGlnTyrGlnGlnGlnIleHisMetAsnLysLeuLeuSerLys
1561 TTCTTGGAGAAGCAGAAGCAATACCAGCAGCAGATCCACATGAACAAACTGCTTTCGAAA

SerIleGluGlnLeuLysGlnProGlySerHisLeuGluGluAlaGluGluGluLeuGln
1621 TCTATTGAACAACTGAAGCAACCAGGCAGTCACCTTGAGGAAGCAGAGGAAGAGCTTCAG

GlyAspGlnAlaMetGlnGluAspArgAlaProSerSerGlyAsnSerThrArgSerAsp
1681 GGGGACCAGGCGATGCAGGAAGACAGAGCGCCCTCTAGTGGCAACAGCACTAGGAGCGAC

SerSerAlaCysValAspAspThrLeuGlyGlnValGlyAlaValLysValLysGluGlu
1741 AGCAGTGCTTGTGTGGATGACACACTGGGACAAGTTGGGGCTGTGAAGGTCAAGGAGGAA

ProValAspSerAspGluAspAlaGlnIleGlnGluMetGluSerGlyGluGlnAlaAla
1801 CCAGTGGACAGTGATGAAGATGCTCAGATCCAGGAAATGGAATCTGGGGAGCAGGCTGCT

PheMetGlnGlnProPheLeuGluProThrHisThrArgAlaLeuSerValArgGlnAla
1861 TTTATGCAACAGCCTTTCCTGGAACCCACGCACACACGTGCGCTCTCTGTGCGCCAAGCT

ProLeuAlaAlaValGlyMetAspGlyLeuGluLysHisArgLeuValSerArgThrHis
1921 CCGCTGGCTGCGGTTGGCATGGATGGATTAGAGAAACACCGTCTCGTCTCCAGGACTCAC

SerSerProAlaAlaSerValLeuProHisProAlaMetAspArgProLeuGlnProGly
1981 TCTTCCCCTGCTGCCTCTGTTTTACCTCACCCAGCAATGGACCGCCCCCTCCAGCCTGGC

SerAlaThrGlyIleAlaTyrAspProLeuMetLeuLysHisGlnCysValCysGlyAsn
2041 TCTGCAACTGGAATTGCCTATGACCCCTTGATGCTGAAACACCAGTGCGTTTGTGGCAAT

SerThrThrHisProGluHisAlaGlyArgIleGlnSerIleTrpSerArgLeuGlnGlu
2101 TCCACCACCCACCCTGAGCATGCTGGACGAATACAGAGTATCTGGTCACGACTGCAAGAA

ThrGlyLeuLeuAsnLysCysGluArgIleGlnGlyArgLysAlaSerLeuGluGluIle
2161 ACTGGGCTGCTAAATAAATGTGAGCGAATTCAAGGTCGAAAAGCCAGCCTGGAGGAAATA

GlnLeuValHisSerGluHisHisSerLeuLeuTyrGlyThrAsnProLeuAspGlyGln
2221 CAGCTTGTTCATTCTGAACATCACTCACTGTTGTATGGCACCAACCCCCTGGACGGACAG

LysLeuAspProArgIleLeuLeuGlyAspAspSerGlnLysPhePheSerSerLeuPro
2281 AAGCTGGACCCCAGGATACTCCTAGGTGATGACTCTCAAAAGTTTTTTTCCTCATTACCT
```

FIG. 22F

```
        CysGlyGlyLeuGlyValAspSerAspThrIleTrpAsnGluLeuHisSerSerGlyAla
2341    TGTGGTGGACTTGGGGTGGACAGTGACACCATTTGGAATGAGCTACACTCGTCCGGTGCT

AlaArgMetAlaValGlyCysValIleGluLeuAlaSerLysValAlaSerGlyGluLeu
2401    GCACGCATGGCTGTTGGCTGTGTCATCGAGCTGGCTTCCAAAGTGGCCTCAGGAGAGCTG

LysAsnGlyPheAlaValValArgProProGlyHisHisAlaGluGluSerThrAlaMet
2461    AAGAATGGGTTTGCTGTTGTGAGGCCCCCTGGCCATCACGCTGAAGAATCCACAGCCATG

GlyPheCysPhePheAsnSerValAlaIleThrAlaLysTyrLeuArgAspGlnLeuAsn
2521    GGGTTCTGCTTTTTTAATTCAGTTGCAATTACCGCCAAATACTTGAGAGACCAACTAAAT

IleSerLysIleLeuIleValAspLeuAspValHisHisGlyAsnGlyThrGlnGlnAla
2581    ATAAGCAAGATATTGATTGTAGATCTGGATGTTCACCATGGAAACGGTACCCAGCAGGCC

PheTyrAlaAspProSerIleLeuTyrIleSerLeuHisArgTyrAspGluGlyAsnPhe
2641    TTTTATGCTGACCCCAGCATCCTGTACATTTCACTCCATCGCTATGATGAAGGGAACTTT

PheProGlySerGlyAlaProAsnGluValArgPheIleSerLeuGluProHisPheTyr
2701    TTCCCTGGCAGTGGAGCCCCAAATGAGGTTCGGTTTATTTCTTTAGAGCCCCACTTTTAT

LeuTyrLeuSerGlyAsnCysIleAla***
2761    TTGTATCTTTCAGGTAATTGCATTGCATGA
```

FIG. 22G

```
   1  GGGGAAGAGAGGCACAGACACAGATAGGAGAAGGGCACCGGCTGGAGCCACTTGCAGGAC
  61  TGAGGGTTTTTGCAACAAAACCCTAGCAGCCTGAAGAACTCTAAGCCAGATGGGGTGGCT

MetHisSerMetIleSerSerValAspVal
 121  GGACGAGAGCAGCTCTTGGCTCAGCAAAGAATGCACAGTATGATCAGCTCAGTGGATGTG

LysSerGluValProValGlyLeuGluProIleSerProLeuAspLeuArgThrAspLeu
 181  AAGTCAGAAGTTCCTGTGGGCCTGGAGCCCATCTCACCTTTAGACCTAAGGACAGACCTC

ArgMetMetMetProValValAspProValValArgGluLysGlnLeuGlnGlnGluLeu
 241  AGGATGATGATGCCCGTGGTGGACCCTGTTGTCCGTGAGAAGCAATTGCAGCAGGAATTA

LeuLeuIleGlnGlnGlnGlnIleGlnLysGlnLeuLeuIleAlaGluPheGlnLys
 301  CTTCTTATCCAGCAGCAGCAACAAATCCAGAAGCAGCTTCTGATAGCAGAGTTTCAGAAA

GlnHisGluAsnLeuThrArgGlnHisGlnAlaGlnLeuGlnGluHisIleLysGluLeu
 361  CAGCATGAGAACTTGACACGGCAGCACCAGGCTCAGCTTCAGGAGCATATCAAGGAACTT

LeuAlaIleLysGlnGlnGlnGluLeuLeuGluLysGluGlnLysLeuGluGlnGlnArg
 421  CTAGCCATAAAACAGCAACAAGAACTCCTAGAAAAGGAGCAGAAACTGGAGCAGCAGAGG

GlnGluGlnGluValGluArgHisArgArgGluGlnGlnLeuProProLeuArgGlyLys
 481  CAAGAACAGGAAGTAGAGAGGCATCGCAGAGAACAGCAGCTTCCTCCTCTCAGAGGCAAA

AspArgGlyArgGluArgAlaValAlaSerThrGluValLysGlnLysLeuGlnGluPhe
 541  GATAGAGGACGAGAAAGGGCAGTGGCAAGTACAGAAGTAAAGCAGAAGCTTCAAGAGTTC

LeuLeuSerLysSerAlaThrLysAspThrProThrAsnGlyLysAsnHisSerValSer
 601  CTACTGAGTAAATCAGCAACGAAAGACACTCCAACTAATGGAAAAAATCATTCCGTGAGC

ArgHisProLysLeuTrpTyrThrAlaAlaHisHisThrSerLeuAspGlnSerSerPro
 661  CGCCATCCCAAGCTCTGGTACACGGCTGCCCACCACACATCATTGGATCAAAGCTCTCCA

ProLeuSerGlyThrSerProSerTyrLysTyrThrLeuProGlyAlaGlnAspAlaLys
 721  CCCCTTAGTGGAACATCTCCATCCTACAAGTACACATTACCAGGAGCACAAGATGCAAAG

AspAspPheProLeuArgLysThrAlaSerGluProAsnLeuLysValArgSerArgLeu
 781  GATGATTTCCCCCTTCGAAAAACTGCCTCTGAGCCCAACTTGAAGGTGCGGTCCAGGTTA

LysGlnLysValAlaGluArgArgSerSerProLeuLeuArgArgLysAspGlyAsnVal
 841  AAACAGAAAGTGGCAGAGAGGAGAAGCAGCCCCTTACTCAGGCGGAAGGATGGAAATGTT

ValThrSerPheLysLysArgMetPheGluValThrGluSerSerValSerSerSerSer
 901  GTCACTTCATTCAAGAAGCGAATGTTTGAGGTGACAGAATCCTCAGTCAGTAGCAGTTCT

ProGlySerGlyProSerSerProAsnAsnGlyProThrGlySerValThrGluAsnGlu
 961  CCAGGCTCTGGTCCCAGTTCACCAAACAATGGGCCAACTGGAAGTGTTACTGAAAATGAG

ThrSerValLeuProProThrProHisAlaGluGlnMetValSerGlnGlnArgIleLeu
1021  ACTTCGGTTTTGCCCCCTACCCCTCATGCCGAGCAAATGGTTTCACAGCAACGCATTCTA

IleHisGluAspSerMetAsnLeuLeuSerLeuTyrThrSerProSerLeuProAsnIle
1081  ATTCATGAAGATTCCATGAACCTGCTAAGTCTTTATACCTCTCCTTCTTTGCCCAACATT

ThrLeuGlyLeuProAlaValProSerGlnLeuAsnAlaSerAsnSerLeuLysGluLys
1141  ACCTTGGGGCTTCCCGCAGTGCCATCCCAGCTCAATGCTTCGAATTCACTCAAAGAAAAG
```

FIG. 22H

```
         GlnLysCysGluThrGlnThrLeuArgGlnGlyValProLeuProGlyGlnTyrGlyGly
1201     CAGAAGTGTGAGACGCAGACGCTTAGGCAAGGTGTTCCTCTGCCTGGGCAGTATGGAGGC

SerIleProAlaSerSerSerHisProHisValThrLeuGluGlyLysProProAsnSer
1261     AGCATCCCGGCATCTTCCAGCCACCCTCATGTTACTTTAGAGGGAAAGCCACCCAACAGC

SerHisGlnAlaLeuLeuGlnHisLeuLeuLeuLysGluGlnMetArgGlnGlnLysLeu
1321     AGCCACCAGGCTCTCCTGCAGCATTTATTATTGAAAGAACAAATGCGACAGCAAAAGCTT

LeuValAlaGlyGlyValProLeuHisProGlnSerProLeuAlaThrLysGluArgIle
1381     CTTGTAGCTGGTGGAGTTCCCTTACATCCTCAGTCTCCCTTGGCAACAAAAGAGAGAATT

SerProGlyIleArgGlyThrHisLysLeuProArgHisArgProLeuAsnArgThrGln
1441     TCACCTGGCATTAGAGGTACCCACAAATTGCCCCGTCACAGACCCCTGAACCGAACCCAG

SerAlaProLeuProGlnSerThrLeuAlaGlnLeuValIleGlnGlnGlnHisGlnGln
1501     TCTGCACCTTTGCCTCAGAGCACGTTGGCTCAGCTGGTCATTCAACAGCAACACCAGCAA

PheLeuGluLysGlnLysGlnTyrGlnGlnGlnIleHisMetAsnLysLeuLeuSerLys
1561     TTCTTGGAGAAGCAGAAGCAATACCAGCAGCAGATCCACATGAACAAACTGCTTTCGAAA

SerIleGluGlnLeuLysGlnProGlySerHisLeuGluGluAlaGluGluGluLeuGln
1621     TCTATTGAACAACTGAAGCAACCAGGCAGTCACCTTGAGGAAGCAGAGGAAGAGCTTCAG

GlyAspGlnAlaMetGlnGluAspArgAlaProSerSerGlyAsnSerThrArgSerAsp
1681     GGGGACCAGGCGATGCAGGAAGACAGAGCGCCCTCTAGTGGCAACAGCACTAGGAGCGAC

SerSerAlaCysValAspAspThrLeuGlyGlnValGlyAlaValLysValLysGluGlu
1741     AGCAGTGCTTGTGTGGATGACACACTGGGACAAGTTGGGGCTGTGAAGGTCAAGGAGGAA

ProValAspSerAspGluAspAlaGlnIleGlnGluMetGluSerGlyGluGlnAlaAla
1801     CCAGTGGACAGTGATGAAGATGCTCAGATCCAGGAAATGGAATCTGGGGAGCAGGCTGCT

PheMetGlnGlnValIleGlyLysAspLeuAlaProGlyPheValIleLysValIleIle
1861     TTTATGCAACAGGTAATAGGCAAAGATTTAGCTCCAGGATTTGTAATTAAAGTCATTATC

***
1921     TGAACATGAAATGCATTGCAGGTTTGGTAAATGGATATGATTTCCTATCAGTTTATATTT
1981     CTCTATGATTTGAGTTCAGTGTTTAAGGATTCTACCTAATGCAGATATATGTATATATCT
2041     ATATAGAGGTCTTTCTATATACTGATCTCTATATAGATATCAATGTTTCATTGAAAATCC
2101     ACTGGTAAGGAAATACCTGTTATACTAAAATTATGATACATAATATCTGAGCAGTTAATA
2161     GGCTTTAAATTTATCCCAAAGCCTGCTACACCAATTACTTCTAAAGAAAACAAATTCACT
2221     GTTATTTTGAGTTTATGTGTTGAGATCAGTGACTGCTGGATAGTCTCCCAGTCTGATCAA
2281     TGAAGCATTCGATTAGTTTTTGATTTTTTGCAACATCTAGAATTTAATTTTCACATCACT
2341     GTACATAATGTATCATACTATAGTCTTGAACACTGTTAAAGGTAGTCTGCCCCTTCCTTC
2401     CTCTCTCTTTTTTTAGTTAAGTAGAAATGTTCTGGTCACCATGCCAGTAGTCCTAGGTTA
2461     TTGTGTAGGTTGCAATTGAACATATTAGGAATACAGGTGGTTTTAAATATATAGATGCAA
2521     ATTGCAGCACTACTTTAAATATTAGATTATGTCTCACATAGCACTGCTCATTTTACTTTT
2581     ATTTTGTGTAATTTGATGACACTGTCTATCAAAAAGAGCAAATGAAGCAGATGCAAATG
2641     TTAGTGAGAAGTAATGTGCAGCATTATGGTCCAATCAGATACAATATTGTGTCTACAATT
2701     GCAAAAAACACAGTAACAGGATGAATATTATCTGATATCAAGTCAAAATCAGTTTGAAAA
2761     GAAGGTGTATCATATTTTATATTGTCACTAGAATCTCTTAAGTATAATTCCATAATGACA
2821     TGGGCATATACCGTAACATTCTGGCAAATAACAATTAGAAAAGATAGGTTTAACAAAAAA
2881     ATTTACTTGTATATAATGCACCTTCAGGAGGACTATGTCCTTTGATGCTATAAAATACAA
2941     ACAACTTTGAAGGCAACAGAAGACACTGTTTATTCAAGTCAGTTCTTTGTCAGGTTCCTG
3001     CTGTTCTCCTACAGAAAAGTGATTCTGTGAGGGTGAACAGGAAATGCCTTGTGGAAACAG
3061     GAAGTCCAAGTGATTCATGTACTGAGGAATGTAGGAAAAAAAATCTGAGGATAGTGCTTT
```

FIG. 22I

```
3121  ACTCTTTCTGTTTTTAAAGGGCACTCTATGAATTGATTTATTGTCTAAGAAAATAACACC
3181  ACAAGTAGGGAAATTGTTACGGAAGCTTTTCACTGGAACATTTCCTTCATATTCCCTTTT
3241  GATATGTTTACCTTGTTTTATAGGTTTACTTTTGTTAAGCTAGTTAAAGGTTCGTTGTAT
3301  TAAGACCCCTTTAATATGGATAATCCAAATTGACCTAGAATCTTTGTGAGGTTTTTTCTA
3361  TTAAAATATTTATATTTCTAAATCCGAGGTATTTCAAGGTGTAGTATCCTATTTCAAAGG
3421  AGATATAGCAGTTTTGCCAAATGTAGACATTGTTCAACTGTATGTTATTGGCACGTGTTG
3481  TTTACATTTTGCTGTGACATTTAAAAATATTTCTTTAAAAATGTTACTGCTAAAGATACA
3541  TTATCCTTTTTAAAAAGTCTCCATTCAAATTAAATTAACATAACTAGAAGTTAGAAAGT
3601  TTAAAAGTTTTCCACATAATGAAAGTCCTTCTGATAATTTGACAAATAGCTATAATAGGA
3661  ACACTCCCTATCACCAACATATTTTGGTTAGTATATTCCTTCATATTAAAATGACTTTTT
3721  GTCAGTTGTTTTGCATTAAAAATATGGCATGCCTAAGATAAAATTGTATATTTTTTCCAT
3781  CTCATAAATATTCATTTTCTTCAAAGTCTTTTTTCAATCTCATAAAAAAGGGATAGTGCA
3841  TCTTTTAAAATACATTTTATTTGGGGAGGAACATGTGGCTGAGCAGACTTTTGTATAATA
3901  TTACTTCAAAGATATGTAATCACAAACAAAAAAAACTATTTTTATAATGTCATTTGAGA
3961  GAGTTTCATCAGTACAGTTGGTGGACGTTAATTGTTTGAATTTGATAGTCTTTGAATTTA
4021  ATCAAGAAACTACCTGGAACCAGTGAAAGGAAAGCTGGACTTAAATAATCTTAGAATTA
4081  ATTGATAAATGTCTCTTTTAAAATCTACTGTATTTATTATAATTTACACCCTTGAAGGTG
4141  ATCTCTTGTTTTGTGTTGTAAATATATTGTTTGTATGTTTCCCTTCTTGCCTTCTGTTAT
4201  AAGTCTCTTCCTTTCTCAAATAAAGTTTTTTTTAAAAG
```

FIG. 23A

```
                        1                                                50
BMY_HDACX_V1    (1)     --------------------------------------------------
BMY_HDACX_V2    (1)     CCACGCGTCCGTAGGAGAAGGGCACCGGCTGGAGCCACTTGCAGGACTGA
HDAC9V1         (1)     --------------------------------------------------
HDAC9V2         (1)     --------------------------------------------------
HDAC9V3         (1)     --------------------------------------------------
CONSENSUS       (1)
                        51                                               100
BMY_HDACX_V1    (1)     --------------------------------------------------
BMY_HDACX_V2    (51)    GGGTTTTTGCAACAAAACCCTAGCAGCCTGAAGAACTCTAAGCCAGGTTT
HDAC9V1         (1)     --------------------------------------------------
HDAC9V2         (1)     --------------------------------------------------
HDAC9V3         (1)     --------------------------------------------------
CONSENSUS       (51)
                        101                                              150
BMY_HDACX_V1    (1)     --------------------------------------------------
BMY_HDACX_V2    (101)   AATTGGTTTCTTTTTCTCGTGGGTAGACTTAATAATTTTCTACGTATTCT
HDAC9V1         (1)     --------------------------------------------------
HDAC9V2         (1)     --------------------------------------------------
HDAC9V3         (1)     --------------------------------------------------
CONSENSUS       (101)
                        151                                              200
BMY_HDACX_V1    (1)     --------------------------------------------------
BMY_HDACX_V2    (151)   GACAAAGAAATAACCCCGAAGCACGTTCCTATTTCCCACCTGCTTGTAGT
HDAC9V1         (1)     ------GGGGAAGAGAGGCACAGACACAGATAGGAGAAGGGCACCGGCTG
HDAC9V2         (1)     ------GGGGAAGAGAGGCACAGACACAGATAGGAGAAGGGCACCGGCTG
HDAC9V3         (1)     ------GGGGAAGAGAGGCACAGACACAGATAGGAGAAGGGCACCGGCTG
CONSENSUS       (151)         GGGGAAGAGAGGCACAGACACAGATAGGAGAAGGGCACCGGCTG
                        201                                              250
BMY_HDACX_V1    (1)     --------------------------------------------------
BMY_HDACX_V2    (201)   TTCGGGATAACCTAAACTCCAGAGAGCTATAGCATCCACTCTGTCCTTT
HDAC9V1         (45)    GAGCCACTTGCAGGACTGAGGGTTTTTGCAACAAAACCCTAGCAGCCTGA
HDAC9V2         (45)    GAGCCACTTGCAGGACTGAGGGTTTTTGCAACAAAACCCTAGCAGCCTGA
HDAC9V3         (45)    GAGCCACTTGCAGGACTGAGGGTTTTTGCAACAAAACCCTAGCAGCCTGA
CONSENSUS       (201)   GAGCCACTTGCAGGACTGAGGGTTTTTGCAACAAAACCCTAGCAGCCTGA
                        251                                              300
BMY_HDACX_V1    (1)     --------------------------------------------------
BMY_HDACX_V2    (251)   CTGCTTTGCACACAGATGGGTGGCTGGACGAGAGCAGCTCTTGGCTCAG
HDAC9V1         (95)    AGAACTCTAAGCCAGATGGGTGGCTGGACGAGAGCAGCTCTTGGCTCAG
HDAC9V2         (95)    AGAACTCTAAGCCAGATGGGTGGCTGGACGAGAGCAGCTCTTGGCTCAG
HDAC9V3         (95)    AGAACTCTAAGCCAGATGGGTGGCTGGACGAGAGCAGCTCTTGGCTCAG
CONSENSUS       (251)   AGAACTCTAAGCCAGATGGGTGGCTGGACGAGAGCAGCTCTTGGCTCAG
                                        * SPLICE JUNCTION: CAG>>>ATG
                        301                                              350
BMY_HDACX_V1    (1)     --------------------------------------------------
BMY_HDACX_V2    (301)   CAAAGAATGCACAGTATGATCAGCTCAGTGGATGTGAAGTCAGAAGTTCC
HDAC9V1         (145)   CAAAGAATGCACAGTATGATCAGCTCAGTGGATGTGAAGTCAGAAGTTCC
HDAC9V2         (145)   CAAAGAATGCACAGTATGATCAGCTCAGTGGATGTGAAGTCAGAAGTTCC
HDAC9V3         (145)   CAAAGAATGCACAGTATGATCAGCTCAGTGGATGTGAAGTCAGAAGTTCC
CONSENSUS       (301)   CAAAGAATGCACAGTATGATCAGCTCAGTGGATGTGAAGTCAGAAGTTCC
                        351                                              400
BMY_HDACX_V1    (1)     --------------------------------------------------
BMY_HDACX_V2    (351)   TGTGGGCCTGGAGCCCATCTCACCTTTAGACCTAAGGACAGACCTCAGGA
HDAC9V1         (195)   TGTGGGCCTGGAGCCCATCTCACCTTTAGACCTAAGGACAGACCTCAGGA
HDAC9V2         (195)   TGTGGGCCTGGAGCCCATCTCACCTTTAGACCTAAGGACAGACCTCAGGA
HDAC9V3         (195)   TGTGGGCCTGGAGCCCATCTCACCTTTAGACCTAAGGACAGACCTCAGGA
CONSENSUS       (351)   TGTGGGCCTGGAGCCCATCTCACCTTTAGACCTAAGGACAGACCTCAGGA
```

FIG. 23B

```
                         401                                              450
BMY_HDACX_V1      (1)    --------------------------------------------------
BMY_HDACX_V2    (401)    TGATGATGCCCGTGGTGGACCCTGTTGTCCGTGAGAAGCAATTGCAGCAG
    HDAC9V1     (245)    TGATGATGCCCGTGGTGGACCCTGTTGTCCGTGAGAAGCAATTGCAGCAG
    HDAC9V2     (245)    TGATGATGCCCGTGGTGGACCCTGTTGTCCGTGAGAAGCAATTGCAGCAG
    HDAC9V3     (245)    TGATGATGCCCGTGGTGGACCCTGTTGTCCGTGAGAAGCAATTGCAGCAG
  CONSENSUS     (401)    TGATGATGCCCGTGGTGGACCCTGTTGTCCGTGAGAAGCAATTGCAGCAG
                         451                                              500
BMY_HDACX_V1      (1)    --------------------------------------------------
BMY_HDACX_V2    (451)    GAATTACTTCTTATCCAGCAGCAGCAACAAATCCAGAAGCAGCTTCTGAT
    HDAC9V1     (295)    GAATTACTTCTTATCCAGCAGCAGCAACAAATCCAGAAGCAGCTTCTGAT
    HDAC9V2     (295)    GAATTACTTCTTATCCAGCAGCAGCAACAAATCCAGAAGCAGCTTCTGAT
    HDAC9V3     (295)    GAATTACTTCTTATCCAGCAGCAGCAACAAATCCAGAAGCAGCTTCTGAT
  CONSENSUS     (451)    GAATTACTTCTTATCCAGCAGCAGCAACAAATCCAGAAGCAGCTTCTGAT
                         501                                              550
BMY_HDACX_V1      (1)    --------------------------------------------------
BMY_HDACX_V2    (501)    AGCAGAGTTTCAGAAACAGCATGAGAACTTGACACGGCAGCACCAGGCTC
    HDAC9V1     (345)    AGCAGAGTTTCAGAAACAGCATGAGAACTTGACACGGCAGCACCAGGCTC
    HDAC9V2     (345)    AGCAGAGTTTCAGAAACAGCATGAGAACTTGACACGGCAGCACCAGGCTC
    HDAC9V3     (345)    AGCAGAGTTTCAGAAACAGCATGAGAACTTGACACGGCAGCACCAGGCTC
  CONSENSUS     (501)    AGCAGAGTTTCAGAAACAGCATGAGAACTTGACACGGCAGCACCAGGCTC
                         551                                              600
BMY_HDACX_V1      (1)    --------------------------------------------------
BMY_HDACX_V2    (551)    AGCTTCAGGAGCATATCAAGTTGCAACAGGAACTTCTAGCCATAAAACAG
    HDAC9V1     (395)    AGCTTCAGGAGCATATCAAG--------GAACTTCTAGCCATAAAACAG
    HDAC9V2     (395)    AGCTTCAGGAGCATATCAAG--------GAACTTCTAGCCATAAAACAG
    HDAC9V3     (395)    AGCTTCAGGAGCATATCAAG--------GAACTTCTAGCCATAAAACAG
  CONSENSUS     (551)    AGCTTCAGGAGCATATCAAG        GAACTTCTAGCCATAAAACAG
                                             *SPLICE ACCEPTOR 1
                                                 *SPLICE ACCEPTOR 2
                         601                                              650
BMY_HDACX_V1      (1)    --------------------------------------------------
BMY_HDACX_V2    (601)    CAACAAGAACTCCTAGAAAAGGAGCAGAAACTGGAGCAGCAGAGGCAAGA
    HDAC9V1     (436)    CAACAAGAACTCCTAGAAAAGGAGCAGAAACTGGAGCAGCAGAGGCAAGA
    HDAC9V2     (436)    CAACAAGAACTCCTAGAAAAGGAGCAGAAACTGGAGCAGCAGAGGCAAGA
    HDAC9V3     (436)    CAACAAGAACTCCTAGAAAAGGAGCAGAAACTGGAGCAGCAGAGGCAAGA
  CONSENSUS     (601)    CAACAAGAACTCCTAGAAAAGGAGCAGAAACTGGAGCAGCAGAGGCAAGA
                         651                                              700
BMY_HDACX_V1      (1)    --------------------------------------------------
BMY_HDACX_V2    (651)    ACAGGAAGTAGAGAGGCATCGCAGAGAACAGCAGCTTCCTCCTCTCAGAG
    HDAC9V1     (486)    ACAGGAAGTAGAGAGGCATCGCAGAGAACAGCAGCTTCCTCCTCTCAGAG
    HDAC9V2     (486)    ACAGGAAGTAGAGAGGCATCGCAGAGAACAGCAGCTTCCTCCTCTCAGAG
    HDAC9V3     (486)    ACAGGAAGTAGAGAGGCATCGCAGAGAACAGCAGCTTCCTCCTCTCAGAG
  CONSENSUS     (651)    ACAGGAAGTAGAGAGGCATCGCAGAGAACAGCAGCTTCCTCCTCTCAGAG
                         701                                              750
BMY_HDACX_V1      (1)    --------------------------------------------------
BMY_HDACX_V2    (701)    GCAAAGATAGAGGACGAGAAAGGGCAGTGGCAAGTACAGAAGTAAAGCAG
    HDAC9V1     (536)    GCAAAGATAGAGGACGAGAAAGGGCAGTGGCAAGTACAGAAGTAAAGCAG
    HDAC9V2     (536)    GCAAAGATAGAGGACGAGAAAGGGCAGTGGCAAGTACAGAAGTAAAGCAG
    HDAC9V3     (536)    GCAAAGATAGAGGACGAGAAAGGGCAGTGGCAAGTACAGAAGTAAAGCAG
  CONSENSUS     (701)    GCAAAGATAGAGGACGAGAAAGGGCAGTGGCAAGTACAGAAGTAAAGCAG
                         751                                              800
BMY_HDACX_V1      (1)    --------------------------------------------------
BMY_HDACX_V2    (751)    AAGCTTCAAGAGTTCCTACTGAGTAAATCAGCAACGAAAGACACTCCAAC
    HDAC9V1     (586)    AAGCTTCAAGAGTTCCTACTGAGTAAATCAGCAACGAAAGACACTCCAAC
    HDAC9V2     (586)    AAGCTTCAAGAGTTCCTACTGAGTAAATCAGCAACGAAAGACACTCCAAC
    HDAC9V3     (586)    AAGCTTCAAGAGTTCCTACTGAGTAAATCAGCAACGAAAGACACTCCAAC
  CONSENSUS     (751)    AAGCTTCAAGAGTTCCTACTGAGTAAATCAGCAACGAAAGACACTCCAAC
                         801                                              850
BMY_HDACX_V1      (1)    --------------------------------------------------
BMY_HDACX_V2    (801)    TAATGGAAAAAATCATTCCGTGAGCCGCCATCCCAAGCTCTGGTACACGG
    HDAC9V1     (636)    TAATGGAAAAAATCATTCCGTGAGCCGCCATCCCAAGCTCTGGTACACGG
    HDAC9V2     (636)    TAATGGAAAAAATCATTCCGTGAGCCGCCATCCCAAGCTCTGGTACACGG
    HDAC9V3     (636)    TAATGGAAAAAATCATTCCGTGAGCCGCCATCCCAAGCTCTGGTACACGG
  CONSENSUS     (801)    TAATGGAAAAAATCATTCCGTGAGCCGCCATCCCAAGCTCTGGTACACGG
```

FIG. 23C

```
                        851                                            900
BMY_HDACX_V1     (1)   --------------------------------------------------
BMY_HDACX_V2   (851)   CTGCCCACCACACATCATTGGATCAAAGCTCTCCACCCCTTAGTGGAACA
HDAC9V1        (686)   CTGCCCACCACACATCATTGGATCAAAGCTCTCCACCCCTTAGTGGAACA
HDAC9V2        (686)   CTGCCCACCACACATCATTGGATCAAAGCTCTCCACCCCTTAGTGGAACA
HDAC9V3        (686)   CTGCCCACCACACATCATTGGATCAAAGCTCTCCACCCCTTAGTGGAACA
CONSENSUS      (851)   CTGCCCACCACACATCATTGGATCAAAGCTCTCCACCCCTTAGTGGAACA
                        901                                            950
BMY_HDACX_V1     (1)   --------------------------------------------------
BMY_HDACX_V2   (901)   TCTCCATCCTACAAGTACACATTACCAGGAGCACAAGATGCAAAGGATGA
HDAC9V1        (736)   TCTCCATCCTACAAGTACACATTACCAGGAGCACAAGATGCAAAGGATGA
HDAC9V2        (736)   TCTCCATCCTACAAGTACACATTACCAGGAGCACAAGATGCAAAGGATGA
HDAC9V3        (736)   TCTCCATCCTACAAGTACACATTACCAGGAGCACAAGATGCAAAGGATGA
CONSENSUS      (901)   TCTCCATCCTACAAGTACACATTACCAGGAGCACAAGATGCAAAGGATGA
                        951                                           1000
BMY_HDACX_V1     (1)   --------------------------------------------------
BMY_HDACX_V2   (951)   TTTCCGCGTTCGAAAAACTGCCTCTGAGCCCAACTTGAAGGTGCGGTCCA
HDAC9V1        (786)   TTTCCCCCTTCGAAAAACTGCCTCTGAGCCCAACTTGAAGGTGCGGTCCA
HDAC9V2        (786)   TTTCCCCCTTCGAAAAACTGCCTCTGAGCCCAACTTGAAGGTGCGGTCCA
HDAC9V3        (786)   TTTCCCCCTTCGAAAAACTGCCTCTGAGCCCAACTTGAAGGTGCGGTCCA
CONSENSUS      (951)   TTTCCCCCTTCGAAAAACTGCCTCTGAGCCCAACTTGAAGGTGCGGTCCA
                       1001                                           1050
BMY_HDACX_V1     (1)   --------------------------------------------------
BMY_HDACX_V2  (1001)   GGTTAAAACAGAAAGTGGCAGAGAGGAGAAGCAGCCCCTTACTCAGGCGG
HDAC9V1        (836)   GGTTAAAACAGAAAGTGGCAGAGAGGAGAAGCAGCCCCTTACTCAGGCGG
HDAC9V2        (836)   GGTTAAAACAGAAAGTGGCAGAGAGGAGAAGCAGCCCCTTACTCAGGCGG
HDAC9V3        (836)   GGTTAAAACAGAAAGTGGCAGAGAGGAGAAGCAGCCCCTTACTCAGGCGG
CONSENSUS     (1001)   GGTTAAAACAGAAAGTGGCAGAGAGGAGAAGCAGCCCCTTACTCAGGCGG
                       1051                                           1100
BMY_HDACX_V1     (1)   --------------------------------------------------
BMY_HDACX_V2  (1051)   AAGGATGGAAATGTTGTCACTTCATTCAAGAAGCGAATGTTTGAGGTGAC
HDAC9V1        (886)   AAGGATGGAAATGTTGTCACTTCATTCAAGAAGCGAATGTTTGAGGTGAC
HDAC9V2        (886)   AAGGATGGAAATGTTGTCACTTCATTCAAGAAGCGAATGTTTGAGGTGAC
HDAC9V3        (886)   AAGGATGGAAATGTTGTCACTTCATTCAAGAAGCGAATGTTTGAGGTGAC
CONSENSUS     (1051)   AAGGATGGAAATGTTGTCACTTCATTCAAGAAGCGAATGTTTGAGGTGAC
                       1101                                           1150
BMY_HDACX_V1     (1)   --------------------------------------------------
BMY_HDACX_V2  (1101)   AGAATCCTCAGTCAGTAGCAGTTCTCCAGGCTCTGGTCCCAGTTCACCAA
HDAC9V1        (936)   AGAATCCTCAGTCAGTAGCAGTTCTCCAGGCTCTGGTCCCAGTTCACCAA
HDAC9V2        (936)   AGAATCCTCAGTCAGTAGCAGTTCTCCAGGCTCTGGTCCCAGTTCACCAA
HDAC9V3        (936)   AGAATCCTCAGTCAGTAGCAGTTCTCCAGGCTCTGGTCCCAGTTCACCAA
CONSENSUS     (1101)   AGAATCCTCAGTCAGTAGCAGTTCTCCAGGCTCTGGTCCCAGTTCACCAA
                       1151                                           1200
BMY_HDACX_V1     (1)   ----------------------GCTGAAAATGAGACTTCGGTTTTGCCC
BMY_HDACX_V2  (1151)   ACAATGGGCCAACTGGAAGTGTTACTGAAAATGAGACTTCGGTTTTGCCC
HDAC9V1        (986)   ACAATGGGCCAACTGGAAGTGTTACTGAAAATGAGACTTCGGTTTTGCCC
HDAC9V2        (986)   ACAATGGGCCAACTGGAAGTGTTACTGAAAATGAGACTTCGGTTTTGCCC
HDAC9V3        (986)   ACAATGGGCCAACTGGAAGTGTTACTGAAAATGAGACTTCGGTTTTGCCC
CONSENSUS     (1151)   ACAATGGGCCAACTGGAAGTGTTACTGAAAATGAGACTTCGGTTTTGCCC
                       1201                                           1250
BMY_HDACX_V1    (28)   CCTACCCCTCATGCCGAGCAAATGGTTTCACAGCAACGCATTCTAATTCA
BMY_HDACX_V2  (1201)   CCTACCCCTCATGCCGAGCAAATGGTTTCACAGCAACGCATTCTAATTCA
HDAC9V1       (1036)   CCTACCCCTCATGCCGAGCAAATGGTTTCACAGCAACGCATTCTAATTCA
HDAC9V2       (1036)   CCTACCCCTCATGCCGAGCAAATGGTTTCACAGCAACGCATTCTAATTCA
HDAC9V3       (1036)   CCTACCCCTCATGCCGAGCAAATGGTTTCACAGCAACGCATTCTAATTCA
CONSENSUS     (1201)   CCTACCCCTCATGCCGAGCAAATGGTTTCACAGCAACGCATTCTAATTCA
                       1251                                           1300
BMY_HDACX_V1    (78)   TGAAGATTCCATGAACCTGCTAAGTCTTTATACCTCTCCTTCTTTGCCCA
BMY_HDACX_V2  (1251)   TGAAGATTCCATGAACCTGCTAAGTCTTTATACCTCTCCTTCTTTGCCCA
HDAC9V1       (1086)   TGAAGATTCCATGAACCTGCTAAGTCTTTATACCTCTCCTTCTTTGCCCA
HDAC9V2       (1086)   TGAAGATTCCATGAACCTGCTAAGTCTTTATACCTCTCCTTCTTTGCCCA
HDAC9V3       (1086)   TGAAGATTCCATGAACCTGCTAAGTCTTTATACCTCTCCTTCTTTGCCCA
CONSENSUS     (1251)   TGAAGATTCCATGAACCTGCTAAGTCTTTATACCTCTCCTTCTTTGCCCA
```

FIG. 23D

```
                         1301                                              1350
BMY_HDACX_V1    (128)  ACATTACCTTGGGGCTTCCCGCAGTGCCATCCCAGCTCAATGCTTCGAAT
BMY_HDACX_V2   (1301)  ACATTACCTTGGGGCTTCCCGCAGTGCCATCCCAGCTCAATGCTTCGAAT
HDAC9V1        (1136)  ACATTACCTTGGGGCTTCCCGCAGTGCCATCCCAGCTCAATGCTTCGAAT
HDAC9V2        (1136)  ACATTACCTTGGGGCTTCCCGCAGTGCCATCCCAGCTCAATGCTTCGAAT
HDAC9V3        (1136)  ACATTACCTTGGGGCTTCCCGCAGTGCCATCCCAGCTCAATGCTTCGAAT
CONSENSUS      (1301)  ACATTACCTTGGGGCTTCCCGCAGTGCCATCCCAGCTCAATGCTTCGAAT
                         1351                                             1400
BMY_HDACX_V1    (178)  TCACTCAAAGAAAAGCAGAAGTGTGAGACGCAGACGCTTAGGCAAGGTGT
BMY_HDACX_V2   (1351)  TCACTCAAAGAAAAGCAGAAGTGTGAGACGCAGACGCTTAGGCAAGGTGT
HDAC9V1        (1186)  TCACTCAAAGAAAAGCAGAAGTGTGAGACGCAGACGCTTAGGCAAGGTGT
HDAC9V2        (1186)  TCACTCAAAGAAAAGCAGAAGTGTGAGACGCAGACGCTTAGGCAAGGTGT
HDAC9V3        (1186)  TCACTCAAAGAAAAGCAGAAGTGTGAGACGCAGACGCTTAGGCAAGGTGT
CONSENSUS      (1351)  TCACTCAAAGAAAAGCAGAAGTGTGAGACGCAGACGCTTAGGCAAGGTGT
                         1401                                             1450
BMY_HDACX_V1    (228)  TCCTCTGCCTGGGCAGTATGGAGGCAGCATCCCGGCATCTTCCAGCCACC
BMY_HDACX_V2   (1401)  TCCTCTGCCTGGGCAGTATGGAGGCAGCATCCCGGCATCTTCCAGCCACC
HDAC9V1        (1236)  TCCTCTGCCTGGGCAGTATGGAGGCAGCATCCCGGCATCTTCCAGCCACC
HDAC9V2        (1236)  TCCTCTGCCTGGGCAGTATGGAGGCAGCATCCCGGCATCTTCCAGCCACC
HDAC9V3        (1236)  TCCTCTGCCTGGGCAGTATGGAGGCAGCATCCCGGCATCTTCCAGCCACC
CONSENSUS      (1401)  TCCTCTGCCTGGGCAGTATGGAGGCAGCATCCCGGCATCTTCCAGCCACC
                         1451                                             1500
BMY_HDACX_V1    (278)  CTCATGTTACTTTAGAGGGAAAGCCACCCAACAGCAGCCACCAGGCTCTC
BMY_HDACX_V2   (1451)  CTCATGTTACTTTAGAGGGAAAGCCACCCAACAGCAGCCACCAGGCTCTC
HDAC9V1        (1286)  CTCATGTTACTTTAGAGGGAAAGCCACCCAACAGCAGCCACCAGGCTCTC
HDAC9V2        (1286)  CTCATGTTACTTTAGAGGGAAAGCCACCCAACAGCAGCCACCAGGCTCTC
HDAC9V3        (1286)  CTCATGTTACTTTAGAGGGAAAGCCACCCAACAGCAGCCACCAGGCTCTC
CONSENSUS      (1451)  CTCATGTTACTTTAGAGGGAAAGCCACCCAACAGCAGCCACCAGGCTCTC
                         1501                                             1550
BMY_HDACX_V1    (328)  CTGCAGCATTTATTATTGAAAGAACAAATGCGACAGCAAAAGCTTCTTGT
BMY_HDACX_V2   (1501)  CTGCAGCATTTATTATTGAAAGAACAAATGCGACAGCAAAAGCTTCTTGT
HDAC9V1        (1336)  CTGCAGCATTTATTATTGAAAGAACAAATGCGACAGCAAAAGCTTCTTGT
HDAC9V2        (1336)  CTGCAGCATTTATTATTGAAAGAACAAATGCGACAGCAAAAGCTTCTTGT
HDAC9V3        (1336)  CTGCAGCATTTATTATTGAAAGAACAAATGCGACAGCAAAAGCTTCTTGT
CONSENSUS      (1501)  CTGCAGCATTTATTATTGAAAGAACAAATGCGACAGCAAAAGCTTCTTGT
                         1551                                             1600
BMY_HDACX_V1    (378)  AGCTGGTGGAGTTCCCTTACATCCTCAGTCTCCCTTGGCAACAAAAGAGA
BMY_HDACX_V2   (1551)  AGCTGGTGGAGTTCCCTTACATCCTCAGTCTCCCTTGGCAACAAAAGAGA
HDAC9V1        (1386)  AGCTGGTGGAGTTCCCTTACATCCTCAGTCTCCCTTGGCAACAAAAGAGA
HDAC9V2        (1386)  AGCTGGTGGAGTTCCCTTACATCCTCAGTCTCCCTTGGCAACAAAAGAGA
HDAC9V3        (1386)  AGCTGGTGGAGTTCCCTTACATCCTCAGTCTCCCTTGGCAACAAAAGAGA
CONSENSUS      (1551)  AGCTGGTGGAGTTCCCTTACATCCTCAGTCTCCCTTGGCAACAAAAGAGA
                         1601                                             1650
BMY_HDACX_V1    (428)  GAATTTCACCTGGCATTAGAGGTACCCACAAATTGCCCCGTCACAGACCC
BMY_HDACX_V2   (1601)  GAATTTCACCTGGCATTAGAGGTACCCACAAATTGCCCCGTCACAGACCC
HDAC9V1        (1436)  GAATTTCACCTGGCATTAGAGGTACCCACAAATTGCCCCGTCACAGACCC
HDAC9V2        (1436)  GAATTTCACCTGGCATTAGAGGTACCCACAAATTGCCCCGTCACAGACCC
HDAC9V3        (1436)  GAATTTCACCTGGCATTAGAGGTACCCACAAATTGCCCCGTCACAGACCC
CONSENSUS      (1601)  GAATTTCACCTGGCATTAGAGGTACCCACAAATTGCCCCGTCACAGACCC
                         1651                                             1700
BMY_HDACX_V1    (478)  CTGAACCGAACCCAGTCTGCACCTTTGCCTCAGAGCACGTTGGCTCAGCT
BMY_HDACX_V2   (1651)  CTGAACCGAACCCAGTCTGCACCTTTGCCTCAGAGCACGTTGGCTCAGCT
HDAC9V1        (1486)  CTGAACCGAACCCAGTCTGCACCTTTGCCTCAGAGCACGTTGGCTCAGCT
HDAC9V2        (1486)  CTGAACCGAACCCAGTCTGCACCTTTGCCTCAGAGCACGTTGGCTCAGCT
HDAC9V3        (1486)  CTGAACCGAACCCAGTCTGCACCTTTGCCTCAGAGCACGTTGGCTCAGCT
CONSENSUS      (1651)  CTGAACCGAACCCAGTCTGCACCTTTGCCTCAGAGCACGTTGGCTCAGCT
                         1701                                             1750
BMY_HDACX_V1    (528)  GGTCATTCAACAGCAACACCAGCAATTCTTGGAGAAGCAGAAGCAATACC
BMY_HDACX_V2   (1701)  GGTCATTCAACAGCAACACCAGCAATTCTTGGAGAAGCAGAAGCAATACC
HDAC9V1        (1536)  GGTCATTCAACAGCAACACCAGCAATTCTTGGAGAAGCAGAAGCAATACC
HDAC9V2        (1536)  GGTCATTCAACAGCAACACCAGCAATTCTTGGAGAAGCAGAAGCAATACC
HDAC9V3        (1536)  GGTCATTCAACAGCAACACCAGCAATTCTTGGAGAAGCAGAAGCAATACC
CONSENSUS      (1701)  GGTCATTCAACAGCAACACCAGCAATTCTTGGAGAAGCAGAAGCAATACC
```

FIG. 23E

```
                        1751                                          1800
BMY_HDACX_V1   (578)  AGCAGCAGATCCACATGAACAAACTGCTTTCGAAATCTATTGAACAACTG
BMY_HDACX_V2  (1751)  AGCAGCAGATCCACATGAACAAAGAATTGCCTATGACCCCTTGATGCTGA
HDAC9V1       (1586)  AGCAGCAGATCCACATGAACAAACTGCTTTCGAAATCTATTGAACAACTG
HDAC9V2       (1586)  AGCAGCAGATCCACATGAACAAACTGCTTTCGAAATCTATTGAACAACTG
HDAC9V3       (1586)  AGCAGCAGATCCACATGAACAAACTGCTTTCGAAATCTATTGAACAACTG
CONSENSUS     (1751)  AGCAGCAGATCCACATGAACAAACTGCTTTCGAAATCTATTGAACAACTG
                                                    *SPLICE JUNCTION:
                                                    CAAA>>GAAA OR CTGC
                        1801                                          1850
BMY_HDACX_V1   (628)  AAGCAACCAGGCAGTCACCTTGAGGAAGCAGAGGAAGAGCTTCAGGGGGA
BMY_HDACX_V2  (1801)  AACACCAGTGCGTTTGTGGCAATTCCACCACCCACCCTGAGCATGCTGGA
HDAC9V1       (1636)  AAGCAACCAGGCAGTCACCTTGAGGAAGCAGAGGAAGAGCTTCAGGGGGA
HDAC9V2       (1636)  AAGCAACCAGGCAGTCACCTTGAGGAAGCAGAGGAAGAGCTTCAGGGGGA
HDAC9V3       (1636)  AAGCAACCAGGCAGTCACCTTGAGGAAGCAGAGGAAGAGCTTCAGGGGGA
CONSENSUS     (1801)  AAGCAACCAGGCAGTCACCTTGAGGAAGCAGAGGAAGAGCTTCAGGGGGA
                        1851                                          1900
BMY_HDACX_V1   (678)  CCAGGCGATGCAGGAAGACAGAGCGCCCTCTAGTGGCAACAGCACTAGGA
BMY_HDACX_V2  (1851)  CGAATACAGAGTATCTGGTCACGACTGCAAGAAACTGGGCTGCTAAATAA
HDAC9V1       (1686)  CCAGGCGATGCAGGAAGACAGAGCGCCCTCTAGTGGCAACAGCACTAGGA
HDAC9V2       (1686)  CCAGGCGATGCAGGAAGACAGAGCGCCCTCTAGTGGCAACAGCACTAGGA
HDAC9V3       (1686)  CCAGGCGATGCAGGAAGACAGAGCGCCCTCTAGTGGCAACAGCACTAGGA
CONSENSUS     (1851)  CCAGGCGATGCAGGAAGACAGAGCGCCCTCTAGTGGCAACAGCACTAGGA
                        1901                                          1950
BMY_HDACX_V1   (728)  GCGACAGCAGTGCTTGTGTGGATGACACACTGGGACAAGTTGGGGCTGTG
BMY_HDACX_V2  (1901)  ATGTGAGCGAATTCAAGGTCGAAAAGCCAGCCTGGAGGAAATACAGCTTG
HDAC9V1       (1736)  GCGACAGCAGTGCTTGTGTGGATGACACACTGGGACAAGTTGGGGCTGTG
HDAC9V2       (1736)  GCGACAGCAGTGCTTGTGTGGATGACACACTGGGACAAGTTGGGGCTGTG
HDAC9V3       (1736)  GCGACAGCAGTGCTTGTGTGGATGACACACTGGGACAAGTTGGGGCTGTG
CONSENSUS     (1901)  GCGACAGCAGTGCTTGTGTGGATGACACACTGGGACAAGTTGGGGCTGTG
                        1951                                          2000
BMY_HDACX_V1   (778)  AAGGTCAAGGAGGAACCAGTGGACAGTGATGAAGATGCTCAGATCCAGGA
BMY_HDACX_V2  (1951)  TTCATTCTGAACATCACTCACTGTTGTATGGCACCAACCCCCTGGACGGA
HDAC9V1       (1786)  AAGGTCAAGGAGGAACCAGTGGACAGTGATGAAGATGCTCAGATCCAGGA
HDAC9V2       (1786)  AAGGTCAAGGAGGAACCAGTGGACAGTGATGAAGATGCTCAGATCCAGGA
HDAC9V3       (1786)  AAGGTCAAGGAGGAACCAGTGGACAGTGATGAAGATGCTCAGATCCAGGA
CONSENSUS     (1951)  AAGGTCAAGGAGGAACCAGTGGACAGTGATGAAGATGCTCAGATCCAGGA
                        2001                                          2050
BMY_HDACX_V1   (828)  AATGGAATCTGGGGAGCAGGCTGCTTTTATGCAACAGCCTTTCCTGGAAC
BMY_HDACX_V2  (2001)  CAGAAGCTGGACCCCAGGATACTCCTAGGTGATGACTCTCAAAAGTTTTT
HDAC9V1       (1836)  AATGGAATCTGGGGAGCAGGCTGCTTTTATGCAACAGCCTTTCCTGGAAC
HDAC9V2       (1836)  AATGGAATCTGGGGAGCAGGCTGCTTTTATGCAACAGCCTTTCCTGGAAC
HDAC9V3       (1836)  AATGGAATCTGGGGAGCAGGCTGCTTTTATGCAACAGGTAATAGGCAAAG
CONSENSUS     (2001)  AATGGAATCTGGGGAGCAGGCTGCTTTTATGCAACAGCCTTTCCTGGAAC
                                                    *SPLICE JUNCTION:
                                                    CAG>>>CCT OR GTA
                        2051                                          2100
BMY_HDACX_V1   (878)  CCACGCACACACGTGCGCTCTCTGTGCGCCAAGCTCCGCTGGCTGCGGTT
BMY_HDACX_V2  (2051)  TTCCTCATTACCTTGTGGTGGACTTGGGGTGGACAGTGACACCATTTGGA
HDAC9V1       (1886)  CCACGCACACACGTGCGCTCTCTGTGCGCCAAGCTCCGCTGGCTGCGGTT
HDAC9V2       (1886)  CCACGCACACACGTGCGCTCTCTGTGCGCCAAGCTCCGCTGGCTGCGGTT
HDAC9V3       (1886)  ATTTAGCTCCAGGATTTGTAATTAAAGTCATTATCTGAACATGAAATGCA
CONSENSUS     (2051)  CCACGCACACACGTGCGCTCTCTGTGCGCCAAGCTCCGCTGGCTGCGGTT
                        2101                                          2150
BMY_HDACX_V1   (928)  GGCATGGATGGATTAGAGAAACACCGTCTCGTCTCCAGGACTCACTCTTC
BMY_HDACX_V2  (2101)  ATGAGCTACACTCGTCCCGTGCTGCACGCATGGCTGTTGGCTGTGTCATC
HDAC9V1       (1936)  GGCATGGATGGATTAGAGAAACACCGTCTCGTCTCCAGGACTCACTCTTC
HDAC9V2       (1936)  GGCATGGATGGATTAGAGAAACACCGTCTCGTCTCCAGGACTCACTCTTC
HDAC9V3       (1936)  TTGCAGGTTTGGTAAATGGATATGATTTCCTATCAGTTTTATATTTCTCA
CONSENSUS     (2101)  GGCATGGATGGATTAGAGAAACACCGTCTCGTCTCCAGGACTCACTCTTC
```

FIG. 23F

```
                        2151                                           2200
BMY_HDACX_V1   (978)   CCCTGCTGCCTCTGTTTTACCTCACCCGGCAATGGACCGCCCCCTCCAGC
BMY_HDACX_V2  (2151)   GAGCTGGCTTCCAAAGTGGCCTCAGGAGAGCTGAAGGTGAGGTCCGGGTT
HDAC9V1       (1986)   CCCTGCTGCCTCTGTTTTACCTCACCCAGCAATGGACCGCCCCCTCCAGC
HDAC9V2       (1986)   CCCTGCTGCCTCTGTTTTACCTCACCCAGCAATGGACCGCCCCCTCCAGC
HDAC9V3       (1986)   TGATTTGAGTTCAGTGTTTAAGGATTCTACCTAATGCAGATATATGTATA
CONSENSUS     (2151)   CCCTGCTGCCTCTGTTTTACCTCACCC GCAATGGACCGCCCCCTCCAGC
                        2201                                           2250
BMY_HDACX_V1  (1028)   CTGGCTCTGCAACTGGAATTGCCTATGACCCCTTGATGCTGAAACACCAG
BMY_HDACX_V2  (2201)   GCATTAAGTGTGGGAAATCCAGAGAAGAAACTGAAACAGACATGTTGTTA
HDAC9V1       (2036)   CTGGCTCTGCAACTGGAATTGCCTATGACCCCTTGATGCTGAAACACCAG
HDAC9V2       (2036)   CTGGCTCTGCAACTGGAATTGCCTATGACCCCTTGATGCTGAAACACCAG
HDAC9V3       (2036)   TATCTATATAGAGGTCTTTCTATATACTGATCTCTATATAGATATCAATG
CONSENSUS     (2201)   CTGGCTCTGCAACTGGAATTGCCTATGACCCCTTGATGCTGAAACACCAG
                        2251                                           2300
BMY_HDACX_V1  (1078)   TGCGTTTGTGGCAATTCCACCACCCACCCTGAGCATGCTGGACGAATACA
BMY_HDACX_V2  (2251)   TGTGGGAATTGGGGGGAGTGTGGCGTGGTAATAAAAGGAAGGGCAGAAGG
HDAC9V1       (2086)   TGCGTTTGTGGCAATTCCACCACCCACCCTGAGCATGCTGGACGAATACA
HDAC9V2       (2086)   TGCGTTTGTGGCAATTCCACCACCCACCCTGAGCATGCTGGACGAATACA
HDAC9V3       (2086)   TTTCATTGAAAATCCACTGGTAAGGAAATACCTGTTATACTAAAATTATG
CONSENSUS     (2251)   TGCGTTTGTGGCAATTCCACCACCCACCCTGAGCATGCTGGACGAATACA
                        2301                                           2350
BMY_HDACX_V1  (1128)   GAGTATCTGGTCACGACTGCAAGAAACTGGGCTGCTAAATAAATGTGAGC
BMY_HDACX_V2  (2301)   AAGAGGGTAGAGATGGCCACTAAGGTGTGATAATAACTCATCTGTACGCA
HDAC9V1       (2136)   GAGTATCTGGTCACGACTGCAAGAAACTGGGCTGCTAAATAAATGTGAGC
HDAC9V2       (2136)   GAGTATCTGGTCACGACTGCAAGAAACTGGGCTGCTAAATAAATGTGAGC
HDAC9V3       (2136)   ATACATAATATCTGAGCAGTTAATAGGCTTTAAATTTATCCCAAAGCCTG
CONSENSUS     (2301)   GAGTATCTGGTCACGACTGCAAGAAACTGGGCTGCTAAATAAATGTGAGC
                        2351                                           2400
BMY_HDACX_V1  (1178)   GAATTCAAGGTCGAAAAGCCAGCCTGGAGGAAATACAGCTTGTTCATTCT
BMY_HDACX_V2  (2351)   GGGAGCAGCTCATCCTGCTCTCAGGGCCTTCTTCTGCCTGAGAACACTCT
HDAC9V1       (2186)   GAATTCAAGGTCGAAAAGCCAGCCTGGAGGAAATACAGCTTGTTCATTCT
HDAC9V2       (2186)   GAATTCAAGGTCGAAAAGCCAGCCTGGAGGAAATACAGCTTGTTCATTCT
HDAC9V3       (2186)   CTACACCAATTACTTCTAAAGAAAACAAATTCACTGTTATTTTGAGTTTA
CONSENSUS     (2351)   GAATTCAAGGTCGAAAAGCCAGCCTGGAGGAAATACAGCTTGTTCATTCT
                        2401                                           2450
BMY_HDACX_V1  (1228)   GAACATCACTCACTGTTGTATGGCACCAACCCCCTGGACGGACAGAAGCT
BMY_HDACX_V2  (2401)   GCAGTCAGGGCCCACCGGTGTCCATGTAAGAGCACAGAGATAATAAGCAA
HDAC9V1       (2236)   GAACATCACTCACTGTTGTATGGCACCAACCCCCTGGACGGACAGAAGCT
HDAC9V2       (2236)   GAACATCACTCACTGTTGTATGGCACCAACCCCCTGGACGGACAGAAGCT
HDAC9V3       (2236)   TGTGTGAGATCAGTGACTGCTGGATAGTCTCCCAGTCTGATCAATGAAG
CONSENSUS     (2401)   GAACATCACTCACTGTTGTATGGCACCAACCCCCTGGACGGACAGAAGCT
                        2451                                           2500
BMY_HDACX_V1  (1278)   GGACCCCAGGATACTCCTAGGTGATGACTCTCAAAAGTTTTTTTCCTCAT
BMY_HDACX_V2  (2451)   AGCTATGGTTCAGGTTAAAAATACCTTTAGTATATACATGTCTGTCATGC
HDAC9V1       (2286)   GGACCCCAGGATACTCCTAGGTGATGACTCTCAAAAGTTTTTTTCCTCAT
HDAC9V2       (2286)   GGACCCCAGGATACTCCTAGGTGATGACTCTCAAAAGTTTTTTTCCTCAT
HDAC9V3       (2286)   CATTCGATTAGTTTTGATTTTTTGCAACATCTAGAATTTAATTTTCACA
CONSENSUS     (2451)   GGACCCCAGGATACTCCTAGGTGATGACTCTCAAAAGTTTTTTTCCTCAT
                        2501                                           2550
BMY_HDACX_V1  (1328)   TACCTTGTGGTGGACTTGGGGTGGACAGTGACACCATTTGGAATGAGCTA
BMY_HDACX_V2  (2501)   CATCCTGAGATTCTCTTTTGAGGCCAATTTTAAAAATATGATTACTGAGAA
HDAC9V1       (2336)   TACCTTGTGGTGGACTTGGGGTGGACAGTGACACCATTTGGAATGAGCTA
HDAC9V2       (2336)   TACCTTGTGGTGGACTTGGGGTGGACAGTGACACCATTTGGAATGAGCTA
HDAC9V3       (2336)   TCACTGTACATAATGTATCATACTATAGTCTTGAACACTGTTAAAGCTAG
CONSENSUS     (2501)   TACCTTGTGGTGGACTTGGGGTGGACAGTGACACCATTTGGAATGAGCTA
                        2551                                           2600
BMY_HDACX_V1  (1378)   CACTCGTCCGGTGCTGCACGCATGGCTGTTGGCTGTGTCATCGAGCTGGC
BMY_HDACX_V2  (2551)   GTGTGTATAAGCTCAGAATACCACCCAGAGAGAGGGAGGCAGAGAAACGT
HDAC9V1       (2386)   CACTCGTCCGGTGCTGCACGCATGGCTGTTGGCTGTGTCATCGAGCTGGC
HDAC9V2       (2386)   CACTCGTCCGGTGCTGCACGCATGGCTGTTGGCTGTGTCATCGAGCTGGC
HDAC9V3       (2386)   TCTGCCCCGTTCCTTCCTCTCTCTTTTTTAGTTAAGTAGAAATGTTCTGG
CONSENSUS     (2551)   CACTCGTCCGGTGCTGCACGCATGGCTGTTGGCTGTGTCATCGAGCTGGC
```

FIG. 23G

```
                      2601                                                2650
BMY_HDACX_V1  (1428)  TTCCAAAGTGGCCTCAGGAGAGCTGAAGAATGGGTTTGCTGTTGTGAGGC
BMY_HDACX_V2  (2601)  AAATACCAGACGGGAAGGATTCGGAGGAGGAACGAAATTGTTGATTAGAA
HDAC9V1       (2436)  TTCCAAAGTGGCCTCAGGAGAGCTGAAGAATGGGTTTGCTGTTGTGAGGC
HDAC9V2       (2436)  TTCCAAAGTGGCCTCAGGAGAGCTGAAGAATGGGTTTGCTGTTGTGAGGC
HDAC9V3       (2436)  TCACCATGCCAGTAGTCCTAGCGTTATTGTGTAGGTTGCAATTGAACATAT
CONSENSUS     (2601)  TTCCAAAGTGGCCTCAGGAGAGCTGAAGAATGGGTTTGCTGTTGTGAGGC
                      2651                                                2700
BMY_HDACX_V1  (1478)  CCCCTGGCCATCACGCTGAAGAATCCACAGCCATGGGGTTCTGCTTTTTT
BMY_HDACX_V2  (2651)  GGGTAATGATCCAGAGTGTGTTTTTCCATGAAAGAACTTAAAAAATGAGC
HDAC9V1       (2486)  CCCCTGGCCATCACGCTGAAGAATCCACAGCCATGGGGTTCTGCTTTTTT
HDAC9V2       (2486)  CCCCTGGCCATCACGCTGAAGAATCCACAGCCATGGGGTTCTGCTTTTTT
HDAC9V3       (2486)  TAGGAATACAGGTGGTTTTAAATATATAGATGCAAATTGCAGCACTACTT
CONSENSUS     (2651)  CCCCTGGCCATCACGCTGAAGAATCCACAGCCATGGGGTTCTGCTTTTTT
                      2701                                                2750
BMY_HDACX_V1  (1528)  AATTCAGTTGCAATTACCGCCAAATACTTGAGAGACCAACTAAATATAAG
BMY_HDACX_V2  (2701)  TATGCTTTATTGTTCTTTTCTTTTTATGGTCTCTTCTTTTCTACATCGTA
HDAC9V1       (2536)  AATTCAGTTGCAATTACCGCCAAATACTTGAGAGACCAACTAAATATAAG
HDAC9V2       (2536)  AATTCAGTTGCAATTACCGCCAAATACTTGAGAGACCAACTAAATATAAG
HDAC9V3       (2536)  TAAATATTAGATTATGTCTCACATAGCACTGCTCATTTTACTTTTATTTT
CONSENSUS     (2701)  AATTCAGTTGCAATTACCGCCAAATACTTGAGAGACCAACTAAATATAAG
                      2751                                                2800
BMY_HDACX_V1  (1578)  CAAGATATTGATTGTAGATCTGGATGTTCACCATGGAAACGGTACCCAGC
BMY_HDACX_V2  (2751)  TGAAAAGAACAATGTCCAAACCCCAGCGTTTCCCAGTCTAAACAATTTAT
HDAC9V1       (2586)  CAAGATATTGATTGTAGATCTGGATGTTCACCATGGAAACGGTACCCAGC
HDAC9V2       (2586)  CAAGATATTGATTGTAGATCTGGATGTTCACCATGGAAACGGTACCCAGC
HDAC9V3       (2586)  GTGTAATTTGATGACACTGTCTATCAAAAAAGAGCAAATGAAGCAGATGC
CONSENSUS     (2751)  CAAGATATTGATTGTAGATCTGGATGTTCACCATGGAAACGGTACCCAGC
                      2801                                                2850
BMY_HDACX_V1  (1628)  AGGCCTTTTATGCTGACCCCAGCATCCTGTACATTTCACTCCATCGCTAT
BMY_HDACX_V2  (2801)  AAAAGCTAGAGACCTGACAGAACGTTGACATTTTATTTGGTATTTTAACAG
HDAC9V1       (2636)  AGGCCTTTTATGCTGACCCCAGCATCCTGTACATTTCACTCCATCGCTAT
HDAC9V2       (2636)  AGGCCTTTTATGCTGACCCCAGCATCCTGTACATTTCACTCCATCGCTAT
HDAC9V3       (2636)  AAATGTTAGTGAGAAGTAATGTGCAGCATTATGGTCCAATCAGATACAAT
CONSENSUS     (2801)  AGGCCTTTTATGCTGACCCCAGCATCCTGTACATTTCACTCCATCGCTAT
                      2851                                                2900
BMY_HDACX_V1  (1678)  GATGAAGGGAACTTTTTCCCTGGCAGTGGAGCCCCAAATGAGGTTGCAAC
BMY_HDACX_V2  (2851)  TGCTATTTAAAGGTACGCCATGTGCGTCTTGAATGCAGTTACCCCAATAA
HDAC9V1       (2686)  GATGAAGGGAACTTTTTCCCTGGCAGTGGAGCCCCAAATGAGGTTGCAAC
HDAC9V2       (2686)  GATGAAGGGAACTTTTTCCCTGGCAGTGGAGCCCCAAATGAGGTTCGGTT
HDAC9V3       (2686)  ATTGTGTCTACAATTGCAAAAAACACAGTAACAGGATGAATATTATCTGA
CONSENSUS     (2851)  GATGAAGGGAACTTTTTCCCTGGCAGTGGAGCCCCAAATGAGGTT G A
                      2901                                                2950
BMY_HDACX_V1  (1728)  AGGCCTTGGAGAAGGGTACAATATAAATATTGCCTGGACAGGTGGCCTTG
BMY_HDACX_V2  (2901)  ACTTTGTTCGTGCTAACACGGCCTTTTAATGCACTAGTTCACACACTTCA
HDAC9V1       (2736)  AGGCCTTGGAGAAGGGTACAATATAAATATTGCCTGGACAGGTGGCCTTG
HDAC9V2       (2736)  TATTTCTTTAGAGCCCCACTTTTATTTGTATCTTTCAGGTAATTGCATTC
HDAC9V3       (2736)  TATCAAGTCAAAATCAGTTTGAAAGAAGGTGTATCATATTTTATATTTGT
CONSENSUS     (2901)  A TC  TTGAGAA    AC  TATA A ATTG CT G      T GC TTG
                      2951                                                3000
BMY_HDACX_V1  (1778)  ATCCTCCCATGGGAGATGTTGAGTACCTTGAAGCATTCAGGACCATCGTG
BMY_HDACX_V2  (2951)  TGACGCAATCTGGGTCGTGATTGATTCGGTATTTTTAGCAATTGCGGGGC
HDAC9V1       (2786)  ATCCTCCCATGGGAGATGTTGAGTACCTTGAAGCATTCAGGACCATCGTG
HDAC9V2       (2786)  CATGA---------------------------------------------
HDAC9V3       (2786)  CACTAGAATCTCTTAAG-------TATAATTCCATAATGACATGGGCATA
CONSENSUS     (2951)     CC C      GG  A       G  C  A  T    A    CGT
                      3001                                                3050
BMY_HDACX_V1  (1828)  AAGCCTGTGGCCAAAGAGTTTGATCCAGACATGGTCTTAGTATCTGCTGG
BMY_HDACX_V2  (3001)  TTAGGGAAATATATTTATCACCAATAACATTGCACTGTGAGTTTGTGTGAA
HDAC9V1       (2836)  AAGCCTGTGGCCAAAGAGTTTGATCCAGACATGGTCTTAGTATCTGCTGG
HDAC9V2       (2791)  --------------------------------------------------
HDAC9V3       (2829)  TACCGTAACATTCTGGCAAATAACAATTAGAAAAGATAGGTTAACAAAA
CONSENSUS     (3001)      A C T     A  GG T AT    AA      TT GT T TG
```

FIG. 23H

```
                        3051                                              3100
BMY_HDACX_V1  (1878)  ATTTGATGCATTGGAAGGCCACACCCCTCCTCTAGGAGGGTACAAAGTGA
BMY_HDACX_V2  (3051)  ACCAAGATAAAATAATTAGGATTACTTTTCTTTATGTCTAGTGAATTTTT
HDAC9V1       (2886)  ATTTGATGCATTGGAAGGCCACACCCCTCCTCTAGGAGGGTACAAAGTGA
HDAC9V2       (2791)  --------------------------------------------------
HDAC9V3       (2879)  AAATTTACTTGTATATAATGCACCTTCAGGAGGACTATGTCCTTTGATGC
CONSENSUS     (3051)  A  T     A T  A      A  CC CT CT TA GA G     AA TG
                        3101                                              3150
BMY_HDACX_V1  (1928)  CGGCAAAATGTTTTGGTCATTTGACGAAGCAATTGATGACATTGGCTGAT
BMY_HDACX_V2  (3101)  ATTCAATTACATGGGACTCTTCCAGTTGTGATTAAAAATGTGGAGTAGGA
HDAC9V1       (2936)  CGGCAAAATGTTTTGGTCATTTGACGAAGCAATTGATGACATTGGCTGAT
HDAC9V2       (2791)  --------------------------------------------------
HDAC9V3       (2929)  TATAAAATACAAACAACT-TTGAAGGCAACAGAAGACACTGTTTATTCAA
CONSENSUS     (3101)       CAAA    T G    TT  A  A CA T GA    TT G TGA
                        3151                                              3200
BMY_HDACX_V1  (1978)  GGACGTGTGGTGTTGGCTCTAGAAGGAGGACATGATCTCACAGCCATCTG
BMY_HDACX_V2  (3151)  ATGTGCACTTCACAATGCAACGTTTGTCCAAGAAGTCTTTACTCTTAACT
HDAC9V1       (2986)  GGACGTGTGGTGTTGGCTCTAGAAGGAGGACATGATCTCACAGCCATCTG
HDAC9V2       (2791)  --------------------------------------------------
HDAC9V3       (2978)  GTCAGTTCTTTGTCAGGTTCCTGCTGTTCTCCTACAGAAAAGTGATTCTG
CONSENSUS     (3151)  G   GT    TGT  GT  G      G   AC T TCT A   C  TCTG
                        3201                                              3250
BMY_HDACX_V1  (2028)  TGATGCATCAGAAGCCTGTGTAAATGCCCTTCTAGCAAATGAGCTGGAGC
BMY_HDACX_V2  (3201)  CTTTAAAAGAGTCAGAGCCTACGGAAATATAATTTTGATAGGTGAGCTCT
HDAC9V1       (3036)  TGATGCATCAGAAGCCTGTGTAAATGCCCTTCTAGGAAATGAGCTGGAGC
HDAC9V2       (2791)  --------------------------------------------------
HDAC9V3       (3028)  TGAGGGTGAACAGGAAATGCCTTGTGGAAACAGGAAGTCCAAGTGATTCA
CONSENSUS     (3201)  TGATG A  A AAG     T    ATG      T  GA A GAG G
                        3251                                              3300
BMY_HDACX_V1  (2078)  CACTTGCAGAAGATATTCTCCACCAAAGCCCGAATATGAATGCTGTTATT
BMY_HDACX_V2  (3251)  ATTTAAAAAGTAGATGTTGCCTGTATATATTTGACATAAGTAGTATTAGGA
HDAC9V1       (3086)  CACTTGCAGAAGATATTCTCCACCAAAGCCCGAATATGAATGCTGTTATT
HDAC9V2       (2791)  --------------------------------------------------
HDAC9V3       (3078)  TGTACTGAGGAATGTAGGAAAAAAAATCTGACGGATAGTGCTTTACTCTTT
CONSENSUS     (3251)         T   AG A    T  C  AA        GAATA   TG  T  TT
                        3301                                              3350
BMY_HDACX_V1  (2128)  TCTTTTACAGAAGATCATTGAAATTCAAAGCAAGTATTGGAAGTCAGTAAG
BMY_HDACX_V2  (3301)  CATTGCTCATCTCAGGGGATATATGGGGTCATTAATGTGGTGCTTACTCT
HDAC9V1       (3136)  TCTTTTACAGAAGATCATTGAAATTCAAAGTATGTCTTTAAAGTTCTCTTA
HDAC9V2       (2791)  --------------------------------------------------
HDAC9V3       (3128)  CTGTTTTTAAAGGGCACTCTATGAATTGATTTATTGTCTAAGAAAATAAC
CONSENSUS     (3301)     TTT     AAG  CA T  A  T         AT T TT  AAG
                        3351                                              3400
BMY_HDACX_V1  (2178)  GATGGTGGCTGTGCCAAGGGGCTGTGCTCTGGCTGGTGCTCAGTTGCAAG
BMY_HDACX_V2  (3351)  TCAGTCTTTACCTTTGAAAATGAGCAAAAAAAAAAAAAAAA---------
HDAC9V1       (3186)  A-------------------------------------------------
HDAC9V2       (2791)  --------------------------------------------------
HDAC9V3       (3178)  ACCACAAGTAGGGAAATTGTTACGGAAGCTTTTCACTGGAACATTTCCTT
CONSENSUS     (3351)                         G
                        3401                                              3450
BMY_HDACX_V1  (2228)  AGGAGACAGAGACCGTTTCTGCCCTGGCCTCCCTAACAGTGGATGTGGAA
BMY_HDACX_V2  (3392)  --------------------------------------------------
HDAC9V1       (3187)  --------------------------------------------------
HDAC9V2       (2791)  --------------------------------------------------
HDAC9V3       (3228)  CATATTCCCTTTTGATATGTTTACCTTGTTTTATAGGTTTACTTTTGTTA
CONSENSUS     (3401)
                        3451                                              3500
BMY_HDACX_V1  (2278)  CAGCCCTTTGCTCAGGAAGACAGCAGAACTGCTGGTGAGCCTATGGAAGA
BMY_HDACX_V2  (3392)  --------------------------------------------------
HDAC9V1       (3187)  --------------------------------------------------
HDAC9V2       (2791)  --------------------------------------------------
HDAC9V3       (3278)  AGCTAGTTAAAGGTTCGTTGTATTAAGACCCCTTTAATATGGATAATCCA
CONSENSUS     (3451)
```

FIG. 23I

```
                         3501                                          3550
BMY_HDACX_V1  (2328)  GGAGCCAGCCTTGTGAAGTGCCAAGTCCCCCTCTGATATTTCCTGTGTGT
BMY_HDACX_V2  (3392)  --------------------------------------------------
     HDAC9V1  (3187)  --------------------------------------------------
     HDAC9V2  (2791)  --------------------------------------------------
     HDAC9V3  (3328)  AATTGACCTAGAATCTTTGTGAGGTTTTTTCTATTAAAATATTTATATTT
   CONSENSUS  (3501)
                         3551                                          3600
BMY_HDACX_V1  (2378)  GACATCATTGTGTATCCCCCCACCCCAGTACCCTCAGACATGTCTTGTCT
BMY_HDACX_V2  (3392)  --------------------------------------------------
     HDAC9V1  (3187)  --------------------------------------------------
     HDAC9V2  (2791)  --------------------------------------------------
     HDAC9V3  (3378)  CTAAATCCGAGGTATTTCAAGGTGTAGTATCCTATTTCAAAGGAGATATA
   CONSENSUS  (3551)
                         3601                                          3650
BMY_HDACX_V1  (2428)  GCTGCCTGGGTGGCACAGATTCAATGGAACATAAACACTGGGCACAAAAT
BMY_HDACX_V2  (3392)  --------------------------------------------------
     HDAC9V1  (3187)  --------------------------------------------------
     HDAC9V2  (2791)  --------------------------------------------------
     HDAC9V3  (3428)  GCAGTTTTGCCAAATGTAGACATTGTTCAACTGTATGTTATTGGCACGTG
   CONSENSUS  (3601)
                         3651                                          3700
BMY_HDACX_V1  (2478)  TCTGAACAGCAGCTTCACTTGTTCTTTGGATGGACTTGAAAGGGCATTAA
BMY_HDACX_V2  (3392)  --------------------------------------------------
     HDAC9V1  (3187)  --------------------------------------------------
     HDAC9V2  (2791)  --------------------------------------------------
     HDAC9V3  (3478)  TTGTTTACATTTTGCTGTGACATTTAAAAATATTTCTTTAAAAATGTTAC
   CONSENSUS  (3651)
                         3701                                          3750
BMY_HDACX_V1  (2528)  AGATTCCTTAAACGTAACCGCTGTGATTCTAGAGTTACAGTAAACCACGA
BMY_HDACX_V2  (3392)  --------------------------------------------------
     HDAC9V1  (3187)  --------------------------------------------------
     HDAC9V2  (2791)  --------------------------------------------------
     HDAC9V3  (3528)  TGCTAAAGATACATTATCCTTTTTTAAAAAGTCTCCATTCAAATTAAATT
   CONSENSUS  (3701)
                         3751                                          3800
BMY_HDACX_V1  (2578)  TTGGAAGAAACTGCTTCCAGCATGCTTTTAATATGCTGGGTGACCCACTC
BMY_HDACX_V2  (3392)  --------------------------------------------------
     HDAC9V1  (3187)  --------------------------------------------------
     HDAC9V2  (2791)  --------------------------------------------------
     HDAC9V3  (3578)  AACATAACTAGAAGTTAGAAAGTTTAAAAGTTTTCCACATAATGAAAGTC
   CONSENSUS  (3751)
                         3801                                          3850
BMY_HDACX_V1  (2628)  CTAGACACCAAGTTTGAACTAGAAACATTCAGTACAGCACTAGATATTGT
BMY_HDACX_V2  (3392)  --------------------------------------------------
     HDAC9V1  (3187)  --------------------------------------------------
     HDAC9V2  (2791)  --------------------------------------------------
     HDAC9V3  (3628)  CTTCTGATAATTTGACAAATAGCTATAATAGGAACACTCCCTATCACCAA
   CONSENSUS  (3801)
                         3851                                          3900
BMY_HDACX_V1  (2678)  TAATTTCAGAAGCTATGACAGCCAGTGAAATTTTGGGCAAAACCTGAGAC
BMY_HDACX_V2  (3392)  --------------------------------------------------
     HDAC9V1  (3187)  --------------------------------------------------
     HDAC9V2  (2791)  --------------------------------------------------
     HDAC9V3  (3678)  CATATTTTGGTTAGTATATTCCTTCATATTAAAATGACTTTTTGTCAGTT
   CONSENSUS  (3851)
                         3901                                          3950
BMY_HDACX_V1  (2728)  ATAGTCATTCCTGACATTCTGATCAGCTTTTTTTGGGGTAATTTGTTTTT
BMY_HDACX_V2  (3392)  --------------------------------------------------
     HDAC9V1  (3187)  --------------------------------------------------
     HDAC9V2  (2791)  --------------------------------------------------
     HDAC9V3  (3728)  GTTTTGCATTAAAAATATGGCATGCCTAAGATAAAATTGTATATTTTTTC
   CONSENSUS  (3901)
```

FIG. 23J

```
                      3951                                               4000
BMY_HDACX_V1  (2778)  CAAACAGTCTTAACTTGTTTACAAGATTTGCTTTTAGCTATGAACGGATC
BMY_HDACX_V2  (3392)  --------------------------------------------------
    HDAC9V1   (3187)  --------------------------------------------------
    HDAC9V2   (2791)  --------------------------------------------------
    HDAC9V3   (3778)  CATCTCATAAATATTCATTTTCTTCAAAGTCTTTTTTCAATCTCATAAAA
  CONSENSUS   (3951)
                      4001                                               4050
BMY_HDACX_V1  (2828)  GTAATTCCACCCAGAATGTAATGTTTCTTGTTTGTTTGTTTTGTTTTGTT
BMY_HDACX_V2  (3392)  --------------------------------------------------
    HDAC9V1   (3187)  --------------------------------------------------
    HDAC9V2   (2791)  --------------------------------------------------
    HDAC9V3   (3828)  AAGGGATAGTGCATCTTTTAAAATACATTTTATTTGGGGAGGAACATGTG
  CONSENSUS   (4001)
                      4051                                               4100
BMY_HDACX_V1  (2878)  AGGGTTTTTTTCTCAACTTTAACACACAGTTCAACTGTTCCTAGTAAAAG
BMY_HDACX_V2  (3392)  --------------------------------------------------
    HDAC9V1   (3187)  --------------------------------------------------
    HDAC9V2   (2791)  --------------------------------------------------
    HDAC9V3   (3878)  GCTGAGCAGACTTTTGTATAATATTACTTCAAAGATATGTAATCACAAAC
  CONSENSUS   (4051)
                      4101                                               4150
BMY_HDACX_V1  (2928)  TTCAAGATGGAGGAACTAGCATGAGGCTTTTTTCAGTATCTCGAAGTCCA
BMY_HDACX_V2  (3392)  --------------------------------------------------
    HDAC9V1   (3187)  --------------------------------------------------
    HDAC9V2   (2791)  --------------------------------------------------
    HDAC9V3   (3928)  AAAAAAAACTATTTTTTATAATGTCATTTGAGAGAGTTTCATCAGTACAG
  CONSENSUS   (4101)
                      4151                                               4200
BMY_HDACX_V1  (2978)  AATGCCAAAGGAACCTCACACACTGTTTGTAATGGTGCAATATTTTATAT
BMY_HDACX_V2  (3392)  --------------------------------------------------
    HDAC9V1   (3187)  --------------------------------------------------
    HDAC9V2   (2791)  --------------------------------------------------
    HDAC9V3   (3978)  TTGGTGGACGTTAATTGTTTGAATTTGATAGTCTTTGAATTTAATCAAGA
  CONSENSUS   (4151)
                      4201                                               4250
BMY_HDACX_V1  (3028)  CACTTTTTTTTAAACATCCCCAACATCTTTGTGTTCTCACACACAGGCAA
BMY_HDACX_V2  (3392)  --------------------------------------------------
    HDAC9V1   (3187)  --------------------------------------------------
    HDAC9V2   (2791)  --------------------------------------------------
    HDAC9V3   (4028)  AACTACCTGGAACCAGTGAAAAGGAAAGCTGGACTTAAATAATCTTAGAA
  CONSENSUS   (4201)
                      4251                                               4300
BMY_HDACX_V1  (3078)  TTTGCAATGTTGCAATTGTGTTGGAGAATGAAGTCCCCCCACCTCCCAGC
BMY_HDACX_V2  (3392)  --------------------------------------------------
    HDAC9V1   (3187)  --------------------------------------------------
    HDAC9V2   (2791)  --------------------------------------------------
    HDAC9V3   (4078)  TTAATTGATAAATGTCTCTTTTAAAATCTACTGTATTTATTATAATTTAC
  CONSENSUS   (4251)
                      4301                                               4350
BMY_HDACX_V1  (3128)  CACACACACATCCTTTGTTCTCATGACAGTAGGTCTGAGCAAATGTTCCA
BMY_HDACX_V2  (3392)  --------------------------------------------------
    HDAC9V1   (3187)  --------------------------------------------------
    HDAC9V2   (2791)  --------------------------------------------------
    HDAC9V3   (4128)  ACCCTTGAAGGTGATCTCTTGTTTTGTGTTGTAAATATATTGTTTGTATG
  CONSENSUS   (4301)
                      4351                                               4400
BMY_HDACX_V1  (3178)  CCAAGCATTTTCAGTGTCTTTGAAAAGCACGTAACTTTTCAAAGGTGGTC
BMY_HDACX_V2  (3392)  --------------------------------------------------
    HDAC9V1   (3187)  --------------------------------------------------
    HDAC9V2   (2791)  --------------------------------------------------
    HDAC9V3   (4178)  TTTCCCTTCTTGCCTTCTGTTATAAGTCTCTTCCTTTCTCAAATAAAGTT
  CONSENSUS   (4351)
```

FIG. 23K

```
                        4401                                              4450
BMY_HDACX_V1    (3228)  TTAATTTGCTGCATATCTATCAAGGACTTATTCACTCACCTTTCCTTTTC
BMY_HDACX_V2    (3392)  --------------------------------------------------
     HDAC9V1    (3187)  --------------------------------------------------
     HDAC9V2    (2791)  --------------------------------------------------
     HDAC9V3    (4228)  TTTTTTAAAAG---------------------------------------
   CONSENSUS    (4401)
                        4451                                              4500
BMY_HDACX_V1    (3278)  TGCCCTCTATCAATTGATTTCTTCTTACCTTTCATCATTCATTCCTTCCT
BMY_HDACX_V2    (3392)  --------------------------------------------------
     HDAC9V1    (3187)  --------------------------------------------------
     HDAC9V2    (2791)  --------------------------------------------------
     HDAC9V3    (4239)  --------------------------------------------------
   CONSENSUS    (4451)
                        4501                                              4550
BMY_HDACX_V1    (3328)  TTAGAAAAACTGAAGATTACCCATAATCTCCTCTTATTACTTGAGGGCCT
BMY_HDACX_V2    (3392)  --------------------------------------------------
     HDAC9V1    (3187)  --------------------------------------------------
     HDAC9V2    (2791)  --------------------------------------------------
     HDAC9V3    (4239)  --------------------------------------------------
   CONSENSUS    (4501)
                        4551                                              4600
BMY_HDACX_V1    (3378)  TGACTATTTAGTTTATTTTGTTTACTTTACAGGTTAACACAGTTGTTTTG
BMY_HDACX_V2    (3392)  --------------------------------------------------
     HDAC9V1    (3187)  --------------------------------------------------
     HDAC9V2    (2791)  --------------------------------------------------
     HDAC9V3    (4239)  --------------------------------------------------
   CONSENSUS    (4551)
                        4601                                              4650
BMY_HDACX_V1    (3428)  TCTGATTGCATTTTATTAACTGTGAAGCCGTTGAAATGAATATCACTTAA
BMY_HDACX_V2    (3392)  --------------------------------------------------
     HDAC9V1    (3187)  --------------------------------------------------
     HDAC9V2    (2791)  --------------------------------------------------
     HDAC9V3    (4239)  --------------------------------------------------
   CONSENSUS    (4601)
                        4651                                              4700
BMY_HDACX_V1    (3478)  GCAACGTTGCTAAATTTCTATGTGTTTGAAATGTGTTAATGAAGGCACTG
BMY_HDACX_V2    (3392)  --------------------------------------------------
     HDAC9V1    (3187)  --------------------------------------------------
     HDAC9V2    (2791)  --------------------------------------------------
     HDAC9V3    (4239)  --------------------------------------------------
   CONSENSUS    (4651)
                        4701                                              4750
BMY_HDACX_V1    (3528)  CTTATTTGTAGTCACCTTGAACTGACTTAACCTAGAAGCTGTGCCTTCTT
BMY_HDACX_V2    (3392)  --------------------------------------------------
     HDAC9V1    (3187)  --------------------------------------------------
     HDAC9V2    (2791)  --------------------------------------------------
     HDAC9V3    (4239)  --------------------------------------------------
   CONSENSUS    (4701)
                        4751                                              4800
BMY_HDACX_V1    (3578)  GTGAAAAAAAAAAAAAAAAAAAAAAAAAAAAAAAAAAAAAAAAAAAAAAA
BMY_HDACX_V2    (3392)  --------------------------------------------------
     HDAC9V1    (3187)  --------------------------------------------------
     HDAC9V2    (2791)  --------------------------------------------------
     HDAC9V3    (4239)  --------------------------------------------------
   CONSENSUS    (4751)
                        4801           4823
BMY_HDACX_V1    (3628)  AAAAAAAAAAAAAAAAAAAAAAA
BMY_HDACX_V2    (3392)  -----------------------
     HDAC9V1    (3187)  -----------------------
     HDAC9V2    (2791)  -----------------------
     HDAC9V3    (4239)  -----------------------
   CONSENSUS    (4801)
```

FIG. 24A

```
                          1                                                 50
      HDAC9V2      (1) ------------------------MHSMISSVDVKSEVPVGLEPIS---P
      HDAC9V1      (1) ------------------------MHSMISSVDVKSEVPVGLEPIS---P
      HDAC9V3      (1) ------------------------MHSMISSVDVKSEVPVGLEPIS---P
   BMY_HDACX_V1    (1) --------------------------------------------------
   BMY_HDACX_V2    (1) ------------------------MHSMISSVDVKSEVPVGLEPIS---P
         HDA5      (1) MNSPNESDGMSGREPSLEILPRTSLHSIPVTVEVKPVLPRAMPSSMGGGG
         HDA4      (1) MSSQSHPDGLSGRDQPVELLNPARVNHMPSTVDVATALPLQVAPSA--VP
     CONSENSUS     (1) M S   DGLSGRD  LEIL      M  M  SVDV    VP L       GG
                         51                                               100
      HDAC9V2     (24) LDLRTDLRMMMP---VVDPVVREKQLQQELLLIQQQQQIQKQLLIAEFQK
      HDAC9V1     (24) LDLRTDLRMMMP---VVDPVVREKQLQQELLLIQQQQQIQKQLLIAEFQK
      HDAC9V3     (24) LDLRTDLRMMMP---VVDPVVREKQLQQELLLIQQQQQIQKQLLIAEFQK
   BMY_HDACX_V1    (1) --------------------------------------------------
   BMY_HDACX_V2   (24) LDLRTDLRMMMP---VVDPVVREKQLQQELLLIQQQQQIQKQLLIAEFQK
         HDA5     (51) GGSPSPVELRGALVGSVDPTLREQQLQQELLALKQQQQLQKQLLFAEFQK
         HDA4     (49) MDLRLDHQFSLP---VAEPALREQQLQQELLALKQKQQIQRQILIAEFQR
     CONSENSUS    (51)              LVG   DP  VRE QLQQELL I Q QQIQKQLL AEFQK
                        101                                               150
      HDAC9V2     (71) QHENLTRQHQAQLQEHIK---ELLAIKQQQELLEKEQK--LEQQRQEQ--
      HDAC9V1     (71) QHENLTRQHQAQLQEHIK---ELLAIKQQQELLEKEQK--LEQQRQEQ--
      HDAC9V3     (71) QHENLTRQHQAQLQEHIK---ELLAIKQQQELLEKEQK--LEQQRQEQ--
   BMY_HDACX_V1    (1) --------------------------------------------------
   BMY_HDACX_V2   (71) QHENLTRQHQAQLQEHIKLQQELLAIKQQQELLEKEQK--LEQQRQEQ--
         HDA5    (101) QHDHLTRQHEVQLQKHLQQQEMLAAKQQQEMLAAKRQQELEQQRQREQQ
         HDA4     (96) QHEQLSRQHEAQLHEHIKQQQEMLAMKHQQELLEHQRK--LERHRQEQ--
     CONSENSUS   (101) QHE LTRQH  QL  HIK QQELLA K QQELL      QELE  RQ  QQ
                        151                                               200
      HDAC9V2    (114) ---EVERHRREQQLPPLRGKDRGRERAVASTEVKQKLQEFLLSKSATKDT
      HDAC9V1    (114) ---EVERHRREQQLPPLRGKDRGRERAVASTEVKQKLQEFLLSKSATKDT
      HDAC9V3    (114) ---EVERHRREQQLPPLRGKDRGRERAVASTEVKQKLQEFLLSKSATKDT
   BMY_HDACX_V1    (1) --------------------------------------------------
   BMY_HDACX_V2  (117) ---EVERHRREQQLPPLRGKDRGRERAVASTEVKQKLQEFLLSKSATKDT
         HDA5    (151) RQEELEKQRLEQQLLILRNKEKSKESAIASTEVKLRLQEFLLSKSKEPTP
         HDA4    (142) ---ELEKQHREQKLQQLKNKEKGKESAVASTEVKMKLQEFVLNKKKALAH
     CONSENSUS   (151)    RQEEVER    EQ L  LR KDR RE AVASTEVK KLQEFLL K
                        201                                               250
      HDAC9V2    (161) PTNGKNHSVSRHPKLWYTAAHHTSLDQSSPPLS---GTSPSYKYTLPGAQ
      HDAC9V1    (161) PTNGKNHSVSRHPKLWYTAAHHTSLDQSSPPLS---GTSPSYKYTLPGAQ
      HDAC9V3    (161) PTNGKNHSVSRHPKLWYTAAHHTSLDQSSPPLS---GTSPSYKYTLPGAQ
   BMY_HDACX_V1    (1) --------------------------------------------------
   BMY_HDACX_V2  (164) PTNGKNHSVSRHPKLWYTAAHHTSLDQSSPPLS---GTSPSYKYTLPGAQ
         HDA5    (201) GG--LNHSLPQHPKCW-G-AHHASLDQSSPPQSGPPGTPPSYKLPLPGPY
         HDA4    (189) RN--LNHCISSDPRYWYGKTQHSSLDQSSPPQS---GVSTSYNHPVLGMY
     CONSENSUS   (201)     NG NH  V  PK WY     H SLDQSSPP  SGPPG    SY  L G
                        251                                               300
      HDAC9V2    (208) DAKDDFPLRKTASEPNLKVRSRLKQKVAERRSSPLLRRKDGNVVTSFKKR
      HDAC9V1    (208) DAKDDFPLRKTASEPNLKVRSRLKQKVAERRSSPLLRRKDGNVVTSFKKR
      HDAC9V3    (208) DAKDDFPLRKTASEPNLKVRSRLKQKVAERRSSPLLRRKDGNVVTSFKKR
   BMY_HDACX_V1    (1) --------------------------------------------------
   BMY_HDACX_V2  (211) DAKDDFPLRKTASEPNLKVRSRLKQKVAERRSSPLLRRKDGNVVTSFKKR
         HDA5    (247) DSRDDFPLRKTASEPNLKVRSRLKQKVAERRSSPLLRRKDGTVISTFKKR
         HDA4    (234) DAKDDFPLRKTASEPNLKLRSRLKQKVAERRSSPLLRRKDGPVVTALKKR
     CONSENSUS   (251) DAKDDFPLRKTASEPNLKVRSRLKQKVAERRSSPLLRRKDG  VVT  KKR
                        301                                               350
      HDAC9V2    (258) MFEVT-----ESSVSSSPGSGPSSPNNGPTGSVTENETSVLPPTPHAEQ
      HDAC9V1    (258) MFEVT-----ESSVSSSPGSGPSSPNNGPTGSVTENETSVLPPTPHAEQ
      HDAC9V3    (258) MFEVT-----ESSVSSSPGSGPSSPNNGPTGSVTENETSVLPPTPHAEQ
   BMY_HDACX_V1    (1) ------------------------------AENETSVLPPTPHAEQ
   BMY_HDACX_V2  (261) MFEVT-----ESSVSSSPGSGPSSPNNGPTGSVTENETSVLPPTPHAEQ
         HDA5    (297) AVEITGAGPGASSVCNSAPGSGPSSPN-SSHSTIANGFTGSVPNIPTEM
         HDA4    (284) PLDVT------DSACSSAPGSGPSSPNNSSGSVSAENGIAPAVPSIPAET
     CONSENSUS   (301)  EVTGAGPG  S   SSPGSGPSSPNN             EN      P    E
```

FIG. 24B

```
                  351                                                  400
HDAC9V2    (303) MVSQQRILIHEDSMNLLSLYTSPSLPNITLGLPAVPSQLNASNSLK----
HDAC9V1    (303) MVSQQRILIHEDSMNLLSLYTSPSLPNITLGLPAVPSQLNASNSLK----
HDAC9V3    (303) MVSQQRILIHEDSMNLLSLYTSPSLPNITLGLPAVPSQLNASNSLK----
BMY_HDACX_V1 (17) MVSQQRILIHEDSMNLLSLYTSPSLPNITLGLPAVPSQLNASNSLK----
BMY_HDACX_V2 (306) MVSQQRILIHEDSMNLLSLYTSPSLPNITLGLPAVPSQLNASNSLK----
HDA5       (346) LPQHRALPLDSSPNQFSLYTSPSLPNISLGLQATVTVTNSHLTASPKLST
HDA4       (328) SLAHRLVAREGSAAPLPLYTSPSLPNITLGLPATGPSAGTAG--------
CONSENSUS  (351)          I        T                 S         KLST
                  401                                                  450
HDAC9V2    (349) --EKQKCETQTLRQGVPLPGQYGGSIPASSSHPHVTLEGKPPNSSHQALL
HDAC9V1    (349) --EKQKCETQTLRQGVPLPGQYGGSIPASSSHPHVTLEGKPPNSSHQALL
HDAC9V3    (349) --EKQKCETQTLRQGVPLPGQYGGSIPASSSHPHVTLEGKPPNSSHQALL
BMY_HDACX_V1 (63) --EKQKCETQTLRQGVPLPGQYGGSIPASSSHPHVTLEGKPPNSSHQALL
BMY_HDACX_V2 (352) --EKQKCETQTLRQGVPLPGQYGGSIPASSSHPHVTLEGKPPNSSHQALL
HDA5       (396) QQEAERQALQSLRQGGTLTGKFMSTSSIPGCLLGVALEGDGSPHGHASLL
HDA4       (370) QQDTERLTLPALQQR-----LSLFPGTHLTPYLSTSPLERDGGAAHSPLL
CONSENSUS  (401) QQE  K   LQ    LG                             H LL
                  451                                                  500
HDAC9V2    (397) QHLLLKEQMRQQKLLV--AGGVPLHPQSPLATKERISPGIRGTHKLPRHR
HDAC9V1    (397) QHLLLKEQMRQQKLLV--AGGVPLHPQSPLATKERISPGIRGTHKLPRHR
HDAC9V3    (397) QHLLLKEQMRQQKLLV--AGGVPLHPQSPLATKERISPGIRGTHKLPRHR
BMY_HDACX_V1 (111) QHLLLKEQMRQQKLLV--AGGVPLHPQSPLATKERISPGIRGTHKLPRHR
BMY_HDACX_V2 (400) QHLLLKEQMRQQKLLV--AGGVPLHPQSPLATKERISPGIRGTHKLPRHR
HDA5       (446) QHVLLLEQARQQSTLI----AVPLHGQSPLVTGERVATSMRTVGKLPRHR
HDA4       (415) QHMVLLEQPPAQAPLVTGLGALPLHAQS-LVGADRVSPSI---HKLRQHR
CONSENSUS  (451) QHLLL EQ  Q   LVTG GGVPLH QSPL   ERIS  IR  KL  HR
                  501                                                  550
HDAC9V2    (445) PLNRTQSAPLPQS--TLAQLVIQQQHQQFLEKQKQ-Y-QQQIHMNKLLSK
HDAC9V1    (445) PLNRTQSAPLPQS--TLAQLVIQQQHQQFLEKQKQ-Y-QQQIHMNKLLSK
HDAC9V3    (445) PLNRTQSAPLPQS--TLAQLVIQQQHQQFLEKQKQ-Y-QQQIHMNKLLSK
BMY_HDACX_V1 (159) PLNRTQSAPLPQS--TLAQLVIQQQHQQFLEKQKQ-Y-QQQIHMNKLLSK
BMY_HDACX_V2 (448) PLNRTQSAPLPQS--TLAQLVIQQQHQQFLEKQKQ-Y-QQQIHMNKELPM
HDA5       (492) PLSRTQSSPLPQSPQALQQLVMQQQHQQFLEKQKQ----QQLQLGKILTK
HDA4       (461) PLGRTQSAPLPQNAQALQHLVIQQQHQQFLEKHKQFQQQQLQMNKIIPK
CONSENSUS  (501) PL RTQSAPLPQ  Q L LVIQQQHQQFLEK KQQYQQQQI M K L
                  551                                                  600
HDAC9V2    (491) SIEQLKQPGSHLEEAEEELQGDQAMQEDRAPSSGNSTRSDSSACVDDTLG
HDAC9V1    (491) SIEQLKQPGSHLEEAEEELQGDQAMQEDRAPSSGNSTRSDSSACVDDTLG
HDAC9V3    (491) SIEQLKQPGSHLEEAEEELQGDQAMQEDRAPSSGNSTRSDSSACVDDTLG
BMY_HDACX_V1 (205) SIEQLKQPGSHLEEAEEELQGDQAMQEDRAPSSGNSTRSDSSACVDDTLG
BMY_HDACX_V2 (494) TP------------------------------------------------
HDA5       (538) TGELPRQPTTHPEETEEELTEQQEVLLGEGALTMPREGSTESESTQEDLE
HDA4       (511) PSEPARQPESHPEETEEELREHQ-ALLDEPYLDRLPGQKEAHAQAGVQVK
CONSENSUS  (551)   E  KQP SH EE EEEL  Q                             L
                  601                                                  650
HDAC9V2    (541) QVGAVKVKEEP-------VDSDEDAQIQEMESGEQAAFMQQPFLEPTHTR
HDAC9V1    (541) QVGAVKVKEEP-------VDSDEDAQIQEMESGEQAAFMQQPFLEPTHTR
HDAC9V3    (541) QVGAVKVKEEP-------VDSDEDAQIQEMESGEQAAFMQQVIGKDLAPG
BMY_HDACX_V1 (255) QVGAVKVKEEP-------VDSDEDAQIQEMESGEQAAFMQQPFLEPTHTR
BMY_HDACX_V2 (496) --------------------------------------------------
HDA5       (588) EEDEEEDGEEEEDCIQVKDEEGESGAEEGPDLEEPGAGYKKLF-SDAQPL
HDA4       (560) QEPIESDEEEAE-------PPREVEPGQRQPSEQELLFRQQALLLEQQRI
CONSENSUS  (601)                    EE EDCIQVK     E
                  651                                                  700
HDAC9V2    (584) ALSVR-QAPLAAVGMD-GLEKHRLVSRTHSSPAASVLPHPAMDRPLQPGS
HDAC9V1    (584) ALSVR-QAPLAAVGMD-GLEKHRLVSRTHSSPAASVLPHPAMDRPLQPGS
HDAC9V3    (584) FVIKVII-------------------------------------------
BMY_HDACX_V1 (298) ALSVR-QAPLAAVGMD-GLEKHRLVSRTHSSPAASVLPHPAMDRPLQPGS
BMY_HDACX_V2 (496) --------------------------------------------------
HDA5       (637) QPLQVYQAPLSLATVP-----HQALGRTQSSPAAPGGMKSPPDQPVKHLF
HDA4       (603) HQLRNYQASMEAAGIPVSFGGHRPLSRAQSSPASATFPVSVQEPPTKPRF
CONSENSUS  (651)       AL   M   H  V R  SSPAA        D P
```

FIG. 24C

```
               701                                                750
HDAC9V2   (632) ATGIAYDPLMLKHQCVCGNSTTHPEHAGRIQSIWSRLQETGLLNKCERIQ
HDAC9V1   (632) ATGIAYDPLMLKHQCVCGNSTTHPEHAGRIQSIWSRLQETGLLNKCERIQ
HDAC9V3   (591) --------------------------------------------------
BMY_HDACX_V1 (346) ATGIAYDPLMLKHQCVCGNSTTHPEHAGRIQSIWSRLQETGLLNKCERIQ
BMY_HDACX_V2 (496) --------------------------------------------------
HDA5      (682) TTGVVYDTFMLKHQCMCGNTHVHPEHAGRIQSIWSRLQETGLLSKCERIR
HDA4      (653) TTGLVYDTLMLKHQCTCGSSSSHPEHAGRIQSIWSRLQETGLRGKCECIR
CONSENSUS (701) TGI YD MLKHQC CG S HPEHAGRIQSIWSRLQETGL KCE I
                <--      HISTONE DEACETYLASE MOTIF (PF00850)    -->

751                                                800
HDAC9V2   (682) GRKASLEEIQLVHSEHHSLLYGTNPLDGQKLDPRILLGDDSQKFFSSLPC
HDAC9V1   (682) GRKASLEEIQLVHSEHHSLLYGTNPLDGQKLDPRILLGDDSQKFFSSLPC
HDAC9V3   (591) --------------------------------------------------
BMY_HDACX_V1 (396) GRKASLEEIQLVHSEHHSLLYGTNPLDGQKLDPRILLGDDSQKFFSSLPC
BMY_HDACX_V2 (496) --------------------------------------------------
HDA5      (732) GRKATLDEIQTVHSEYHTLLYGTSPLNRQKLDSKKLLGPISQKMYAVLPC
HDA4      (703) GRKATLEELQTVHSEAHTLLYGTNPLNRQKLDSKKLLG-SLASVFVRLPC
CONSENSUS (751) GRKASLEEIQ VHSE HSLLYGT PL QKLD R LLG       F LPC
                <--      HISTONE DEACETYLASE MOTIF (PF00850)    -->

801                                                850
HDAC9V2   (732) GGLGVDSDTIWNELHSSGAARMAVGCVIELASKVASGELKNGFAVVRPPG
HDAC9V1   (732) GGLGVDSDTIWNELHSSGAARMAVGCVIELASKVASGELKNGFAVVRPPG
HDAC9V3   (591) --------------------------------------------------
BMY_HDACX_V1 (446) GGLGVDSDTIWNELHSSGAARMAVGCVIELASKVASGELKNGFAVVRPPG
BMY_HDACX_V2 (496) --------------------------------------------------
HDA5      (782) GGIGVDSDTVWNEMHSSSAVRMAVGCLLELAFKVAAGELKNGFAIIRPPG
HDA4      (752) GGVGVDSDTIWNEVHSAGAARLAVGCVVELVFKVATGELKNGFAVVRPPG
CONSENSUS (801) GGLGVDSDTIWNELHSS A RMAVGCVIEL KVA GELKNGFAVVRPPG
                <--      HISTONE DEACETYLASE MOTIF (PF00850)    -->

851                                                900
HDAC9V2   (782) HHAEESTAMGFCFFNSVAITAKYLRDQLNISKILIVDLDVHHGNGTQQAF
HDAC9V1   (782) HHAEESTAMGFCFFNSVAITAKYLRDQLNISKILIVDLDVHHGNGTQQAF
HDAC9V3   (591) --------------------------------------------------
BMY_HDACX_V1 (496) HHAEESTAMGFCFFNSVAITAKYLRDQLNISKILIVDLDVHHGNGTQQAF
BMY_HDACX_V2 (496) --------------------------------------------------
HDA5      (832) HHAEESTAMGFCFFNSVAITAKLLQQKLNVGKVLIVDWDIHHGNGTQQAF
HDA4      (802) HHAEESTPMGFCYFNSVAVAAKLLQQRLSVSKILIVDWDVHHGNGTQQAF
CONSENSUS (851) HHAEEST MGFCFFNSVAI AK L  L I KILIVD DVHHGNGTQQAF
                <--      HISTONE DEACETYLASE MOTIF (PF00850)    -->

901                                                950
HDAC9V2   (832) YADPSILYISLHRYDEGNFFPGSGAPNEVRFISLEPHFYLYLSGNCIA--
HDAC9V1   (832) YADPSILYISLHRYDEGNFFPGSGAPNEVGTGLGEGYNINIAWTGGLDPP
HDAC9V3   (591) --------------------------------------------------
BMY_HDACX_V1 (546) YADPSILYISLHRYDEGNFFPGSGAPNEVGTGLGEGYNINIAWTGGLDPP
BMY_HDACX_V2 (496) --------------------------------------------------
HDA5      (882) YNDPSVLYISLHRYDNGNFFPGSGAPEEVGGGPGVGYNVNVAWTGGVDPP
HDA4      (852) YSDPSVLYMSLHRYDDGNFFPGSGAPDEVGTGPGVGFNVNMAFTGGLDPP
CONSENSUS (901) Y DPSILYISLHRYD GNFFPGSGAP EV              L PP
                <--      HISTONE DEACETYLASE MOTIF (PF00850)    -->

951                                                1000
HDAC9V2   (880) --------------------------------------------------
HDAC9V1   (882) MGDVEYLEAFRTIVKPVAKEFDPDMVLVSAGFDALEGHTPPLGGYKVTAK
HDAC9V3   (591) --------------------------------------------------
BMY_HDACX_V1 (596) MGDVEYLEAFRTIVKPVAKEFDPDMVLVSAGFDALEGHTPPLGGYKVTAK
BMY_HDACX_V2 (496) --------------------------------------------------
HDA5      (932) IGDVEYLTAFRTVVMPIAHEFSPDVVLVSAGFDAVEGHLSPLGGYSVTAR
HDA4      (902) MGDAEYLAAFRTVVMPIASEFAPDVVLVSSGFDAVEGHPTPLGGYNLSAR
CONSENSUS (951) MGD EYL AFRTIV PIA EF PDMVLVSAGFDALEGH  PLGGY VTAK
                <--      HISTONE DEACETYLASE MOTIF (PF00850)    -->
```

FIG. 24D

```
                  1001                                              1050
   HDAC9V2  (880) --------------------------------------------------
   HDAC9V1  (932) CFGHLTKQLMTLADGRVVLALEGGHDLTAICDASEACVNALLGNELEPLA
   HDAC9V3  (591) --------------------------------------------------
BMY_HDACX_V1 (646) CFGHLTKQLMTLADGRVVLALEGGHDLTAICDASEACVNALLGNELEPLA
BMY_HDACX_V2 (496) --------------------------------------------------
      HDA5  (982) CFGHLTRQLMTLAGGRVVLALEGGHDLTAICDASEACVSALLSVELQPLD
      HDA4  (952) CFGYLTKQLMGLAGGRIVLALEGGHDLTAICDASEACVSALLGNELDPLP
 CONSENSUS (1001) CFGHLTKQLM LA GRVVLALEGGHDLTAICDASEACV ALL  EL PL
                  <--     HISTONE DEACETYLASE MOTIF (PF00850)  -->

1051                                              1100
   HDAC9V2  (880) --------------------------------------------------
   HDAC9V1  (982) EDILHQSPNMNAVISLQKIIEIQSMSLKFS--------------------
   HDAC9V3  (591) --------------------------------------------------
BMY_HDACX_V1 (696) EDILHQSPNMNAVISLQKIIEIQSKYWKSVRMVAVPRGCAL--AGAQLQE
BMY_HDACX_V2 (496) --------------------------------------------------
      HDA5 (1032) EAVLQQKPNINAVATLEKVIEIQSKHWSCVQKFAAGLGRSLREAQAGETE
      HDA4 (1002) EKVLQQRPNANAVRSMEKVMEIHSKYWRCLQRTTSTAGRSLIEAQTCENE
 CONSENSUS (1051) E IL Q PN NAV SL KIIEI S            G SL EA       E
                  1101                     1141
   HDAC9V2  (880) ----------------------------------------
   HDAC9V1 (1012) ----------------------------------------
   HDAC9V3  (591) ----------------------------------------
BMY_HDACX_V1 (744) ETETVSAL----ASLTVDVEQPFAQEDSRTAGEPMEEEPAL
BMY_HDACX_V2 (496) ----------------------------------------
      HDA5 (1082) EAETVSAMALLSVGAEQAQAAAAREHSPRPAEEPMEQEPAL
      HDA4 (1052) EAETVTAMASLSVGKPAEK----RP----DEEPMEEEPPL
 CONSENSUS (1101) E ETVSAMA LS           R      EPME EP L
```

FIG. 25A

```
BMY_HDAL1    ------------------------------------------------------------
BMY_HDAL2    ------------------------------------------------------------
BMY_HDAL3    ------------------------------------------------------------
HDAC9C       MHSMISSVDVKSEVPVGLEPISPLDLRTDLRMMMPVVDPVVREKQLQQELLLIQQQQQIQ
HDACX_V1     ------------------------------------------------------------
HDACX_V2     MHSMISSVDVKSEVPVGLEPISPLDLRTDLRMMMPVVDPVVREKQLQQELLLIQQQQQIQ

BMY_HDAL1    ------------------------------------------------------------
BMY_HDAL2    ------------------------------------------------------------
BMY_HDAL3    ------------------------------------------------------------
HDAC9C       KQLLIAEFQKQHENLTRQHQAQLQEHIKLQQELLAIKQQQELLEKEQKLEQQRQEQEVER
HDACX_V1     ------------------------------------------------------------
HDACX_V2     KQLLIAEFQKQHENLTRQHQAQLQEHIKLQQELLAIKQQQELLEKEQKLEQQRQEQEVER

BMY_HDAL1    ------------------------------------------------------------
BMY_HDAL2    ------------------------------------------------------------
BMY_HDAL3    ------------------------------------------------------------
HDAC9C       HRREQQLPPLRGKDRGRERAVASTEVKQKLQEFLLSKSATKDTPTNGKNHSVSRHPKLWY
HDACX_V1     ------------------------------------------------------------
HDACX_V2     HRREQQLPPLRGKDRGRERAVASTEVKQKLQEFLLSKSATKDTPTNGKNHSVSRHPKLWY

BMY_HDAL1    ------------------------------------------------------------
BMY_HDAL2    ------------------------------------------------------------
BMY_HDAL3    ------------------------------------------------------------
HDAC9C       TAAHHTSLDQSSPPLSGTSPSYKYTLPGAQDAKDDFPLRKTASEPNLKVRSRLKQKVAER
HDACX_V1     ------------------------------------------------------------
HDACX_V2     TAAHHTSLDQSSPPLSGTSPSYKYTLPGAQDAKDDFPLRKTASEPNLKVRSRLKQKVAER

BMY_HDAL1    ------------------------------------------------------------
BMY_HDAL2    ------------------------------------------------------------
BMY_HDAL3    ------------------------------------------------------------
HDAC9C       RSSPLLRRKDGNVVTSFKKRMFEVTESSVSSSSPGSGPSSPNNGPTGSVTENETSVLPPT
HDACX_V1     ---------------------------------------------AENETSVLPPT
HDACX_V2     RSSPLLRRKDGNVVTSFKKRMFEVTESSVSSSSPGSGPSSPNNGPTGSVTENETSVLPPT

BMY_HDAL1    ------------------------------------------------------------
BMY_HDAL2    ------------------------------------------------------------
BMY_HDAL3    ------------------------------------------------------------
HDAC9C       PHAEQMVSQQRILIHEDSMNLLSLYTSPSLPNITLGLPAVPSQLNASNSLKEKQKCETQT
HDACX_V1     PHAEQMVSQQRILIHEDSMNLLSLYTSPSLPNITLGLPAVPSQLNASNSLKEKQKCETQT
HDACX_V2     PHAEQMVSQQRILIHEDSMNLLSLYTSPSLPNITLGLPAVPSQLNASNSLKEKQKCETQT

BMY_HDAL1    ------------------------------------------------------------
BMY_HDAL2    ------------------------------------------------------------
BMY_HDAL3    ------------------------------------------------------------
HDAC9C       LRQGVPLPGQYGGSIPASSSHPHVTLEGKPPNSSHQALLQHLLLKEQMRQQKLLVAGGVP
HDACX_V1     LRQGVPLPGQYGGSIPASSSHPHVTLEGKPPNSSHQALLQHLLLKEQMRQQKLLVAGGVP
HDACX_V2     LRQGVPLPGQYGGSIPASSSHPHVTLEGKPPNSSHQALLQHLLLKEQMRQQKLLVAGGVP
```

FIG. 25B

```
BMY_HDAL1    ------------------------------------------------------------
BMY_HDAL2    ------------------------------------------------------------
BMY_HDAL3    ------------------------------------------------------------
HDAC9C       LHPQSPLATKERISPGIRGTHKLPRHRPLNRTQSAPLPQSTLAQLVIQQHQQFLEKQKQ
HDACX_V1     LHPQSPLATKERISPGIRGTHKLPRHRPLNRTQSAPLPQSTLAQLVIQQHQQFLEKQKQ
HDACX_V2     LHPQSPLATKERISPGIRGTHKLPRHRPLNRTQSAPLPQSTLAQLVIQQHQQFLEKQKQ

BMY_HDAL1    ------------------------------------------------------------
BMY_HDAL2    ------------------------------------------------------------
BMY_HDAL3    ------------------------------------------------------------
HDAC9C       YQQQIHMNKLLSKSIEQLKQPGSHLEEAEEELQGDQAMQEDRAPSSGNSTRSDSSACVDD
HDACX_V1     YQQQIHMNKLLSKSIEQLKQPGSHLEEAEEELQGDQAMQEDRAPSSGNSTRSDSSACVDD
HDACX_V2     YQQQIHMNKELPMTP---------------------------------------------

BMY_HDAL1    ------------------------------------------------------------
BMY_HDAL2    ------------------------------------------------------------
BMY_HDAL3    ------------------------------------------------------------
HDAC9C       TLGQVGAVKVKEEPVDSDEDAQIQEMESGEQAAFMQQPFLEPTHTRALSVRQAPLAAVGM
HDACX_V1     TLGQVGAVKVKEEPVDSDEDAQIQEMESGEQAAFMQQPFLEPTHTRALSVRQAPLAAVGM
HDACX_V2     ------------------------------------------------------------

BMY_HDAL1    -------------------------------GIAYDPLMLKHQCVCGNSTTHPEH
BMY_HDAL2    ------------------------------------------------------------
BMY_HDAL3    ------------------------------------------------------------
HDAC9C       DGLEKHRLVSRTHSSPAASVLPHPAMDRPLQPGSATGIAYDPLMLKHQCVCGNSTTHPEH
HDACX_V1     DGLEKHRLVSRTHSSPAASVLPHPAMDRPLQPGSATGIAYDPLMLKHQCVCGNSTTHPEH
HDACX_V2     ------------------------------------------------------------

BMY_HDAL1    AGRIQSIWSRLQETGLLNKCERIQGRKASLEEIQLVHSEHHSLLYGTNPLDGQKLDPRIL
BMY_HDAL2    ------------------------------------------------------------
BMY_HDAL3    ------------------------------------------------------------
HDAC9C       AGRIQSIWSRLQETGLLNKCERIQGRKASLEEIQLVHSEHHSLLYGTNPLDGQKLDPRIL
HDACX_V1     AGRIQSIWSRLQETGLLNKCERIQGRKASLEEIQLVHSEHHSLLYGTNPLDGQKLDPRIL
HDACX_V2     ------------------------------------------------------------

BMY_HDAL1    LGDDSQKFFSSLPCGGLGVST---------------------------------------
BMY_HDAL2    -----------------VDSDTIWNELHSSGAARMAVGCVIELASKVASGELKNGFAVV
BMY_HDAL3    ------------------------------------------------------------
HDAC9C       LGDDSQKFFSSLPCGGLGVDSDTIWNELHSSGAARMAVGCVIELASKVASGELKNGFAVV
HDACX_V1     LGDDSQKFFSSLPCGGLGVDSDTIWNELHSSGAARMAVGCVIELASKVASGELKNGFAVV
HDACX_V2     ------------------------------------------------------------

BMY_HDAL1    ------------------------------------------------------------
BMY_HDAL2    RPPGHHAEESTAMGFCFFNSVAITAKYLRDQLNISKILIVDLDVHHGNTQQAFYADPSI
BMY_HDAL3    ------------------------------------------------------------
HDAC9C       RPPGHHAEESTAMGFCFFNSVAITAKYLRDQLNISKILIVDLDVHHGNTQQAFYADPSI
HDACX_V1     RPPGHHAEESTAMGFCFFNSVAITAKYLRDQLNISKILIVDLDVHHGNTQQAFYADPSI
HDACX_V2     ------------------------------------------------------------
```

FIG. 25C

```
BMY_HDAL1    ----------------------------------------------------------------
BMY_HDAL2    LYISLHRYDEGNFFPGSGAPNEVGTGLGEGYNINIAWTGGLDPPMGDVEYLEAFRLVLLS
BMY_HDAL3    -----------------------------------------------------------RTIVKP
HDAC9C       LYISLHRYDEGNFFPGSGAPNEVGTGLGEGYNINIAWTGGLDPPMGDVEYLEAFRTIVKP
HDACX_V1     LYISLHRYDEGNFFPGSGAPNEVGTGLGEGYNINIAWTGGLDPPMGDVEYLEAFRTIVKP
HDACX_V2     ----------------------------------------------------------------

BMY_HDAL1    ----------------------------------------------------------------
BMY_HDAL2    L---------------------------------------------------------------
BMY_HDAL3    VAKEFDPDMVLVSAGFDALEGHTPPLGGYKVTAKCFGHLTKQLMTLADGRVVLALEGGHD
HDAC9C       VAKEFDPDMVLVSAGFDALEGHTPPLGGYKVTAKCFGHLTKQLMTLADGRVVLALEGGHD
HDACX_V1     VAKEFDPDMVLVSAGFDALEGHTPPLGGYKVTAKCFGHLTKQLMTLADGRVVLALEGGHD
HDACX_V2     ----------------------------------------------------------------

BMY_HDAL1    ----------------------------------------------------------------
BMY_HDAL2    ----------------------------------------------------------------
BMY_HDAL3    LTAICDASEACVNALLGNELEPLAEDILHQSPNMNAVISLQKIIEIQSKYWKSVRMVAVP
HDAC9C       LTAICDASEACVNALLGNELEPLAEDILHQSPNMNAVISLQKIIEIQSKYWKSVRMVAVP
HDACX_V1     LTAICDASEACVNALLGNELEPLAEDILHQSPNMNAVISLQKIIEIQSKYWKSVRMVAVP
HDACX_V2     ----------------------------------------------------------------

BMY_HDAL1    ----------------------------------------------------------------
BMY_HDAL2    ----------------------------------------------------------------
BMY_HDAL3    RGCALAGAQLQEETETVSALASLTVDVEQPFAQEDSRTAGEPMEEEPAL
HDAC9C       RGCALAGAQLQEETETVSALASLTVDVEQPFAQEDSRTAGEPMEEEPAL
HDACX_V1     RGCALAGAQLQEETETVSALASLTVDVEQPFAQEDSRTAGEPMEEEPAL
HDACX_V2     ----------------------------------------------------------------
```

HUMAN HISTONE DEACETYLASE, HDAC9C

RELATED APPLICATIONS

This application is a divisional application of non-provisional application U.S. Ser. No. 10/172,094, filed Jun. 14, 2002, now U.S. Pat. No. 7,199,227, which claims benefit to provisional application U.S. application Ser. No. 60/298,296, filed Jun. 14, 2001, which is incorporated by reference in its entirety.

FIELD OF THE INVENTION

The present invention relates to novel members of the histone deacetylase (HDAC) family, including BMY_HDAL1, BMY_HDAL2, BMY_HDAL3, BMY_HDACX_v1, BMY_HDACX_v2, and HDAC9c. Specifically related are nucleic acids encoding the polypeptide sequences, vectors comprising the nucleic acid sequences, and antibodies that bind to the encoded polypeptides. In addition, the invention relates to pharmaceutical compositions and diagnostic reagents comprising one or more of the disclosed HDAC components. The present invention also relates to methods of treating a disease or disorder caused by malfunction of an HDAC, e.g., due to mutation or altered gene expression. The invention further relates to methods of using a modulator of an HDAC of the present invention to treat or ameliorate a disease state. Also related are methods for devising antisense therapies and prophylactic treatments using the HDACs of the invention. In particular, the disclosed HDAC components and methods may be used to prevent, diagnose, and treat diseases and disorders associated with abnormal cell growth or proliferation, cell differentiation, or cell survival, e.g., neoplasias, cancers, and tumors, such as breast and prostate cancers or tumors, and neurodegerative diseases.

BACKGROUND OF THE INVENTION

Chromatin is a dynamic protein-DNA complex which is modulated by post-translational modifications. These modifications, in turn, regulate cellular processes such as gene transcription and replication. Key chromatin modifications include the acetylation and deacetylation of nucelosomal histone proteins. Acetylation is catalyzed by histone acetylases (HATs), whereas deacetylation is catalyzed by deacetylases (HDACs or HDAs). HDACs catalyze the removal of acetyl groups from the N-termini of histone core proteins to produce more negatively charged chromatin. This results in chromatin compaction, which shuts down gene transcription. In addition, inhibition of HDACs results in the accumulation of hyperacetylated histones. This, in turn, is implicated in a variety of cellular responses, including altered gene expression, cell differentiation, and cell-cycle arrest (see, generally, S. G. Gray et al., 2001, *Exp. Cell Res.* 262(2):75-83, and U.S. Pat. Nos. 6,110,697 and 6,068,987 to Dulski et al.).

The HDAC gene family is composed of two distinct classes. Class I HDACs are related to the yeast transcriptional regulator, RPD3. Class II HDACs include a subgroup of proteins containing a C-terminal catalytic domain as well as a separate N-terminal domain with transcriptional repression activity. Class III HDAC proteins are related to the yeast sir2 protein and require NAD for activity. Class I HDACs are predominantly nuclear, whereas class II HDACs are transported between the cytoplasm and nucleus as part of the regulation of cellular proliferation and/or differentiation (reviewed in S. Khochbin et al., 2001, *Curr. Opin. Genet Dev.* 11(2):162-6).

The best characterized substrates for HDACs include histone or histone-like peptide sequences containing N-terminal lysines. However, non-histone HDAC substrates have also been identified, including several transcription factors. Non-histone substrates for HDACs include p53, androgen receptor, LEF1/TCF4 (B. R. Henderson et al., 2002, *J. Biol. Chem.*, published online on May 1, 2002 as Manuscript M110602200), GATA-1, and estrogen receptor-alpha (reviewed in D. M. Vigushin et al., 2002, *Anticancer Drugs* 13(1):1-13). For these substrates, deacetylation has been shown to regulate DNA/protein interactions or protein stability. Such molecules may therefore represent therapeutic targets of HDACs. Importantly, the histone deacetylase function of HDACs represses transcription by removing the acetyl moieties from amino terminal lysines on histones, thereby resulting in a compact chromatin structure. In contrast, the non-histone deacetylase function of HDACs can either repress or activate transcription.

There has been considerable interest in modulating the activity of HDACs for the treatment of a variety of diseases, particularly cancer. Several small molecule inhibitors of HDAC have shown anti-proliferative activities on a number of tumor cell lines and potent anti-tumor activity in pre-clinical tumor xenograft models, most recently, CBHA (D. C. Coffey et al., 2001, *Cancer Res.* 61(9):3591-4), pyroxamide, (L. M. Butler et al, 2001, *Clin. Cancer Res.* 7(4):962-70), and CHAP31 (Y. Komatsu et al., 2001, *Cancer Res.* 61(11):4459-66). Several inhibitors are presently being evaluated as single agents and in combination regimens with cytotoxic agents for the treatment of advanced malignancies (reviewed in P. A. Marks et al., *Curr. Opin. Oncol.* 2001 November; 13(6):477-83). Thus, HDAC inhibitors are being developed as anti-tumor agents, as well as agents useful for gene therapy (McInerney et al., 2000, *Gene Ther.* 7(8):653-663).

Small molecule inhibitors of HDAC activity that have undergone extensive analysis include trichostatin A (TSA), trapoxin, SAHA (V. M. Richon et al., 2001, *Blood Cells Mol. Dis.* 27(1):260-4), CHAPs (Y. Komatsu et al., 2001, *Cancer Res.* 61(11):4459-66), MS-27-275 (reviewed in M. Yoshida et al., 2001, *Cancer Chemother. Pharmacol.* 48 Suppl. 1:S20-6), depsipeptide (FR901228; FK228; see, e.g., V. Sandor et al., 2002, *Clin. Cancer Res.* 8(3):718-28), and CI-994 (see, e.g., P. M. LoRusso et al., 1996, *New Drugs* 14(4):349-56; S. Prakash et al., 2001, *Invest. New Drugs* 19(1):1-11). Trichostatin A and trapoxin have been reported to be reversible and irreversible inhibitors, respectively, of mammalian histone deacetylase (Yoshida et al, 1995, *Bioassays,* 17(5):423-430). Trichostatin A has also been reported to inhibit partially purified yeast histone deacetylase (Sanchez del Pino et al., 1994, *Biochem. J.,* 303:723-729). Moreover, trichostatin A is an antifungal antibiotic and has been shown to have anti-trichomonal activity and cell differentiating activity in murine erythroleukemia cells, as well as the ability to induce phenotypic reversion in ras-transformed fibroblast cells (see e.g. U.S. Pat. No. 4,218,478; and Yoshida et al., 1995, *Bioassays,* 17(5):423-430, and references cited therein). Trapoxin A, a cyclic tetrapeptide, induces morphological reversion of v-sis-transformed NIH/3T3 cells (Yoshida and Sugita, 1992, *Jap. J. Cancer Res.,* 83(4):324-328).

The therapeutic effects of HDAC inhibition are believed to occur through the induction of differentiation and/or apoptosis through the up-regulation of genes such as the cyclin dependent kinase inhibitors, p21 and p27 (see, e.g., W. Wharton et al., 2000, *J. Biol. Chem.* 275(43):33981-7; L. Huang et al., 2000, *Mol. Med.* 6(10):849-66). Although known HDAC inhibitors are efficacious as anti-tumor agents, they are also associated with toxicity (see, e.g., V. Sandor et al., 2002, *Clin.*

Cancer Res. 8(3):718-28). Such toxicity is believed to be caused by a non-selective mechanism of targeting multiple HDACs. Despite the potent anti-tumor activity of HDAC inhibitors, it is still unclear which HDACs are necessary to produce an anti-proliferative response. Furthermore, little progress has been made in comparing the HDAC gene expression profiles in tumor versus normal cells. Differential HDAC expression may underlie the tumor-selective responses of HDAC inhibition. In addition, a cellular growth advantage may be conferred by the expression of particular HDACs. Therefore, there is a need for further insight into the consequences of selective HDAC inhibition, or activation.

SUMMARY OF THE INVENTION

The present invention provides novel histone deacetylase (HDAC) nucleic acid sequences and their encoded polypeptide products, also called histone deacetylase like (HDAL) sequences and products herein, as well as methods and reagents for modulating HDACs.

It is an aspect of this invention to provide new HDAC nucleic acid or protein sequences, or cell lines overexpressing HDAC nucleic acid and/or encoded protein, for use in assays to identify small molecules which modulate HDAC activity, preferably antagonize HDAC activity.

It is another aspect of the present invention to employ HDAC protein structural data for the in silico identification of small molecules which modulate HDAC activity. This structural data could be generated by experimental techniques (for example, X-Ray crystallography or NMR spectroscopy) or by computational modeling based on available histone deacetylase structures (for example, M. S. Finnin et al., 1999, Nature, 401(6749):188-193).

Another aspect of the present invention provides modulators of HDAC activity, e.g., antagonists or inhibitors, and their use to treat neoplastic cells, e.g., cancer cells and tumor cells. In one aspect of the invention, breast or prostate cancers or tumors are treated using the HDAC modulators. The modulators of the invention can be employed alone or in combination with standard anti-cancer regimens for neoplastic cell, e.g., tumor and cancer, treatments.

In addition, the present invention provides diagnostic reagents (i.e., biomarkers) for the detection of cancers, tumors, or neoplastic growth. In one embodiment, HDAC (e.g., HDAC9c) nucleic acids or anti-HDAC antibodies are used to detect the presence of specific cancers or tumors, such as breast or prostate cancers or tumors.

It is yet another aspect of the present invention to employ HDAC inhibitors in the regulation of the differentiation state of normal cells such as hematopoietic stem cells. According to this invention, a method is provided for the use of modulators of HDAC in ex vivo therapies, particularly as a means to modulate the expression of gene therapeutic vectors.

Yet another aspect of this invention is to provide antisense nucleic acids and oligonucleotides for use in the regulation of HDAC and HDAL gene transcription or translation.

An additional aspect of this invention pertains to the use of HDAC nucleic acid sequences and antibodies directed against the produced protein for prognosis or susceptibility for certain disorders (e.g., breast or prostate cancer).

Further aspects, features and advantages of the present invention will be better appreciated upon a reading of the detailed description of the invention when considered in connection with the accompanying figures/drawings.

BRIEF DESCRIPTION OF THE FIGURES

The file of this patent contains at least one figure executed in color. Copies of this patent with color figure(s) will be provided by the Patent and Trademark Office upon request and payment of the necessary fee.

FIG. 1 shows the novel BMY_HDAL1 partial nucleic acid (cDNA) sequence (SEQ ID NO:1) and the encoded amino acid sequence (SEQ ID NO:2) of the BMY_HDAL1 polypeptide product. The top line in each group of FIG. 1 presents the BMY_HDAL1 protein sequence (SEQ ID NO:2) in 3-letter IUPAC form; the middle line presents the nucleotide sequence of the BMY_HDAL1 coding strand (i.e., SEQ ID NO:1); and the bottom line presents the nucleotide sequence of the reverse strand (SEQ ID NO:3).

FIGS. 2A and 2B show the amino acid sequences of the novel histone deacetylase-like proteins BMY_HDAL1 (SEQ ID NO:2), BMY_HDAL2 (SEQ ID NO:4) and BMY_HDAL3 (SEQ ID NO:5) aligned with the following known histone deacetylase proteins: S. cerevisiae HDA1 (SC_HDA1), (SEQ ID NO:6); human HDAC4 (HDA4), (SEQ ID NO:7); human HDAC5 (HDA5), (SEQ ID NO:8); human HDAC7 (HDA7), (SEQ ID NO:9) and to a histone deacetylase-like protein ACUC from Aquifex aeolicus (AQUIFEX_HDAL), (SEQ ID NO:10), (M. S. Finnin et al., 1999, Nature, 401(6749):188-193). Residues identical among all proteins are in shown in black text on a gray background. The sequences were aligned using the ClustalW algorithm as implemented in the VectorNTI sequence analysis package (1998, 5.5 Ed., Informax, Inc.) with a gap opening penalty of 10, a gap extension penalty of 0.1 and no end gap penalties.

FIGS. 3A and 3B show a GenewiseDB comparison of BMY_HDAL1 amino acid sequence (SEQ ID NO:2) and human HDAC5 (HDA5) amino acid sequence (SEQ ID NO:8). Genewise results from HDA5_HUMAN_run2 applied to AC002088 nucleic acid (coding) sequence. (SEQ ID NO:11).

FIG. 4 presents the results of sequence motif analysis of motifs within the BMY_HDAL1 amino acid sequence.

FIG. 5 shows the novel BMY_HDAL2 partial nucleic acid (cDNA) sequence (SEQ ID NO:12) and the encoded amino acid sequence (SEQ ID NO:4) of the BMY_HDAL2 polypeptide product. The top line in each group of FIG. 5 presents the BMY_HDAL2 protein sequence (SEQ ID NO:4) in 3-letter IUPAC form; the middle line presents the nucleotide sequence of the BMY_HDAL2 coding strand (i.e., SEQ ID NO:12); and the bottom line presents the nucleotide sequence of the reverse strand (SEQ ID NO:13).

FIG. 6 presents a GenewiseDB comparison of the BMY_HDAL2 amino acid sequence (SEQ ID NO:4) and human HDAC5 (HDA5) amino acid sequence (SEQ ID NO:8). Genewise results from HDA5_HUMAN_run3 applied to AC002410 nucleic acid sequence (SEQ ID NO:14).

FIG. 7 shows PROSITE motifs identified in the predicted amino acid sequence of the novel BMY_HDAL2 (SEQ ID NO:4). MOTIFS are from: bmy_hdal2.aa.fasta.

FIGS. 8A and 8B show the sequences of the N- and C-terminal sequences of BMY_HDAL3 as determined from BAC AC004994 and BAC AC004744. FIG. 8A presents the most N-terminal region of the BMY_HDAL3 amino acid sequence (SEQ ID NO:15) presented herein as encoded by the human genomic BAC AC004994 polynucleotide sequence (SEQ ID NO:17). FIG. 8B presents an additional C-terminal portion of the BMY_HDAL3 amino acid sequence (SEQ ID NO:16) as encoded by human genomic BAC AC004744 polynucleotide sequence (SEQ ID NO:18).

FIG. 9 shows partial transcripts identified from the AC004994 polynucleotide sequence (SEQ ID NO:17) and from the AC004744 polynucleotide sequence (SEQ ID NO:18) assembled into a single contig, which was designated BMY_HDAL3 (SEQ ID NO:19) using the VectorNTI ContigExpress program (Informax, Inc.).

FIG. 10 presents the BMY_HDAL3 partial nucleic acid sequence (SEQ ID NO:19) and the encoded amino acid sequence (SEQ ID NO:5) based on the assembled BMY_HDAL3 sequence described in FIG. 9. The top line in each group of FIG. 10 presents the BMY_HDAL3 protein sequence (SEQ ID NO:5) in 3-letter IUPAC form; the middle line presents the nucleotide sequence of the BMY_HDAL3 coding strand (i.e., SEQ ID NO:19); and the bottom line presents the nucleotide sequence of the reverse strand (SEQ ID NO:20).

FIG. 11 presents the results of the GCG Motifs program used to analyze the BMY_HDAL3 partial predicted amino acid sequence for motifs in the PROSITE collection (K. Hofmann et al., 1999, *Nucleic Acids Res.*, 27(1):215-219) with no allowed mismatches.

FIG. 12 shows a multiple sequence alignment of the novel human HDAC, BMY_HDAL3, amino acid sequence (SEQ ID NO:5) with the amino acid sequence of AAC78618 (SEQ ID NO:21) and with the amino acid sequence of AAD15364 (SEQ ID NO:22). AA78618 is a histone deacetylase-like protein predicted by genefinding and conceptual translation of AC004994 and which was entered in Genbank. AAD15364 is a similar predicted protein derived from AC004744 and entered in Genbank. AAC78618, AAD15364 and BMY_HDAL3 were aligned using the ClustalW algorithm as implemented in the VectorNTI sequence analysis package (1998, 5.5 Ed., Informax, Inc.) with a gap opening penalty of 10, a gap extension penalty of 0.1 and no end gap penalties. Residues identical among all proteins are shown in white text on a black background; conserved residues are shown in black text on a gray background.

FIG. 13 shows a BLASTN alignment of the AA287983 polynucleotide sequence (SEQ ID NO:23) and BMY_HDAL3 polynucleotide sequence from SEQ ID NO:19. Genbank accession AA287983 is a human EST sequence (GI # 1933807; Incyte template 1080282.1) which was identified by BLASTN searches against the Incyte LifeSeq database using the NCBI Blast algorithm (S. F. Altschul et al., 1997, *Nucl. Acids Res.*, 25(17):3389-3402) with default parameters. The AA287983 human EST was isolated from a germinal B-cell library. No additional ESTs are included in the Incyte template derived from this cluster (Incyte gene ID 180282).

FIGS. 14A-14H present other histone deacetylase sequences, as shown in FIGS. 2A and 2B. FIG. 14A: Aquifex ACUC protein amino acid sequence (SEQ ID NO:10); FIG. 14B: *Saccharomyces cerevisiae* histone deacetylase 1 amino acid sequence (SEQ ID NO:6); FIG. 14C: *Homo sapiens* histone deacetylase 4 amino acid sequence (SEQ ID NO:7); FIG. 14D: *Homo sapiens* histone deacetylase 5 amino acid sequence (SEQ ID NO:8); FIG. 14E: *Homo sapiens* histone deacetylase 7 amino acid sequence (SEQ ID NO:9); FIG. 14F: Human EST AA287983 nucleic acid sequence (SEQ ID NO:23); FIG. 14G: Human predicted protein AAD15364 amino acid sequence (SEQ ID NO:22); and FIG. 14H: Human predicted protein AAC78618 amino acid sequence (SEQ ID NO:21).

FIGS. 15A-15C depict the nucleotide and amino acid sequence information for HDAC9c. The polypeptide sequence (SEQ ID NO:87) is shown using the standard 3-letter abbreviation for amino acids. The DNA sequence (SEQ ID NO:88) of the coding strand is also shown. FIGS. 15D-15F depict an amino acid sequence alignment of HDAC9c. The predicted amino acid sequence of HDAC9c (SEQ ID NO:87) was aligned to previously identified HDACs, including HDAC9 (AY032737; SEQ ID NO:89), HDAC9a (AY032738; SEQ ID NO:90), and HDAC4 (ALF132608; SEQ ID NO:91), using ClustalW (D. G. Higgins et al., 1996, *Methods Enzymol.* 266:383-402). Identical amino acids are shown in white text on a black background; conserved amino acids are shown in black text on a gray background.

FIGS. 16A-16C depict expression levels of HDAC9 and HDAC9c in human cancer cell lines and normal adult tissue. FIG 16A: Northern blot analysis of HDAC9 and HDAC9c expression in normal adult tissue. FIG 16B: Quantitative PCR mRNA analysis of HDAC9 and HDAC9c expression in human tumor cell lines. FIG 16C: Nuclease protection assay analysis of HDAC9 and HDAC9c expression in human tumor cell lines. FIG. 16D shows the nucleotide sequence of HDAC9c used to derive the probes used for Northern blotting and nuclease protection analysis (SEQ ID NO:92). The probes were derived from the HDAC9c nucleotide sequence, and were predicted to hybridize to HDAC9c and HDAC9 (AY032737), but not HDAC9a (AY032738).

FIGS. 17A-17C illustrate the increase of HDAC9 and HDAC9c gene expression in human cancer tissues. FIGS. 17A-17B: Summary of HDAC9 and HDAC9c expression in selected tissues, as assayed by in situ hybridization. FIG. 17C: Photomicrographs of representative cells showing HDAC9 and HDAC9c or actin staining.

FIG. 18 shows HDAC9c-mediated induction of morphological transformation of NIH/3T3 cells. The panels show photomicrographs of soft agar growth of vector (upper panel), FGF8 (middle panel) and HDAC9c (lower panel) transfected NIH/3T3 cells. Cells are shown at 10× magnification.

FIGS. 20A-20C depict the nucleotide and amino acid sequence information for BMY_HDACX variant 1, also called BMY_HDACX_v1 and HDACX_v1. BMY_HDACX_v1 represents a partial cDNA sequence obtained from cells expressing a transcript variant of human HDAC9. The polypeptide sequence (SEQ ID NO:93) is shown using the standard 3-letter abbreviation for amino acids. The DNA sequence (SEQ ID NO:94) of the coding strand is also shown.

FIGS. 21A-21B depict the nucleotide and amino acid sequence information for BMY_HDACX variant 2, also called BMY_HDACX_v2 and HDACX_v2. BMY_HDACX_v2 represents a full-length sequence of a novel transcript variant (i.e., splice product) of HDAC9. The polypeptide sequence (SEQ ID NO:95) is shown using the standard 3-letter abbreviation for amino acids. The DNA sequence (SEQ ID NO:96) of the coding strand is also shown.

FIGS. 22A-22I depict the nucleotide and amino acid sequence information for the previously identified HDAC9 transcript variants. FIGS. 22A-22C: HDAC9 variant 1 (HDAC9v1; NCBI Ref. Seq. NM_058176). The polypeptide sequence (SEQ ID NO:89) is shown using the standard 3-letter abbreviation for amino acids. The DNA sequence (SEQ ID NO:97) of the coding strand is also shown. FIGS. 22D-22F: HDAC9 variant 2 (HDAC9v2; NCBI Ref. Seq. NM_058177). The polypeptide sequence (SEQ ID NO:90) is shown using the standard 3-letter abbreviation for amino acids. The DNA sequence (SEQ ID NO:98) of the coding strand is also shown. FIGS. 22G-22I: HDAC9 variant 3 (HDAC9v3; NCBI Ref. Seq. NM_014707). The polypeptide sequence (SEQ ID NO:99) is shown using the standard 3-letter abbreviation for amino acids. The DNA sequence (SEQ ID NO:100) of the coding strand is also shown.

FIGS. 23A-23K depict a multiple sequence alignment of nucleotide sequences representing known and novel HDAC9 splice products. The cDNAs for BMY_HDACX-v1 (SEQ ID NO:94) and BMY_HDACX_v2 (SEQ ID NO:96) nucleotide sequences were aligned to the three reported splice products of the HDAC9 gene, including HDAC9v1 (NCBI Ref. Seq. NM_058176; SEQ ID NO:97), HDAC9v2 (NCBI Ref. Seq. NM_058177; SEQ ID NO:98), and HDAC9v3 (NCBI Ref. Seq. NM_014707; SEQ ID NO:100) using the sequence alignment program ClustalW (D. G. Higgins et al., 1996, Methods Enzymol. 266:383-402). The consensus sequence is shown on the bottom line (SEQ ID NO:106). Identical nucleotides are shown in white text on a black background. Selected splice junctions are indicated below the alignment; these junctions were identified by comparison of the cDNA sequences to the assembled genomic contig NT_00798.1 using the Sim4 algorithm (L. Florea et al., 1998, Genome Res. 8:967-74). It is noted that the HDAC9 (AY032737) nucleotide and amino acid sequences are identical to the HDAC9v1 (NM_058176) nucleotide and amino acid sequences. Similarly, the HDAC9a (AY032738) nucleotide and amino acid sequences are identical to the HDAC9v2 (NM_058177) nucleotide and amino acid sequences.

FIGS. 24A-24D depict a multiple sequence alignment of amino acid sequences representing known and novel HDAC polypeptides. The amino acid sequences encoded by transcript variants BMY_HDACX_v1 (SEQ ID NO:93) and BMY_HDACX v2 (SEQ ID NO:95) were aligned to amino acid sequences encoded by known splice variants of human histone deacetylase 9 including HDAC9v1 (NCBI Ref. Seq. NM_058176; SEQ ID NO:89), HDAC9v2 (NCBI Ref Seq. NM_058177; SEQ ID NO:90), and HDAC9v3 (NCBI Ref. Seq. NM_014707; SEQ ID NO:99), and to human histone deacetylases 4 and 5 (HDA5, SEQ ID NO:8; HDA4, SEQ ID NO:7) using the multiple sequence alignment program ClustalW (D. G. Higgins et al., 1996, Methods Enzymol. 266:383-402). The consensus sequence is shown on the bottom line (SEQ ID NO:107). Residues conserved among all polypeptides are shown in white text on a black background; residues conserved in a majority of polypeptides are shown in black text on a gray background.

FIGS. 25A-25C depict a multiple sequence alignment of amino acid sequences showing novel HDAC polypeptides. The amino acid sequences of BMY_HDAL1 (SEQ ID NO:2), BMY_HDAL2 (SEQ ID NO:4), BMY_HDAL3 (SEQ ID NO:5), HDAC9c (SEQ ID NO:87), HDACX_v1 (SEQ ID NO:93), and HDACX_v2 (SEQ ID NO:95) were aligned using the T-Coffee program (C. Notredame et al., 2000, J. Mol. Biol. 302:205-217; C. Notredame et al., 1998, Bioinformatics 14:407-422). Identical residues are shown in black text on a gray background.

DESCRIPTION OF THE INVENTION

Figure 17C:
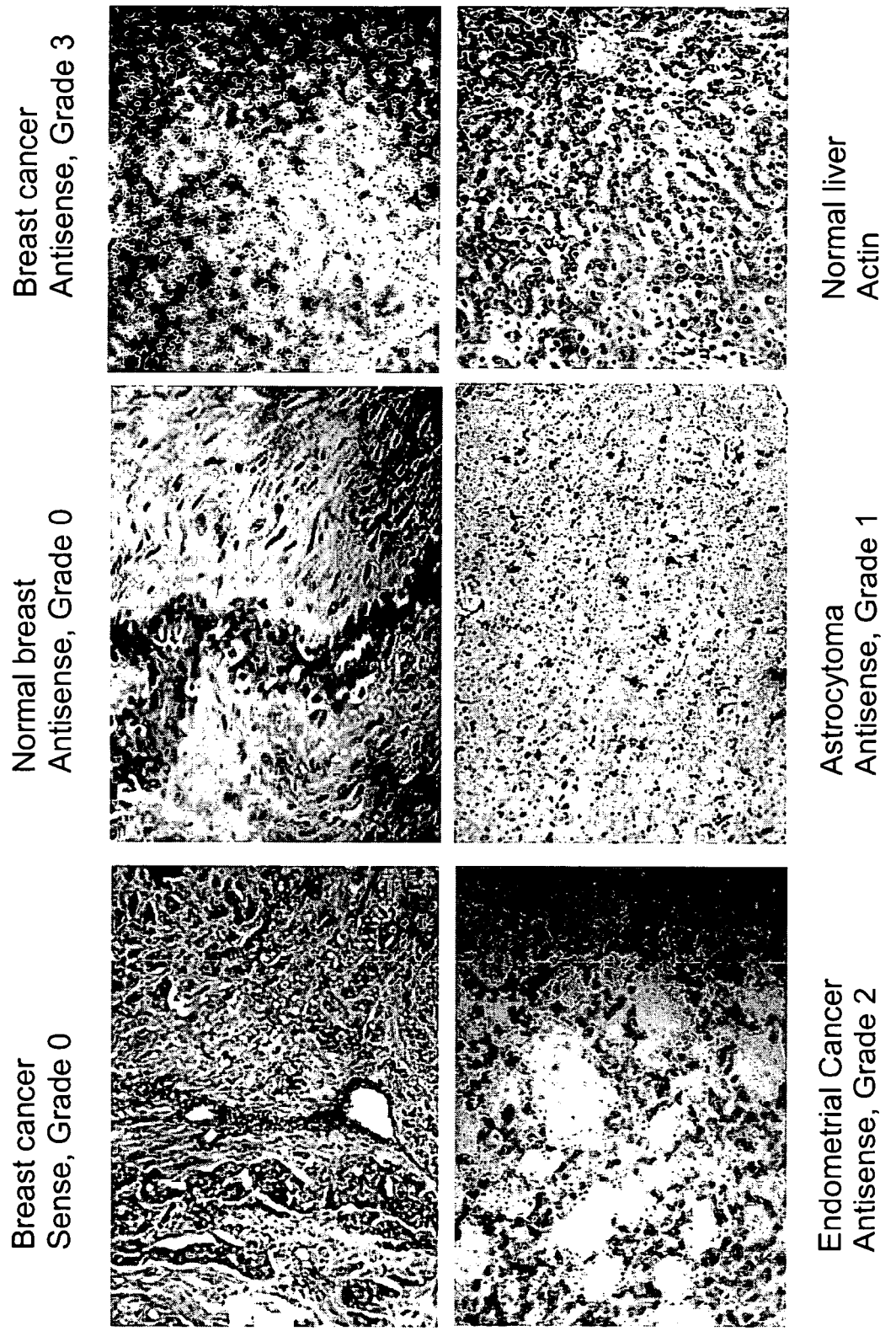

The present invention discloses several novel HDAC nucleotide sequences and encoded products. New members of the histone deacetylase protein family have been identified as having identity to known HDACs. Three new HDACs are referred to as BMY_HDAL1, BMY_HDAL2, and BMY_HDAL3 herein, wherein HDAL signifies histone deacetylase like proteins in current nomenclature. These proteins are most similar to the known human histone deacetylase, HDAC9. Novel HDAC9 splice variants, termed HDACX_v1 and HDACX_v2, have also been identified. In addition, HDAC9c, an HDAC9-related family member, has been newly identified and cloned. The nucleic acid sequences encoding the novel HDAC polypeptides are provided together with the description of the means employed to obtain these novel molecules. Such HDAC products can serve as protein deacetylases, which are useful for disease treatment and/or diagnosis of diseases and disorders associated with cell growth or proliferation, cell differentiation, and cell survival, e.g., neoplastic cell growth, cancers, and tumors.

As shown herein, HDAC9 expression is elevated in tumor cell lines, as determined by quantitative PCR analysis. Elevated expression of HDAC9 was also observed in clinical specimens of human tumor tissue compared to normal tissue, using in situ hybridization (ISH) and an HDAC9-specific riboprobe. Further, cell biological assessment of HDAC9c revealed that overexpression of HDAC9c confers a growth advantage to normal fibroblasts. These results indicate that HDAC9c can be used as a diagnostic marker for tumor progression and that selective HDAC9c inhibitors can be used to target specific cancer or tumor types, such as breast and prostate cancers or tumors.

Definitions

The following definitions are provided to more fully describe the present invention in its various aspects. The definitions are intended to be useful for guidance and elucidation, and are not intended to limit the disclosed invention and its embodiments.

HDAC polypeptides (or proteins) refer to the amino acid sequence of isolated, and preferably substantially purified, human histone deacetylase proteins isolated as described herein. HDACs may also be obtained from any species, preferably mammalian, including mouse, rat, non-human primates, and more preferably, human; and from a variety of sources, including natural, synthetic, semi-synthetic, or recombinant. The probes and oligos described may be used in obtaining HDACs from mammals other than humans. The present invention more particularly provides six new human HDAC family members, namely, BMY_HDAL1, BMY_HDAL2, BMY_HDAL3, HDACX_v1, HDACX_v2, and HDAC9c, their polynucleotide sequences (e.g., SEQ ID NO:1, SEQ ID NO:12, SEQ ID NO:19, SEQ ID NO:88, SEQ ID NO:94, SEQ ID NO:96, and sequences complementary thereto), and encoded products (e.g., SEQ ID NO:2, SEQ ID NO:4, SEQ ID NO:5, SEQ ID NO:87, SEQ ID NO:93, and SEQ ID NO:95).

An agonist (e.g., activator) refers to a molecule which, when bound to, or interactive with, an HDAC polypeptide, or a functional fragment thereof, increases or prolongs the duration of the effect of the HDAC polypeptide. Agonists may include proteins, nucleic acids, carbohydrates, or any other molecules that bind to and modulate the effect of an HDAC polypeptide. An antagonist (e.g., inhibitor, blocker) refers to a molecule which, when bound to, or interactive with, an HDAC polypeptide, or a functional fragment thereof, decreases or eliminates the amount or duration of the biological or immunological activity of the HDAC polypeptide. Antagonists may include proteins, nucleic acids, carbohydrates, antibodies, or any other molecules that decrease, reduce or eliminate the effect and/or function of an HDAC polypeptide.

"Nucleic acid sequence", as used herein, refers to an oligonucleotide, nucleotide, or polynucleotide (e.g., DNA, cDNA, RNA), and fragments or portions thereof, and to DNA or RNA of genomic or synthetic origin which may be single- or double-stranded, and represent the sense (coding) or antisense (non-coding) strand. By way of nonlimiting example, fragments include nucleic acid sequences that can be about 10 to 60 contiguous nucleotides in length, preferably, at least 15-60 contiguous nucleotides in length, and also preferably include fragments that are at least 70-100 contiguous nucleotides, or which are at least 1000 contiguous nucleotides or greater in length. Nucleic acids for use as probes or primers may differ in length as described herein.

In specific embodiments, HDAC polynucleotides of the present invention can comprise at least 15, 20, 25, 50, 100, 150, 200, 250, 300, 350, 400, 450, 500, 600, 700, 800, 900, 1000, 1195, 1200, 1500, 2000, 2160, 2250, 2500, 2755, or 2900 contiguous nucleotides of SEQ ID NO:1, SEQ ID NO:12, SEQ ID NO:19, SEQ ID NO:88, SEQ ID NO:94, SEQ ID NO:96, or a sequence complementary thereto. Additionally, a polynucleotide of the invention can comprise a specific region of a HDAC nucleotide sequence, e.g., a region encoding the C-terminal sequence of the HDAC polypeptide. Such polynucleotides can comprise, for example, nucleotides 3024-4467 of HDAC9c (SEQ ID NO:88), nucleotides 2156-3650 of HDACX_v1 (SEQ ID NO:94), nucleotides 1174-3391 of HDACX_v2 (SEQ ID NO:96), or portions or fragments thereof.

As specific examples, polynucleotides of the invention may comprise at least 183 contiguous nucleotides of SEQ ID NO:88; or at least 17 contiguous nucleotides of SEQ ID NO:96. As additional examples, the polynucleotides of the invention may comprise nucleotides 1 to 3207 of SEQ ID NO:88; nucleotides 1 to 2340 of SEQ ID NO:94; or nucleotides 307 to 1791 of SEQ ID NO:96. Further, the polynucleotides of the invention may comprise nucleotides 4 to 3207 of SEQ ID NO:88, wherein said nucleotides encode amino acids 2 to 1069 of SEQ ID NO:87 lacking the start methionine; or nucleotides 310 to 1791 of SEQ ID NO:96, wherein said nucleotides encode amino acids 2 to 495 of SEQ ID NO:95 lacking the start methionine. In addition, polynucleotides of the invention may comprise nucleotides 3024-3207 of SEQ ID NO:88; or nucleotides 1174-1791 of SEQ ID NO:96.

"Amino acid sequence" as used herein refers to an oligopeptide, peptide, polypeptide, or protein sequence, and fragments or portions thereof, and to naturally occurring or synthetic molecules. Amino acid sequence fragments are typically from about 4 or 5 to about 35, preferably from about 5 to about 15 or 25 amino acids in length and, optimally, retain the biological activity or function of an HDAC polypeptide. However, it will be understood that larger amino acid fragments can be used, depending on the purpose therefor, e.g., fragments of from about 15 to about 50 or 60 amino acids, or greater.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule. In addition, the terms HDAC polypeptide and HDAC protein are frequently used interchangeably herein to refer to the encoded product of an HDAC nucleic acid sequence of the present invention.

A variant of an HDAC polypeptide can refer to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Minor variations may also include amino acid deletions or insertions, or both. Guidance in determining which amino acid residues may be substituted, inserted, or deleted without abolishing functional biological or immunological activity may be found using computer programs well known in the art, for example, DNASTAR software.

An allele or allelic sequence is an alternative form of an HDAC nucleic acid sequence. Alleles may result from at least one mutation in the nucleic acid sequence and may yield altered mRNAs or polypeptides whose structure or function may or may not be altered. Any given gene, whether natural or recombinant, may have none, one, or many allelic forms. Common mutational changes that give rise to alleles are generally ascribed to natural deletions, additions, or substitutions of nucleotides. Each of these types of changes may occur alone, or in combination with the others, one or more times in a given sequence.

Altered nucleic acid sequences encoding an HDAC polypeptide include nucleic acid sequences containing deletions, insertions and/or substitutions of different nucleotides resulting in a polynucleotide that encodes the same or a functionally equivalent HDAC polypeptide. Altered nucleic acid sequences may further include polymorphisms of the polynucleotide encoding an HDAC polypeptide; such polymorphisms may or may not be readily detectable using a particular oligonucleotide probe. The encoded protein may also contain deletions, insertions, or substitutions of amino acid residues, which produce a silent change and result in a functionally equivalent HDAC protein of the present invention. Deliberate amino acid substitutions may be made on the basis of similarity in polarity, charge, solubility, hydrophobicity, hydrophilicity, and/or the amphipathic nature of the residues, as long as the biological activity or function of the HDAC protein is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; and phenylalanine and tyrosine.

"Peptide nucleic acid" (PNA) refers to an antisense molecule or anti-gene agent which comprises an oligonucleotide ("oligo") linked to a peptide backbone of amino acid residues, which terminates in lysine. PNA typically comprise oligos of at least 5 nucleotides linked to amino acid residues. These small molecules stop transcript elongation by binding to their complementary strand of nucleic acid (P. E. Nielsen et al., 1993, *Anticancer Drug Des.*, 8:53-63). PNA may be pegylated to extend their lifespan in the cell where they preferentially bind to complementary single stranded DNA and RNA.

Oligonucleotides or oligomers refer to a nucleic acid sequence, preferably comprising contiguous nucleotides, typically of at least about 6 nucleotides to about 60 nucleotides, preferably at least about 8 to 10 nucleotides in length, more preferably at least about 12 nucleotides in length, e.g., about 15 to 35 nucleotides, or about 15 to 25 nucleotides, or about 20 to 35 nucleotides, which can be typically used, for example, as probes or primers, in PCR amplification assays, hybridization assays, or in microarrays. It will be understood that the term oligonucleotide is substantially equivalent to the terms primer, probe, or amplimer, as commonly defined in the art. It will also be appreciated by those skilled in the pertinent art that a longer oligonucleotide probe, or mixtures of probes, e.g., degenerate probes, can be used to detect longer, or more complex, nucleic acid sequences, for example, genomic DNA. In such cases, the probe may comprise at least 20-200 nucleotides, preferably, at least 30-100 nucleotides, more preferably, 50-100 nucleotides.

Amplification refers to the production of additional copies of a nucleic acid sequence and is generally carried out using polymerase chain reaction (PCR) technologies, which are well known and practiced in the art (See, D. W. Dieffenbach and G. S. Dveksler, 1995, *PCR Primer, a Laboratory Manual*, Cold Spring Harbor Press, Plainview, N.Y.).

Microarray is an array of distinct polynucleotides or oligonucleotides synthesized on a substrate, such as paper, nylon, or other type of membrane; filter; chip; glass slide; or any other type of suitable solid support.

The term antisense refers to nucleotide sequences, and compositions containing nucleic acid sequences, which are complementary to a specific DNA or RNA sequence. The term "antisense strand" is used in reference to a nucleic acid strand that is complementary to the "sense" strand. Antisense (i.e., complementary) nucleic acid molecules include PNA and may be produced by any method, including synthesis or transcription. Once introduced into a cell, the complementary nucleotides combine with natural sequences produced by the cell to form duplexes that block either transcription or translation. The designation "negative" is sometimes used in reference to the antisense strand, and "positive" is sometimes used in reference to the sense strand.

The term consensus refers to the sequence that reflects the most common choice of base or amino acid at each position among a series of related DNA, RNA, or protein sequences. Areas of particularly good agreement often represent conserved functional domains.

A deletion refers to a change in either nucleotide or amino acid sequence and results in the absence of one or more nucleotides or amino acid residues. By contrast, an insertion (also termed "addition") refers to a change in a nucleotide or amino acid sequence that results in the addition of one or more nucleotides or amino acid residues, as compared with the naturally occurring molecule. A substitution refers to the replacement of one or more nucleotides or amino acids by different nucleotides or amino acids.

A derivative nucleic acid molecule refers to the chemical modification of a nucleic acid encoding, or complementary to, an encoded HDAC polypeptide. Such modifications include, for example, replacement of hydrogen by an alkyl, acyl, or amino group. A nucleic acid derivative encodes a polypeptide that retains the essential biological and/or functional characteristics of the natural molecule. A derivative polypeptide is one that is modified by glycosylation, pegylation, or any similar process that retains the biological and/or functional or immunological activity of the polypeptide from which it is derived.

The term "biologically active", i.e., functional, refers to a protein or polypeptide or peptide fragment thereof having structural, regulatory, or biochemical functions of a naturally occurring molecule. Likewise, "immunologically active" refers to the capability of the natural, recombinant, or synthetic HDAC, or any oligopeptide thereof, to induce a specific immune response in appropriate animals or cells, for example, to generate antibodies, and to bind with specific antibodies.

An HDAC-related protein refers to the HDAC and HADL proteins or polypeptides described herein, as well as other human homologs of these HDAC or HDAL sequences, in addition to orthologs and paralogs (homologs) of the HDAC or HADL sequences in other species, ranging from yeast to other mammals, e.g., homologous histone deacetylase. The term ortholog refers to genes or proteins that are homologs via speciation, e.g., closely related and assumed to have common descent based on structural and functional considerations. Orthologous proteins function as recognizably the same activity in different species. The term paralog refers to genes or proteins that are homologs via gene duplication, e.g., duplicated variants of a gene within a genome. (See, W. M. Fritch, 1970, *Syst. Zool.*, 19:99-113.

It will be appreciated that, under certain circumstances, it may be advantageous to provide homologs of one of the novel HDAC polypeptides which function in a limited capacity as one of either an HDAC agonist (i.e., mimetic), or an HDAC antagonist, in order to promote or inhibit only a subset of the biological activities of the naturally-occurring form of the protein. Thus, specific biological effects can be elicited by treatment with a homolog of limited function, and with fewer side effects, relative to treatment with agonists or antagonists which are directed to all of the biological activities of naturally-occurring forms of HDAC proteins.

Homologs (i.e., isoforms or variants) of the novel HDAC polypeptides can be generated by mutagenesis, such as by discrete point mutation(s), or by truncation. For example, mutation can yield homologs that retain substantially the same, or merely a subset of, the biological activity of the HDAC polypeptide from which it was derived. Alternatively, antagonistic forms of the protein can be generated which are able to inhibit the function of the naturally-occurring form of the protein, such as by competitively binding to an HDAC substrate, or HDAC-associated protein. Non-limiting examples of such situations include competing with wild-type HDAC in the binding of p53 or a histone. Also, agonistic forms of the protein can be generated which are constitutively active, or have an altered $K_{cat}$ or $K_m$ for deacylation reactions. Thus, the HDAC protein and homologs thereof may be either positive or negative regulators of transcription and/or replication.

The term hybridization refers to any process by which a strand of nucleic acid binds with a complementary strand through base pairing.

The term "hybridization complex" refers to a complex formed between two nucleic acid sequences by virtue of the formation of hydrogen bonds between complementary G and C bases and between complementary A and T bases. The hydrogen bonds may be further stabilized by base stacking interactions. The two complementary nucleic acid sequences hydrogen bond in an anti-parallel configuration. A hybridization complex may be formed in solution (e.g., $C_o t$ or $R_o t$ analysis), or between one nucleic acid sequence present in solution and another nucleic acid sequence immobilized on a solid support (e.g., membranes, filters, chips, pins, or glass slides, or any other appropriate substrate to which cells or their nucleic acids have been affixed).

The terms stringency or stringent conditions refer to the conditions for hybridization as defined by nucleic acid composition, salt and temperature. These conditions are well known in the art and may be altered to identify and/or detect identical or related polynucleotide sequences in a sample. A variety of equivalent conditions comprising either low, moderate, or high stringency depend on factors such as the length and nature of the sequence (DNA, RNA, base composition), reaction milieu (in solution or immobilized on a solid substrate), nature of the target nucleic acid (DNA, RNA, base composition), concentration of salts and the presence or absence of other reaction components (e.g., formamide, dextran sulfate and/or polyethylene glycol) and reaction temperature (within a range of from about 5° C. below the melting temperature of the probe to about 20° C. to 25° C. below the melting temperature). One or more factors may be varied to generate conditions, either low or high stringency, that are different from but equivalent to the aforementioned conditions.

As will be understood by those of skill in the art, the stringency of hybridization may be altered in order to identify or detect identical or related polynucleotide sequences. As will be further appreciated by the skilled practitioner, Tm can be approximated by the formulas as known in the art, depending on a number of parameters, such as the length of the hybrid or probe in number of nucleotides, or hybridization buffer ingredients and conditions (See, for example, T. Maniatis et al., *Molecular Cloning: A Laboratory Manual*, Cold Spring Harbor Laboratory, Cold Spring Harbor, N.Y., 1982 and J. Sambrook et al., *Molecular Cloning: A Laboratory Manual*, Cold Spring Harbor Laboratory, Cold Spring Harbor, N.Y., 1989; *Current Protocols in Molecular Biology*, Eds. F. M. Ausubel et al., Vol. 1, "Preparation and Analysis of DNA", John Wiley and Sons, Inc., 1994-1995, *Suppls.* 26, 29, 35 and 42; pp. 2.10.7-2.10.16; G. M. Wahl and S. L. Berger (1987; *Methods Enzymol.* 152:399-407); and A. R. Kimmel, 1987; *Methods of Enzymol.*, 152:507-511). As a general guide, Tm decreases approximately 1° C.-1.5° C. with every 1% decrease in sequence homology. Also, in general, the stability of a hybrid is a function of sodium ion concentration and temperature. Typically, the hybridization reaction is initially performed under conditions of low stringency, followed by washes of varying, but higher stringency. Reference to hybridization stringency, e.g., high, moderate, or low stringency, typically relates to such washing conditions.

Thus, by way of nonlimiting example, high stringency refers to conditions that permit hybridization of those nucleic acid sequences that form stable hybrids in 0.018M NaCl at about 65° C. (i.e., if a hybrid is not stable in 0.018M NaCl at about 65° C., it will not be stable under high stringency conditions). High stringency conditions can be provided, for instance, by hybridization in 50% formamide, 5× Denhart's solution, 5×SSPE (saline sodium phosphate EDTA) (1×SSPE buffer comprises 0.15 M NaCl, 10 mM $Na_2HPO_4$, 1 mM EDTA), (or 1×SSC buffer containing 150 mM NaCl, 15 mM $Na_3$ citrate·$2H_2O$, pH 7.0), 0.2% SDS at about 42° C., followed by washing in 1×SSPE (or saline sodium citrate, SSC) and 0.1% SDS at a temperature of at least about 42° C., preferably about 55° C., more preferably about 65° C.

Moderate stringency refers, by way of nonlimiting example, to conditions that permit hybridization in 50% formamide, 5× Denhart's solution, 5×SSPE (or SSC), 0.2% SDS at 42° C. (to about 50° C.), followed by washing in 0.2×SSPE (or SSC) and 0.2% SDS at a temperature of at least about 42° C., preferably about 55° C., more preferably about 65° C.

Low stringency refers, by way of nonlimiting example, to conditions that permit hybridization in 10% formamide, 5× Denhart's solution, 6×SSPE (or SSC), 0.2% SDS at 42° C., followed by washing in 1×SSPE (or SSC) and 0.2% SDS at a temperature of about 45° C., preferably about 50° C.

For additional stringency conditions, see T. Maniatis et al., *Molecular Cloning: A Laboratory Manual*, Cold Spring Harbor Laboratory, Cold Spring Harbor, N.Y. (1982). It is to be understood that the low, moderate and high stringency hybridization/washing conditions may be varied using a variety of ingredients, buffers and temperatures well known to and practiced by the skilled practitioner.

The terms complementary or complementarity refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between single stranded molecules. The degree of complementarity between nucleic acid strands has significant effects on the efficiency and strength of hybridization between nucleic acid strands. This is of particular importance in amplification reactions, which depend upon binding between nucleic acids strands, as well as in the design and use of PNA molecules.

The term homology refers to a degree of complementarity. There may be partial sequence homology or complete homology, wherein complete homology is equivalent to identity, e.g., 100% identity. A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (e.g., Southern or Northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. Nonetheless, conditions of low stringency do not permit non-specific binding; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Those having skill in the art will know how to determine percent identity between/among sequences using, for example, algorithms such as those based on the CLUSTALW computer program (J. D. Thompson et al., 1994, *Nucleic Acids Research*, 2(22):4673-4680), or FASTDB, (Brutlag et al., 1990, *Comp. App. Biosci.*, 6:237-245), as known in the art. Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations.

Also available to those having skill in this art are the BLAST and BLAST 2.0 algorithms (Altschul et al., 1977, *Nucl. Acids Res.*, 25:3389-3402 and Altschul et al., 1990, *J. Mol. Biol.*, 215:403-410). The BLASTN program for nucleic acid sequences uses as defaults a wordlength (W) of 11, an expectation (E) of 10, M=5, N=4, and a comparison of both strands. For amino acid sequences, the BLASTP program uses as defaults a wordlength (W) of 3, and an expectation (E) of 10. The BLOSUM62 scoring matrix (Henikoff and Henikoff, 1989, *Proc. Natl. Acad. Sci., USA*, 89:10915) uses alignments (B) of 50, expectation (E) of 10, M=5, N=4, and a comparison of both strands.

An HDAC polynucleotide of the present invention may show at least 27.7%, 35%, 40%, 44.1%, 48.2%, 50%, 55.4%, 58.6%, 59.8%, 60%, 60.2%, 67.8%, 70%, 80%, 81.5%, 85%, 90%, 91%, 92%, 93%, 94%, 94.2%, 94.4%, 95%, 96%, 97%, 97.2%, 97.5%, 98%, 99%, 99.1%, 99.2%, 99.3%, 99.4%, 99.5%, 99.6%, 99.7%, 99.8%, or 99.9% identity to a sequence provided in SEQ ID NO:1, SEQ ID NO:12, SEQ ID NO:19, SEQ ID NO:88, SEQ ID NO:94, SEQ ID NO:96, or a sequence complementary thereto. An HDAC polypeptide of the present invention may show at least 25%, 35%, 40%, 45%, 48.1%, 55.2%, 55.3%, 60%, 65%, 70%, 72%, 75%, 79%, 80%, 80.6%, 85%, 90%, 91%, 92%, 93%, 94%, 94.2%, 95%, 96%, 97%, 97.2%, 97.5%, 98%, 99%, 99.1%, 99.2%, 99.3%, 99.4%, 99.5%, 99.6%, 99.7%, 99.8%, or 99.9% identity to a sequence provided in any one of SEQ ID NO:2, SEQ ID NO:4, SEQ ID NO:5, SEQ ID NO:87, SEQ ID NO:93, or SEQ ID NO:95.

In a preferred aspect of the invention, a HDAC polynucleotide shows at least 60.2%, 81.5%, or 94.4% identity to the HDAC9c nucleotide sequence (SEQ ID NO:88 or a sequence complementary thereto); or at least 27.7%, 48.2%, or 55.4% identity to the HDACX_v2 nucleotide sequence (SEQ ID NO:96 or a sequence complementary thereto). A HDAC polypeptide of the invention preferably shows at least 55.2%, 80.6%, or 94.2% identity to the HDAC9c amino acid sequence (SEQ ID NO:87); at least 55.3% identity to the HDACX_v2 amino acid sequence (SEQ ID NO:95); at least 72% identity to the amino acid sequence of BMY_HDAL1 (SEQ ID NO:2); at least 79% identity to the amino acid sequence of BMY_HDAL2 (SEQ ID NO:4); or at least 70% identity to the amino acid sequence of BMY_HDAL3 (SEQ ID NO:5).

A composition comprising a given polynucleotide sequence refers broadly to any composition containing the given polynucleotide sequence. The composition may comprise a dry formulation or an aqueous solution. Compositions comprising the polynucleotide sequences (e.g., SEQ ID NO:1, SEQ ID NO:12, SEQ ID NO:19, SEQ ID NO:88, SEQ ID NO:94, or SEQ ID NO:96) encoding the novel HDAC polypeptides of this invention, or fragments thereof, or complementary sequences thereto, may be employed as hybridization probes. The probes may be stored in freeze-dried form and may be in association with a stabilizing agent such as a carbohydrate. In hybridizations, the probe may be employed in an aqueous solution containing salts (e.g., NaCl), detergents or surfactants (e.g., SDS) and other components (e.g., Denhardt's solution, dry milk, salmon sperm DNA, and the like).

The term "substantially purified" refers to nucleic acid sequences or amino acid sequences that are removed from their natural environment, i.e., isolated or separated by a variety of means, and are at least 60% free, preferably 75% to 85% free, and most preferably 90% or greater free from other components with which they are naturally associated.

The term sample, or biological sample, is meant to be interpreted in its broadest sense. A biological sample suspected of containing nucleic acid encoding an HDAC protein, or fragments thereof, or an HDAC protein itself, may comprise a body fluid, an extract from cells or tissue, chromosomes isolated from a cell (e.g., a spread of metaphase chromosomes), organelle, or membrane isolated from a cell, a cell, nucleic acid such as genomic DNA (in solution or bound to a solid support such as for Southern analysis), RNA (in solution or bound to a solid support such as for Northern analysis), cDNA (in solution or bound to a solid support), a tissue, a tissue print and the like.

Transformation refers to a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and partial bombardment. Such "transformed" cells include stably transformed cells in which the inserted DNA is capable of replication either as an autonomously replicating plasmid or as part of the host chromosome. Transformed cells also include those cells that transiently express the inserted DNA or RNA for limited periods of time.

The term "mimetic" refers to a molecule, the structure of which is developed from knowledge of the structure of an HDAC protein, or portions thereof, and as such, is able to effect some or all of the actions of HDAC proteins.

The term "portion" with regard to a protein (as in "a portion of a given protein") refers to fragments or segments, for example, peptides, of that protein. The fragments may range in size from four or five amino acid residues to the entire amino acid sequence minus one amino acid. Thus, a protein "comprising at least a portion of the amino acid sequence of the HDAC molecules presented herein can encompass a full-length human HDAC polypeptide, and fragments thereof.

In specific embodiments, HDAC polypeptides of the invention can comprise at least 5, 10, 20, 30, 50, 70, 100, 200, 300, 400, 500, 600, 700, 720, 750, 800, 920, or 950 contiguous amino acid residues of SEQ ID NO:2, SEQ ID NO:4, SEQ ID NO:5, SEQ ID NO:87, SEQ ID NO:93, or SEQ ID NO:95. Additionally, a polypeptide of the invention can comprise a specific region, e.g., the C-terminal region, of a HDAC amino acid sequence. Such polypeptides can comprise, for example, amino acids 1009-1069 of HDAC9c (SEQ ID NO:87), amino acids 720-780 of HDACX_v1 (SEQ ID NO:93), or portions or fragments thereof.

The term antibody refers to intact molecules as well as fragments thereof, such as Fab, F(ab')$_2$, Fv, which are capable of binding an epitopic or antigenic determinant. Antibodies that bind to the HDAC polypeptides can be prepared using intact polypeptides or fragments containing small peptides of interest or prepared recombinantly for use as the immunizing antigen. The polypeptide or oligopeptide used to immunize an animal can be derived from the transition of RNA or synthesized chemically, and can be conjugated to a carrier protein, if desired. Commonly used carriers that are chemically coupled to peptides include bovine serum albumin (BSA), keyhole limpet hemocyanin (KLH), and thyroglobulin. The coupled peptide is then used to immunize the animal (e.g, a mouse, a rat, or a rabbit).

The term "humanized" antibody refers to antibody molecules in which amino acids have been replaced in the non-antigen binding regions, e.g., the complementarity determining regions (CDRs), in order to more closely resemble a human antibody, while still retaining the original binding capability, e.g., as described in U.S. Pat. No. 5,585,089 to C. L. Queen et al., which is a nonlimiting example. Fully humanized antibodies, such as those produced transgenically or recombinantly, are also encompassed herein.

The term "antigenic determinant" refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to an antigenic determinants. An antigenic determinant may compete with the intact antigen (i.e., the immunogen used to elicit the immune response) for binding to an antibody.

The terms "specific binding" or "specifically binding" refer to the interaction between a protein or peptide and a binding molecule, such as an agonist, an antagonist, or an antibody. The interaction is dependent upon the presence of a particular structure (e.g., an antigenic determinant or epitope, or a structural determinant) of the protein that is recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The term "correlates with expression of a polynucleotide" indicates that the detection of the presence of ribonucleic acid that is similar to one or more of the HDAC sequences provided herein by Northern analysis is indicative of the presence of mRNA encoding an HDAC polypeptide in a sample and thereby correlates with expression of the transcript from the polynucleotide encoding the protein.

An alteration in the polynucleotide of an HDAC nucleic acid sequence comprises any alteration in the sequence of the polynucleotides encoding an HDAC polypeptide, including deletions, insertions, and point mutations that may be detected using hybridization assays. Included within this definition is the detection of alterations to the genomic DNA sequence which encodes an HDAC polypeptide (e.g., by alterations in the pattern of restriction fragment length polymorphisms capable of hybridizing to the HDAC nucleic acid sequences presented herein, (i.e., SEQ ID NO:1, SEQ ID NO:12, SEQ ID NO:19, SEQ ID NO:88, SEQ ID NO:94, and/or SEQ ID NO:96), the inability of a selected fragment of a given HDAC sequence to hybridize to a sample of genomic DNA (e.g., using allele-specific oligonucleotide probes), and improper or unexpected hybridization, such as hybridization to a locus other than the normal chromosomal locus for the polynucleotide sequence encoding an HDAC polypeptide (e.g., using fluorescent in situ hybridization (FISH) to metaphase chromosome spreads).

DESCRIPTION OF EMBODIMENTS OF THE PRESENT INVENTION

In one of its embodiments, the present invention is directed to a novel HDAC termed, BMY_HDAL1, which is encoded by the human BAC clones AC016186, AC00755 and AC002088. The BMY_HDAL1 nucleic acid (cDNA) sequence is provided as SEQ ID NO:1; the BMY_HDAL1 amino acid sequence encoded by the BMY_HDAL1 nucleic acid sequence is presented as SEQ ID NO:2. (FIG. 1).

BMY_HDAL1 was identified by HMM analysis using PFAM model PF00850. (Example 1). The PFAM-HMM database is a collection of protein families and domains and contains multiple protein alignments (A. Bateman et al., 1999, *Nucleic Acids Research*, 27:260-262). BMY_HDAL1 is most closely related to the known human histone deacetylase HDAC5; the two proteins are 71% identical and 77% similar over 105 amino acids, as determined by the GCG Gap program with a gap weight of 8 and a length weight of 2. The gene structure and predicted cDNA and protein sequence of BMY_HDAL1 were determined by comparison to the known human histone deacetylase HDAC5 using the GenewiseDB program to analyze human BAC AC002088 (E. Birney and R. Durbin, 2000, *Genome Res.*, 10(4):547-548).

Sequence motifs of BMY_HDAL1 were examined using the GCG Motifs program to ascertain if there were motifs common to other known proteins in the PROSITE collection (K. Hofmann et al., 1999, *Nucleic Acids Res.*, 27(1):215-219) with no allowed mismatches. Motifs programs typically search for protein motifs by searching protein sequences for regular-expression patterns described in the PROSITE Dictionary. FIG. 4 shows PROSITE motifs identified in the partial predicted amino acid sequence of BMY_HDAL1.

In another embodiment, the present invention is directed to the novel HDAC termed BMY_HDAL2, a novel human histone deacetylase-like protein encoded by genomic BACs AC002410. The BMY_HDAL2 nucleic acid sequence (SEQ ID NO:12) and its encoded polypeptide (SEQ ID NO:4) are presented in FIG. 5. BMY_HDAL2 was identified by hidden Markov model searches using the PFAM HMM PF00850 to search predicted proteins from human genomic DNA. BMY_HDAL2 is most closely related to the known human histone deacetylase HDAC5; the two proteins are 78% identical and 86% similar over 163 amino acids as determined by the GCG Gap program with a gap weight of 8 and a length weight of 2. The gene structure and predicted cDNA and protein sequences of BMY_HDAL2 were determined by comparison to BMY_HDA5 using the GenewiseDB program (E. Birney and R. Durbin, 2000, *Genome Res.*, 10(4):547-548).

Sequence motifs of BMY_HDAL2 were examined using the GCG Motifs program to ascertain if there were motifs in the PROSITE collection (K. Hofmann et al., 1999, *Nucleic Acids Res.*, 27(1):215-219) with no allowed mismatches. FIG. 7 shows PROSITE motifs identified in the partial predicted amino acid sequence of BMY_HDAL2.

In addition, the genomic location surrounding BMY_HDAL2 was investigated. Based on the genomic location of BAC AC002410 as reported by the NCBI MapViewer, BMY_HDAL2 has been localized to chromosome 7 region q36.

In another embodiment, the present invention further provides a third HDAC termed BMY_HDAL3. The BMY_HDAL3 nucleic acid sequence (SEQ ID NO:19) and its encoded polypeptide (SEQ ID NO:5) are presented in FIG. 10. BMY_HDAL3 is encoded by the human genomic BAC clones AC004994 and AC004744. BMY_HDAL3 was identified by HMM analysis using PFAM model PF00850 to search predicted proteins generated from human genomic DNA sequences using Genscan. BMY_HDAL3 is most closely related to the known human histone deacetylase HDAC5; the two proteins are 69% identical over 1122 amino acids as determined by the GCG Gap program with a gap weight of 8 and a length weight of 2.

The partial transcripts identified from BAC clones AC004994 (SEQ ID NO:15) and AC004744 (SEQ ID NO:16) were assembled into a single contig (designated BMY_HDAL3) using the VectorNTI ContigExpress program (Informax). (FIG. 9). The gene structure and predicted cDNA and protein sequence of BMY_HDAL3 were determined by comparison to the known human histone deacetylase HDAC5 using the GenewiseDB program (K. Hofmann et al., 1999, *Nucleic Acids Res.*, 27(1):215-219) and are presented in FIG. 9. The most N-terminal region of the BMY_HDAL3 sequence described herein is encoded by human genomic BAC AC004994. (FIG. 8A).

BMY_HDAL3 has been localized to chromosome 7, region q36 based on the locations reported for AC004994 and by the NCBI MapViewer.

Sequence motifs of BMY_HDAL3 were examined using the GCG Motifs program to ascertain if there were motifs in the PROSITE collection (K. Hofmann et al., 1999, *Nucleic Acids Res.*, 27(1):215-219) with no allowed mismatches. FIG. 11 shows PROSITE motifs identified in the partial predicted amino acid sequence of BMY_HDAL3. FIG. 12 shows a multiple sequence alignment of the novel human HDAC, BMY_HDAL3, amino acid sequence (SEQ ID NO:5) with the amino acid sequence of AAC78618 (SEQ ID NO:21) and with the amino acid sequence of AAD15364 (SEQ ID NO:22). AAC78618 is a histone deacetylase-like protein predicted by genefinding and conceptual translation of AC004994 and which was entered in Genbank. AAD15364 is a similar predicted protein derived from AC004744 and entered in Genbank. AAC78618, AAD15364 and BMY_HDAL3 were aligned using the ClustalW algorithm as implemented in the VectorNTI sequence analysis package (1998, 5.5 Ed., Informax, Inc.) with a gap opening penalty of 10, a gap extension penalty of 0.1 and no end gap penalties.

Novel HDAC9 variants, termed HDACX_v1 and HDACX_v2, have also been identified. In addition, HDAC9c, an HDAC9-related family member, has been newly identified and cloned.

HDAC Polynucleotides and Polypeptides

The present invention encompasses novel HDAC nucleic acid sequences (e.g., SEQ ID NO:1, SEQ ID NO:12, SEQ ID NO:19, SEQ ID NO:88, SEQ ID NO:94, SEQ ID NO:96, and sequences complementary thereto) encoding newly discovered histone deacetylase like polypeptides (e.g., SEQ ID NO:2, SEQ ID NO:4, SEQ ID NO:5, SEQ ID NO:87, SEQ ID NO:93, and SEQ ID NO:95). These HDAC polynucleotides, polypeptides, or compositions thereof, can be used in methods for screening for antagonists or inhibitors of the activity or function of HDACs.

In another of its embodiments, the present invention encompasses new HDAC polypeptides comprising the amino acid sequences of, e.g., SEQ ID NO:2, SEQ ID NO:4, SEQ ID NO:5, SEQ ID NO:87, SEQ ID NO:93, and SEQ ID NO:95, and as shown in FIG. 1, FIG. 5, FIG. 10, FIGS. 15A-15C, FIGS. 20A-20C, and FIGS. 21A-21B.

The HDAC polypeptides as described herein show close similarity to HDAC proteins, including HDAC5 and HDAC9. FIGS. 2A and 2B portray the structural similarities among the novel HDAC polypeptides and several other proteins, namely Aquifex HDAL, Human HDAC4, Human HDAC5, Human HDAC7, and *Saccharomyces cerevisiae* HDA1. FIGS. 15D-15F show the amino acid sequence similarity and identity shared by HDAC9c and previously identified HDAC9 amino acid sequences. FIGS. 23A-23K show the nucleotide sequence identity shared by HDACX_v1, HDACX_v2, and previously identified HDAC9 nucleotide sequences.

Variants of the disclosed HDAC polynucleotides and polypeptides are also encompassed by the present invention. In some cases, a HDAC polynucleotide variant (i.e., variant of SEQ ID NO:1, SEQ ID NO:12, SEQ ID NO:19, SEQ ID NO:88, SEQ ID NO:94, or SEQ ID NO:96) will encode an amino acid sequence identical to a HDAC sequence (e.g., SEQ ID NO:2, SEQ ID NO:4, SEQ ID NO:5, SEQ ID NO:87, SEQ ID NO:93, and SEQ ID NO:95). This is due to the redundancy (degeneracy) of the genetic code, which allows for silent mutations. In other cases, a HDAC polynucleotide variant will encode a HDAC polypeptide variant (i.e., a variant of SEQ ID NO:2, SEQ ID NO:4, SEQ ID NO:5, SEQ ID NO:87, SEQ ID NO:93, or SEQ ID NO:95). Preferably, an HDAC polypeptide variant has at least 75 to 80%, more preferably at least 85 to 90%, and even more preferably at least 90% or greater amino acid sequence identity to one or more of the HDAC amino acid sequences (e.g., SEQ ID NO:2, SEQ ID NO:4, SEQ ID NO:5, SEQ ID NO:87, SEQ ID NO:93, and SEQ ID NO:95) as disclosed herein, and which retains at least one biological or other functional characteristic or activity of the HDAC polypeptide. Most preferred is a variant having at least 95% amino acid sequence identity to the amino acid sequences set forth in SEQ ID NO:2, SEQ ID NO:4, SEQ ID NO:5, SEQ ID NO:87, SEQ ID NO:93, and SEQ ID NO:95.

An amino acid sequence variant of the HDAC proteins can be categorized into one or more of three classes: substitutional, insertional, or deletional variants. Such variants are typically prepared by site-specific mutagenesis of nucleotides in the DNA encoding the HDAC protein, using cassette or PCR mutagenesis, or other techniques that are well known and practiced in the art, to produce DNA encoding the variant.

Thereafter, the DNA is expressed in recombinant cell culture as described herein. Variant HDAC protein fragments having up to about 100-150 residues may be prepared by in vitro synthesis using conventional techniques.

Amino acid sequence variants are characterized by the predetermined nature of the variation, a feature that sets them apart from naturally occurring allelic or interspecies variations of an HDAC amino acid sequence. The variants typically exhibit the same qualitative biological activity as that of the naturally occurring analogue, although variants can also be selected having modified characteristics. While the site or region for introducing an amino acid sequence variation is predetermined, the mutation per se need not be predetermined. For example, in order to optimize the performance of a mutation at a given site, random mutagenesis may be performed at the target codon or region, and the expressed HDAC variants can be screened for the optimal combination of desired activity. Techniques for making substitution mutations at predetermined sites in DNA having a known sequence are well known, for example, M13 primer mutagenesis and PCR mutagenesis. Screening of the mutants is accomplished using assays of HDAC protein activity, for example, for binding domain mutations, competitive binding studies may be carried out.

Amino acid substitutions are typically of single residues; insertions usually are on the order of from one to twenty amino acids, although considerably larger insertions may be tolerated. Deletions range from about one to about 20 residues, although in some cases, deletions may be much larger.

Substitutions, deletions, insertions, or any combination thereof, may be used to arrive at a final HDAC derivative. Generally, these changes affect only a few amino acids to minimize the alteration of the molecule. However, larger changes may be tolerated in certain circumstances. When small alterations in the characteristics of the HDAC protein are desired or warranted, substitutions are generally made in accordance with the following table:

| Original Residue | Conservative Substitution(s) |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in the above Table. For example, substitutions may be made which more significantly affect the structure of the polypeptide backbone in the area of the alteration, for example, the alpha-helical, or beta-sheet structure; the charge or hydrophobicity of the molecule at the target site; or the bulk of the side chain. The substitutions which generally are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl, or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) a residue that does not have a side chain, e.g., glycine.

While HDAC variants will ordinarily exhibit the same qualitative biological activity or function, and elicit the same immune response, as the naturally occurring analogue, the variants are also selected to modify the characteristics of HDAC proteins as needed. Alternatively, the variant may be designed such the that biological activity of the HDAC protein is altered, e.g., improved.

In another embodiment, the present invention encompasses polynucleotides that encode the novel HDAC polypeptides disclosed herein. Accordingly, any nucleic acid sequence that encodes the amino acid sequence of an HDAC polypeptide of the invention can be used to produce recombinant molecules that express that HDAC protein. In a particular embodiment, the present invention encompasses the novel human HDAC polynucleotides comprising the nucleic acid sequences of SEQ ID NO:1, SEQ ID NO:12, SEQ ID NO:19, SEQ ID NO:88, SEQ ID NO:94, and SEQ ID NO:96 as shown in FIG. 1, FIG. 5, FIG. 10, FIGS. 15A-15C, FIGS. 20A-20C, and FIGS. 21A-21B. More particularly, the present invention embraces cloned full-length open reading frame human HDAC9c deposited at the American Type Culture Collection (ATCC), 10801 University Boulevard, Manassas, Va. 20110-2209 on Jun. 12, 2002 under ATCC Accession No. PTA-4454 according to the terms of the Budapest Treaty.

As will be appreciated by the skilled practitioner in the art, the degeneracy of the genetic code results in the production of more than one appropriate nucleotide sequence encoding the HDAC polypeptides of the present invention. Some of the sequences bear minimal homology to the nucleotide sequences of any known and naturally occurring gene. Accordingly, the present invention contemplates each and every possible variation of nucleotide sequence that could be made by selecting combinations based on possible codon choices. These combinations are made in accordance with the standard triplet genetic code as applied to the nucleotide sequence of a naturally occurring HDAC protein, and all such variations are to be considered as being embraced herein.

Although nucleotide sequences which encode the HDAC polypeptides and variants thereof are preferably capable of hybridizing to the nucleotide sequence of the naturally occurring HDAC polypeptides under appropriately selected conditions of stringency, it may be advantageous to produce nucleotide sequences encoding the HDAC polypeptides, or derivatives thereof, which possess a substantially different codon usage. Codons may be selected to increase the rate at which expression of the peptide/polypeptide occurs in a particular prokaryotic or eukaryotic host in accordance with the frequency with which particular codons are utilized by the host, for example, in plant cells or yeast cells or amphibian cells. Other reasons for substantially altering the nucleotide sequence encoding the HDAC polypeptides, and derivatives, without altering the encoded amino acid sequences, include the production of mRNA transcripts having more desirable properties, such as a greater half-life, than transcripts produced from the naturally occurring sequence.

The present invention also encompasses production of DNA sequences, or portions thereof, which encode the HDAC polypeptides, and derivatives of these polypeptides, entirely by synthetic chemistry. After production, the synthetic sequence may be inserted into any of the many available expression vectors and cell systems using reagents that are well known and practiced by those in the art. Moreover, synthetic chemistry may be used to introduce mutations into a sequence encoding an HDAC polypeptide, or any fragment thereof.

Also encompassed by the present invention are polynucleotide sequences that are capable of hybridizing to the HDAC nucleotide sequences presented herein, such as those shown in SEQ ID NO:1, SEQ ID NO:12, SEQ ID NO:19, SEQ ID NO:88, SEQ ID NO:94, and SEQ ID NO:96, or sequences complementary thereto, under various conditions of stringency. Hybridization conditions are typically based on the melting temperature (Tm) of the nucleic acid binding complex or probe (See, G. M. Wahl and S. L. Berger, 1987; Methods Enzymol., 152:399407 and A. R. Kimmel, 1987; Methods of Enzymol., 152:507-511), and may be used at a defined stringency. For example, included in the present invention are sequences capable of hybridizing under moderately stringent conditions to the HDAC nucleic acid sequences of SEQ ID NO:1, SEQ ID NO:12, or SEQ ID NO:19, SEQ ID NO:88, SEQ ID NO:94, and SEQ ID NO:96, and other sequences which are degenerate to those which encode the HDAC polypeptides (e.g., as a nonlimiting example: prewashing solution of 2×SSC, 0.5% SDS, 1.0 mM EDTA, pH 8.0, and hybridization conditions of 50° C., 5×SSC, overnight).

In another embodiment of the present invention, polynucleotide sequences or fragments (peptides) thereof which encode the HDAC polypeptide may be used in recombinant DNA molecules to direct the expression of the HDAC polypeptide products, or fragments or functional equivalents thereof, in appropriate host cells. Because of the inherent degeneracy of the genetic code, other DNA sequences, which encode substantially the same or a functionally equivalent amino acid sequences, may be produced, and these sequences may be used to express recombinant HDAC polypeptides.

As will be appreciated by those having skill in the art, it may be advantageous to produce HDAC polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter HDAC polypeptide-encoding sequences for a variety of reasons, including, but not limited to, alterations which modify the cloning, processing, and/or expression of the gene products. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and the like.

In another embodiment of the present invention, natural, modified, or recombinant nucleic acid sequences, or a fragment thereof, encoding the HDAC polypeptides may be ligated to a heterologous sequence to encode a fusion protein. For example, for screening peptide libraries for inhibitors or modulators of HDAC activity or binding, it may be useful to encode a chimeric HDAC protein or peptide that can be recognized by a commercially available antibody. A fusion protein may also be engineered to contain a cleavage site located between an HDAC protein-encoding sequence and the heterologous protein sequence, so that the HDAC protein may be cleaved and purified away from the heterologous moiety.

In another embodiment, ligand-binding assays are useful to identify inhibitor or antagonist compounds that interfere with the function of the HDAC protein, or activator compounds that stimulate the function of the HDAC protein. Preferred are inhibitor or antagonist compounds. Such assays are useful even if the function of a protein is not known. These assays are designed to detect binding of test compounds (i.e., test agents) to particular target molecules, e.g., proteins or peptides. The detection may involve direct measurement of binding. Alternatively, indirect indications of binding may involve stabilization of protein structure, or disruption or enhancement of a biological function. Non-limiting examples of useful ligand-binding assays are detailed below.

One useful method for the detection and isolation of binding proteins is the Biomolecular Interaction Assay (BIAcore) system developed by Pharmacia Biosensor and described in the manufacturer's protocol (LKB Pharmacia, Sweden). The BIAcore system uses an affinity purified anti-GST antibody to immobilize GST-fusion proteins onto a sensor chip. The sensor utilizes surface plasmon resonance, which is an optical phenomenon that detects changes in refractive indices. Accordingly, a protein of interest, e.g., an HDAC polypeptide, or fragment thereof, of the present invention, is coated onto a chip and test compounds (i.e., test agents) are passed over the chip. Binding is detected by a change in the refractive index (surface plasmon resonance).

A different type of ligand-binding assay involves scintillation proximity assays (SPA), as described in U.S. Pat. No. 4,568,649. In a modification of this assay currently undergoing development, chaperoning are used to distinguish folded and unfolded proteins. A tagged protein is attached to SPA beads, and test compounds are added. The bead is then subjected to mild denaturing conditions, such as, for example, heat, exposure to SDS, and the like, and a purified labeled chaperonin is added. If a test compound (i.e., test agent) has bound to a target protein, the labeled chaperonin will not bind; conversely, if no test compound has bound, the protein will undergo some degree of denaturation and the chaperonin will bind. In another type of ligand binding assay, proteins containing mitochondrial targeting signals are imported into isolated mitochondria in vitro (Hurt et al., 1985, *EMBO J.*, 4:2061-2068; Eilers and Schatz, 1986, *Nature*, 322:228-231).

In a mitochondrial import assay, expression vectors are constructed in which nucleic acids encoding particular target proteins are inserted downstream of sequences encoding mitochondrial import signals. The chimeric proteins are synthesized and tested for their ability to be imported into isolated mitochondria in the absence and presence of test compounds. A test compound that binds to the target protein should inhibit its uptake into isolated mitochondria in vitro.

Another type of ligand-binding assay suitable for use according to the present invention is the yeast two-hybrid system (Fields and Song, 1989, *Nature*, 340:245-246). The yeast two-hybrid system takes advantage of the properties of the GAL4 protein of the yeast *S. cerevisiae*. The GAL4 protein is a transcriptional activator required for the expression of genes encoding enzymes involving the utilization of galactose. GAL4 protein consists of two separable and functionally essential domains: an N-terminal domain, which binds to specific DNA sequences (UASG); and a C-terminal domain containing acidic regions, which is necessary to activate transcription. The native GAL4 protein, containing both domains, is a potent activator of transcription when yeast cells are grown on galactose medium. The N-terminal domain binds to DNA in a sequence-specific manner but is unable to activate transcription. The C-terminal domain contains the activating regions but cannot activate transcription because it fails to be localized to UASG. In the two-hybrid system, a system of two hybrid proteins containing parts of GAL4: (1) a GAL4 DNA-binding domain fused to a protein 'X', and (2) a GAL4 activation region fused to a protein 'Y'. If X and Y can form a protein-protein complex and reconstitute proximity of the GAL4 domains, transcription of a gene regulated by UASG occurs. Creation of two hybrid proteins, each containing one of the interacting proteins X and Y, allows the activation region of UASG to be brought to its normal site of action.

The binding assay described in Fodor et al., 1991, *Science*, 251:767-773, which involves testing the binding affinity of test compounds for a plurality of defined polymers synthesized on a solid substrate, may also be useful. Compounds that bind to an HDAC polypeptide, or portions thereof, according to this invention are potentially useful as agents for use in therapeutic compositions.

In another embodiment, sequences encoding an HDAC polypeptide may be synthesized in whole, or in part, using chemical methods well known in the art (See, for example, M. H. Caruthers et al., 1980, *Nucl. Acids Res. Symp. Ser.*, 215-223 and T. Horn, T et al., 1980, *Nucl. Acids Res. Symp. Ser.*, 225-232). Alternatively, an HDAC protein or peptide itself may be produced using chemical methods to synthesize the amino acid sequence of the HDAC polypeptide or peptide, or a fragment or portion thereof. For example, peptide synthesis can be performed using various solid-phase techniques (J. Y. Roberge et al., 1995, *Science*, 269:202-204) and automated synthesis may be achieved, for example, using the ABI 431A Peptide Synthesizer (PE Biosystems).

The newly synthesized peptide can be substantially purified by preparative high performance liquid chromatography (e.g., T. Creighton, 1983, *Proteins, Structures and Molecular Principles*, WH Freeman and Co., New York, N.Y), by reversed-phase high performance liquid chromatography, or other purification methods as are known in the art. The composition of the synthetic peptides may be confirmed by amino acid analysis or sequencing (e.g., the Edman degradation procedure; Creighton, supra). In addition, the amino acid sequence of an HDAC polypeptide, peptide, or any portion thereof, may be altered during direct synthesis and/or combined using chemical methods with sequences from other proteins, or any part thereof, to produce a variant polypeptide.

Expression of Human HDAC Proteins

To express a biologically active/functional HDAC polypeptide or peptide, the nucleotide sequences encoding the HDAC polypeptides, or functional equivalents, may be inserted into an appropriate expression vector, i.e., a vector which contains the necessary elements for the transcription and translation of the inserted coding sequence. Methods that are well known to and practiced by those skilled in the art may be used to construct expression vectors containing sequences encoding an HDAC polypeptide or peptide and appropriate transcriptional and translational control elements. These methods include in vitro recombinant DNA techniques, synthetic techniques, and in vivo genetic recombination. Such techniques are described in J. Sambrook et al., 1989, *Molecular Cloning, A Laboratory Manual*, Cold Spring Harbor Press, Plainview, N.Y. and in F. M. Ausubel et al., 1989, *Current Protocols in Molecular Biology*, John Wiley & Sons, New York, N.Y.

A variety of expression vector/host systems may be utilized to contain and express sequences encoding an HDAC polypeptide or peptide. Such expression vector/host systems include, but are not limited to, microorganisms such as bacteria transformed with recombinant bacteriophage, plasmid, or cosmid DNA expression vectors; yeast or fungi transformed with yeast or fungal expression vectors; insect cell systems infected with virus expression vectors (e.g., baculovirus); plant cell systems transformed with virus expression vectors (e.g., cauliflower mosaic virus (CaMV) and tobacco mosaic virus (TMV)), or with bacterial expression vectors (e.g., Ti or pBR322 plasmids); or animal cell systems. The host cell employed is not limiting to the present invention.

"Control elements" or "regulatory sequences" are those non-translated regions of the vector, e.g., enhancers, promoters, 5' and 3' untranslated regions, which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, La Jolla, Calif.) or PSPORT1 plasmid (Life Technologies), and the like, may be used. The baculovirus polyhedrin promoter may be used in insect cells. Promoters or enhancers derived from the genomes of plant cells (e.g., heat shock, RUBISCO; and storage protein genes), or from plant viruses (e.g., viral promoters or leader sequences), may be cloned into the vector. In mammalian cell systems, promoters from mammalian genes or from mammalian viruses are preferred. If it is necessary to generate a cell line that contains multiple copies of the sequence encoding an HDAC polypeptide or peptide, vectors based on SV40 or EBV may be used with an appropriate selectable marker.

In bacterial systems, a number of expression vectors may be selected, depending upon the use intended for the expressed HDAC product. For example, when large quantities of expressed protein are needed for the induction of antibodies, vectors that direct high level expression of fusion proteins that are readily purified may be used. Such vectors include, but are not limited to, the multifunctional *E. coli* cloning and expression vectors such as BLUESCRIPT (Stratagene), in which the sequence encoding an HDAC polypeptide, or peptide, may be ligated into the vector in-frame with sequences for the amino-terminal Met and the subsequent 7 residues of β-galactosidase, so that a hybrid protein is produced; pIN vectors (See, G. Van Heeke and S. M. Schuster, 1989, *J. Biol. Chem.*, 264:5503-5509); and the like. pGEX vectors (Promega, Madison, Wis.) may also be used to express foreign polypeptides, as fusion proteins with glutathione S-transferase (GST). In general, such fusion proteins are soluble and can be easily purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. (For reviews, see F. M. Ausubel et al., supra, and Grant et al., 1987, *Methods Enzymol.*, 153:516-544).

Should plant expression vectors be desired and used, the expression of sequences encoding an HDAC polypeptide or peptide may be driven by any of a number of promoters. For example, viral promoters such as the 35S and 19S promoters of CaMV may be used alone or in combination with the omega leader sequence from TMV (N. Takamatsu, 1987, *EMBO J.*, 6:307-311). Alternatively, plant promoters such as the small subunit of RUBISCO, or heat shock promoters, may be used (G. Coruzzi et al., 1984, *EMBO J.*, 3:1671-1680; R. Broglie et al., 1984, *Science*, 224:838-843; and J. Winter et al., 1991, *Results Probl. Cell Differ.* 17:85-105). These constructs can be introduced into plant cells by direct DNA transformation or pathogen-mediated transfection. Such techniques are described in a number of generally available reviews (See, for example, S. Hobbs or L. E. Murry, In: McGraw Hill *Yearbook of Science and Technology* (1992) McGraw Hill, New York, N.Y.; pp. 191-196).

An insect system may also be used to express an HDAC polypeptide or peptide. For example, in one such system, *Autographa californica* nuclear polyhedrosis virus (AcNPV) is used as a vector to express foreign genes in *Spodoptera frugiperda* cells or in *Trichoplusia larvae*. The sequences encoding an HDAC polypeptide or peptide may be cloned into a non-essential region of the virus such as the polyhedrin gene and placed under control of the polyhedrin promoter. Successful insertion of the HDAC polypeptide or peptide will render the polyhedrin gene inactive and produce recombinant virus lacking coat protein. The recombinant viruses may then be used to infect, for example, *S. frugiperda* cells or *Trichoplusia larvae* in which the HDAC polypeptide or peptide product may be expressed (E. K. Engelhard et al., 1994, *Proc. Nat. Acad. Sci.*, 91:3224-3227).

In mammalian host cells, a number of viral-based expression systems may be utilized. In cases where an adenovirus is used as an expression vector, sequences encoding an HDAC polypeptide or peptide may be ligated into an adenovirus transcription/translation complex containing the late promoter and tripartite leader sequence. Insertion in a non-essential E1 or E3 region of the viral genome may be used to obtain a viable virus which is capable of expressing the HDAC polypeptide or peptide in infected host cells (J. Logan and T. Shenk, 1984, *Proc. Natl. Acad. Sci.*, 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding an HDC polypeptide or peptide. Such signals include the ATG initiation codon and adjacent sequences. In cases where sequences encoding an HDAC polypeptide or peptide, its initiation codon, and upstream sequences are inserted into the appropriate expression vector, no additional transcriptional or translational control signals may be needed. However, in cases where only coding sequence, or a fragment thereof, is inserted, exogenous translational control signals, including the ATG initiation codon, should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system that is used, such as those described in the literature (D. Scharf et al., 1994, *Results Probl. Cell Differ.*, 20:125-162).

Moreover, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells having specific cellular machinery and characteristic mechanisms for such post-translational activities (e.g., COS, CHO, HeLa, MDCK, HEK293, and W138) are available from the American Type Culture Collection (ATCC), American Type Culture Collection (ATCC), 10801 University Boulevard, Manassas, Va. 20110-2209, and may be chosen to ensure the correct modification and processing of the foreign protein.

For long-term, high-yield production of recombinant proteins, stable expression is preferred. For example, cell lines which stably express an HDAC protein may be transformed using expression vectors which may contain viral origins of replication and/or endogenous expression elements and a selectable marker gene on the same, or on a separate, vector. Following the introduction of the vector, cells may be allowed to grow for 1-2 days in an enriched cell culture medium before they are switched to selective medium. The purpose of the selectable marker is to confer resistance to selection, and its presence allows the growth and recovery of cells that successfully express the introduced sequences. Resistant clones of stably transformed cells may be proliferated using tissue culture techniques appropriate to the cell type.

Any number of selection systems may be used to recover transformed cell lines. These include, but are not limited to, the Herpes Simplex Virus thymidine kinase (HSV TK), (M. Wigler et al., 1977, *Cell*, 11:223-32) and adenine phosphoribosyltransferase (I. Lowy et al., 1980, *Cell*, 22:817-23) genes which can be employed in tk⁻ or aprt⁻ cells, respectively. Also, anti-metabolite, antibiotic or herbicide resistance can be used as the basis for selection; for example, dhfr, which confers resistance to methotrexate (M. Wigler et al., 1980, *Proc. Natl. Acad. Sci.*, 77:3567-70); npt, which confers resistance to the aminoglycosides neomycin and G-418 (F. Colbere-Garapin et al., 1981, *J. Mol. Biol.*, 150:1-14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (S. C. Hartman and R. C. Mulligan, 1988, *Proc. Natl. Acad. Sci.*, 85:8047-51). Recently, the use of visible markers has gained popularity with such markers as the anthocyanins, β-glucuronidase and its substrate GUS, and luciferase and its substrate luciferin, which are widely used not only to identify transformants, but also to quantify the amount of transient or stable protein expression that is attributable to a specific vector system (C. A. Rhodes et al., 1995, *Methods Mol. Biol.*, 55:121-131).

Although the presence/absence of marker gene expression suggests that the gene of interest is also present, the presence and expression of the desired gene of interest may need to be confirmed. For example, if an HDAC nucleic acid sequence is inserted within a marker gene sequence, recombinant cells containing sequences encoding the HDAC polypeptide or peptide can be identified by the absence of marker gene function. Alternatively, a marker gene can be placed in tandem with a sequence encoding an HDAC polypeptide or peptide under the control of a single promoter. Expression of the marker gene in response to induction or selection usually indicates co-expression of the tandem gene.

Alternatively, host cells which contain the nucleic acid sequence encoding an HDAC polypeptide or peptide and which express the HDAC product may be identified by a variety of procedures known to those having skill in the art. These procedures include, but are not limited to, DNA-DNA or DNA-RNA hybridizations and protein bioassay or immunoassay techniques, including membrane, solution, or chip based technologies, for the detection and/or quantification of nucleic acid or protein.

Preferably, the HDAC polypeptide or peptide of this invention is substantially purified after expression. HDAC proteins and peptides can be isolated or purified in a variety of ways known to and practiced by those having skill in the art, depending on what other components may be present in the sample. Standard purification methods include electrophoretic, molecular, immunological and chromatographic techniques, including, but not limited to, ion exchange, hydrophobic affinity and reverse phase HPLC chromatography, and chromatofocusing. For example, an HDAC protein or peptide can be purified using a standard anti-HDAC antibody column. Ultrafiltration and diafiltration techniques, in conjunction with protein concentration, are also useful. For general guidance in suitable purification techniques, see R. Scopes, 1982, *Protein Purification*, Springer-Verlag, N.Y. As will be understood by the skilled practitioner, the degree of purification necessary will vary depending on the intended use of the HDAC protein or peptide; in some instances, no purification will be necessary.

In addition to recombinant production, fragments of an HDAC polypeptide or peptide may be produced by direct peptide synthesis using solid-phase techniques (J. Merrifield, 1963, *J. Am. Chem. Soc.*, 85:2149-2154). Protein synthesis may be performed using manual techniques or by automation. Automated synthesis may be achieved, for example, using ABI 431A Peptide Synthesizer (PE Biosystems). If desired, various fragments of an HDAC polypeptide can be chemically synthesized separately and then combined using chemical methods to produce the full length molecule.

Detection of Human HDAC Polynucleotide

The presence of polynucleotide sequences encoding an HDAC polypeptide or this invention can be detected by DNA-DNA or DNA-RNA hybridization, or by amplification using probes or portions or fragments of polynucleotides encoding the HDAC polypeptide. Nucleic acid amplification based assays involve the use of oligonucleotides or oligomers, based on the sequences encoding a particular HDAC polypeptide or peptide, to detect transformants containing DNA or RNA encoding an HDAC polypeptide or peptide.

A wide variety of labels and conjugation techniques are known and employed by those skilled in the art and may be used in various nucleic acid and amino acid assays. Means for producing labeled hybridization or PCR probes for detecting sequences related to polynucleotides encoding an HDAC polypeptide or peptide include oligo-labeling, nick translation, end-labeling, or PCR amplification using a labeled nucleotide. Alternatively, the sequences encoding an HDAC polypeptide, or any portions or fragments thereof, may be cloned into a vector for the production of an mRNA probe. Such vectors are known in the art, are commercially available, and may be used to synthesize RNA probes in vitro by addition of an appropriate RNA polymerase, such as T7, T3, or SP(6) and labeled nucleotides. These procedures may be conducted using a variety of commercially available kits (e.g., Amersham Pharmacia Biotech, Promega and U.S. Biochemical Corp.).

Suitable reporter molecules or labels which may be used include radionucleotides, enzymes, fluorescent, chemiluminescent, or chromogenic agents, as well as substrates, cofactors, inhibitors, magnetic particles, and the like. Non-limiting examples of labels include radioisotopes, such as $^3$H, $^{14}$C, and $^{32}$P, and non-radioactive molecules, such as digoxigenin. In addition, nucleic acid molecules may be modified using known techniques, for example, using RNA or DNA analogs, phosphorylation, dephosphorylation, methylation, or demethylation.

Human HDAC Polypeptides—Production, Detection, Isolation

Host cells transformed with nucleotide sequences encoding an HDAC protein or peptide, or fragments thereof, may be cultured under conditions suitable for the expression and recovery of the protein from cell culture. The protein produced by a recombinant cell may be secreted or contained intracellularly depending on the sequence and/or the vector used. As will be understood by those having skill in the art, expression vectors containing polynucleotides which encode an HDAC protein or peptide may be designed to contain signal sequences that direct secretion of the HDAC protein or peptide through a prokaryotic or eukaryotic cell membrane.

Other constructions may be used to join nucleic acid sequences encoding an HDAC protein or peptide to a nucleotide sequence encoding a polypeptide domain that will facilitate purification of soluble proteins. Such purification facilitating domains include, but are not limited to, metal chelating peptides such as histidine-tryptophan modules that allow purification on immobilized metals; protein A domains that allow purification on immobilized immunoglobulin; and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and the HDAC protein or peptide may be used to facilitate purification. One such expression vector provides for expression of a fusion protein containing HDAC-encoding sequence and a nucleic acid encoding 6 histidine residues preceding a thioredoxin or an enterokinase cleavage site. The histidine residues facilitate purification on IMAC (immobilized metal ion affinity chromatography) as described by J. Porath et al., 1992, *Prot. Exp. Purif.*, 3:263-281, while the enterokinase cleavage site provides a means for purifying from the fusion protein. For a discussion of suitable vectors for fusion protein production, see D. J. Kroll et al., 1993; *DNA Cell Biol.*, 12:441-453.

Human artificial chromosomes (HACs) may be used to deliver larger fragments of DNA than can be contained and expressed in a plasmid vector. HACs are linear microchromosomes which may contain DNA sequences of 10K to 10M in size, and contain all of the elements that are required for stable mitotic chromosome segregation and maintenance (See, J. J. Harrington et al., 1997, *Nature Genet.*, 15:345-355). HACs of 6 to 10M are constructed and delivered via conventional delivery methods (e.g., liposomes, polycationic amino polymers, or vesicles) for therapeutic purposes.

A variety of protocols for detecting and measuring the expression of an HDAC polypeptide using either polyclonal or monoclonal antibodies specific for the protein are known and practiced in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive with two non-interfering epitopes on the HDAC polypeptide is preferred, but a competitive binding assay may also be employed. These and other assays are described in the art as represented by the publication of R. Hampton et al., 1990; *Serological Methods, a Laboratory Manual*, APS Press, St Paul, Minn. and D. E. Maddox et al., 1983; *J. Exp. Med.*, 158:1211-1216).

For use with these assays, amino acid sequences (e.g., polypeptides, peptides, antibodies, or antibody fragments) may be attached to a label capable of providing a detectable signal, either directly or indirectly, including, but not limited to, radioisotope, fluorescent, and enzyme labels. Fluorescent labels include, for example, Cy3, Cy5, Alexa, BODIPY, fluorescein (e.g., Fluor X, DTAF, and FITC), rhodamine (e.g., TRITC), auramine, Texas Red, AMCA blue, and Lucifer Yellow. Preferred isotope labels include $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re. Preferred enzyme labels include peroxidase, β-glucuronidase, β-D-glucosidase, β-D-galactosidase, urease, glucose oxidase plus peroxidase, and alkaline phosphatase (see, e.g., U.S. Pat. Nos. 3,654,090; 3,850,752 and 4,016,043). Enzymes can be conjugated by reaction with bridging molecules such as carbodiimides, diisocyanates, glutaraldehyde, and the like. Enzyme labels can be detected visually, or measured by calorimetric, spectrophotometric, fluorospectrophotometric, amperometric, or gasometric techniques. Other labeling systems, such as avidin/biotin, Tyramide Signal Amplification (TSA™), are known in the art, and are commercially available (see, e.g., ABC kit, Vector Laboratories, Inc., Burlingame, Calif.; NEN® Life Science Products, Inc., Boston, Mass.).

A compound that interacts with a histone deacetylase according to the present invention may be one that is a substrate for the enzyme, one that binds the enzyme at its active site, or one that otherwise acts to alter enzyme activity by binding to an alternate site. A substrate may be acetylated histones, or a labeled acetylated peptide fragment derived therefrom, such as AcGly-Ala-Lys,(.epsilon.-Ac)-Arg-His-Arg-Lys,(.epsilon.-Ac)-ValNH$_2$, or other synthetic or naturally occurring substrates. Examples of compounds that bind to histone deacetylase are known inhibitors such as n-butyrate, trichostatin, trapoxin and SAHA (S. Swendeman et al., 1999, *Cancer Res.*, 59(17):4392-4399). The compound that interacts with a histone deacetylase is preferably labeled to allow easy quantification of the level of interaction between the compound and the enzyme. A preferred radiolabel is tritium.

The test compound (i.e., test agent) may be a synthetic compound, a purified preparation, crude preparation, or an initial extract of a natural product obtained from plant, microorganism or animal sources.

One aspect of the present method is based on test compound-induced inhibition of histone deacetylase activity. The enzyme inhibition assay involves adding histone deacetylase or an extract containing histone deacetylase to mixtures of an enzyme substrate and the test compound, both of which are present in known concentrations. The amount of the enzyme is chosen such that approximately 20% of the substrate is consumed during the assay. The assay is carried out with the test compound at a series of different dilution levels. After a period of incubation, the labeled portion of the substrate released by enzymatic action is separated and counted. The assay is generally carried out in parallel with a negative control (i.e., no test compound) and a positive control (i.e., containing a known enzyme inhibitor instead of a test compound). The concentration of the test compound at which 50% of the enzyme activity is inhibited (IC$_{50}$) is determined using art recognized method.

Although enzyme inhibition is the most direct measure of the inhibitory activity of the test compound, results obtained from a competitive binding assay in which the test compound competes with a known inhibitor for binding to the enzyme active site correlate well with the results obtained from enzyme inhibition assay described above. The binding assay represents a more convenient way to assess enzyme inhibition, because it allows the use of a crude extract containing histone deacetylase rather than partially purified enzyme. The use of a crude extract may not always be suitable in the enzyme inhibition assay because other enzymes present in the extract may act on the histone deacetylase substrate.

The competition binding assay is carried out by adding a histone deacetylase, or an extract containing histone deacetylase activity, to a mixture of the test compound and a labeled inhibitor, both of which are present in the mixture in known concentrations. After incubation, the enzyme-inhibitor complex is separated from the unbound labeled inhibitors and unlabeled test compound, and counted. The concentration of the test compound required to inhibit 50% of the binding of the labeled inhibitor to the histone deacetylase ($IC_{50}$) is calculated.

In one method suitable for this invention, the $IC_{50}$ of test compounds against host histone deacetylase is determined using either the enzyme inhibition assay or the binding assay as described above, to identify those compounds that have selectivity for a particular type of histone deacetylase over that of a host.

Anti-Human HDAC Antibodies and Uses Thereof

Antagonists or inhibitors of the HDAC polypeptides of the present invention may be produced using methods that are generally known in the art. In particular, purified HDAC polypeptides or peptides, or fragments thereof, can be used to produce antibodies, or to screen libraries of pharmaceutical agents or other compounds, particularly, small molecules, to identify those which specifically bind to the novel HDACs of this invention.

Antibodies specific for an HDAC polypeptide, or immunogenic peptide fragments thereof, can be generated using methods that have long been known and conventionally practiced in the art. Such antibodies may include, but are not limited to, polyclonal, monoclonal, chimeric, single chain, Fab fragments, and fragments produced by an Fab expression library. Neutralizing antibodies, (i.e., those which inhibit dimer formation) are especially preferred for therapeutic use.

For the production of antibodies, various hosts including goats, rabbits, sheep, rats, mice, humans, and others, can be immunized by injection with HDAC polypeptide, or any peptide fragment or oligopeptide thereof, which has immunogenic properties. Depending on the host species, various adjuvants may be used to increase the immunological response. Nonlimiting examples of suitable adjuvants include Freund's (incomplete), mineral gels such as aluminum hydroxide or silica, and surface active substances such as lysolecithin, pluronic polyols, polyanions, peptides, oil emulsions, KLH, and dinitrophenol. Adjuvants typically used in humans include BCG (bacilli Calmette Guérin) and *Corynebacterium parvum*.

Preferably, the peptides, fragments, or oligopeptides used to induce antibodies to HDAC polypeptides (i.e., immunogens) have an amino acid sequence having at least five amino acids, and more preferably, at least 7-10 amino acids. It is also preferable that the immunogens are identical to a portion of the amino acid sequence of the natural protein; they may also contain the entire amino acid sequence of a small, naturally occurring molecule. The peptides, fragments or oligopeptides may comprise a single epitope or antigenic determinant or multiple epitopes. Short stretches of HDAC amino acids may be fused with those of another protein, such as KLH, and antibodies are produced against the chimeric molecule.

Monoclonal antibodies to HDAC polypeptides, or immunogenic fragments thereof, may be prepared using any technique which provides for the production of antibody molecules by continuous cell lines in culture. These include, but are not limited to, the hybridoma technique, the human B-cell hybridoma technique, and the EBV-hybridoma technique (G. Kohler et al., 1975, *Nature*, 256:495-497; D. Kozbor et al., 1985, *J. Immunol. Methods*, 81:3142; R. J. Cote et al., 1983, *Proc. Natl. Acad. Sci. USA*, 80:2026-2030; and S. P. Cole et al., 1984, *Mol. Cell Biol.*, 62:109-120). The production of monoclonal antibodies is well known and routinely used in the art.

In addition, techniques developed for the production of "chimeric antibodies," the splicing of mouse antibody genes to human antibody genes to obtain a molecule with appropriate antigen specificity and biological activity can be used (S. L. Morrison et al., 1984, *Proc. Natl. Acad. Sci. USA*, 81:6851-6855; M. S. Neuberger et al., 1984, *Nature*, 312:604-608; and S. Takeda et al., 1985, *Nature*, 314:452-454). Alternatively, techniques described for the production of single chain antibodies may be adapted, using methods known in the art, to produce HDAC polypeptide- or peptide-specific single chain antibodies. Antibodies with related specificity, but of distinct idiotypic composition, may be generated by chain shuffling from random combinatorial immunoglobulin libraries (D. R. Burton, 1991, *Proc. Natl. Acad. Sci. USA*, 88:11120-3). Antibodies may also be produced by inducing in vivo production in the lymphocyte population or by screening recombinant immunoglobulin libraries or panels of highly specific binding reagents as disclosed in the literature (R. Orlandi et al., 1989, *Proc. Natl. Acad. Sci. USA*, 86:3833-3837 and G. Winter et al., 1991, *Nature*, 349:293-299).

Antibody fragments that contain specific binding sites for an HDAC polypeptide or peptide may also be generated. For example, such fragments include, but are not limited to, $F(ab')_2$ fragments which can be produced by pepsin digestion of the antibody molecule and Fab fragments which can be generated by reducing the disulfide bridges of the $F(ab')_2$ fragments. Alternatively, Fab expression libraries may be constructed to allow rapid and easy identification of monoclonal Fab fragments with the desired specificity (W. D. Huse et al., 1989, *Science*, 254. 1275-1281).

Various immunoassays can be used for screening to identify antibodies having the desired specificity. Numerous protocols for competitive binding or immunoradiometric assays using either polyclonal or monoclonal antibodies with established specificities are well known in the art. Such immunoassays typically involve measuring the formation of complexes between an HDAC polypeptide and its specific antibody. A two-site, monoclonal-based immunoassay utilizing monoclonal antibodies reactive with two non-interfering HDAC epitopes is preferred, but a competitive binding assay may also be employed (Maddox, supra).

Antibodies which specifically bind HDAC epitopes can also be used in immunohistochemical staining of tissue samples to evaluate the abundance and pattern of expression of each of the provided HDAC polypeptides. Anti-HDAC antibodies can be used diagnostically in immuno-precipitation and immunoblotting techniques to detect and evaluate HDAC protein levels in tissue as part of a clinical testing procedure. For instance, such measurements can be useful in predictive evaluations of the onset or progression of proliferative or differentiation disorders. Similarly, the ability to monitor HDAC protein levels in an individual can allow the determination of the efficacy of a given treatment regimen for an individual afflicted with such a disorder. The level of HDAC polypeptide may be measured from cells in a bodily fluid, such as in samples of cerebral spinal fluid or amniotic fluid, or can be measured in tissue, such as produced by biopsy. Diagnostic assays using anti-HDAC antibodies can include, for example, immunoassays designed to aid in early diagnosis of a disorder, particularly ones that are manifest at birth. Diagnostic assays using anti-HDAC polypeptide antibodies can also include immunoassays designed to aid in early diagnosis and phenotyping of neoplastic or hyperplastic disorders.

Another application of anti-HDAC antibodies according to the present invention is in the immunological screening of cDNA libraries constructed in expression vectors such as λgt11, λgt 18-23, λZAP, and λORF8. Messenger libraries of this type, having coding sequences inserted in the correct reading frame and orientation, can produce fusion proteins. For example, λgt11 will produce fusion proteins whose amino termini contain β-galactosidase amino acid sequences and whose carboxy termini contain a foreign polypeptide. Antigenic epitopes of an HDAC protein, e.g. other orthologs of a particular HDAC protein or other paralogs from the same species, can then be detected with antibodies by, for example, reacting nitrocellulose filters lifted from infected plates with anti-HDAC antibodies. Positive phage detected by this assay can then be isolated from the infected plate. Thus, the presence of HDAC homologs can be detected and cloned from other animals, as can alternative isoforms (including splice variants) from humans.

Therapeutics/Treatments/Methods of Use Involving HDACs

In an embodiment of the present invention, the polynucleotide encoding an HDAC polypeptide or peptide, or any fragment or complement thereof, may be used for therapeutic purposes. In one aspect, antisense to the polynucleotide encoding a novel HDAC polypeptide may be used in situations in which it would be desirable to block the transcription of HDAC mRNA. In particular, cells may be transformed or transfected with sequences complementary to polynucleotides encoding an HDAC polypeptide. Thus, complementary molecules may be used to modulate human HDAC polynucleotide and polypeptide activity, or to achieve regulation of gene function. Such technology is now well known in the art, and sense or antisense oligomers or oligonucleotides, or larger fragments, can be designed from various locations along the coding or control regions of polynucleotide sequences encoding the HDAC polypeptides. For antisense therapeutics, the oligonucleotides in accordance with this invention preferably comprise at least 3 to 50 nucleotides of a sequence complementary to SEQ ID NO:1, SEQ ID NO:12, SEQ ID NO:19, SEQ ID NO:88, SEQ ID NO:94, or SEQ ID NO:96. It is more preferred that such oligonucleotides and analogs comprise at least 8 to 25 nucleotides, and still more preferred to comprise at least 12 to 20 nucleotides of this sequence.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express nucleic acid sequences that are complementary to the nucleic acid sequences encoding the novel HDAC polypeptides and peptides of the present invention. These techniques are described both in J. Sambrook et al., supra and in F. M. Ausubel et al., supra.

A preferred approach for in vivo introduction of nucleic acid into a cell is by use of a viral vector containing nucleic acid, e.g. a cDNA encoding the particular HDAC polypeptide desired. Infection of cells with a viral vector has the advantage that a large proportion of the targeted cells can receive the nucleic acid. In addition, molecules encoded within the viral vector, e.g., by a cDNA contained in the viral vector, are expressed efficiently in cells that have taken up viral vector nucleic acid. As mentioned, retrovirus vectors, adenovirus vectors and adeno-associated virus vectors are exemplary recombinant gene delivery system for the transfer of exogenous genes in vivo, particularly into humans. These vectors provide efficient delivery of genes into cells, and the transferred nucleic acids are stably integrated into the chromosomal DNA of the host.

In addition to the above-illustrated viral transfer methods, non-viral methods can also be employed to yield expression of an HDAC polypeptide in the cells and/or tissue of an animal. Most non-viral methods of gene transfer rely on normal mechanisms used by mammalian cells for the uptake and intracellular transport of macromolecules. In preferred embodiments, non-viral gene delivery systems rely on endocytic pathways for the uptake of the novel HDAC polypeptide-encoding gene by the targeted cell. Exemplary gene delivery systems of this type include liposomal derived systems, poly-lysine conjugates, and artificial viral envelopes.

In clinical settings, the gene delivery systems for a therapeutic HDAC gene can be introduced into a patient by any of a number of methods, each of which is familiar in the art. For instance, a pharmaceutical preparation of the gene delivery system can be introduced systematically, e.g., by intravenous injection, and specific transduction of the protein in the target cells occurs predominantly from the specificity of transfection provided by the gene delivery vehicle, cell-type or tissue-type expression due to the transcriptional regulatory sequences controlling expression of the receptor gene, or a combination thereof.

In other aspects. the initial delivery of a recombinant HDAC gene is more limited, for example, with introduction into an animal being quite localized. For instance, the gene delivery vehicle can be introduced by catheter (see, U.S. Pat. No. 5,328,470) or by stereotactic injection (e.g., Chen et al., 1994, *Proc. Natl. Acad. Sci. USA*, 91:3054-3057). An HDAC nucleic acid sequence (gene), e.g., sequences represented by SEQ ID NO:1, SEQ ID NO:12, SEQ ID NO:19, SEQ ID NO:88, SEQ ID NO:94, and/or SEQ ID NO:96, or a fragment thereof, can be delivered in a gene therapy construct by electroporation using techniques described, for example, by Dev et al. (1994, *Cancer Treat. Rev.*, 20:105-115).

The gene encoding an HDAC polypeptide can be turned off by transforming a cell or tissue with an expression vector that expresses high levels of an HDAC polypeptide-encoding polynucleotide, or a fragment thereof. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and even longer if appropriate replication elements are designed to be part of the vector system.

Modifications of gene expression can be obtained by designing antisense molecules or complementary nucleic acid sequences (DNA, RNA, or PNA), to the control, 5', or regulatory regions of the genes encoding the novel HDAC polypeptides, (e.g., signal sequence, promoters, enhancers, and introns). Oligonucleotides derived from the transcription initiation site, e.g., between positions −10 and +10 from the start site, are preferable. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described (See, for example, J. E. Gee et al., 1994, In: B. E. Huber and B. I. Carr, *Molecular and Immunologic Approaches*, Futura Publishing Co., Mt. Kisco, N.Y.). The antisense molecule or complementary sequence may also be designed to block translation of mRNA by preventing the transcript from binding to ribosomes.

Ribozymes, i.e., enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Suitable examples include engineered hammerhead motif ribozyme molecules that can specifically and efficiently catalyze endonucleolytic cleavage of sequences encoding the HDAC polypeptides.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes according to the invention may be prepared by any method known in the art for the synthesis of nucleic acid molecules. Such methods include techniques for chemically synthesizing oligonucleotides, for example, solid phase phosphoramidite chemical synthesis. Alternatively, RNA molecules may be generated by in vitro and in vivo transcription of DNA sequences encoding the human HDACs of the present invention. Such DNA sequences may be incorporated into a wide variety of vectors with suitable RNA polymerase promoters such as T7 or SP. Alternatively, the cDNA constructs that constitutively or inducibly synthesize complementary HDAC RNA can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl (rather than phosphodiesterase linkages) within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and are equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods that are well known in the art.

In another embodiment of the present invention, an expression vector containing the complement of the polynucleotide encoding an HDAC polypeptide, or an antisense HDAC oligonucleotide, may be administered to an individual to treat or prevent a disease or disorder associated with uncontrolled or neoplastic cell growth, hyperactivity or stimulation, for example. A variety of specialized oligonucleotide delivery techniques may be employed, for example, encapsulation in unilamellar liposomes and reconstituted Sendai virus envelopes for RNA and DNA delivery (Arad et al., 1986, *Biochem. Biophys. Acta.,* 859:88-94).

In another embodiment, the proteins, antagonists, antibodies, agonists, complementary sequences, or vectors of the present invention can be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Any of the therapeutic methods described above may be applied to any individual in need of such therapy, including, for example, mammals such as dogs, cats, cows, horses, rabbits, monkeys, and most preferably, humans.

Another aspect of the present invention involves a method for modulating one or more of growth, differentiation, or survival of a mammalian cell by modulating HDAC bioactivity, e.g., by inhibiting the deacetylase activity of HDAC proteins, or disrupting certain protein-protein interactions. In general, whether carried out in vivo, in vitro, ex vivo, or in situ, the method comprises treating a cell with an effective amount of an HDAC therapeutic so as to alter, relative to an effect in the absence of treatment, one or more of (i) rate of growth or proliferation, (ii) differentiation, or (iii) survival of the cell. Accordingly, the method can be carried out with HDAC therapeutics, such as peptide and peptidomimetics, or other molecules identified in the drug screening methods as described herein which antagonize the effects of a naturally-occurring HDAC protein on a cell.

Other HDAC therapeutics include antisense constructs for inhibiting expression of HDAC proteins, and dominant negative mutants of HDAC proteins which competitively inhibit protein-substrate and/or protein-protein interactions upstream and downstream of the wild-type HDAC protein. In an exemplary embodiment, an antisense method is used to treat tumor cells by antagonizing HDAC activity and blocking cell cycle progression. The method includes, but is not limited to, the treatment of testicular cells, so as modulate spermatogenesis; the modulation of osteogenesis or chondrogenesis, comprising the treatment of osteogenic cells or chondrogenic cell, respectively, with an HDAC polypeptide. In addition, HDAC polypeptides can be used to modulate the differentiation of progenitor cells, e.g., the method can be used to cause differentiation of hematopoietic cells, neuronal cells, or other stem/progenitor cell populations, to maintain a cell in a differentiated state, and/or to enhance the survival of a differentiated cell, e.g., to prevent apoptosis or other forms of cell death.

The present method is applicable, for example, to cell culture techniques, such as in the culturing of hematopoietic cells and other cells whose survival or differentiation state is dependent on HDAC function. Moreover, HDAC agonists and antagonists can be used for therapeutic intervention, such as to enhance survival and maintenance of cells, as well as to influence organogenic pathways, such as tissue patterning and other differentiation processes. As an example, such a method is practiced for modulating, in an animal, cell growth, cell differentiation or cell survival, and comprises administering a therapeutically effective amount of an HDAC polypeptide to alter, relative the absence of HDAC treatment, one or more of (i) rate of cell growth or proliferation, (ii) cell differentiation, and/or (iii) cell survival of one or more cell types in an animal.

In another of its aspects the present invention provides a method of determining if a subject, e.g., a human patient, is at risk for a disorder characterized by unwanted cell proliferation or aberrant control of differentiation. The method includes detecting, in a tissue of the subject, the presence or the absence of a genetic lesion characterized by at least one of (i) a mutation of a gene encoding an HDAC protein, e.g. represented in one of SEQ ID NO:1, SEQ ID NO:12, SEQ ID NO:19, SEQ ID NO:88, SEQ ID NO:94, or SEQ ID NO:96, or a homolog thereof, or (ii) the mis-expression of an HDAC gene. More specifically, detecting the genetic lesion includes ascertaining the existence of at least one of a deletion of one or more nucleotides from an HDAC gene; an addition of one or more nucleotides to the gene, a substitution of one or more nucleotides of the gene, a gross chromosomal rearrangement of the gene; an alteration in the level of a messenger RNA transcript of the gene; the presence of a non-wild type splicing pattern of an mRNA transcript of the gene; or a non-wild type level of the protein.

For example, detecting a genetic lesion can include (i) providing a probe/primer including an oligonucleotide containing a region of nucleotide sequence which hybridizes to a sense or antisense sequence of an HDAC gene, e.g., a nucleic acid represented in one of SEQ ID NO:1, SEQ ID NO:12, SEQ ID NO:19, SEQ ID NO:88, SEQ ID NO:94, or SEQ ID NO:96, or naturally occurring mutants thereof, or 5' or 3' flanking sequences naturally associated with the HDAC gene; (ii) exposing the probe/primer to nucleic acid of the tissue; and (iii) detecting, by hybridization of the probe/primer to the nucleic acid, the presence or absence of the genetic lesion; e.g., wherein detecting the lesion comprises utilizing the probe/primer to determine the nucleotide sequence of the HDAC gene and, optionally, of the flanking nucleic acid sequences. For instance, the probe/primer can be employed in a polymerase chain reaction (PCR) or in a ligation chain reaction (LCR). In alternative embodiments, the level of an HDAC protein is detected in an immunoassay using an antibody that is specifically immunoreactive with the HDAC protein.

Methods and Therapeutic Uses Related to Cell Modulation

Another aspect of the present invention relates to a method of inducing and/or maintaining a differentiated state, enhancing survival, and/or inhibiting (or alternatively, potentiating) the proliferation of a cell, by contacting cells with an agent that modulates HDAC-dependent transcription. In view of the apparently broad involvement of HDAC proteins in the control of chromatin structure and, in turn, transcription and replication, the present invention contemplates a method for generating and/or maintaining an array of different tissue both in vitro and in vivo. An "HDAC therapeutic," whether inhibitory or potentiating with respect to modulating histone deacetylation, can be, as appropriate, any of the preparations described herein, including isolated polypeptides, gene therapy constructs, antisense molecules, peptidomimetics, or agents identified in the drug and bioactive screening assays and methods described herein.

As an aspect of the present invention, the HDAC modulatory (i.e., inhibitory or stimulatory) compounds are likely to play an important role in effecting cellular proliferation. There are a wide variety of pathological cell proliferative conditions for which HDAC therapeutic agents of the present invention may be used in treatment. For instance, such agents can provide therapeutic benefits in the inhibition of an anomalous cell proliferation. Nonlimiting examples of diseases and conditions that may benefit from such methods include various cancers and leukemias, psoriasis, bone diseases, fibroproliferative disorders, e.g., those involving connective tissues, atherosclerosis and other smooth muscle proliferative disorders, as well as chronic inflammation.

Non-limiting cancer types include carcinoma (e.g., adenocarcinoma), sarcoma, myeloma, leukemia, and lymphoma, and mixed types of cancers, such as adenosquamous carcinoma, mixed mesodermal tumor, carcinosarcoma, and teratocarcinoma. Representative cancers include, but are not limited to, bladder cancer, lung cancer, breast cancer, colon cancer, rectal cancer, endometrial cancer, ovarian cancer; head and neck cancer, prostate cancer, and melanoma. Specifically included are AIDS-related cancers (e.g., Kaposi's Sarcoma, AIDS-related lymphoma), bone cancers (e.g., osteosarcoma, malignant fibrous histiocytoma of bone, Ewing's Sarcoma, and related cancers), and hematologic/blood cancers (e.g., adult acute lymphoblastic leukemia, childhood acute lymphoblastic leukemia, adult acute myeloid leukemia, childhood acute myeloid leukemia, chronic lymphocytic leukemia, chronic myelogenous leukemia, hairy cell leukemia, cutaneous T-cell lymphoma, adult Hodgkin's disease, childhood Hodgkin's disease, Hodgkin's disease during pregnancy, mycosis fungoides, adult non-Hodgkin's lymphoma, childhood non-Hodgkin's lymphoma, non-Hodgkin's lymphoma during pregnancy, primary central nervous system lymphoma, Sezary syndrome, cutaneous T-cell lymphoma, Waldenstrom's macroglobulinemia, multiple myeloma/plasma cell neoplasm, myelodysplastic syndrome, and myeloproliferative disorders).

Also included are brain cancers (e.g., adult brain tumor, childhood brain stem glioma, childhood cerebellar astrocytoma, childhood cerebral astrocytoma, childhood ependymoma, childhood medulloblastoma, supratentorial primitive neuroectodermal and pineal, and childhood visual pathway and hypothalamic glioma), digestive/gastrointestinal cancers (e.g., anal cancer, extrahepatic bile duct cancer, gastrointestinal carcinoid tumor, colon cancer, esophageal cancer, gallbladder cancer, adult primary liver cancer, childhood liver cancer, pancreatic cancer, rectal cancer, small intestine cancer, and gastric cancer), musculoskeletal cancers (e.g., childhood rhabdomyosarcoma, adult soft tissue sarcoma, childhood soft tissue sarcoma, and uterine sarcoma), and endocrine cancers (e.g., adrenocortical carcinoma, gastrointestinal carcinoid tumor, islet cell carcinoma (endocrine pancreas), parathyroid cancer, pheochromocytoma, pituitary tumor, and thyroid cancer).

Further included are neurologic cancers (e.g., neuroblastoma, pituitary tumor, and primary central nervous system lymphoma), eye cancers (e.g., intraocular melanoma and retinoblastoma), genitourinary cancers (e.g., bladder cancer, kidney (renal cell) cancer, penile cancer, transitional cell renal pelvis and ureter cancer, testicular cancer, urethral cancer, Wilms' tumor and other childhood kidney tumors), respiratory/thoracic cancers (e.g., non-small cell lung cancer, small cell lung cancer, malignant mesothelioma, and malignant thymoma), germ cell cancers (e.g., childhood extracranial germ cell tumor and extragonadal germ cell tumor), skin cancers (e.g., melanoma, and merkel cell carcinoma), gynecologic cancers (e.g., cervical cancer, endometrial cancer, gestational trophoblastic tumor, ovarian epithelial cancer, ovarian germ cell tumor, ovarian low malignant potential tumor, uterine sarcoma, vaginal cancer, and vulvar cancer), and unknown primary cancers.

In certain aspects of the inventions, the disclosed HDAC inhibitors, antisense molecules, anti-HDAC antibodies, or antibody fragments can be used as treatments for breast or prostate cancers. In particular, HDAC9c inhibitors, HDAC9c antisense molecules, anti-HDAC9c antibodies, or fragments thereof, can be used. Specific breast cancers include, but are not limited to, non-invasive cancers, such as ductal carcinoma in situ (DCIS), intraductal carcinoma lobular carcinoma in situ (LCIS), papillary carcinoma, and comedocarcinoma, or invasive cancers, such as adenocarcinomas, or carcinomas, e.g., infiltrating ductal carcinoma, infiltrating lobular carcinoma, infiltrating ductal and lobular carcinoma, medullary carcinoma, mucinous (colloid) carcinoma, comedocarcinoma, Paget's Disease, papillary carcinoma, tubular carcinoma, and inflammatory carcinoma. Specific prostate cancers may include adenocarcinomas and sarcomas, or pre-cancerous conditions, such as prostate intraepithelial neoplasia (PIN).

In addition to proliferative disorders, the present invention envisions the use of HDAC therapeutics for the treatment of differentiation disorders resulting from, for example, de-differentiation of tissue which may (optionally) be accompanied by abortive reentry into mitosis, e.g. apoptosis. Such degenerative disorders include chronic neurodegenerative diseases of the nervous system, including Alzheimer's disease, Parkinson's disease, Huntington's chorea, amylotrophic lateral sclerosis (ALS) and the like, as well as spinocerebellar degenerations. Other differentiation disorders include, for example, disorders associated with connective tissue, such as can occur due to de-differentiation of chondrocytes or osteocytes, as well as vascular disorders which involve de-differentiation of endothelial tissue and smooth muscle cells, gastric ulcers characterized by degenerative changes in glandular cells, and renal conditions marked by failure to differentiate, e.g. Wilm's tumors.

It will also be recognized that, by transient use of modulators of HDAC activities, in vivo reformation of tissue can be accomplished, for example, in the development and maintenance of organs. By controlling the proliferative and differentiation potential for different cell types, HDAC therapeutics can be used to re-form injured tissue, or to improve grafting and morphology of transplanted tissue. As an example, HDAC antagonists and agonists can be employed in a differential manner to regulate different stages of organ repair after physical, chemical or pathological insult or injury. Such regimens can be utilized, for example, in the repair of cartilage, increasing bone density, liver repair subsequent to a partial hepatectomy, or to promote regeneration of lung tissue in the treatment of emphysema. The present method is also applicable to cell culture techniques.

More specifically, HDAC therapeutics can be used to induce differentiation of uncommitted progenitor cells, thus giving rise to a committed progenitor cell, or causing further restriction of the developmental fate of a committed progenitor cell toward becoming a terminally differentiated cell. As an example, methods involving HDAC therapeutics can be used in vitro, ex vivo, or in vivo to induce and/or to maintain the differentiation of hematopoietic cells into erythrocytes and other cells of the hematopoietic cell lineage. Illustratively, the effect of erythropoietin (EPO) on the growth of EPO-responsive erythroid precursor cells is increased to influence their differentiation into red blood cells. Also, as an example, the amount of EPO, or other differentiating agent, that is required for growth and/or differentiation is reduced based on the administration of an inhibitor of histone deacetylation. (PCT/US92/07737).

Accordingly, HDAC therapeutics as described, particularly those that antagonize HDAC deacetylase activity, can be administered alone or in conjunction with EPO, for example, in a suitable carrier, to vertebrates to promote erythropoiesis. Alternatively, ex vivo cell treatments are suitable. Similar types of treatments can be used for a variety of disease states, including use in individuals who require bone marrow transplants (e.g., patients with aplastic anemia, acute leukemias, recurrent lymphomas, or solid tumors). As an example, prior to receiving a bone marrow transplant, a recipient is prepared by ablating or removing endogenous hematopoietic stem cells. Such treatment is typically performed by total body irradiation, or by delivery of a high dose of an alkylating agent or other chemotherapeutic cytotoxic agent (Anklesaria et al., 1987, Proc. Natl. Acad. Sci. USA), 84:7681-7685). Following the preparation of the recipient, donor bone marrow cells are injected intravenously. Optionally, HDAC therapeutics could be contacted with the cells ex vivo or administered to the subject with the re-implanted cells.

In addition, there may be cell-type specific HDAC proteins, and/or some cell types may be more sensitive to the modulation of HDAC deacetylase activities. Even within a cell type, the stage of differentiation or position in the cell cycle could influence a cell's response to a modulatory HDAC therapeutic agent. Accordingly, the present invention contemplates the use of agents that modulate histone deacetylase activity to specifically inhibit or activate certain cell types. As an illustrative example, T cell proliferation could be preferentially inhibited so as to induce tolerance by a procedure similar to that used to induce tolerance using sodium butyrate (see, for example, PCT/US93/03045). Accordingly, HDAC therapeutics may be used to induce antigen specific tolerance in any situation in which it is desirable to induce tolerance, such as autoimmune diseases, in allogeneic or xenogeneic transplant recipients, or in graft versus host (GVH) reactions. Tolerance is typically induced by presenting the tolerizing compound (e.g., an HDAC inhibitor compound) substantially concurrently with the antigen, i.e., within a time period that is reasonably close to that in which the antigen is administered. Preferably, the HDAC therapeutic is administered after presentation of the antigen, so that the cumulative effect will occur after the particular repertoire of $T_H$ cells begins to undergo clonal expansion. Additionally, the present invention contemplates the application of HDAC therapeutics for modulating morphogenic signals involved in organogenic pathways. Thus, it is apparent that compositions comprising HDAC therapeutics can be employed for both cell culture and therapeutic methods involving the generation and maintenance of tissue.

In a further aspect, HDAC therapeutics are useful in increasing the amount of protein produced by a cell, including a recombinant cell. Suitable cells may comprise any primary cell isolated from any animal, cultured cells, immortalized cells, transfected or transformed cells, and established cell lines. Animal cells preferably will include cells which intrinsically have an ability to produce a desired protein; cells which are induced to have an ability to produce a desired protein, for example, by stimulation with a cytokine such as an interferon or an interleukin; genetically engineered cells into which a gene encoding a desired protein is introduced. The protein produced by the process can include peptides or proteins, including peptide-hormone or proteinaceous hormones such as any useful hormone, cytokine, interleukin, or protein which it may be desirable to be produced in purified form and/or in large quantity.

In specific aspects, the HDAC inhibitors, antisense molecules, anti-HDAC antibodies, or antibody fragments of the invention can be used in combination with other HDAC inhibitory agents, e.g., trichostatin A (D. M. Vigushin et al., 2001, *Clin. Cancer Res.* 7(4):971-6); trapoxin A (Itazaki et al., 1990, *J. Antibiot.* 43:1524-1532), MS-275 (T. Suzuki et al., 1999, *J. Med. Chem.* 42(15):3001-3), CHAPs (Y. Komatsu et al., 2001, *Cancer Res.* 61(11):4459-66), CI-994 (see, e.g., P. M. LoRusso et al., 1996, *New Drugs* 14(4):349-56), SAHA (V. M. Richon et al., 2001, *Blood Cells Mol. Dis.* 27(1):260-4), depsipeptide (FR901228; FK228; V. Sandor et al., 2002, *Clin. Cancer Res.* 8(3):718-28), CBHA (D. C. Coffey et al., 2001, *Cancer Res.* 61(9):3591-4), pyroxamide, (L. M. Butler et al, 2001, *Clin. Cancer Res.* 7(4):962-70), CHAP31 (Y. Komatsu et al., 2001, *Cancer Res.* 61(11):4459-66), HC-toxin (Liesch et al., 1982, *Tetrahedron* 38:45-48), chlamydocin (Closse et al., 1974, *Helv. Chim. Acta* 57:533-545), Cly-2 (Hirota et al., 1973, *Agri. Biol. Chem.* 37:955-56), WF-3161 (Umehana et al., 1983, J. Antibiot 36, 478-483; M. Kawai et al., 1986, *J. Med. Chem.* 29(11):2409-11), Tan-1746 (Japanese Patent No. 7196686 to Takeda Yakuhin Kogyo KK), apicidin (S. H. Kwon et al., 2002, *J. Biol. Chem.* 277 (3):2073-80), and analogs thereof.

Screening Methods

The novel HDAC proteins, peptides and nucleic acids can be used in screening assays to identify candidate bioactive agents or drugs that modulate HDAC bioactivity, preferably HDAC inhibitors, for potential use to treat neoplastic disorders, for example, to kill cancer cells and tumor cells exhibiting uncontrolled cell growth for numerous reasons, e.g., the lack of a suppressor molecule such as p53. In addition, HDAC proteins and encoding nucleic acids, as well as the bioactive agents that modulate HDAC activity or function, can be used as effectors in methods to regulate cell growth, e.g., to kill neoplastic cells.

The HDAC polynucleotides and polypeptides can also be modulated by interactive molecules. By "modulate" herein is meant that the bioactivity of HDAC is altered, i.e., either increased or decreased. In a preferred embodiment, HDAC function is inhibited. The HDACs can be used as targets to screen for inhibitors of HDAC, e.g., naturally-occurring HDAC, function, bioactivity, or expression in neoplastic cells and/or uncontrolled cell growth. Examples of HDAC biological activity include the ability to modulate the proliferation of cells. For example, inhibiting histone deacetylation causes cells to arrest in the G1 and G2 phases of the cell cycle. The biochemical activity associated with the novel HDAC proteins of the present invention are also characterized in terms of binding to and (optionally) catalyzing the deacetylation of an acetylated histone. Another biochemical property of certain HDAC proteins involves binding to other cellular proteins, such as RbAp48 (Qian et al., 1993, *Nature*, 364:648), or Sin3A. (see, e.g., WO 97/35990)

Generally, in performing screening methods, HDAC polypeptide or peptide can be non-diffusably bound to an insoluble support having isolated sample receiving areas (e.g. a microtiter plate, an array, etc.). The criteria for suitable insoluble supports are that they can be made of any composition to which polypeptides can be bound; they are readily separated from soluble material; and they are otherwise compatible with the overall method of screening. The surface of such supports may be solid or porous and of any convenient size or shape. Examples of suitable insoluble supports include microtiter plates, arrays, membranes and beads. These are typically made of glass, plastic (e.g., polystyrene), polysaccharides, nylon or nitrocellulose. Microtiter plates and arrays are especially convenient, because a large number of assays can be carried out simultaneously, using small amounts of reagents and samples. The particular manner of binding the polypeptide is not crucial, so long as it is compatible with the reagents and overall methods of the invention, maintains the activity of the peptide and is nondiffusable.

Preferred methods of binding include the use of antibodies (which should not hinder the binding of HDACs to associated proteins), direct binding to "sticky" or ionic supports, chemical crosslinking, etc. Following binding of the polypeptide, excess unbound material is removed by washing. The sample receiving areas may then be blocked as needed through incubation with bovine serum albumin (BSA), casein or other innocuous/nonreactive protein.

A candidate bioactive agent is added to the assay. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. The term "agent" as used herein describes any molecule, e.g., protein, oligopeptide, small organic molecule, polysaccharide, polynucleotide, etc., having the capability of directly or indirectly altering the activity or function of HDAC polypeptides. Generally a plurality of assay mixtures are run in parallel with different agent concentrations to obtain a differential response to the various concentrations. Typically, one of these concentrations serves as a negative control, i.e., at zero concentration, or below the level of detection.

Candidate agents encompass numerous chemical classes, though typically they are organic molecules, preferably small organic compounds having a molecular weight of more than 100 and less than about 10,000 daltons, preferably, less than about 2000 to 5000 daltons, as a nonlimiting example. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. In addition, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

The determination of the binding of the candidate biomolecule or agent to an HDAC polypeptide may be accomplished in a number of ways practiced in the art. In one aspect, the candidate bioactive agent is labeled, and binding is determined directly. Where the screening assay is a binding assay, one or more of the molecules may be joined to a label, where the label can directly or indirectly provide a detectable signal. Various labels include radioisotopes, enzymes, fluorescent and chemiluminescent compounds, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule which allows detection, in accordance with known procedures. In some embodiments, only one of the components is labeled. Alternatively, more than one component may be labeled with different labels; for example, the HDAC polypeptide may be labeled with one fluorophor and the candidate agent labeled with another In one embodiment, the candidate bioactive agent is labeled. Labeled candidate bioactive agents are incubated with an HDAC polypeptide for a time sufficient to allow binding, if present. Incubations may be performed at any temperature which facilitates optimal activity, typically between 4° C. and 40° C. Incubation periods are selected for optimum activity, but may also be optimized to facilitate rapid high throughput screening. Typically between 0.1 and 1 hour is sufficient. Excess reagent is generally removed or washed away. The presence or absence of the labeled component is detected to determine and indicate binding.

A variety of other reagents may be included in the screening assay. Such reagents include, but are not limited to, salts, neutral proteins, e.g. albumin, detergents, etc., which may be used to facilitate optimal protein-protein binding and/or to reduce non-specific or background interactions. In addition, reagents that otherwise improve the efficiency of the assay, such as protease inhibitors, nuclease inhibitors, anti-microbial agents, etc. may be used. Further, the mixture of components in the method may be added in any order that provides for the requisite binding.

Kits are included as an embodiment of the present invention which comprise containers with reagents necessary to screen test compounds. Depending on the design of the test and the types of compounds to be screened, such kits include human HDAC polynucleotide, polypeptide, or peptide and instructions for performing the assay.

Inhibitors of the enzymatic activity of each of the novel HDAC polypeptides can be identified using assays which measure the ability of an agent to inhibit catalytic conversion of a substrate by the HDAC proteins provided by the present invention. For example, the ability of the novel HDAC proteins to deacetylate a histone substrate, such as histone H4, in the presence and absence of a candidate inhibitor, can be determined using standard enzymatic assays.

A number of methods have been employed in the art for assaying histone deacetylase activity, and can be incorporated in the drug screening assays of the present invention. Preferably, the assay method will employ a labeled acetyl group linked to appropriate histone lysine residues as substrates. In other embodiments, a histone substrate peptide can be labeled with a group whose signal is dependent on the simultaneous presence or absence of an acetyl group, e.g., the label can be a fluorogenic group whose fluorescence is modulated (either quenched or potentiated) by the presence of the acetyl moiety.

Using standard enzymatic analysis, the ability of a test agent (i.e., test compound) to cause a statistically significant change in substrate conversion by a histone deacetylase can be measured, and as desirable, inhibition constants, e.g., $K_i$ values, can be calculated. The histone substrate can be provided as a purified or semi-purified polypeptide or as part of a cell lysate. Likewise, the histone deacetylase can be provided to a reaction mixture as a purified or semi-purified polypeptide, or as a cell lysate. Accordingly, the reaction mixtures can range from reconstituted protein mixtures derived with purified preparations of histones and deacetylases, to mixtures of cell lysates, e.g., by admixing baculovirus lysates containing recombinant histones and deacetylases.

As an example, the histone substrate for assays described herein can be provided by isolation of radiolabeled histones from metabolically labeled cells. Cells such as HeLa cells can be labeled in culture by the addition of [$^3$H]acetate (New England Nuclear) to the culture media. (Hay et al., 1983, *J. Biol. Chem.*, 258:3726-3734). The addition of an HDAC inhibitor, such as butyrate, trapoxin and the like, can be used to increase the abundance of acetylated histones in the cells. Radiolabeled histones can be isolated from the cells by extraction with $H_2SO_4$ (Marushige et al., 1966, *J. Mol. Biol.*, 15:160-174). Briefly, cells are homogenized in buffer, centrifuged to isolate a nuclear pellet, and the subsequently homogenized nuclear pellet is centrifuged through sucrose. The resulting chromatin pellet extracted by addition of $H_2SO_4$ to yield [$^3$H]acetyl-labeled histones. Alternatively, nucleosome preparations containing [$^3$H]acetyl-labeled histones can be isolated from metabolically labeled cells. As known in the art, nucleosomes can be isolated from cell preparations by sucrose gradient centrifugation (e.g., Hay et al., 1983, *J. Biol. Chem.*, 258:3726-3734 and Noll, 1967, *Nature*, 215:360-363), and polynucleosomes can be prepared by NaCl precipitation from micrococcal nuclease digested cells (Hay et al., supra).

Similar procedures for isolating labeled histones from other cells types, including yeast, have been described. (See for example, Alonso et al., 1986, *Biochem Biophys Acta*, 866:161-169 and Kreiger et al, 1974, *J. Biol. Chem.*, 249:332 334). Also, histones are generated by recombinant gene expression, and include an exogenous tag (e.g., an HA epitope, a poly(his) sequence, and the like) which facilitates purification from cell extracts. Further, whole nuclei can be isolated from metabolically labeled cells by micrococcal nuclease digestion (Hay et al., supra).

The deacetylase substrate can also be provided as an acetylated peptide including a sequence corresponding to the sequence around the specific lysyl residues acetylated on histones, e.g., peptidyl portions of the core histones H2A, H2B, H3, or H4. Such fragments can be produced by cleavage of acetylated histones derived from metabolically labeled cells, e.g., by treatment with proteolytic enzymes or cyanogen bromide (Kreiger et al., supra). The acetylated peptide can also be provided by standard solid phase synthesis using acetylated lysine residues (Id.).

The activity of a histone deacetylase in assay detection methods involving use of [$^3$H]acetyl-labeled histones is detected by measuring the release of [$^3$H]acetate by standard scintillation techniques. As an illustrative example, a reaction mixture is provided which contains a recombinant HDAC protein suspended in buffer, along with a sample of [$^3$H] acetyl-labeled histones and (optionally) a test compound. The reaction mixture is maintained at a desired temperature and pK such as 22° C. at pH 7.8, for several hours, and the reaction is terminated by boiling, or another form of denaturation. Released [$^3$H]acetate is extracted and counted. For example, the quenched reaction mixture can be acidified with concentrated HCl and used to create a biphasic mixture with ethyl acetate. The resulting two-phase system is thoroughly mixed, centrifuged, and the ethyl acetate phase collected and counted by standard scintillation methods. Other methods for detecting acetate release will be easily recognized by those having skill in the art.

In yet another aspect, the drug screening assay is designed to include a reagent cell recombinantly expressing one or more of a target protein or HDAC protein. The ability of a test agent to alter the activit of the HDAC protein can be detected by analysis of the recombinant cell. For instance, agonists and antagonists of the HDAC biological activity can by detected by scoring for alterations in growth or differentiation (phenotype) of the cell. General techniques for detecting these characteristics are well known, and will vary with respect to the source of the particular reagent cell utilized in any given assay. For example, quantification of cell proliferation in the presence and absence of a candidate agent can be measured by using a number of techniques well known in the art, including simple measurement of population growth curves.

Where an assay involves proliferation in a liquid medium, turbidimetric techniques (i.e. absorbance/transmittance of light of a given wavelength through the sample) can be utilized. For example, in a case in which the reagent cell is a yeast cell, measurement of absorbance of light at a wavelength at between 540 and 600 nm can provide a conveniently fast measure of cell growth. Moreover, the ability of yeast cells to form colonies in solid medium (e.g. agar) can be used to readily score for proliferation. In other embodiments, an HDAC substrate protein, such as a histone, can be provided as a fusion protein which permits the substrate to be isolated from cell lysates and the degree of acetylation detected. Each of these techniques is suitable for high throughput analysis necessary for rapid screening of large numbers of candidate HDAC modulatory agents.

In addition, in assays in which the ability of an agent to cause or reverse a transformed phenotype is being determined, cell growth in solid or semi-solid medium, such as agar, can further aid in establishing whether a mammalian cell is transformed. Visual inspection of the morphology of the reagent cell can also be used to determine whether the biological activity of the targeted HDAC protein has been affected by the added agent. By illustration, the ability of an agent to influence an apoptotic phenotype which is mediated in some way by a recombinant HDAC protein can be assessed by visual microscopy. Similarly, the formation of certain cellular structures as part of normal cell differentiation, such as the formation of neuritic processes, can be visualized under a light microscope.

The nature of the effect of a test agent on a reagent cell can be assessed by measuring levels of expression of specific genes, e.g., by reverse transcription PCR. Another method of scoring for an effect on HDAC activity is by detecting cell-type specific marker expression through immunofluorescent staining. Many such markers are known in the art for which antibodies are readily available. For example, the presence of chondroitin sulfate proteoglycans, as well as type-II collagen, is correlated with cartilage production in chondrocytes, and each can be detected by immunostaining. Similarly, the human kidney differentiation antigen gp160, human aminopeptidase A, is a marker of kidney induction, and the cytoskeletal protein troponin I is a marker of heart induction.

Also, the alteration of expression of a reporter gene construct provided in the reagent cell provides a means of detecting an effect on HDAC activity. For example, reporter gene constructs designed using transcriptional regulatory sequences, e.g. the promoters, for developmentally regulated genes can be used to drive the expression of a detectable marker, such as a luciferase gene. For example, the construct can be prepared using the promoter sequence from a gene expressed in a particular differentiation phenotype.

Pharmaceutical Compositions

A further embodiment of the present invention embraces the administration of a pharmaceutical composition, in conjunction with a pharmaceutically acceptable carrier, diluent, or excipient, for any of the above-described therapeutic uses and effects. Such pharmaceutical compositions may comprise HDAC nucleic acid, polypeptide, or peptides, antibodies to HDAC polypeptides or peptides, or fragments thereof, mimetics, agonists (e.g., activators), antagonists (e.g., inhibitors, blockers) of the HDAC polypeptide, peptide, or polynucleotide. The compositions may be administered alone or in combination with at least one other agent, such as a stabilizing compound, which may be administered in any sterile, biocompatible pharmaceutical (or physiologically compatible) carrier, including, but not limited to, saline, buffered saline, dextrose, and water. The compositions may be administered to a patient alone, or in combination with other agents, drugs, hormones, or biological response modifiers. Preferred are compositions comprising one or more HDAC inhibitors.

The pharmaceutical compositions for use in the present invention can be administered by any number of routes including, but not limited to, parenteral oral, intravenous, intramuscular, intra-arterial, intramedullary, intrathecal, intraventricular, transdermal, subcutaneous, intraperitoneal, intranasal, ophthalmic, enteral, topical, sublingual, vaginal, or rectal means.

Transdermal patches have the added advantage of providing controlled delivery of a compound of the present invention to the body. Such dosage forms can be made by dissolving or dispersing a deacetylase inhibitor in the proper medium. Absorption enhancers can also be used to increase the flux of the deacetylase inhibitor across the skin. The rate of such flux can be controlled by either providing a rate controlling membrane or dispersing the deacetylase inhibitor in a polymer matrix or gel.

Ophthalmic formulations, eye ointments, powders, solutions and the like, are also contemplated as being within the scope of this invention.

In addition to the active ingredients (i.e., an HDAC antagonist compound), the pharmaceutical compositions may contain suitable pharmaceutically acceptable carriers or excipients comprising auxiliaries which facilitate processing of the active compounds into preparations that can be used pharmaceutically. Further details on techniques for formulation and administration are provided in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained by the combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropyl-methylcellulose, or sodium carboxymethylcellulose; gums, including arabic and tragacanth, and proteins such as gelatin and collagen. If desired, disintegrating or solubilizing agents may be added, such as cross-linked polyvinyl pyrrolidone, agar, alginic acid, or a physiologically acceptable salt thereof, such as sodium alginate.

Dragee cores may be used in conjunction with physiologically suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification, or to characterize the quantity of active compound, i.e., dosage.

Pharmaceutical preparations which can be used orally include push-fit capsules made of gelatin, as well as soft, scaled capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. In addition, suspensions of the active compounds may be prepared as appropriate oily injection suspensions. Suitable lipophilic solvents or vehicles include fatty oils such as sesame oil, or synthetic fatty acid esters, such as ethyloleate or triglycerides, or liposomes. Optionally, the suspension may also contain suitable stabilizers or agents which increase the solubility of the compounds to allow for the preparation of highly concentrated solutions.

For topical or nasal administration, penetrants or permeation agents that are appropriate to the particular barrier to be permeated are used in the formulation. Such penetrants and permeation enhancers are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, and the like. Salts tend to be more soluble in aqueous solvents, or other protonic solvents, than are the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, combined with a buffer prior to use. After the pharmaceutical compositions have been prepared, they can be placed in an appropriate container and labeled for treatment of an indicated condition. For administration of an HDAC inhibitor compound, such labeling would include amount, frequency, and method of administration.

Pharmaceutical compositions suitable for use in the present invention include compositions wherein the active ingredients are contained in an effective amount to achieve the intended purpose. The determination of an effective dose or amount is well within the capability of those skilled in the art. For any compound, the therapeutically effective dose can be estimated initially either in cell culture assays, e.g., using neoplastic cells, or in animal models, usually mice, rabbits, dogs, or pigs. The animal model may also be used to determine the appropriate concentration range and route of administration. Such information can then be used and extrapolated to determine useful doses and routes for administration in humans.

A therapeutically effective dose refers to that amount of active ingredient, for example, an HDAC inhibitor or antagonist compound, antibodies to an HDAC polypeptide or peptide, agonists of HDAC polypeptides, which ameliorates, reduces, or eliminates the symptoms or the condition. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio of toxic to therapeutic effects is the therapeutic index, which can be expressed as the ratio, $LD_{50}/ED_{50}$. Pharmaceutical compositions which exhibit large therapeutic indices are preferred. The data obtained from cell culture assays and animal studies are used in determining a range of dosages for human use. Preferred dosage contained in a pharmaceutical composition is within a range of circulating concentrations that include the $ED_{50}$ with little or no toxicity. The dosage varies within this range depending upon the dosage form employed, sensitivity of the patient, and the route of administration.

The exact dosage will be determined by the practitioner, who will consider the factors related to the individual requiring treatment. Dosage and administration are adjusted to provide sufficient levels of the active moiety or to maintain the desired effect. Factors which may be taken into account include the severity of the individual's disease state, general health of the patient, age, weight, and gender of the patient, diet, time and frequency of administration, drug combination(s), reaction sensitivities, and tolerance/response to therapy. As a general guide, long-acting pharmaceutical compositions may be administered every 3 to 4 days, every week, or once every two weeks, depending on half-life and clearance rate of the particular formulation.

Normal dosage amounts may vary from 0.1 to 100,000 micrograms (µg), up to a total dose of about 1 gram (g), depending upon the route of administration. Guidance as to particular dosages and methods of delivery is provided in the literature and is generally available to practitioners in the art. Those skilled in the art will employ different formulations for nucleotides than for proteins or their inhibitors. Similarly, delivery of polynucleotides or polypeptides will be specific to particular cells, conditions, locations, and the like.

Assays and Diagnostics

In another embodiment of the present invention, antibodies which specifically bind to the HDAC polypeptides or peptides of the present invention may be used for the diagnosis of conditions or diseases characterized by expression (or overexpression) of an HDAC polynucleotide or polypeptide, or in assays to monitor patients being treated modulatory compounds of HDAC polypeptides, or, for example, HDAC antagonists or inhibitors. The antibodies useful for diagnostic purposes may be prepared in the same manner as those described above for use in therapeutic methods. Diagnostic assays for the HDAC polypeptides include methods which utilize the antibody and a label to detect the protein in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

Several assay protocols including ELISA, RIA, and FACS for measuring an HDAC polypeptide or peptide are known in the art and provide a basis for diagnosing altered or abnormal levels of HDAC polypeptide expression. Normal or standard values for HDAC polypeptide expression are established by combining body fluids or cell extracts taken from normal mammalian subjects, preferably human, with antibody to HDAC polypeptide or peptide under conditions suitable for complex formation. The amount of standard complex formation may be quantified by various methods; photometric means are preferred. Quantities of HDAC polypeptide or peptide expressed in subject sample, control sample, and disease samples from biopsied tissues are compared with the standard values. Deviation between standard and subject values establishes the parameters for diagnosing disease.

In one embodiment of the present invention, anti-HDAC antibodies (e.g., anti-HDAC9c antibodies) can be used in accordance with established methods to detect the presence of specific cancers or tumors, such as breast or prostate cancers or tumors. Representative cancers and cancer types are listed above.

According to another embodiment of the present invention, the polynucleotides encoding the novel HDAC polypeptides may be used for diagnostic purposes. The polynucleotides which may be used include oligonucleotide sequences, complementary RNA and DNA molecules, and PNAs. The polynucleotides may be used to detect and quantify HDAC-encoding nucleic acid expression in biopsied tissues in which expression (or under or overexpression) of HDAC polynucleotide may be correlated with disease. The diagnostic assay may be used to distinguish between the absence, presence, and excess expression of HDAC, and to monitor regulation of HDAC polynucleotide levels during therapeutic treatment or intervention.

In a related aspect, hybridization with PCR probes which are capable of detecting polynucleotide sequences, including genomic sequences, encoding an HDAC polypeptide, or closely related molecules, may be used to identify nucleic acid sequences which encode an HDAC polypeptide. The specificity of the probe, whether it is made from a highly specific region, e.g., about 8 to 10 or 12 or 15 contiguous nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding the HDAC polypeptide, alleles thereof, or related sequences.

Probes may also be used for the detection of related sequences, and should preferably contain at least 50%, preferably at least 80%, of the nucleotides encoding an HDAC polypeptide. The hybridization probes of this invention may be DNA or RNA and may be derived from the nucleotide sequence of SEQ ID NO:1, SEQ ID NO:12, SEQ ID NO:19, SEQ ID NO:88, SEQ ID NO:94, or SEQ ID NO:96, or from genomic sequence including promoter, enhancer elements, and introns of the naturally occurring HDAC protein.

The nucleotide sequences of the novel HDAC genes presented herein will further allow for the generation of probes and primers designed for use in identifying and/or cloning HDAC homologs in other cell types, e.g. from other tissues, as well as HDAC homologs from other organisms. For example, the present invention also provides a probe/primer comprising a substantially purified oligonucleotide, which oligonucleotide comprises a region of nucleotide sequence that hybridizes under stringent conditions to at least 10 consecutive nucleotides of sense or anti-sense sequence selected from the group consisting of HDAC SEQ ID NO:1, SEQ ID NO:12, SEQ ID NO:19, SEQ ID NO:88, SEQ ID NO:94, or SEQ ID NO:96, or naturally occurring mutants thereof. Primers based on the nucleic acid represented in SEQ ID NO:1, SEQ ID NO:12, SEQ ID NO:19, SEQ ID NO:88, SEQ ID NO:94, or SEQ ID NO:96, or as presented in the tables herein, can be used in PCR reactions to clone HDAC homologs. Likewise, probes based on the HDAC sequences provided herein can be used to detect transcripts or genomic sequences encoding the same or homologous proteins. The probe preferably comprises a label moiety attached thereto and is able to be detected, e.g., the label moiety is selected from radioisotopes, fluorescent compounds, chemiluminescent compounds, enzymes, enzyme co-factors, and the like.

Such probes can also be used as a part of a diagnostic test kit for identifying cells or tissue which mis-express an HDAC protein, such as by measuring a level of an HDAC encoding nucleic acid in a sample of cells from a patient; e.g., detecting HDAC mRNA levels, or determining whether a genomic HDAC gene has been mutated or deleted. To this end, nucleotide probes can be generated from the HDAC sequences herein which facilitate histological screening of intact tissue and tissue samples for the presence (or absence) of HDAC-encoding transcripts. Similar to the diagnostic uses of anti-HDAC antibodies, the use of probes directed to HDAC messages, or to genomic HDAC sequences, can be used for both predictive and therapeutic evaluation of allelic mutations which might be manifest in, for example, neoplastic or hyperplastic disorders (e.g. unwanted cell growth), or the abnormal differentiation of tissue. Used in conjunction with immunoassays as described herein, the oligonucleotide probes can help facilitate the determination of the molecular basis for a developmental disorder which may involve some abnormality associated with expression (or lack thereof) of an HDAC protein. For instance, variation in polypeptide synthesis can be differentiated from a mutation in a coding sequence.

Accordingly, the present invention provides a method for determining if a subject is at risk for a disorder characterized by aberrant cell proliferation and/or differentiation. Such a method can be generally characterized as comprising detecting, in a sample of cells from a subject, the presence or absence of a genetic lesion characterized by at least one of (i) an alteration affecting the integrity of a gene or nucleic acid sequence encoding an HDAC polypeptide, or (ii) the mis-expression of an HDAC gene. To illustrate, such genetic lesions can be detected by ascertaining the existence of at least one of (i) a deletion of one or more nucleotides from an HDAC gene, (ii) an addition of one or more nucleotides to an HDAC gene, (iii) a substitution of one or more nucleotides of an HDAC gene, (iv) a gross chromosomal rearrangement of an HDAC gene, (v) a gross alteration in the level of a messenger RNA transcript of an HDAC gene, (vii) aberrant modification of an HDAC gene, such as of the methylation pattern of the genomic DNA, (vii) the presence of a non-wild type splicing pattern of a messenger RNA transcript of an HDAC gene, (viii) a non-wild type level of an HDAC polypeptide, and (ix) inappropriate post-translational modification of an HDAC polypeptide. Accordingly, the present invention provides a large number of assay techniques for detecting lesions in an HDAC gene, and importantly, provides the ability to distinguish between different molecular causes underlying HDAC-dependent aberrant cell growth, proliferation and/or differentiation.

Methods for producing specific hybridization probes for DNA encoding the HDAC polypeptides include the cloning of nucleic acid sequence that encodes the HDAC polypeptides, or HDAC derivatives, into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of detector/reporter groups, e.g., radionuclides such as $^{32}P$ or $^{35}S$, or enzymatic labels, such as alkaline phosphatase coupled to the probe via avidin/biotin coupling systems, and the like.

The polynucleotide sequences encoding the HDAC polypeptides may be used in Southern or Northern analysis, dot blot, or other membrane-based technologies; in PCR technologies; or in dip stick, pin, ELISA or chip assays utilizing fluids or tissues from patient biopsies to detect the status of, e.g., levels or overexpression of HDAC, or to detect altered HDAC expression. Such qualitative or quantitative methods are well known in the art.

In a particular aspect, the nucleotide sequences encoding the HDAC polypeptides may be useful in assays that detect activation or induction of various tumors, neoplasms or cancers. The nucleotide sequences encoding the HDAC polypeptides may be labeled by standard methods, and added to a fluid or tissue sample from a patient under conditions suitable for the formation of hybridization complexes. After a suitable incubation period, the sample is washed and the signal is quantified and compared with a standard value. If the amount of signal in the biopsied or extracted sample is significantly altered from that of a comparable control sample, the nucleotide sequence has hybridized with nucleotide sequence present in the sample, and the presence of altered levels of nucleotide sequence encoding the HDAC polypeptides in the sample indicates the presence of the associated disease. Such assays may also be used to evaluate the efficacy of a particular therapeutic treatment regimen in animal studies, in clinical trials, or in monitoring the treatment of an individual patient.

In one embodiment of the present invention, HDAC (e.g., HDAC9c) nucleic acids can be used in accordance with established methods to detect the presence of specific cancers or tumors, such as breast or prostate cancers or tumors. Representative cancers and cancer types are listed herein above.

To provide a basis for the diagnosis of disease associated with HDAC expression, a normal or standard profile for expression is established. This may be accomplished by combining body fluids or cell extracts taken from normal subjects, either animal or human, with a sequence, or a fragment thereof, which encodes an HDAC polypeptide, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject (patient) values is used to establish the presence of disease.

Once disease is established and a treatment protocol is initiated, hybridization assays may be repeated on a regular basis to evaluate whether the level of expression in the patient begins to approximate that which is observed in a normal individual. The results obtained from successive assays may be used to show the efficacy of treatment over a period ranging from several days to months.

With respect to cancer, the presence of an abnormal amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier, thereby preventing the development or further progression of the cancer.

Additional diagnostic uses for oligonucleotides designed from the nucleic acid sequences encoding the novel HDAC polypeptides may involve the use of PCR. Such oligomers may be chemically synthesized, generated enzymatically, or produced from a recombinant source. Oligomers will preferably comprise two nucleotide sequences, one with sense orientation (5'→3') and another with antisense (3'-5'), employed under optimized conditions for identification of a specific gene or condition. The same two oligomers, nested sets of oligomers, or even a degenerate pool of oligomers may be employed under less stringent conditions for detection and/or quantification of closely related DNA or RNA sequences.

Methods suitable for quantifying the expression of HDAC include radiolabeling or biotinylating nucleotides, co-amplification of a control nucleic acid, and standard curves onto which the experimental results are interpolated (P. C. Melby et al., 1993, *J. Immunol. Methods,* 159:235-244; and C. Duplaa et al., 1993, *Anal. Biochem.,* 229-236). The speed of quantifying multiple samples may be accelerated by running the assay in an ELISA format where the oligomer of interest is presented in various dilutions and a spectrophotometric or calorimetric response gives rapid quantification.

In another embodiment of the present invention, oligonucleotides, or longer fragments derived from the HDAC polynucleotide sequences described herein, may be used as targets in a microarray. The microarray can be used to monitor the expression level of large numbers of genes simultaneously (to produce a transcript image), and to identify genetic variants, mutations and polymorphisms. This information may be used to determine gene function, to understand the genetic basis of a disease, to diagnose disease, and to develop and monitor the activities of therapeutic agents. In a particular aspect, the microarray is prepared and used according to the methods described in WO 95/11995 (Chee et al.); D. J. Lockhart et al., 1996, *Nature Biotechnology,* 14:1675-1680; and M. Schena et al., 1996, *Proc. Natl. Acad. Sci. USA,* 93:10614-10619). Microarrays are further described in U.S. Pat. No. 6,015,702 to P. Lal et al.

In another embodiment of this invention, a nucleic acid sequence which encodes one or more of the novel HDAC polypeptides may also be used to generate hybridization probes which are useful for mapping the naturally occurring genomic sequence. The sequences may be mapped to a particular chromosome, to a specific region of a chromosome, or to artificial chromosome constructions (HACs), yeast artificial chromosomes (YACs), bacterial artificial chromosomes (BACs), bacterial PI constructions, or single chromosome cDNA libraries, as reviewed by C. M. Price, 1993, *Blood Rev.,* 7:127-134 and by B. J. Trask, 1991, *Trends Genet.,* 7:149-154.

In another embodiment of the present invention, an HDAC polypeptide, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between an HDAC polypeptide, or portion thereof, and the agent being tested, may be measured utilizing techniques commonly practiced in the art and as described above.

Another technique for drug screening which may be used provides for high throughput screening of compounds having suitable binding affinity to the protein of interest as described in WO 84/03564. In this method, as applied to HDAC protein, large numbers of different small test compounds are synthesized on a solid substrate, such as plastic pins or some other surface. The test compounds are reacted with an HDAC polypeptide, or fragments thereof, and washed. Bound HDAC polypeptide is then detected by methods well known in the art. Purified HDAC polypeptide can also be coated directly onto plates for use in the aforementioned drug screening techniques. Alternatively, non-neutralizing antibodies can be used to capture the peptide and immobilize it on a solid support.

Other screening and small molecule (e.g., drug) detection assays which involve the detection or identification of small molecules that can bind to a given protein, i.e., an HDAC protein, are encompassed by the present invention. Particularly preferred are assays suitable for high throughput screening methodologies. In such binding-based screening or detection assays, a functional assay is not typically required. All that is needed is a target protein, preferably substantially purified, and a library or panel of compounds (e.g., ligands, drugs, small molecules) to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, Gen. Eng. News 20(8)). The assay allows the detection of small molecules (e.g., drugs, ligands) that bind to expressed, and preferably purified, HDAC polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

In a further embodiment of this invention, competitive drug screening assays can be used in which neutralizing antibodies capable of binding an HDAC polypeptide specifically compete with a test compound for binding to HDAC polypeptide. In this manner, the antibodies can be used to detect the presence of any peptide which shares one or more antigenic determinants with an HDAC polypeptide.

In yet another of its aspects, the present invention provides the identification of compounds with optimum therapeutic indices, or drugs or compounds which have therapeutic indices more favorable than known HDAC inhibitors, such as trapoxin, tichostatin, sodium butyrate, and the like. The identification of such compounds can be made by the use of differential screening assays which detect and compare drug mediated inhibition of deacetylase activity between two or more different HDAC-like enzymes, or which compare drug mediated inhibition of formation of complexes involving two or more different types of HDAC-like proteins.

For example, an assay can be designed for side-by-side comparison of the effect of a test compound on the deacetylase activity or protein interactions of tissue-type specific HDAC proteins. Given the apparent diversity of HDAC proteins, it is probable that different functional HDAC activities, or HDAC complexes, exist and in certain instances, are localized to particular tissue or cell types. Thus, test compounds can be screened to identify agents that are able to inhibit the tissue-specific formation of only a subset of the possible repertoire of HDAC/regulatory protein complexes, or which preferentially inhibit certain HDAC enzymes. For instance, an "interaction trap assay" can be derived using two or more different human HDAC "bait" proteins, while the "fish" protein is constant in each, e.g., a human RbAp48 construct. Running the interaction trap side-by-side permits the detection of agents which have a greater effect (e.g., statistically significant) on the formation of one of the HDAC/RbAp48 complexes than on the formation of the other HDAC complexes. (See, e.g., WO 97/35990).

Similarly, differential screening assays can be used to exploit the difference in protein interactions and/or catalytic mechanisms of mammalian HDAC proteins and yeast RPD3 proteins, for example, in order to identify agents which display a statistically significant increase in specificity for inhibiting the yeast enzyme relative to the mammalian enzyme. Thus, lead compounds which act specifically on pathogens, such as fungus involved in mycotic infections, can be developed. By way of illustration, assays can be used to screen for agents which may ultimately be useful for inhibiting at least one fungus implicated in pathologies such as candidiasis, aspergillosis, mucomycosis, blastomycosis, geotrichosis, cryptococcosis, chromoblastomycosis, coccidiomycosis, conidiosporosis, histoplasmosis, maduromycosis, rhinosporidosis, nocaidiosis, para actinomycosis, penicilliosis, monoliasis, or sporotrichosis.

As an example, if the mycotic infection to which treatment is desired is candidiasis, the described assay can involve comparing the relative effectiveness of a test compound on inhibiting the deacetylase activity of a mammalian HDAC protein with its effectiveness in inhibiting the deacetylase activity of an RPD3 homolog that has been cloned from yeast selected from the group consisting of *Candida albicans*, *Candida stellatoidea*, *Candida tropicalis*, *Candida parapsilosis*, *Candida krusei*, *Candida pseudotropicalis*, *Candida quillermondii*, or *Candida rugosa*. Such an assay can also be used to identify anti-fungal agents which may have therapeutic value in the treatment of aspergillosis by selectively targeting RPD3 homologs cloned from yeast such as *Aspergillus fumigatus*, *Aspergillus flavus*, *Aspergillus niger*, *Aspergillus nidulans*, or *Aspergillus terreus*. Where the mycotic infection is muco-mycosis, the RPD3 deacetylase can be derived from yeast such as *Rhizopus arrhizus*, *Rhizopus oryzae*, *Absidja corymbiera*, *Absidia ramosa*, or *Mucor pusillus*.

Sources of other RPD3 activities for comparison with a mammalian HDAC activity include the pathogen *Pneumocystis carinii*.

In addition to such HDAC therapeutic uses, anti-fungal agents developed from such differential screening assays can be used, for example, as preservatives in foodstuff, feed supplement for promoting weight gain in livestock, or in disinfectant formulations for treatment of non-living matter, e.g., for decontaminating hospital equipment and rooms. In a similar fashion, side by side comparison of the inhibition of a mammalian HDAC protein and an insect HDAC-related protein, will permit selection of HDAC inhibitors which are capable of discriminating between the human/mammalian and insect enzymes. Accordingly, the present invention envisions the use and formulations of HDAC therapeutics in insecticides, such as for use in management of insects like the fruit fly.

In yet another embodiment, certain of the subject HDAC inhibitors can be selected on the basis of inhibitory specificity for plant HDAC-related activities relative to the mammalian enzyme. For example, a plant HDAC-related protein can be disposed in a differential screen with one or more of the human enzymes to select those compounds of greatest selectivity for inhibiting the plant enzyme. Thus, the present invention specifically contemplates formulations of HDAC inhibitors for agricultural applications, such as in the form of a defoliant or the like.

In many drug screening programs that test libraries of compounds and natural extracts, high throughput assays are desirable in order to maximize the number of compounds surveyed in a given period of time. Assays performed in cell-free systems, such as may be derived with purified or semi-purified proteins, are often preferred as "primary" screens in that they can be rapidly generated to permit the quick development and relatively easy detection of an alteration in a molecular target which is mediated by a test compound. In addition, the effects of cellular toxicity and/or bioavailability of the test compound can be generally ignored in an in vitro system, since the assay is focused primarily on the effect of the drug on the molecular target which may be manifest in an alteration of binding affinity with upstream or downstream elements.

Accordingly, in an exemplary screening assay, a reaction mixture is generated to include an HDAC polypeptide, compound(s) of interest, and a "target polypeptide", e.g., a protein, which interacts with the HDAC polypeptide, whether as a substrate or by some other protein-protein interaction. Exemplary target polypeptides include histones, RbAp48 polypeptides, p53 polypeptides, and/or combinations thereof, or with other transcriptional regulatory proteins (such as myc, max, etc.). Detection and quantification of complexes containing the HDAC protein provide a means for determining a compound's efficacy at inhibiting (or potentiating) complex formation between the HDAC and the target polypeptide. The efficacy of the compound can be assessed by generating dose response curves from data obtained using various concentrations of the test compound. Moreover, a control assay can also be performed to provide a baseline for comparison. In the control assay, isolated and purified HDAC polypeptide is added to a composition containing the target polypeptide and the formation of a complex is quantified in the absence of the test compound.

Complex formation between an HDAC polypeptide and the target polypeptide may be detected by a variety of techniques. Modulation of the formation of complexes can be quantified using, for example, detectably labeled proteins such as radiolabeled, fluorescently labeled, or enzymatically labeled HDAC polypeptides, by immunoassay, by chromatography, or by detecting the intrinsic activity of the acetylase.

Transgenics and Knock Outs

The present invention further encompasses transgenic non-human mammals, preferably mice, that comprise a recombinant expression vector harboring a nucleic acid sequence that encodes a human HDAC (e.g., SEQ ID NO:2, SEQ ID NO:4, SEQ ID NO:5, SEQ ID NO:87, SEQ ID NO:93, or SEQ ID NO:95).

Transgenic non-human mammals useful to produce recombinant proteins are well known to the skilled practitioner, as are the expression vectors necessary and the techniques for generating transgenic animals. Generally, the transgenic animal comprises a recombinant expression vector in which the nucleotide sequence that encodes a human HDAC is operably linked to a tissue specific promoter whereby the coding sequence is only expressed in that specific tissue. For example, the tissue specific promoter can be a mammary cell specific promoter and the recombinant protein so expressed is recovered from the animal's milk.

The transgenic animals, particularly transgenic mice, containing a nucleic acid molecule which encodes a novel human HDAC may be used as animal models for studying in vivo the overexpression of HDAC and for use in drug evaluation and discovery efforts to find compounds effective to inhibit or modulate the activity of HDAC, such as for example compounds for treating disorders, diseases, or conditions related to cell proliferation and neoplastic cell growth, for example.

One having ordinary skill in the art using standard techniques, such as those taught in U.S. Pat. No. 4,873,191, issued Oct. 10, 1989 to Wagner and in U.S. Pat. No. 4,736,866, issued Apr. 12, 1988 to Leder, can produce transgenic animals which produce human HDAC, and use the animals in drug evaluation and discovery projects.

The transgenic non-human animals according to this aspect of the present invention can express a heterologous HDAC-encoding gene, or which have had one or more genomic HDAC genes disrupted in at least one of the tissue or cell types of the animal. Accordingly, the invention features an animal model for developmental diseases, which animal has one or more HDAC alleles which are improperly expressed. For example, a mouse can be bred which has one or more HDAC alleles deleted or otherwise rendered inactive. Such a mouse model can then be used to study disorders arising from improperly expressed HDAC genes, as well as for evaluating potential therapies for similar disorders.

Another aspect of transgenic animals are those animals which contain cells harboring an HDAC transgene according to the present invention and which preferably express an exogenous HDAC protein in one or more cells in the animal. An HDAC transgene can encode the wild-type form of the protein, or can encode homologs thereof, including both agonists and antagonists, as well as antisense constructs. Preferably, the expression of the transgene is restricted to specific subsets of cells, tissues or developmental stages utilizing, for example, cis-acting sequences that control expression in the desired pattern. According to the invention, such mosaic expression of an HDAC protein can be essential for many forms of lineage analysis and can also provide a means to assess the effects of, for example, lack of HDAC expression which might grossly alter development in small portions of tissue within an otherwise normal embryo. Toward this end, tissue specific regulatory sequences and conditional regulatory sequences can be used to control the expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which permit the regulated expression of a recombinase that catalyzes the genetic recombination of a target sequence. The phrase "target sequence" in this instance refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the present HDAC proteins.

For example, excision of a target sequence which interferes with the expression of a recombinant HDAC gene, such as one which encodes an antagonistic homolog or an antisense transcript, can be designed to activate the expression of that gene. This interference with expression of an encoded product can result from a variety of mechanisms, such as spatial separation of the HDAC gene from the promoter element, or an internal stop codon. Moreover, the transgene can be made so that the coding sequence of the gene is flanked by recombinase recognition sequences and is initially transfected into cells in a 3' to 5' orientation with respect to the promoter element. In this case, inversion of the target sequence will reorient the subject gene by placing the 5' end of the coding sequence in an orientation with respect to the promoter element which allows for promoter driven transcriptional activation.

Illustratively, transgenic non-human animals are produced by introducing transgenes into the germline of the non-human animal. Embryonic target cells at various developmental stages can be used to introduce transgenes. Different methods are used depending on the stage of development of the embryonic target cell. The zygote is a preferred target for microinjection.

In the mouse, the male pronucleus reaches the size of approximately 20 micrometers in diameter which allows reproducible injection of 1-2 pl of DNA solution. The use of zygotes as a target for gene transfer has a major advantage in that in most cases the injected DNA will be incorporated into the host gene before the first cleavage (e.g., Brinster et al., 1985, Proc. Natl. Acad. Sci. USA, 82:4438-4442). As a consequence, all cells of the transgenic non-human animal will carry the incorporated transgene. This will generally also be reflected in the efficient transmission of the transgene to offspring of the founder mice since 50% of the germ cells will harbor the transgene. Microinjection of zygotes is the preferred method for incorporating HDAC transgenes.

In addition, retroviral infection can also be used to introduce HDAC transgenes into a non human animal. The developing non-human embryo can be cultured in vitro to the blastocyst stage. During this time, the blastomeres are targets for retroviral infection (R. Jaenisch, 1976, Proc. Natl. Acad. Sci. USA., 73:1260-1264). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the transgene is typically a replication-defective retrovirus carrying the transgene (Jahner et al., 1985, Proc. Natl. Acad. Sci. USA., 82:6927 6931; Van der Putten et al., 1985, Proc. Natl. Acad. Sci. USA., 82:6148-6152). Transfection is easily and efficiently obtained by culturing the blastomeres on a monolayer of virus-producing cells (Stewart et al., 1987, EMBO J., 6:383-388).

Alternatively, infection can be performed at a later developmental stage. For example, virus or virus-producing cells can be injected into the blastocoele (e.g., Jahner et al., 1982, Nature, 298:623-628). Most of the founder animals win be mosaic for the transgene, because incorporation occurs only in the subset of cells which formed the transgenic non-human animal. Further, the founders may contain various retroviral insertions of the transgene at different positions in the genome which generally will segregate in the offspring. It is also possible to introduce transgenes into the germline by intrauterine retroviral infection of the midgestation embryo (Jahner et al., 1982, supra).

A third type of target cell for transgene introduction is the embryonic stem cell (ES). ES cells are obtained from preimplantation embryos that are cultured in vitro and fused with embryos (Evans et al., 1981, Nature, 292:154-156; Bradley et al., 1984, Nature, 309:255-258; Gossler et al., 1986, Proc. Natl. Acad. Sci. USA., 83:9065-9069; and Robertson et al., 1986, Nature, 322:445-448). Cultured ES cell lines are available. Transgenes can be efficiently introduced into the ES cells by DNA transfection or by retrovirus-mediated transduction. Transformed ES cells can thereafter be combined with blastocysts from a non-human animal. The ES cells then colonize the embryo and contribute to the germ line of the resulting chimeric animal. See, e.g., R. Jaenisch, 1988, Science, 240:1468-1474.

Methods for making HDAC knock-out animals, or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination, to insert recombinase target sequences flanking portions of an endogenous HDAC gene, such that tissue specific and/or temporal control of inactivation of an HDAC gene sequence or allele can be controlled as above.

In knock-outs, transgenic mice may be generated which are homozygous for a mutated, non-functional HDAC gene which is introduced into the animals using well known techniques. Surviving knock-out mice produce no functional HDAC and thus are useful to study the function of HDAC. Furthermore, the mice may be used in assays to study the effects of test compounds in HDAC deficient animals. For instance, HDAC-deficient mice can be used to determine if, how and to what extent HDAC inhibitors will effect the animal and thus address concerns associated with inhibiting the activity of the molecule.

More specifically, methods of generating genetically deficient knock-out mice are well known and are disclosed in M. R. Capecchi, 1989, Science, 244:1288-1292 and P. Li et al., 1995, Cell, 80:401-411. For example, a human HDAC cDNA clone can be used to isolate a murine HDAC genomic clone. The genomic clone can be used to prepare an HDAC targeting construct which can disrupt the HDAC gene in the mouse by homologous recombination. The targeting construct contains a non-functioning portion of an HDAC gene which inserts in place of the functioning portion of the native mouse gene. The non-functioning insert generally contains an insertion in the exon that encodes the active region of the HDAC polypeptide. The targeting construct can contain markers for both positive and negative selection. The positive selection marker allows for the selective elimination of cells which do not carry the marker, while the negative selection marker allows for the elimination of cells that carry the marker.

For example, a first selectable marker is a positive marker that will allow for the survival of cells carrying it. In some instances, the first selectable marker is an antibiotic resistance gene, such as the neomycin resistance gene, which can be placed within the coding sequence of a novel HDAC gene to render it non-functional, while at the same time rendering the construct selectable. The antibiotic resistance gene is within the homologous region which can recombine with native sequences. Thus, upon homologous recombination, the non-functional and antibiotic resistance selectable gene sequences will be taken up. Knock-out mice may be used as models for studying inflammation-related disorders and screening compounds for treating these disorders.

The targeting construct also contains a second selectable marker which is a negative selectable marker. Cells with the negative selectable marker will be eliminated. The second selectable marker is outside the recombination region. Thus, if the entire construct is present in the cell, both markers will be present. If the construct has recombined with native sequences, the first selectable marker will be incorporated into the genome and the second will be lost. The herpes simplex virus thymidine kinase (HSV tk) gene is an example of a negative selectable marker which can be used as a second marker to eliminate cells that carry it. Cells with the HSV tk gene are selectively killed in the presence of gangcyclovir.

Cells are transfected with targeting constructs and then selected for the presence of the first selection marker and the absence of the second. Constructs/DNA are then injected into the blastocyst stage and implanted into pseudopregnant females. Chimeric offspring which are capable of transferring the recombinant genes in their germline are selected, mated and their offspring examined for heterozygous carriers of the recombined genes. Mating of the heterozygous offspring can then be used to generate fully homozygous offspring which constitute HDAC-deficient knock-out mice.

EMBODIMENTS OF THE INVENTION

An isolated polynucleotide encoding a histone deacetylase polypeptide comprising an amino acid sequence selected from the group consisting of SEQ ID NO:2, SEQ ID NO:4, SEQ ID NO:5, SEQ ID NO:87, SEQ ID NO:93, and SEQ ID NO:95.

An isolated polynucleotide encoding an amino acid sequence selected from the group consisting of:
  a. an amino acid sequence comprising residues 1009-1069 of SEQ ID NO:87; and
  b. an amino acid sequence comprising residues 720-780 of SEQ ID NO:93.

An isolated polynucleotide comprising a nucleotide sequence selected from the group consisting of SEQ ID NO:1, SEQ ID NO:12, SEQ ID NO:19, SEQ ID NO:88, SEQ ID NO:94, and SEQ ID NO:96.

An isolated polynucleotide comprising a nucleotide sequence selected from the group consisting of:
  a. a nucleotide sequence which is at least 60% identical to SEQ ID NO:1;
  b. a nucleotide sequence which is at least 60% identical to SEQ ID NO:12;
  c. a nucleotide sequence which is at least 60% identical to SEQ ID NO:19;
  d. a nucleotide sequence which is at least 67.8% identical to SEQ ID NO:88;
  e. a nucleotide sequence which is at least 70% identical to SEQ ID NO:94;
  f. a nucleotide sequence which is at least 59.8% identical to SEQ ID NO:96;
  g. a nucleotide sequence which is at least 94.4% identical to nucleotides 1 to 3207 of SEQ ID NO:88;
  h. a nucleotide sequence which is at least 55.4% identical to nucleotides 307 to 1791 of SEQ ID NO:96.
  i. a nucleotide sequence comprising nucleotides 1 to 3207 of SEQ ID NO:88;
  j. a nucleotide sequence comprising nucleotides 1 to 2340 of SEQ ID NO:94;
  k. a nucleotide sequence comprising nucleotides 307 to 1791 of SEQ ID NO:96;
  l. a nucleotide sequence comprising nucleotides 4 to 3207 of SEQ ID NO:88 wherein said nucleotides encode amino acids 2 to 1069 of SEQ ID NO:87 lacking the start methionine; and
  m. a nucleotide sequence comprising nucleotides 310 to 1791 of SEQ ID NO:96 wherein said nucleotides encode amino acids 2 to 495 of SEQ ID NO:95 lacking the start methionine.

An isolated polynucleotide comprising a nucleotide sequence selected from the group consisting of:
  a. a nucleotide sequence comprising at least 25 contiguous nucleotides of SEQ ID NO 1;
  b. a nucleotide sequence comprising at least 25 contiguous nucleotides of SEQ ID NO:12;
  c. a nucleotide sequence comprising at least 25 contiguous nucleotides of SEQ ID NO:19;
  d. a nucleotide sequence comprising at least 2755 contiguous nucleotides of SEQ ID NO:88;
  e. a nucleotide sequence comprising at least 2160 contiguous nucleotides of SEQ ID NO:94;
  f. a nucleotide sequence comprising at least 1195 contiguous nucleotides of SEQ ID NO:96;
  g. a nucleotide sequence comprising at least 183 contiguous nucleotides of SEQ ID NO:88; and
  h. a nucleotide sequence comprising at least 17 contiguous nucleotides of SEQ ID NO:96.

An isolated polynucleotide comprising a nucleotide sequence selected from the group consisting of:
  a. a nucleotide sequence comprising nucleotides 3024-4467 of SEQ ID NO:88;
  b. a nucleotide sequence comprising nucleotides 2156-3650 of SEQ ID NO:94;
  c. a nucleotide sequence comprising nucleotides 1174-3391 of SEQ ID NO:96;
  d. a nucleotide sequence comprising nucleotides 3024-3207 of SEQ ID NO:88; and
  e. a nucleotide sequence comprising nucleotides 1174-1791 of SEQ ID NO:96.

An primer comprising a nucleotide sequence selected from the group consisting of SEQ ID NO:24-27, SEQ ID NO:28-35, SEQ ID NO:39-46, SEQ ID NO:47-62, SEQ ID NO:65-66, SEQ ID NO:67-74, SEQ ID NO:75-82, and SEQ ID NO:104-105.

A probe comprising a nucleotide sequence selected from the group consisting of SEQ ID NO:36, SEQ ID NO:63-64, SEQ ID NO:83-86, SEQ ID NO92, and SEQ ID NO:101-103.

A cell line comprising the isolated polynucleotide according to any one of the preceding embodiments.

A gene delivery vector comprising the isolated polynucleotide according to any one of the preceding embodiments.

An expression vector comprising the isolated polynucleotide according to any one of the preceding embodiments.

A host cell comprising the expression vector according to any one of the preceding embodiments, wherein the host cell is selected from the group consisting of bacterial, yeast, insect, mammalian, and human cells.

An isolated polypeptide comprising an amino acid sequence selected from the group consisting of SEQ ID NO:2, SEQ ID NO:4, SEQ ID NO:5, SEQ ID NO:87, SEQ ID NO:93, and SEQ ID NO:95.

An isolated polypeptide comprising an amino acid sequence selected from the group consisting of:
  a. an amino acid sequence which is at least 72% identical to SEQ ID NO:2;
  b. an amino acid sequence which is at least 79% identical to SEQ ID NO:4;
  c. an amino acid sequence which is at least 70% identical to SEQ ID NO:5;
  d. an amino acid sequence which is at least 94.2% identical to SEQ ID NO:87;
  e. an amino acid sequence which is at least 95% identical to SEQ ID NO:93; and
  f. an amino acid sequence which is at least 55.3% identical to SEQ ID NO:95.

An isolated polypeptide comprising an amino acid sequence selected from the group consisting of:
  a. an amino acid sequence comprising at least 8 contiguous amino acids of SEQ ID NO:2;
  b. an amino acid sequence comprising at least 8 contiguous amino acids of SEQ ID NO:4;
  c. an amino acid sequence comprising at least 8 contiguous amino acids of SEQ ID NO:5;

d. an amino acid sequence comprising at least 920 contiguous amino acids of SEQ ID NO:87;
e. an amino acid sequence comprising at least 720 contiguous amino acids of SEQ ID NO:93; and
f. an amino acid sequence comprising at least 400 contiguous amino acids of SEQ ID NO:95.

An isolated polypeptide comprising an amino acid sequence selected from the group consisting of:
a. an amino acid sequence comprising residues 1009-1069 of SEQ ID NO:87; and
b. an amino acid sequence comprising residues 720-780 of SEQ ID NO:93.

An isolated fusion protein comprising the isolated polypeptide according to any one of the preceding embodiments.

An antibody which binds specifically to the isolated polypeptide according to any one of the preceding embodiments, wherein the antibody is selected from the group consisting of polyclonal and monoclonal antibodies.

An antibody which binds specifically to the isolated fusion protein according to any one of the preceding embodiments.

An antisense polynucleotide comprising a nucleotide sequence that is complementary to at least 20 contiguous nucleotides of the isolated polynucleotide according to any one of the preceding embodiments.

An antisense polynucleotide comprising a nucleotide sequence selected from the group consisting of SEQ ID NO:36, SEQ ID NO:63-64, and SEQ ID NO:83-86.

An expression vector comprising the antisense polynucleotide according to any one of the preceding embodiments.

A pharmaceutical composition comprising the monoclonal antibody according to any one of the preceding embodiments, and a physiologically acceptable carrier, diluent, or excipient.

A pharmaceutical composition comprising the antisense polynucleotide according to any one of the preceding embodiments and a physiologically acceptable carrier, diluent, or excipient.

A pharmaceutical composition comprising the expression vector according to any one of the preceding embodiments, and a physiologically acceptable carrier, diluent, or excipient.

A pharmaceutical composition comprising the gene delivery vector according to any one of the preceding embodiments, and a physiologically acceptable carrier, diluent, or excipient.

A pharmaceutical composition comprising the host cell according to any one of the preceding embodiments, and a physiologically acceptable carrier, diluent, or excipient.

A pharmaceutical composition comprising the modulating agent according to any one of the following embodiments, and a physiologically acceptable carrier, diluent, or excipient.

A method of treating cancer comprising administering the pharmaceutical composition according to any one of the preceding embodiments in an amount effective for treating the cancer.

In various aspects, the cancer is selected from the group consisting of bladder cancer, lung cancer, breast cancer, colon cancer, rectal cancer, endometrial cancer, ovarian cancer, head and neck cancer, prostate cancer, and melanoma.

In other aspects, the breast cancer is selected from the group consisting of ductal carcinoma in situ, intraductal carcinoma lobular carcinoma in situ, papillary carcinoma, and comedocarcinoma, adenocarcinomas, and carcinomas, such as infiltrating ductal carcinoma, infiltrating lobular carcinoma, infiltrating ductal and lobular carcinoma, medullary carcinoma, mucinous carcinoma, comedocarcinoma, Paget's Disease, papillary carcinoma, tubular carcinoma, and inflammatory carcinoma.

In further aspects, the prostate cancer is selected from the group consisting of adenocarcinomas and sarcomas, and pre-cancerous conditions, such as prostate intraepithelial neoplasia.

A method of diagnosing a cancer comprising:
a. incubating the isolated polynucleotide according to any one of the preceding embodiments with a biological sample under conditions to allow the isolated polynucleotide to amplify a polynucleotide in the sample to produce a amplification product; and
b. measuring levels of amplification product formed in (a), wherein an alteration in these levels compared to standard levels indicates diagnosis of the cancer.

In various aspects, the cancer is selected from the group consisting of bladder cancer, lung cancer, breast cancer, colon cancer, rectal cancer, endometrial cancer, ovarian cancer, head and neck cancer, prostate cancer, and melanoma.

In other aspects, the breast cancer is selected from the group consisting of ductal carcinoma in situ, intraductal carcinoma lobular carcinoma in situ, papillary carcinoma, and comedocarcinoma, adenocarcinomas, and carcinomas, such as infiltrating ductal carcinoma, infiltrating lobular carcinoma, infiltrating ductal and lobular carcinoma, medullary carcinoma, mucinous carcinoma, comedocarcinoma, Paget's Disease, papillary carcinoma, tubular carcinoma, and inflammatory carcinoma.

In further aspects, the prostate cancer is selected from the group consisting of adenocarcinomas and sarcomas, and pre-cancerous conditions, such as prostate intraepithelial neoplasia.

A method of diagnosing cancer comprising:
a. contacting the antibody according to any one of the preceding embodiments with a biological sample under conditions to allow the antibody to associate with a polypeptide in the sample to form a complex; and
b. measuring levels of complex formed in (a), wherein an alteration in these levels compared to standard levels indicates diagnosis of the cancer.

In various aspects, the cancer is selected from the group consisting of bladder cancer, lung cancer, breast cancer, colon cancer, rectal cancer, endometrial cancer, ovarian cancer, head and neck cancer, prostate cancer, and melanoma.

In other aspects, the breast cancer is selected from the group consisting of ductal carcinoma in situ, intraductal carcinoma lobular carcinoma in situ, papillary carcinoma, and comedocarcinoma, adenocarcinomas, and carcinomas, such as infiltrating ductal carcinoma, infiltrating lobular carcinoma, infiltrating ductal and lobular carcinoma, medullary carcinoma, mucinous carcinoma, comedocarcinoma, Paget's Disease, papillary carcinoma, tubular carcinoma, and inflammatory carcinoma.

In further aspects, the prostate cancer is selected from the group consisting of adenocarcinomas and sarcomas, and pre-cancerous conditions, such as prostate intraepithelial neoplasia.

A method of detecting a histone deacetylase polynucleotide comprising:
  a. incubating the isolated polynucleotide according to any one of the preceding embodiments with a biological sample under conditions to allow the polynucleotide to hybridize with a polynucleotide in the sample to form a complex; and
  b. identifying the complex formed in (a), wherein identification of the complex indicates detection of a histone deacetylase polynucleotide.

A method of detecting a histone deacetylase polypeptide comprising:
  a. incubating the antibody according to any one of the preceding embodiments with a biological sample under conditions to allow the antibody to associate with a polypeptide in the sample to form a complex; and
  b. identifying the complex formed in (a), wherein identification of the complex indicates detection of a histone deacetylase polypeptide.

A method of screening test agents to identify modulating agents capable of altering deacetylase activity of a histone deacetylase polypeptide comprising:
  a. contacting the isolated polypeptide according to any one of the preceding embodiments with test agents under conditions to allow the polypeptide to associate with one or more test agents; and
  b. selecting test agents that alter the deacetylase activity of the polypeptide, whereby this alteration indicates identification of modulating agents.

In various aspects, the modulating agents are selected from the group consisting of antagonists and inhibitors of histone deacetylase activity.

In other aspects, the modulating agents are selected from the group consisting of agonists or activators of histone deacetylase activity.

A method for screening test agents to identify modulating agents which inhibit or antagonize deacetylation activity of a histone deacetylase, comprising:
  a. combining an isolated polypeptide according any one of the preceding embodiments having a histone deacetylase activity with a histone deacetylase substrate and a test agent in a reaction mixture; and
  b. determining the conversion of the substrate to product; wherein a statistically significant decrease in the conversion of the substrate in the presence of the test agent indicates identification of a modulating agent which inhibits or antagonizes the deacetylation activity of histone deacetylase.

A method for screening test agents to identify modulating agents that inhibit or antagonize interaction of histone deacetylase with a histone deacetylase binding protein, comprising:
  a. combining the isolated polypeptide according any one of the preceding embodiments having a histone deacetylase activity with the histone deacetylase binding protein and a test agent in a reaction mixture; and
  b. detecting the interaction of the polypeptide with the histone deacetylase binding protein to form a complex; wherein a statistically significant decrease in the interaction of the polypeptide and protein in the presence of the test agent indicates identification of a modulating agent which inhibits or antagonizes interaction of the histone deacetylase polypeptide with the histone deacetylase binding protein.

In various aspects, one or both of the histone deacetylase polypeptide and the histone deacetylase binding protein is a fusion protein.

In other aspects, at least one of the histone deacetylase polypeptide and the histone deacetylase binding protein comprises a detectable label for detecting the formation of the complex.

In a further aspect, the interaction of the histone deacetylase polypeptide and the histone deacetylase binding protein is detected in a two-hybrid assay system.

A method of screening a library of molecules or compounds to identify at least one molecule or compound therein which specifically binds to a histone deacetylase polynucleotide, comprising:
  a. combining the isolated polynucleotide according to any one of the preceding embodiments with a library of molecules or compounds under conditions to allow specific binding of the polynucleotide to at least one of the molecules or compounds; and
  b. detecting the specific binding in (a), thereby identifying a molecule or compound which specifically binds to the histone deacetylase polynucleotide. In various aspects, the library comprises molecules selected from the group consisting of selected from the group consisting of DNA molecules, RNA molecules, artificial chromosomes, PNAs, peptides, and polypeptides.

In one aspect, the detecting is performed by the use of high throughput screening.

A method of treating a disease or disorder associated with abnormal cell growth or proliferation in a mammal comprising administrating the antagonist or inhibitor of histone deacetylase polypeptide according to any one of the preceding embodiments in an amount effective to treat the disease or disorder.

In various aspects, the disease or disorder is selected from neoplasms, tumors and cancers.

A method of treating a disease or disorder associated with abnormal cell growth or proliferation in a mammal comprising administrating the antisense polynucleotide according to any one of the preceding embodiments in an amount effective to treat the disease or disorder.

In various aspects, the disease or disorder is selected from neoplasms, tumors and cancers.

A method of modulating one or more of cell growth or proliferation, cell differentiation, or cell survival of a eukaryotic cell, comprising combining the cell with an effective amount of a modulating agent that alters the deacetylase activity of a histone deacetylase polypeptide comprising an amino acid sequence selected from the group consisting of SEQ ID NO:2, SEQ ID NO:4, SEQ ID NO:5, SEQ ID NO:87, SEQ ID NO:93, and SEQ ID NO:95, and thereby modulating the rate of one or more of cell growth or proliferation, cell differentiation, or cell survival of the eukaryotic cell, relative to the effect on the eukaryotic cells in the absence of the modulating agent.

EXAMPLES

The Examples below are provided to illustrate the subject invention and are not intended to limit the invention in any way.

Example 1

Identification of Novel HDAC Gene Fragments

Gene fragments encoding the novel HDAC (HDAL) polypeptides of this invention were identified by a combination of the following methods. Homology-based searches using the TBLASTN program (S. F. Altschul et al., 1997, *Nucl. Acids Res.*, 25(17):3389-3402) were performed to compare known histone deacetylases with human genomic (gDNA) and EST sequences. EST or gDNA sequences having significant homology to one or more of phosphatases (expect score less than or equal to $1\times10^{-3}$) were retained for further analysis.

Hidden Markov Model (HMM) searches using PFAM motifs (listed in Table 2) (A. Bateman et al., 1999, *Nucleic Acids Research*, 27:260-262 and E. L. Sonnhammer et al., 1997, *Proteins*, 28(3):405-420) to search human genomic sequence using the Genewise program. EST or gDNA sequences having a significant score (greater than or equal to 10) with any of the following motifs were retained for further analysis.

HMM searches using PFAM motifs (listed in Table 1) to search predicted protein sequences identified by GENSCAN analysis of human genomic sequence (C. Burge and S. Karlin, 1997, *J. Mol. Biol.*, 268(1):78-94). gDNA sequences having a significant score (greater than or equal to 10) with any of the following motifs were retained for further analysis.

TABLE 1

PFAM motifs used to identify histone deacetylases

| Motif Name | PFAM Accession # | Description |
| --- | --- | --- |
| Hist_deacetyl | PF00850 | Histone deacetylase family (length 342) |

Once a bacterial artificial chromosome (BAC) encoding a novel histone deacetylase-like protein was identified by any of the methods listed above, its predicted protein sequence was used to identify the most closely related known histone deacetylase using the BLASTP program(NCBI). This known protein was used as the query for a GenewiseDB search of the original BAC and all nearby BACs (identified by the Golden Path tiling map, UCSC). The results were used to identify additional potential exons, intron/exon boundaries, partial transcript cDNA sequence and partial predicted protein sequence for the novel HDAC gene. The Primer3 program (S. Rozen et al., 1998, 0.6 Ed., Whitehead Institute Center for Genomic Research, Cambridge, Mass.) was used to design PCR primers within single exons and between adjacent exons and to design antisense 80mer probes for use in isolating cDNA clones.

Example 2

Analysis of HDACs

Enzymatic Activity Measurements

Constructs representing the open reading frames of the identified novel sequences are engineered in frame with c-MYC or FLAG epitopes using commercially available mammalian expression vectors. These plasmids are transfected into HEK293 or COS7 cells and novel HDAC protein expression are analyzed by Western blot analysis of protein lysates from the transfectants using anti-MYC epitope or anti-FLAG epitope antibodies.

MYC or FLAG tagged-HDAC proteins are immunoprecipitated from the lysates and incubated with {$^3$H} acetate- or fluorescent-labeled acetylated proteins. Release of {$^3$H} acetate or decrease in fluorescent signal intensity is used to establish the activity of the putative HDACs. The effects of pan-HDAC chemical inhibitors on the enzymatic activity of the novel HDACs is also assessed and compared with the activity of known HDAC proteins and their inhibition with these chemical agents.

Transcriptional Assays

HDAC proteins have been shown to positively or negatively regulate transcriptional pathways. The ability of the novel HDAC proteins to repress or activate the constitutive or regulated activity of transcriptional reporter plasmids is assessed. These assays are performed using transient transfections of mammalian expression constructs encoding the novel HDAC proteins with reporter plasmid constructs of containing response elements of specific transcriptional pathways (e.g., p53, AP1, androgen receptor, LEF1/TCF4), a minimal promoter and a reporter gene product (e.g., alkaline phosphatase, luciferase, green fluorescent protein).

Alternatively, the novel HDACs are transfected into cell lines engineered to stably express these transcriptional reporter plasmids. Because the consequence of HDAC expression could be inhibitory or stimulatory, the effects of the novel HDAC proteins on these transcriptional responses are monitored in the presence and absence of activators of the pathway. Similar to enzymatic activity measurements, pan-inhibitors of the known HDACs are also examined to establish the enzymatic activity of the novel HDAC gene products as protein deacetylases.

Expression Analysis

Initial insights into the role of the novel HDACs in normal physiology and disease states is assessed by a variety of expression analyses. Quantitative reverse transcriptase polymerase chain reaction (RT-PCR) using primers specific to the novel sequences is implemented to evaluate the expression of novel HDAC mRNA in a variety of normal cell lines and tissue as well as a spectrum of human tumor cell lines. Expression profiles of novel HDACs are confirmed using Northern blot analysis or ribonuclease protection assays.

In addition, tissue arrays containing a variety of patient organ samples and arrays of malignant tissue are evaluated by in situ hybridization to gain further insights into the association of the novel HDAC proteins with particular physiological responses and in neoplasia.

Subcellular Localization

The subcellular localization of MYC- or FLAG-tagged novel HDAC proteins is determined upon ectopic expression in mammalian cells. Cells are fixed, permeabilized and incubated with anti-MYC or anti-FLAG antibodies to detect expressed protein. The localization of tagged proteins is then detected using CY3 or FITC-conjugated secondary antibodies and visualized by fluorescent microscopy. These studies can determine if the assayed HDACs deacetylate nuclear or cytoplasmic protein substrates.

Example 3

Oligonucleotides for the Isolation of HDACs

BMY HDAL1

Based on the predicted gene structure of BMY_HDAL1, the Primer3 program designed the following PCR primers and probe oligos for isolation of cDNAs. Table 2 presents single exon primers and probes for BMY_HDAL1 cDNA isolation. Table 3 presents multiple exon primers for BMY_HDAL1 cDNA isolation. Table 4 presents BMY_HDAL1 capture oligonucleotides. As shown below in Table 5, a separately designed primer set was used to test for BMY_HDAL1 expression using a cDNA pool from human placenta and the following human tumor cell lines including Caco-2, LS174-T, MIP, HCT-116, A2780, OVCAR-3, HL60, A431, Jurkat, A549, PC3 and LnCAP cells.

BMY HDAL2

Based on the predicted gene structure of BMY_HDAL2, the Primer3 program designed the following PCR primers and probe oligonucleotides for isolation of cDNAs. BMY_HDAL2 single exon primers and probes are shown in Table 6. Multiple exon primers for BMY-HDAL2 cDNA isolation are shown in Table 7. BMY_HDAL2 capture oligonucleotides are shown in Table 8. As shown in Table 9, a separately designed primer set was used to test for BMY_HDAL2 expression using a cDNA pool from human placenta and the following human tumor cell lines: Caco-2, LS174-T, MIP, HCT-116, A2780, OVCAR-3, HL60, A431, Jurkat, A549, PC3 and LnCAP cells.

BMY HDAL3

Based on the predicted gene structure of BMY_HDAL3, the Primer3 program designed the following PCR primers and probe oligonucleotides for isolation of cDNAs. For BMY_HDAL3, the following primer sets were designed from the AC002410 sequence using Primer3. Single exon primers for the novel BMY-HDAL3 isolation are shown in Table 10. Multiple exon primers for BMY_HDAL3 isolation are presented in Table 11. BMY_HDAL3 capture oligonucleotides are shown in Table 12.

TABLE 2

| Template | Primer Set | Product Size | Left Primer Start, Length | Sequence | Tm | Right Primer Start, Length | Sequence | Tm |
|---|---|---|---|---|---|---|---|---|
| BMY_HDAL1 exon 1 | 1 | 118 | 16, 20 | ccttgatgctgaaacaccag (SEQ ID NO: 24) | 59.3 | 133, 21 | tcacatttatttagcagccca (SEQ ID NO: 25) | 58.3 |
| BMY_HDAL1 exon 1 | 2 | 119 | 16, 20 | ccttgatgctgaaacaccag (SEQ ID NO: 26) | 59.3 | 134, 22 | ctcacatttatttagcagccca (SEQ ID NO: 27) | 59.3 |

TABLE 3

| Template | Primer Set | Product Size | Left Primer Start, Length | Sequence | Tm | Right Primer Start, Length | Sequence | Tm |
|---|---|---|---|---|---|---|---|---|
| BMY_HDAL1 exons 1_2 | 1 | 148 | 67, 20 | agcatgctggacgaatacag (SEQ ID NO: 28) | 58.9 | 234, 20 | ttggtgccatacaacagtga (SEQ ID NO: 29) | 58.5 |
| BMY_HDAL1 exons 1_2 | 2 | 199 | 16, 20 | ccttgatgctgaaacaccag (SEQ ID NO: 30) | 59.3 | 234, 20 | ttggtgccatacaacagtga (SEQ ID NO: 31) | 58.5 |
| BMY_HDAL1 exons 2_3 | 1 | 110 | 60, 20 | tcactgttgtatggcaccaa (SEQ ID NO: 32) | 58.5 | 189, 20 | ccaagtccaccacaaggtaa (SEQ ID NO: 33) | 58.5 |
| BMY_HDAL1 exons 2_3 | 2 | 104 | 60, 20 | tcactgttgtatggcaccaa (SEQ ID NO: 34) | 58.5 | 183, 20 | ccaccacaaggtaatgagga (SEQ ID NO: 35) | 58.4 |

TABLE 4

| Oligo | | | Capture Probe |
|---|---|---|---|
| Template | Number | Start, Size | Sequence (ANTISENSE) |
| BMY_HDAL2 exon 1 | 1 | 36, 77 | gtttcttgcagtcgtgaccagatactctgtattcgtccagcatgctcagggtgggtggtggaattgccacaaacgca (SEQ ID NO: 36) |

TABLE 5

| HDAL Gene | 5'-oligo primer sequence (5'-3') | 3'-oligo primer sequence (5'-3') | Predicted Product | Product observed |
|---|---|---|---|---|
| HDAL1 | ggaattgcctatgaccccttga (SEQ ID NO: 37) | tgtacttaccccaagtccaccaca (SEQ ID NO: 38) | 316 nt | yes |

TABLE 6

| Template | Primer Set | Product Size | Left Primer Start, Length | Sequence | Tm | Right Primer Start, Length | Sequence | Tm |
|---|---|---|---|---|---|---|---|---|
| BMY_HDAL2 exon 1 | 1 | 102 | 2, 20 | ggacagtgacaccatttgga (SEQ ID NO: 39) | 59.4 | 103, 19 | agctctcctgaggccactt (SEQ ID NO: 40) | 59.1 |
| BMY_HDAL2 exon 1 | 2 | 100 | 2, 20 | ggacagtgacaccatttgga (SEQ ID NO: 41) | 59.4 | 101, 19 | ctctcctgaggccactttg (SEQ ID NO: 42) | 58.5 |

TABLE 6-continued

| Template | Primer Set Set | Pro-duct Size | Left Primer Start, Length | Sequence | Tm | Right Primer Start, Length | Sequence | Tm |
|---|---|---|---|---|---|---|---|---|
| BMY_HDAL2 exon 4 | NA | | | | | | | |
| BMY_HDAL2 exon 5 | 1 | 103 | 10, 20 | gccttggagaagggtacaat (SEQ ID NO: 43) | 58.1 | 112, 23 | gaaagaagtaccaacctgaatgc (SEQ ID NO: 44) | 59.2 |
| BMY_HDAL2 exon 5 | 2 | 102 | 10, 20 | gccttggagaagggtacaat (SEQ ID NO: 45) | 58.1 | 111, 22 | aaagaagtaccaacctgaatgc (SEQ ID NO: 46) | 57.4 |

TABLE 7

| Template | Primer Set Set | Product Size | Left Primer Start, Length | Sequence | Tm | Right Primer Start, Length | Sequence | Tm |
|---|---|---|---|---|---|---|---|---|
| BMY_HDAL2 exons 1-2 | 1 | 157 | 2, 20 | ggacagtgacaccatttgga (SEQ ID NO: 47) | 59.4 | 178, 2 | tgtggattcttcagcgtgat (SEQ ID NO: 48) | 59.2 |
| BMY_HDAL2 exons 1-2 | 2 | 126 | 2, 20 | ggacagtgacaccatttgga (SEQ ID NO: 49) | 59.4 | 147, 20 | ctcacaacagcaaacccatt (SEQ ID NO: 50) | 58.6 |
| BMY_HDAL2 exons 2-3 | 1 | 107 | 0, 20 | aatgggtttgctgttgtgag (SEQ ID NO: 51) | 58.6 | 126, 20 | tctctcaagtatttggcggt (SEQ ID NO: 52) | 57.4 |
| BMY_HDAL2 exons 2-3 | 2 | 108 | 0, 20 | aatgggtttgctgttgtgag (SEQ ID NO: 53) | 58.6 | 127, 20 | gtctctcaagtatttggcgg (SEQ ID NO: 54) | 57.4 |
| BMY_HDAL2 exons 3-4 | 1 | 130 | 23, 20 | ttgcaattaccgccaaatac (SEQ ID NO: 55) | 58.6 | 172, 20 | gaaatgtacaggatgctggg (SEQ ID NO: 56) | 58.0 |
| BMY_HDAL2 exons 3-4 | 2 | 131 | 22, 20 | gttgcaattaccgccaaata (SEQ ID NO: 57) | 58.561 | 172, 20 | gaaatgtacaggatgctggg (SEQ ID NO: 58) | 58.019 |
| BMY_HDAL2 exons 4-5 | 1 | 105 | 45, 20 | cccagcatcctgtacatttc (SEQ ID NO: 59) | 58.019 | 169, 20 | attgtaccctctccaaggc (SEQ ID NO: 60) | 58.121 |
| BMY_HDAL2 exons 4-5 | 2 | 113 | 69, 20 | catcgctatgatgaagggaa (SEQ ID NO: 61) | 58.671 | 201, 18 | ggatcaaggccacctgtc (SEQ ID NO: 62) | 58.969 |

TABLE 8

| Template | Set Oligo Number | Capture Probe Start, Size | Sequence (ANTISENSE) |
|---|---|---|---|
| BMY_HDAL2 exon 1 | No oligo | | |
| BMY_HDAL2 exon 4 | 1 | 23, 80 | tgccagggaaaaagttcccttcatcatagcgatggagtgaaatgtacaggatgctggggtcagcataaaaggcctgctgg (SEQ ID NO: 63) |
| BMY_HDAL2 exon 4 | 2 | 19, 79 | gggaaaaagttcccttcatcatagcgatggagtgaaatgtacaggatgctggggtcagcataaaaggcctgctgggtac (SEQ ID NO: 64) |

TABLE 9

| HDAL Gene | 5'-oligo primer sequence (5'-3') | 3'-oligo primer sequence (5'-3') | Predicted Product | Product observed |
|---|---|---|---|---|
| HDAL2 | gtggacagtgacaccatttgga (SEQ ID NO: 65) | ggagaaagaagtaccaacctgaatgctt (SEQ ID NO: 66) | 489 nt | yes |

TABLE 10

| Template | Primer Set Set | Product Size | Left Primer Start, Length | Sequence | Tm | Right Primer Start, Length | Sequence | Tm |
|---|---|---|---|---|---|---|---|---|
| BMY_HDAL3 exon 1 | 1 | 100 | 18, 20 | gtggccaaagagtttgatcc (SEQ ID NO: 67) | 60 | 117, 20 | ttgccgtcactttgtaccct (SEQ ID NO: 68) | 60 |
| BMY_HDAL3 exon 1 | 2 | 100 | 18, 20 | gtggccaaagagtttgatcc (SEQ ID NO: 69) | 60 | 117, 19 | ttgccgtcactttgtaccc (SEQ ID NO: 70) | 59 |
| BMY_HDAL3 | 1 | 120 | 4, 20 | tggtcatttgacgaagcaat | 59 | 123, 20 | agaagggcatttacacaggc | 59 |

TABLE 10-continued

| Template | Primer Set | Product Size | Left Primer Start, Length | Sequence | Tm | Right Primer Start, Length | Sequence | Tm |
|---|---|---|---|---|---|---|---|---|
| exon 2 BMY_HDAL3 exon 2 | 2 | 119 | 4, 20 | (SEQ ID NO: 71) tggtcatttgacgaagcaat (SEQ ID NO: 73) | 59 | 122, 20 | (SEQ ID NO: 72) gaagggcatttacacaggct (SEQ ID NO: 74) | 59 |

TABLE 11

| Template | Primer Set | Product Size | Left Primer Start, Length | Sequence | Tm | Right Primer Start, Length | Sequence | Tm |
|---|---|---|---|---|---|---|---|---|
| BMY_HDAL3 exons 1-2 | 1 | 147 | 95, 20 | aggagggtacaaagtgacgg (SEQ ID NO: 75) | 59 | 261, 20 | agggcatttacacaggcttc (SEQ ID NO: 76) | 59 |
| BMY_HDAL3 exons 1-2 | 2 | 146 | 95, 20 | aggagggtacaaagtgacgg (SEQ ID NO: 77) | 59 | 260, 20 | gggcatttacacaggcttct (SEQ ID NO: 78) | 59 |
| BMY_HDAL3 exons 2-3 | 1 | 160 | 25, 20 | gatgacattggctgatggac (SEQ ID NO: 79) | 59 | 204, 20 | agcattcatattcgggcttt (SEQ ID NO: 80) | 59 |
| BMY_HDAL3 exons 2-3 | 2 | 181 | 4, 20 | tggtcatttgacgaagcaat (SEQ ID NO: 81) | 59 | 204, 20 | agcattcatattcgggcttt (SEQ ID NO: 82) | 59 |

TABLE 12

| Template | Set | Capture Probe Start, Size | Sequence (ANTISENSE) |
|---|---|---|---|
| BMY_HDAL3 exon 1 | 1 | 32, 80 | tcactttgtaccctcctagaggaggggtgtggccttccaatgcatcaaatccagcagatactaagaccatgtctggatca (SEQ ID NO: 83) |
| BMY_HDAL3 exon 1 | 2 | 19, 80 | tcctagaggaggggtgtggccttccaatgcatcaaatccagcagatactaagaccatgtctggatcaaactctttggcca (SEQ ID NO: 84) |
| BMY_HDAL3 exon 2 | 1 | 27, 80 | ggcttctgatgcatcacagatggctgtgagatcatgtcctccttctagagccaacaccacacgtccatcagccaatgtca (SEQ ID NO: 85) |
| BMY_HDAL3 exon 2 | 2 | 27, 80 | ggcttctgatgcatcacagatggctgtgagatcatgtcctccttctagagccaacaccacacgtccatcagccaatgtca (SEQ ID NO: 86) |

Example 4

Complementary Polynucleotides

Antisense molecules or nucleic acid sequence complementary to an HDAC protein-encoding sequence, or any part thereof, can be used to decrease or to inhibit the expression of naturally occurring HDAC. Although the use of antisense or complementary oligonucleotides comprising about 15 to 35 base-pairs is described, essentially the same procedure is used with smaller or larger nucleic acid sequence fragments. An oligonucleotide based on the coding sequence of an HDAC polypeptide or peptide, for example, as shown in FIG. 1, FIG. 5, FIG. 10, FIGS. 15A-15C, FIGS. 20A-20C, and FIGS. 21A-21B, and as depicted in SEQ ID NO:1, SEQ ID NO:12, SEQ ID NO:19, SEQ ID NO:88, SEQ ID NO:94, or SEQ ID NO:96, for example, is used to inhibit expression of naturally occurring HDAC. The complementary oligonucleotide is typically designed from the most unique 5' sequence and is used either to inhibit transcription by preventing promoter binding to the coding sequence, or to inhibit translation by preventing the ribosome from binding to an HDAC protein-encoding transcript.

Using a portion SEQ ID NO:1, SEQ ID NO:12, SEQ ID NO:19, SEQ ID NO:88, SEQ ID NO:94, or SEQ ID NO:96, for example, an effective antisense oligonucleotide includes any of about 15-35 nucleotides spanning the region which translates into the signal or 5' coding sequence of the HDAC polypeptide. Appropriate oligonucleotides are designed using OLIGO 4.06 software and the HDAC coding sequence (e.g., SEQ ID NO:1, SEQ ID NO:12, SEQ ID NO:19, SEQ ID NO:88, SEQ ID NO:94, or SEQ ID NO:96).

Example 5

Northern Blot Analysis for HDACs

Northern Blot analysis is used to detect the presence of a transcript of a gene and involves the hybridization of a labeled nucleotide sequence to a membrane on which RNA from a particular cell or tissue type has been bound (See, J. Sambrook et al., supra). Analogous computer techniques using BLAST (S. F. Altschul, 1993, J. Mol. Evol., 36:290-300 and S. F. Altschul et al., 1990, J. Mol. Evol., 215:403-410) are used to search for identical or related molecules in nucleotide databases, such as GenBank or the LIFESEQ database (Incyte Pharmaceuticals). This analysis is much more rapid and less labor-intensive than performing multiple, membrane-based hybridizations. In addition, the sensitivity of the computer search can be modified to determine whether any particular match is categorized as being exact (identical) or homologous.

The basis of the search is the product score, which is defined as follows: (% sequence identity×maximum BLAST score)/100. The product score takes into account both the degree of similarity between two sequences and the length of the sequence match. For example, with a product score of 40, the match will be exact within a 1-2% error; at 70, the match will be exact. Homologous molecules are usually identified by selecting those which show product scores between 15 and 40, although lower scores may identify related molecules. The results of Northern analysis are reported as a list of libraries in which the transcript encoding HDAC polypeptides occurs. Abundance and percent abundance are also reported. Abundance directly reflects the number of times that a particular transcript is represented in a cDNA library, and percent abundance is abundance divided by the total number of sequences that are examined in the cDNA library.

Example 6

Microarrays for Analysis of HDACs

For the production of oligonucleotides for a microarray, an HDAC sequence, e.g., a novel HDAC having SEQ ID NO:1, SEQ ID NO:12, SEQ ID NO:19, SEQ ID NO:88, SEQ ID NO:94, or SEQ ID NO:96, for example, is examined using a computer algorithm which starts at the 3' end of the nucleotide sequence. The algorithm identifies oligomers of defined length that are unique to the gene, have a GC content within a range that is suitable for hybridization and lack predicted secondary structure that would interfere with hybridization. The algorithm identifies specific oligonucleotides of 20 nucleotides in length, i.e., 20-mers. A matched set of oligonucleotides is created in which one nucleotide in the center of each sequence is altered. This process is repeated for each gene in the microarray, and double sets of 20-mers are synthesized in the presence of fluorescent or radioactive nucleotides and arranged on the surface of a substrate. When the substrate is a silicon chip, a light-directed chemical process is used for deposition (WO 95/11995, M. Chee et al.).

Alternatively, a chemical coupling procedure and an ink jet device is used to synthesize oligomers on the surface of a substrate. (WO 95/25116, J. D. Baldeschweiler et al.). As another alternative, a "gridded" array that is analogous to a dot (or slot) blot is used to arrange and link cDNA fragments or oligonucleotides to the surface of a substrate using, for example, a vacuum system, or thermal, UV, mechanical, or chemical bonding techniques. A typical array may be produced by hand, or by using available materials and equipment, and may contain grids of 8 dots, 24 dots, 96 dots, 384 dots, 1536 dots, or 6144 dots. After hybridization, the microarray is washed to remove any non-hybridized probe, and a detection device is used to determine the levels and patterns of radioactivity or fluorescence. The detection device may be as simple as X-ray film, or as complicated as a light scanning apparatus. Scanned fluorescent images are examined to determine degree of complementarity and the relative abundance/expression level of each oligonucleotide sequence in the microarray.

Example 7

Purification of HDAC Polypeptides

Naturally occurring or recombinant HDAC polypeptide is substantially purified by immunoaffinity chromatography using antibodies specific for an HDAC polypeptide, or a peptide derived therefrom. An immunoaffinity column is constructed by covalently coupling anti-HDAC polypeptide antibody to an activated chromatographic resin, such as CNBr-activated SEPHAROSE (Amersham Pharmacia Biotech). After the coupling, the resin is blocked and washed according to the manufacturer's instructions.

Medium containing HDAC polypeptide is passed over the immunoaffinity column, and the column is washed under conditions that allow the preferential absorbance of the HDAC polypeptide (e.g., high ionic strength buffers in the presence of detergent). The column is eluted under conditions that disrupt antibody/HDAC polypeptide binding (e.g., a buffer of pH 2-3, or a high concentration of a chaotrope, such as urea or thiocyanate ion), and HDAC polypeptide is collected.

Example 8

Identification of Molecules that Interact with HDAC Polypeptides

HDAC polypeptides, or biologically active fragments thereof, are labeled with $^{125}$I Bolton-Hunter reagent (Bolton et al., 1973, Biochem. J., 133:529). Candidate molecules previously arrayed in wells of a multi-welled plate are incubated with the labeled HDAC polypeptide, washed, and any wells having labeled HDAC polypeptide-candidate molecule complexes are assayed. Data obtained using different concentrations of HDAC polypeptide are used to calculate values for the number, affinity and association of an HDAC polypeptide with the candidate molecules.

Another method suitable for identifying proteins, peptides or other molecules that interact with an HDAC polypeptide include ligand binding assays such as the yeast-two hybrid system as described hereinabove.

Example 9

Identification and Cloning of HDAC9c

Bioinformatic searches of the assembled human genome sequence were performed using a conserved consensus sequence derived from the catalytic domain of class I and class II HDACs. Three gene fragments (HDAL1, HDAL2, HDAL3) were identified from the assembled sequence of human chromosome 7q36 that encoded amino acids sequence with homology to class II HDACs. Biotinylated single stranded oligonucleotides representing unique sequences from these predicted gene fragments of the following sequence were prepared:

```
HDAL1, 5-gtttcttgcagtcgtgaccagatactctgattcgtccagcatgctcagggt    (SEQ ID NO:101)
gggtgggtggaattgccacaaacgca;

HDAL2, 5'-tgccagggaaaaagt tcccttcatcatagcgatggagtgaaatgtaca    (SEQ ID NO:102)
ggatgctggggtcagcataaaaggcctgctgg;
```

-continued and

HDAL3, 5' tgatccagacatggtcttagtatctgctggatttgatgcattggaaggcca (SEQ ID NO:103)
cacccctcctctaggagggtacaaagtga.

The biotinylated oligonucleotides were hybridized to fractions of cDNA prepared from human placenta, and positive sequences were identified by PCR. Three of the clones identified (HDACX1A, HDACX2A, and HDACX3A) contained overlapping cDNAs that showed sequence identity to the predicted gene fragments. These cDNAs encoded a novel sequence, designated HDAC9c (FIGS. 15A-15C), that shared homology to class II HDACs. A full length HIDAC9c construct was prepared by combining a 1.3 kb BamHI-PstI fragment from the HDACX2A clone with a 3.5 kb PstI-NotI fragment from the HDACX3A. These fragments were ligated into mammalian expression vectors pcDNA3.1 and pcDNA4.0. The resulting constructs were evaluated by DNA sequencing to confirm the identity of the inserts. The HDAC9c pcDNA3.1 construct was deposited at the American Type Culture Collection (ATCC), 10801 University Boulevard, Manassas, Va. 20110-2209 on Jun. 12, 2002 under ATCC Accession No. PTA-4454 according to the terms of the Budapest Treaty.

Three fragments that encoded homology to class II HDACs were identified from the assembled sequence of human chromosome 7q36. Subsequent cDNA cloning bioinformatics analysis revealed that these gene fragments encoded a single class II HDAC, comprising a protein of 1147 amino acids. This sequence was provisionally designated as HDAC-9, and later renamed HDAC9c. During the course of this work, similar sequences were reported by Zhou et al. (2001, *Proc. Natl. Acad. Sci. USA* 98:10572-7), including two isoforms related to class II HDAC proteins. Sequence alignments revealed the HDAC-9 sequence was closely related to the previously identified HDAC9 sequences (GenBank Accession Nos. AY032737 and AY032738). However, the published sequences lacked a large portion of the C-terminal domain common to known class HDAC proteins (FIGS. 15D-15F).

One of the HDAC9 isoforms (HDAC9a, (GenBank Accession No. AY032738) lacked ~ 185 C-terminal amino acids compared to other HDAC family members. Another isoform of HDAC9 (HDAC9, (GenBank Accession No. AY032737) lacked approximately 65 C-terminal amino acids compared to other HDAC family members. In contrast to these sequences, the HDAC9c sequence, also designated as HDAC-X, contained more than 50 additional amino acids at its C-terminus (FIGS. 15D-15F). The HDAC9c sequence was deemed to represent the full-length version of HDAC9. Notably, HDAC9c contained an LQQ sequence motif at positions 123-125. This motif was missing in the HDAC9 C-terminal truncated isoforms, but was conserved in other HDAC family members. Thus, the LQQ sequence motif may be important for the function of the HDAC9c protein. No other motifs were identified by PFAM analysis (A. Bateman et al., 2002, *Nucl. Acids Res.* 30:276-80).

Example 10

Expression Profiling For HDAC9 And HDAC9c

To determine the distribution of HDAC9 and HDAC9c in adult normal tissues, the expression profile of HDAC9 and HDAC9c was examined by Northern blot analysis. Northern blotting was performed as described (Sambrook et al., *Molecular Cloning: A Laboratoy Manual*, 2$^{nd}$ Edition). Tissue samples were obtained from CLONTECH (Palo Alto, Calif). The probe for Northern blotting was derived from nucleotides 2917-3211 of HDAC9c (FIG. 16D; SEQ ID NO:92). Two > 8.0 kb HDAC9 and HDAC9c transcripts were detected at low levels in brain, skeletal muscle, stomach, and trachea tissue (FIG. 16A). Upon longer exposure, HDAC9 and HDAC9c mRNA was also detected in mammary gland and prostate tissue (FIG. 16A).

Given the low level of expression in normal tissues, experiments were performed to determine the expression of HDAC9 and HDAC9c in human tumor cell lines. HDAC9 and HDAC9c mRNA expression levels were evaluated by quantitative PCR analysis on first-strand cDNA prepared from a variety of human tumor cell lines (ATCC, Rockville, Md.). HDAC9 and HDAC9c levels were normalized to GAPDH mRNA levels within the samples, and RNA levels were quantified using the fluorophore SYBR green. For amplification, HDAC9 and HDAC9c primers were used: forward primer 5'-gtgacaccatttggaatgagctac (SEQ ID NO: 104); and reverse primer 5'ttggaagccagctcgatgac (SEQ ID NO:105). HDAC9 and HDAC9c expression was found to be elevated in ovarian, breast, and certain lung cancer cell lines (FIG. 16B). In contrast, HDAC9 and HDAC9c was poorly expressed in tumor cell lines derived from colon tumor specimens (FIG. 16B).

To confirm these results, nuclease protection experiments were performed on RNAs isolated from select tumor cell displaying a range of HDAC9 and HDAC9c expression. Nuclease protection was performed using $^{35}$S-labled UTP as a radioactive precursor for a in accordance with published methods (Sambrook et al., *Molecular Cloning: A Laboratory Manual*, 2$^{nd}$ Edition). The riboprobe sequence was derived from nucleotides 2917-3211 in HDAC9c (FIG. 16D; SEQ ID NO:92). Brain tissue was included as a control to show nonnal tissue expression levels. The profile of HDAC9 and HDAC9c expression observed by quantitative RT-PCR was confirmed by nuclease protection (i.e., A2780 > MDA-MB453 > MCF7; FIG. 16C). The pervasive expression of HDAC9 and HDAC9c in tumor cell lines of diverse origin, and the low level expression of HDAC9 and HDAC9c in normal adult tissue, suggested that the expression of this gene was regulated in tumor progression.

Example 11

In Situ Hybridization To Analyze HDAC9 And HDAC9c Expression

To further analyze the upregulation of HDAC9 and HDAC9c in tumor cells, a variety of human tumor and nonnal tissue specimens were subjected to in situ hybridization using an HDAC9c antisense riboprobe and tissue microarrays. A $^{35}$S-labeled eRNA riboprobe was prepared from a 295 bp cDNA fragment from the HDAC9c coding region (FIG. 16D; SEQ ID NO:92). This fragment encoded the most divergent region of the HDAC9c protein. The riboprobe was hybridized to paraffin-embedded clinical tissue specimens derived from normal or cancerous tissues, and processed by standard procedures (Lorenzi et al., 1999, *Oncogene* 18:4742-4755). Hybridized sections were incubated for 3 to 6 weeks, and the level and localization of HDAC9 and HDAC9c staining was evaluated by microscopy. Staining levels were quantified by a board-certified pathologist.

HDAC9 and HDAC9c mRNA levels were generally below the limit of detection (staining level =0) in normal tissues, including breast, kidney, testis, and liver tissues. Low to moderate levels of HDAC9 and HDAC9c mRNA (staining level =1-2) were detected in lymph node, brain, adrenal gland, pancreas, bladder, lung, and gastric tissues (data not shown). Normal breast and prostate tissue showed average staining levels of 0 and 1, respectively (FIGS. 17A-17C). A dramatic increase in HDAC9 and HDAC9c mRNA expression was detected in breast tumor (average staining level =2-3) and prostate tumor (average staining level =2) tissues (FIGS. 17A-17C). Preliminary data also showed increased expression of HDAC9 and HDAC9c in endometrial and ovarian tumors. Thus, HDAC9 and HDAC9c was expressed at very low levels in normal adult peripheral tissues, but was overexpressed in a variety of tumors, including breast and prostate adenocarcinomas. This suggested that HDAC9 and HDAC9c expression correlated with the progression of breast and prostate tumors.

Example 12

Effect of HDAC9c on Cellular Transformation

Results of the experiments, above, indicated that elevated HDAC9c expression was associated with certain tumor cells. To further investigate its involvement in tumorogenesis, HDAC9c was evaluated for its ability to morphologically transform mouse fibroblasts. HDAC9c in pcDNA3.1 was introduced by calcium phosphate transfection into $1.5 \times 10^5$ NIH/3T3 cells (ATCC, Rockville, Md.) in duplicate at 1.0 µg/10 cm plate. One set of cultures received growth medium (DMEM containing 5% calf serum) while the parallel culture received growth medium containing 750 µg/ml of G418 to develop stable clonal populations.

After 10-14 days in culture, unselected plates were stained with Geimsa (Sigma-Aldrich, St. Louis, Mo.), and morphologically transformed foci were visualized. Selected clones were examined for growth in soft agar at $10^5$, $10^4$, or $10^3$ cells/15 mm well following standard protocols. After 2-3 weeks in culture, colonies were visualized by microscopy and tetrazolium violet staining. HDAC9c transfectants produced some foci in monolayer culture (data not shown). However, the response was not robust, suggesting that higher levels HDAC9c expression levels were required to transform NIH/3T3 cells.

HDAC9c transfectants were also evaluated for anchorage-independent growth. NIH/3T3 cells stably transfected with HDAC9c or FGF8 constructs, or vector alone, were suspended in soft agar containing growth medium and cultured for 2-3 weeks. FGF8 is a cDNA that potently transforms NIH/3T3 through autocrine stimulation of endogenous FGF receptors (Lorenzi et al., 1995, Oncogene 10:2051-2055). In vector transfectants, very few colonies greater than 50 µm in diameter were observed after three weeks in culture (FIG. 18). In contrast, FGF8 transfectants produced several colonies greater than 50 µm after three weeks (FIG. 18). HDAC9c transfectants also produced significant colony growth compared to vector transfectants, but less than that observed for FGF8 transfectants (FIG. 18). These results suggested that overexpression of HDAC9c induced an oncogenic phenotype in mouse fibroblasts.

Example 13

Effect of HDAC9c on the Actin Cytoskeleton

Changes in the actin cytoskeleton often accompany the transformed phenotype of cells expressing oncogenes such as Ras, Rho, or src. In general, gene products that affect cell adhesion or motility are associated with changes in the actin cytoskeleton. To investigate whether the transformation induced by HDAC9c was associated with changes in the cytoskeletal architecture, NIH/3T3 transfectants expressing HDAC9c were subjected to fluorescent staining with TRITC-conjugated phalloidin to visualize filamentous actin (F-actin).

In these experiments, a HDAC4 construct was used as a control. For the control construct, full-length HDAC4 cDNA was amplified by RT-PCR from first-strand cDNA based on the sequence reported by Grozinger et al. (*Proc. Natl. Acad. Sci. USA* 96:4868-4873), and cloned into pcDNA3.1. Mass-selected stable NIH/3T3 clones of HDAC9c (in pcDNA3.1), Ras, HDAC4, or vector alone, were plated in 8 well chamber slides in duplicate and allowed to adhere overnight in growth medium (DMEM high glucose containing 10% calf serum). Cells were subsequently serum-starved for 18 hours and one set was stimulated with 10% calf serum for 15 minutes. The cultures were fixed for 30 minutes in 4% paraformaldehyde, permeabilized in 0.02% Triton-X100, and incubated with TRITC or FITC conjugated phalloidin (Sigma, St. Louis, Mo.) for 2 hours. Filamentous actin was visualized by fluorescence microscopy, and images were captured with a digital camera.

Figure 19:
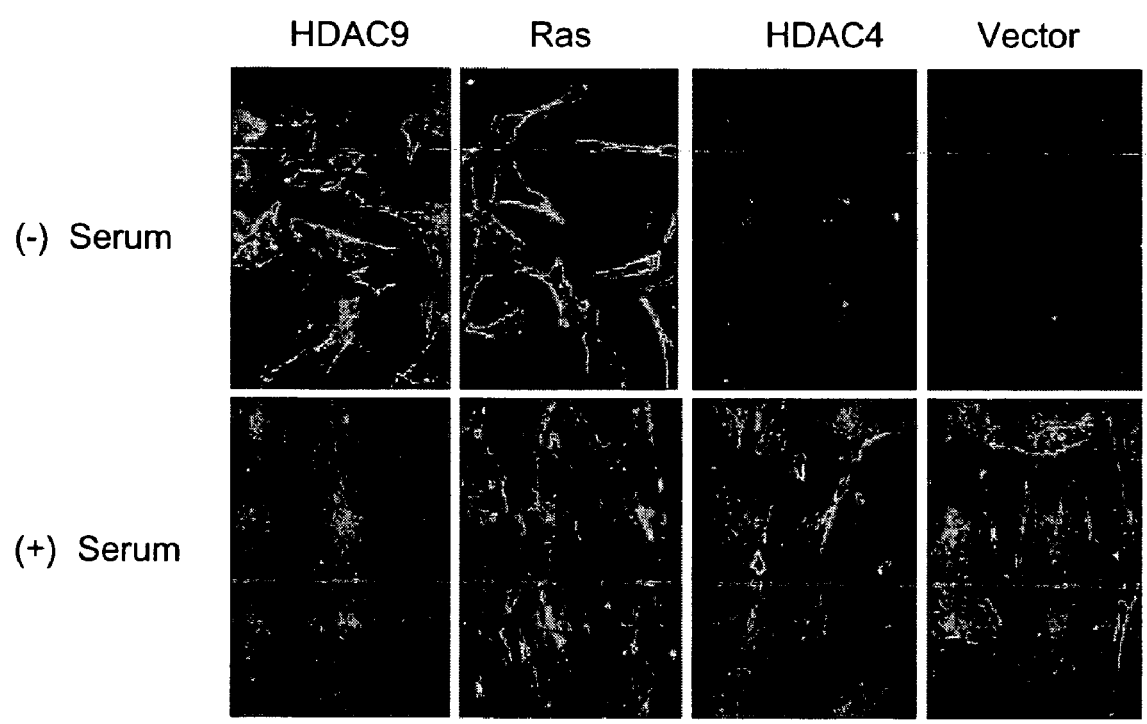
FIG. 19 shows HDAC9c induction of actin stress fiber formation in NIH/3T3 cells. Stable NIH/3T3 cells expressing the indicated constructs were stained with phalloidin-TRITC and visualized by fluorescent microscopy.

In parental NIH/3T3 cells (data not shown) or vector transfectants, low levels of F-actin stress fiber formation were observed following serum starvation for 18 hours (FIG. 19). Stimulation of these cells for 15 minutes with serum promoted an extensive stress fiber network (FIG. 19), indicating that the extracellular signals regulating these pathways were intact in these cells. A dramatic increase in stress fiber content and organization was observed in serum starved HDAC9c-expressing cells (FIG. 19), indicating that that expression of HDAC9c was sufficient to induce reorganization of the actin cytoskeleton. In contrast, no stress fiber formation was observed in serum starved NIH/3T3 cells expressing the HDAC4 protein (FIG. 19). These results suggested that induction of actin stress fiber formation underlay the transformed phenotype associated with expression of HDAC9c.

CONCLUSION

Inhibitors of HDAC activity are involved in the regulation of cellular proliferation, apoptosis, and differentiation of a variety of cell types. However, little is known about the role of individual HDACs in tumor cells or in their genesis. In accordance with the present invention, a unique HDAC isoform, HDAC9c, has been identified and characterized. HDAC9 shows restricted expression in normal adult tissues, but is overexpressed in several primary human tumors, including those derived from breast and prostate cancers. The overexpression of HDAC9c in in vitro models promoted the oncogenic transformation of fibroblasts and this transformed phenotype was associated with the induction of actin cytoskeletal stress fiber formation. These results suggest a functional consequence of HDAC9c overexpression is the promotion and/or maintenance of the transformation state of certain tumor cells.

Members of the HDAC protein family have been shown to possess potent ability to repress transcription. For instance, tumor suppressor genes p21 and gelsolin are expressed upon HDAC inhibition (Sowa et al., 1999, *Cancer Res.* 59(17): 4266-70; Saito et al., 1999, *Proc. Natl. Acad. Sci. USA* 96:4592-4597). It is interesting to note that gelsolin negatively regulates the formation of the actin cytoskeleton (Sun et al., 1999, *J. Biol. Chem.* 274:33179-33182). In contrast, actin cytoskeleton formation is positively regulated by HDAC9c expression (FIG. 19). Thus, HDAC9c inhibition or overexpression may regulate gelsolin levels, and this regulation may underlie the cytoskeletal changes mediated by HDAC9c.

HDAC9 was overexpressed greater than 90% of the breast and prostate tumor specimens examined compared to corresponding tissue from normal patients (FIGS. 17A-17B). By comparison, the epidermal growth factor (EGF) receptor, erbB2, has been estimated to be overexpressed in roughly 30% of certain tumor types (King et al., 1985, *Science* 229: 974-976). These observations strongly suggest that HDAC9c can be used as a diagnostic marker for breast or prostate tumorigenesis. Hormonal signaling is critical to the progression and treatment of breast cancers, and HDAC9 has been implicated in transcription (Zhou et al., *Proc. Natl. Acad. Sci. USA* 98:10572-10577). Without wishing to be bound by theory, it is possible that HDAC9 regulates estrogen or androgen responsive promoters in these tumor cells. As shown herein, HDAC9 expression is increased in primary cancers, and restricted in normal tissue expression. Further, HDAC9c expression induces oncogenic transformation. The sum of these observations indicates that HDAC9c can be used as a diagnostic and/or therapeutic target for certain tumors or cancers, in particular, breast and prostate tumors or cancers.

Example 14

HDAC9 Splice Variants

Using the methods described herein, HDAC9 splice variants were identified, including BMY_HDACX variant 1 (FIGS. 20A-20C; SEQ ID NO:94; also called BMY_HDACX_v1 and HDACX_v1) and BMY_HDACX variant 2 (FIGS. 21A-21B; SEQ ID NO:96; also called BMY_HDACX_v2 and HDACX v2). The cDNA sequences for BMY_ HDACX_v1 (SEQ ID NO:94) and BMY_HDACX_v2 (SEQ ID NO:96) were aligned to the nucleotide sequences of three reported splice products of the HDAC9 gene, including HDAC9v1 (NCBI Ref. Seq. NM_058176; FIGS. 22A-22C; SEQ ID NO:97), HDAC9v2 (NCBI Ref. Seq. NM_058177; FIGS. 22D-22F; SEQ ID NO:98), and HDAC9v3 (NCBI Ref. Seq. NM_014707; FIGS. 22G-22I; SEQ ID NO:100). The sequence alignment produced by ClustalW (D. G. Higgins et al., 1996, *Methods Enzymol.* 266:383-402) is shown in FIGS. 23A-23K.

ClustalW sequence alignments indicated that the HDAC9c amino acid sequence showed 80.5% identity to the HDAC9a (AY032738) amino acid sequence, 94.1% identity to the HDAC9 (AY032737) amino acid sequence, and 55.1% identity to the HDAC5 (AF132608) amino acid sequence. The HDAC9c nucleotide sequence showed 81.4% identity to the HDAC9a (AY032738) nucleotide sequence, 94.3% identity to the HDAC9 (AY032737) nucleotide sequence, and 60.1% identity to the HDAC5 (AF132608) nucleotide sequence. In addition, the HDACX_v2 amino acid sequence showed 55.2% identity to the most closely related amino acid sequence, and the HDACX_v2 nucleotide sequence showed 55.3% identity to the HDAC9a (AY032738) nucleotide sequence, 48.1% identity to the HDAC9 (AY032737) nucleotide sequence, and 27.6% identity to the HDAC5 (AF132608) nucleotide sequence.

Additional amino acid sequence alignments are shown in FIGS. 24A-24D and FIGS. 25A-25C. For reference, the SEQ ID NOs of the sequences of the present invention are listed in the table shown below.

| Description | SEQ ID NO: |
|---|---|
| BMY_HDAL1 nucleic acid sequence | SEQ ID NO:1 |
| BMY_HDAL1 amino acid sequence | SEQ ID NO:2 |
| BMY_HDAL1 reverse nucleic acid sequence | SEQ ID NO:3 |
| BMY_HDAL2 amino acid sequence | SEQ ID NO:4 |
| BMY_HDAL3 amino acid sequence | SEQ ID NO:5 |
| SC_HDA1 amino acid sequence | SEQ ID NO:6 |
| Human HDAC4 amino acid sequence | SEQ ID NO:7 |
| Human HDAC5 amino acid sequence | SEQ ID NO:8 |
| Human HDAC7 amino acid sequence | SEQ ID NO:9 |
| Aquifex ACUC HDAL amino acid sequence | SEQ ID NO:10 |
| AC002088 nucleic acid sequence | SEQ ID NO:11 |
| BMY_HDAL2 nucleic acid sequence | SEQ ID NO:12 |
| BMY_HDAL2 reverse nucleic acid sequence | SEQ ID NO:13 |
| AC002410 nucleic acid sequence | SEQ ID NO:14 |
| N-terminus of BMY_HDAL3 | SEQ ID NO:15 |
| C-terminus of BMY_HDAL3 | SEQ ID NO:16 |
| BAC AC004994 nucleic acid sequence | SEQ ID NO:17 |
| BAG AC004744 nucleic acid sequence | SEQ ID NO:18 |
| BMY_HDAL3 nucleic acid sequence | SEQ ID NO:19 |
| BMY_HDAL3 reverse strand nucleic acid sequence | SEQ ID NO:20 |
| AAC78618 amino acid sequence | SEQ ID NO:21 |
| AAD15364 amino acid sequence | SEQ ID NO:22 |
| AA287983 nucleic acid sequence | SEQ ID NO:23 |
| BMY_HDAL1 single exon primer | SEQ ID NO:24 |
| BMY_HDAL1 single exon primer | SEQ ID NO:25 |
| BMY_HDAL1 single exon primer | SEQ ID NO:26 |
| BMY_HDAL1 single exon primer | SEQ ID NO:27 |
| BMY_HDAL1 multiple exon primer | SEQ ID NO:28 |
| BMY_HDAL1 multiple exon primer | SEQ ID NO:29 |
| BMY_HDAL1 multiple exon primer | SEQ ID NO:30 |
| BMY_HDAL1 multiple exon primer | SEQ ID NO:31 |
| BMY_HDAL1 multiple exon primer | SEQ ID NO:32 |
| BMY_HDAL1 multiple exon primer | SEQ ID NO:33 |
| BMY_HDAL1 multiple exon primer | SEQ ID NO:34 |
| BMY_HDAL1 multiple exon primer | SEQ ID NO:35 |
| BMY_HDAL1 capture oligonucleotide | SEQ ID NO:36 |
| BMY_HDAL1 5' oligo primer | SEQ ID NO:37 |

| Description | SEQ ID NO: |
|---|---|
| BMY_HDAL1 3' oligo primer | SEQ ID NO:38 |
| BMY_HDAL2 single exon primer | SEQ ID NO:39 |
| BMY_HDAL2 single exon primer | SEQ ID NO:40 |
| BMY_HDAL2 single exon primer | SEQ ID NO:41 |
| BMY_HDAL2 single exon primer | SEQ ID NO:42 |
| BMY_HDAL2 single exon primer | SEQ ID NO:43 |
| BMY_HDAL2 single exon primer | SEQ ID NO:44 |
| BMY_HDAL2 single exon primer | SEQ ID NO:45 |
| BMY_HDAL2 single exon primer | SEQ ID NO:46 |
| BMY_HDAL2 multiple exon primer | SEQ ID NO:47 |
| BMY_HDAL2 multiple exon primer | SEQ ID NO:48 |
| BMY_HDAL2 multiple exon primer | SEQ ID NO:49 |
| BMY_HDAL2 multiple exon primer | SEQ ID NO:50 |
| BMY_HDAL2 multiple exon primer | SEQ ID NO:51 |
| BMY_HDAL2 multiple exon primer | SEQ ID NO:52 |
| BMY_HDAL2 multiple exon primer | SEQ ID NO:53 |
| BMY_HDAL2 multiple exon primer | SEQ ID NO:54 |
| BMY_HDAL2 multiple exon primer | SEQ ID NO:55 |
| BMY_HDAL2 multiple exon primer | SEQ ID NO:56 |
| BMY_HDAL2 multiple exon primer | SEQ ID NO:57 |
| BMY_HDAL2 multiple exon primer | SEQ ID NO:58 |
| BMY_HDAL2 multiple exon primer | SEQ ID NO:59 |
| BMY_HDAL2 multiple exon primer | SEQ ID NO:60 |
| BMY_HDAL2 multiple exon primer | SEQ ID NO:61 |
| BMY_HDAL2 multiple exon primer | SEQ ID NO:62 |
| BMY_HDAL2 capture oligonucleotide | SEQ ID NO:63 |
| BMY_HDAL2 capture oligonucleotide | SEQ ID NO:64 |
| BMY_HDAL2 5' oligo primer | SEQ ID NO:65 |
| BMY_HDAL2 3' oligo primer | SEQ ID NO:66 |
| BMY_HDAL3 single exon primer | SEQ ID NO:67 |
| BMY_HDAL3 single exon primer | SEQ ID NO:68 |
| BMY_HDAL3 single exon primer | SEQ ID NO:69 |
| BMY_HDAL3 single exon primer | SEQ ID NO:70 |
| BMY_HDAL3 single exon primer | SEQ ID NO:71 |
| BMY_HDAL3 single exon primer | SEQ ID NO:72 |
| BMY_HDAL3 single exon primer | SEQ ID NO:73 |
| BMY_HDAL3 single exon primer | SEQ ID NO:74 |
| BMY_HDAL3 multiple exon primer | SEQ ID NO:75 |
| BMY_HDAL3 multiple exon primer | SEQ ID NO:76 |
| BMY_HDAL3 multiple exon primer | SEQ ID NO:77 |
| BMY_HDAL3 multiple exon primer | SEQ ID NO:78 |
| BMY_HDAL3 multiple exon primer | SEQ ID NO:79 |
| BMY_HDAL3 multiple exon primer | SEQ ID NO:80 |
| BMY_HDAL3 multiple exon primer | SEQ ID NO:81 |
| BMY_HDAL3 multiple exon primer | SEQ ID NO:82 |
| BMY_HDAL3 capture oligo | SEQ ID NO:83 |
| BMY_HDAL3 capture oligo | SEQ ID NO:84 |
| BMY_HDAL3 capture oligo | SEQ ID NO:85 |
| BMY_HDAL3 capture oligo | SEQ ID NO:86 |
| HDAC9c amino acid sequence | SEQ ID NO:87 |
| HDAC9c nucleotide sequence | SEQ ID NO:88 |
| HDAC9 (AY032737) amino acid sequence | SEQ ID NO:89 |
| HDAC9a (AY032738) amino acid sequence | SEQ ID NO:90 |
| HDAC4 (ALF132608) amino acid sequence | SEQ ID NO:91 |
| HDAC9 probe | SEQ ID NO:92 |
| BMY_HDACX_v1 amino acid sequence | SEQ ID NO:93 |
| BMY_HDACX_v1 nucleotide sequence | SEQ ID NO:94 |
| BMY_HDACX_v2 amino acid sequence | SEQ ID NO:95 |
| BMY_HDACX_v2 nucleotide sequence | SEQ ID NO:96 |
| HDAC9v1 (NM_058176) amino acid sequence | SEQ ID NO:89 |
| HDAC9v1 (NM_058176) nucleotide sequence | SEQ ID NO:97 |
| HDAC9v2 (NM_058177) amino acid sequence | SEQ ID NO:90 |
| HDAC9v2 (NM_058177) nucleotide sequence | SEQ ID NO:98 |
| HDAC9v3 (NM_014707) amino acid sequence | SEQ ID NO:99 |
| HDAC9v3 (NM_014707) nucleotide sequence | SEQ ID NO:100 |
| HDAL1 primer | SEQ ID NO:101 |
| HDAL2 primer | SEQ ID NO:102 |
| HDAL3 primer | SEQ ID NO:103 |
| HDAC9 forward primer | SEQ ID NO:104 |
| HDAC9 reverse primer | SEQ ID NO:105 |
| HDAC consensus nucleotide sequence | SEQ ID NO:106 |
| HDAC consensus amino acid sequence | SEQ ID NO:107 |

The contents of all patents, patent applications, published PCT applications and articles, books, references, reference manuals and abstracts cited herein are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. An isolated polypeptide comprising a polypeptide sequence selected from the group consisting of:
   (a) an isolated polypeptide comprising amino acids 1 to 1069 of SEQ ID NO:87;
   (b) an isolated polypeptide comprising amino acids 2 to 1069 of SEQ ID NO:87;
   (c) an isolated polypeptide comprising the polypeptide sequence encoded by nucleotides 1 to 3207 of SEQ ID NO:88; and
   (d) an isolated polypeptide comprising the polypeptide sequence encoded by nucleotides 4 to 3207 of SEQ ID NO:88.

2. The isolated polypeptide of claim 1, wherein said polypeptide is (a).

3. The isolated polypeptide of claim 1, wherein said polypeptide is (b).

4. The isolated polypeptide of claim 1, wherein said polypeptide is (c).

5. The isolated polypeptide of claim 1, wherein said polypeptide is (d).

6. An isolated polypeptide produced by a method comprising:
   (a) culturing an isolated recombinant host cell comprising a vector that comprises the coding region encoding the polypeptide of claim 1 under conditions such that said polypeptide is expressed; and
   (b) recovering said polypeptide.

7. The isolated polypeptide of claim 1 further comprising a heterologous polypeptide sequence.

8. An isolated polypeptide comprising at least 920 contiguous amino acids of SEQ ID NO:87.

9. An isolated polypeptide encoded by cDNA clone, HDAC9c, contained in ATCC Deposit No: PTA-4454.

* * * * *

SEQUENCE LISTING

```
<160> NUMBER OF SEQ ID NOS: 127

<210> SEQ ID NO 1
<211> LENGTH: 315
<212> TYPE: DNA
<213> ORGANISM: Homo sapiens
<220> FEATURE:
<221> NAME/KEY: CDS
<222> LOCATION: (1)..(315)

<400> SEQUENCE: 1 gga att gcc tat gac ccc ttg atg ctg aaa cac cag tgc gtt tgt ggc      48
Gly Ile Ala Tyr Asp Pro Leu Met Leu Lys His Gln Cys Val Cys Gly
 1               5                  10                  15 aat tcc acc acc cac cct gag cat gct gga cga ata cag agt atc tgg      96
Asn Ser Thr Thr His Pro Glu His Ala Gly Arg Ile Gln Ser Ile Trp
             20                  25                  30 tca cga ctg caa gaa act ggg ctg cta aat aaa tgt gag cga att caa     144
Ser Arg Leu Gln Glu Thr Gly Leu Leu Asn Lys Cys Glu Arg Ile Gln
         35                  40                  45 ggt cga aaa gcc agc ctg gag gaa ata cag ctt gtt cat tct gaa cat     192
Gly Arg Lys Ala Ser Leu Glu Glu Ile Gln Leu Val His Ser Glu His
     50                  55                  60 cac tca ctg ttg tat ggc acc aac ccc ctg gac gga cag aag ctg gac     240
His Ser Leu Leu Tyr Gly Thr Asn Pro Leu Asp Gly Gln Lys Leu Asp
 65                  70                  75                  80 ccc agg ata ctc cta ggt gat gac tct caa aag ttt ttt tcc tca tta     288
Pro Arg Ile Leu Leu Gly Asp Asp Ser Gln Lys Phe Phe Ser Ser Leu
                 85                  90                  95 cct tgt ggt gga ctt ggg gta agt aca                                 315
Pro Cys Gly Gly Leu Gly Val Ser Thr
            100                 105

<210> SEQ ID NO 2
<211> LENGTH: 105
<212> TYPE: PRT
<213> ORGANISM: Homo sapiens

<400> SEQUENCE: 2

Gly Ile Ala Tyr Asp Pro Leu Met Leu Lys His Gln Cys Val Cys Gly
 1               5                  10                  15

Asn Ser Thr Thr His Pro Glu His Ala Gly Arg Ile Gln Ser Ile Trp
             20                  25                  30

Ser Arg Leu Gln Glu Thr Gly Leu Leu Asn Lys Cys Glu Arg Ile Gln
         35                  40                  45

Gly Arg Lys Ala Ser Leu Glu Glu Ile Gln Leu Val His Ser Glu His
     50                  55                  60

His Ser Leu Leu Tyr Gly Thr Asn Pro Leu Asp Gly Gln Lys Leu Asp
 65                  70                  75                  80

Pro Arg Ile Leu Leu Gly Asp Asp Ser Gln Lys Phe Phe Ser Ser Leu
                 85                  90                  95

Pro Cys Gly Gly Leu Gly Val Ser Thr
            100                 105
```

```
<210> SEQ ID NO 3
<211> LENGTH: 95
<212> TYPE: PRT
<213> ORGANISM: Homo sapiens

<400> SEQUENCE: 3

Leu Leu Phe Leu Gln Leu Glu Pro Leu Ala Glu Asp Ile Leu His Gln
 1               5                  10                  15

Ser Pro Asn Met Asn Ala Val Ile Ser Leu Gln Lys Ile Ile Glu Ile
             20                  25                  30

Gln Ser Lys Tyr Trp Lys Ser Val Arg Met Val Ala Val Pro Arg Gly
         35                  40                  45

Cys Ala Leu Ala Gly Ala Gln Leu Gln Glu Glu Thr Glu Thr Val Ser
     50                  55                  60

Ala Leu Ala Ser Leu Thr Val Asp Val Glu Gln Pro Phe Ala Gln Glu
 65                  70                  75                  80

Asp Ser Arg Thr Ala Gly Glu Pro Met Glu Glu Pro Ala Leu
                 85                  90                  95

<210> SEQ ID NO 4
<211> LENGTH: 163
<212> TYPE: PRT
<213> ORGANISM: Homo sapiens

<400> SEQUENCE: 4

Val Asp Ser Asp Thr Ile Trp Asn Glu Leu His Ser Ser Gly Ala Ala
 1               5                  10                  15

Arg Met Ala Val Gly Cys Val Ile Glu Leu Ala Ser Lys Val Ala Ser
             20                  25                  30

Gly Glu Leu Lys Asn Gly Phe Ala Val Val Arg Pro Gly His His
         35                  40                  45

Ala Glu Glu Ser Thr Ala Met Gly Phe Cys Phe Phe Asn Ser Val Ala
     50                  55                  60

Ile Thr Ala Lys Tyr Leu Arg Asp Gln Leu Asn Ile Ser Lys Ile Leu
 65                  70                  75                  80

Ile Val Asp Leu Asp Val His His Gly Asn Gly Thr Gln Gln Ala Phe
                 85                  90                  95

Tyr Ala Asp Pro Ser Ile Leu Tyr Ile Ser Leu His Arg Tyr Asp Glu
            100                 105                 110

Gly Asn Phe Phe Pro Gly Ser Gly Ala Pro Asn Glu Val Gly Thr Gly
            115                 120                 125

Leu Gly Glu Gly Tyr Asn Ile Asn Ile Ala Trp Thr Gly Gly Leu Asp
        130                 135                 140

Pro Pro Met Gly Asp Val Glu Tyr Leu Glu Ala Phe Arg Leu Val Leu
145                 150                 155                 160

Leu Ser Leu

<210> SEQ ID NO 5
<211> LENGTH: 175
<212> TYPE: PRT
<213> ORGANISM: Homo sapiens

<400> SEQUENCE: 5

Arg Thr Ile Val Lys Pro Val Ala Lys Glu Phe Asp Pro Asp Met Val
 1               5                  10                  15

Leu Val Ser Ala Gly Phe Asp Ala Leu Glu Gly His Thr Pro Pro Leu
             20                  25                  30
```

```
Gly Gly Tyr Lys Val Thr Ala Lys Cys Phe Gly His Leu Thr Lys Gln
            35                  40                  45

Leu Met Thr Leu Ala Asp Gly Arg Val Val Leu Ala Leu Glu Gly Gly
 50                  55                  60

His Asp Leu Thr Ala Ile Cys Asp Ala Ser Glu Ala Cys Val Asn Ala
 65                  70                  75                  80

Leu Leu Gly Asn Glu Leu Glu Pro Leu Ala Glu Asp Ile Leu His Gln
                 85                  90                  95

Ser Pro Asn Met Asn Ala Val Ile Ser Leu Gln Lys Ile Ile Glu Ile
                100                 105                 110

Gln Ser Lys Tyr Trp Lys Ser Val Arg Met Val Ala Val Pro Arg Gly
            115                 120                 125

Cys Ala Leu Ala Gly Ala Gln Leu Gln Glu Glu Thr Glu Thr Val Ser
130                 135                 140

Ala Leu Ala Ser Leu Thr Val Asp Val Glu Gln Pro Phe Ala Gln Glu
145                 150                 155                 160

Asp Ser Arg Thr Ala Gly Glu Pro Met Glu Glu Glu Pro Ala Leu
                165                 170                 175

<210> SEQ ID NO 6
<211> LENGTH: 706
<212> TYPE: PRT
<213> ORGANISM: Saccharomyces cerevisiae

<400> SEQUENCE: 6

Met Asp Ser Val Met Val Lys Lys Glu Val Leu Glu Asn Pro Asp His
 1               5                  10                  15

Asp Leu Lys Arg Lys Leu Glu Glu Asn Lys Glu Glu Asn Ser Leu
             20                  25                  30

Ser Thr Thr Ser Lys Ser Lys Arg Gln Val Ile Val Pro Val Cys Met
            35                  40                  45

Pro Lys Ile His Tyr Ser Pro Leu Lys Thr Gly Leu Cys Tyr Asp Val
 50                  55                  60

Arg Met Arg Tyr His Ala Lys Ile Phe Thr Ser Tyr Phe Glu Tyr Ile
 65                  70                  75                  80

Asp Pro His Pro Glu Asp Pro Arg Arg Ile Tyr Arg Ile Tyr Lys Ile
                 85                  90                  95

Leu Ala Glu Asn Gly Leu Ile Asn Asp Pro Thr Leu Ser Gly Val Asp
                100                 105                 110

Asp Leu Gly Asp Leu Met Leu Lys Ile Pro Val Arg Ala Ala Thr Ser
            115                 120                 125

Glu Glu Ile Leu Glu Val His Thr Lys Glu His Leu Glu Phe Ile Glu
130                 135                 140

Ser Thr Glu Lys Met Ser Arg Glu Glu Leu Leu Lys Glu Thr Glu Lys
145                 150                 155                 160

Gly Asp Ser Val Tyr Phe Asn Asn Asp Ser Tyr Ala Ser Ala Arg Leu
                165                 170                 175

Pro Cys Gly Gly Ala Ile Glu Ala Cys Lys Ala Val Val Glu Gly Arg
                180                 185                 190

Val Lys Asn Ser Leu Ala Val Val Arg Pro Gly His His Ala Glu
            195                 200                 205

Pro Gln Ala Ala Gly Gly Phe Cys Leu Phe Ser Asn Val Ala Val Ala
210                 215                 220

Ala Lys Asn Ile Leu Lys Asn Tyr Pro Glu Ser Val Arg Arg Ile Met
```

-continued

```
            225                 230                 235                 240
Ile Leu Asp Trp Asp Ile His His Gly Asn Gly Thr Gln Lys Ser Phe
                245                 250                 255
Tyr Gln Asp Asp Gln Val Leu Tyr Val Ser Leu His Arg Phe Glu Met
            260                 265                 270
Gly Lys Tyr Tyr Pro Gly Thr Ile Gln Gly Gln Tyr Asp Gln Thr Gly
                275                 280                 285
Glu Gly Lys Gly Glu Gly Phe Asn Cys Asn Ile Thr Trp Pro Val Gly
            290                 295                 300
Gly Val Gly Asp Ala Glu Tyr Met Trp Ala Phe Glu Gln Val Val Met
305                 310                 315                 320
Pro Met Gly Arg Glu Phe Lys Pro Asp Leu Val Ile Ile Ser Ser Gly
                325                 330                 335
Phe Asp Ala Ala Asp Gly Asp Thr Ile Gly Gln Cys His Val Thr Pro
                340                 345                 350
Ser Cys Tyr Gly His Met Thr His Met Leu Lys Ser Leu Ala Arg Gly
                355                 360                 365
Asn Leu Cys Val Val Leu Glu Gly Gly Tyr Asn Leu Asp Ala Ile Ala
            370                 375                 380
Arg Ser Ala Leu Ser Val Ala Lys Val Leu Ile Gly Glu Pro Pro Asp
385                 390                 395                 400
Glu Leu Pro Asp Pro Leu Ser Asp Pro Lys Pro Val Ile Glu Met
                405                 410                 415
Ile Asp Lys Val Ile Arg Leu Gln Ser Lys Tyr Trp Asn Cys Phe Arg
                420                 425                 430
Arg Arg His Ala Asn Ser Gly Cys Asn Phe Asn Glu Pro Ile Asn Asp
                435                 440                 445
Ser Ile Ile Ser Lys Asn Phe Pro Leu Gln Lys Ala Ile Arg Gln Gln
            450                 455                 460
Gln Gln His Tyr Leu Ser Asp Glu Phe Asn Phe Val Thr Leu Pro Leu
465                 470                 475                 480
Val Ser Met Asp Leu Pro Asp Asn Thr Val Leu Cys Thr Pro Asn Ile
                485                 490                 495
Ser Glu Ser Asn Thr Ile Ile Val Val His Asp Thr Ser Asp Ile
                500                 505                 510
Trp Ala Lys Arg Asn Val Ile Ser Gly Thr Ile Asp Leu Ser Ser Ser
            515                 520                 525
Val Ile Ile Asp Asn Ser Leu Asp Phe Ile Lys Trp Gly Leu Asp Arg
            530                 535                 540
Lys Tyr Gly Ile Ile Asp Val Asn Ile Pro Leu Thr Leu Phe Glu Pro
545                 550                 555                 560
Asp Asn Tyr Ser Gly Met Ile Thr Ser Gln Glu Val Leu Ile Tyr Leu
                565                 570                 575
Trp Asp Asn Tyr Ile Lys Tyr Phe Pro Ser Val Ala Lys Ile Ala Phe
                580                 585                 590
Ile Gly Ile Gly Asp Ser Tyr Ser Gly Ile Val His Leu Leu Gly His
                595                 600                 605
Arg Asp Thr Arg Ala Val Thr Lys Thr Val Ile Asn Phe Leu Gly Asp
            610                 615                 620
Lys Gln Leu Lys Pro Leu Val Pro Leu Val Asp Glu Thr Leu Ser Glu
625                 630                 635                 640
Trp Tyr Phe Lys Asn Ser Leu Ile Phe Ser Asn Ser His Gln Cys
                645                 650                 655
```

```
Trp Lys Glu Asn Glu Ser Arg Lys Pro Arg Lys Lys Phe Gly Arg Val
            660                 665                 670

Leu Arg Cys Asp Thr Asp Gly Leu Asn Asn Ile Ile Glu Glu Arg Phe
            675                 680                 685

Glu Glu Ala Thr Asp Phe Ile Leu Asp Ser Phe Glu Glu Trp Ser Asp
            690                 695                 700

Glu Glu
705

<210> SEQ ID NO 7
<211> LENGTH: 1084
<212> TYPE: PRT
<213> ORGANISM: Homo sapiens

<400> SEQUENCE: 7

Met Ser Ser Gln Ser His Pro Asp Gly Leu Ser Gly Arg Asp Gln Pro
  1               5                  10                  15

Val Glu Leu Leu Asn Pro Ala Arg Val Asn His Met Pro Ser Thr Val
             20                  25                  30

Asp Val Ala Thr Ala Leu Pro Leu Gln Val Ala Pro Ser Ala Val Pro
         35                  40                  45

Met Asp Leu Arg Leu Asp His Gln Phe Ser Leu Pro Val Ala Glu Pro
     50                  55                  60

Ala Leu Arg Glu Gln Gln Leu Gln Gln Glu Leu Leu Ala Leu Lys Gln
 65                  70                  75                  80

Lys Gln Gln Ile Gln Arg Gln Ile Leu Ile Ala Glu Phe Gln Arg Gln
                 85                  90                  95

His Glu Gln Leu Ser Arg Gln His Glu Ala Gln Leu His Glu His Ile
            100                 105                 110

Lys Gln Gln Gln Glu Met Leu Ala Met Lys His Gln Gln Glu Leu Leu
        115                 120                 125

Glu His Gln Arg Lys Leu Glu Arg His Arg Gln Glu Gln Glu Leu Glu
    130                 135                 140

Lys Gln His Arg Glu Gln Lys Leu Gln Gln Leu Lys Asn Lys Glu Lys
145                 150                 155                 160

Gly Lys Glu Ser Ala Val Ala Ser Thr Glu Val Lys Met Lys Leu Gln
                165                 170                 175

Glu Phe Val Leu Asn Lys Lys Ala Leu Ala His Arg Asn Leu Asn
            180                 185                 190

His Cys Ile Ser Ser Asp Pro Arg Tyr Trp Tyr Gly Lys Thr Gln His
        195                 200                 205

Ser Ser Leu Asp Gln Ser Pro Pro Gln Ser Gly Val Ser Thr Ser
    210                 215                 220

Tyr Asn His Pro Val Leu Gly Met Tyr Asp Ala Lys Asp Phe Pro
225                 230                 235                 240

Leu Arg Lys Thr Ala Ser Glu Pro Asn Leu Lys Leu Arg Ser Arg Leu
                245                 250                 255

Lys Gln Lys Val Ala Glu Arg Arg Ser Ser Pro Leu Leu Arg Arg Lys
            260                 265                 270

Asp Gly Pro Val Val Thr Ala Leu Lys Lys Arg Pro Leu Asp Val Thr
        275                 280                 285

Asp Ser Ala Cys Ser Ser Ala Pro Gly Ser Gly Pro Ser Ser Pro Asn
    290                 295                 300

Asn Ser Ser Gly Ser Val Ser Ala Glu Asn Gly Ile Ala Pro Ala Val
```

-continued

```
            305                 310                 315                 320

Pro Ser Ile Pro Ala Glu Thr Ser Leu Ala His Arg Leu Val Ala Arg
                325                 330                 335

Glu Gly Ser Ala Ala Pro Leu Pro Leu Tyr Thr Ser Pro Ser Leu Pro
                340                 345                 350

Asn Ile Thr Leu Gly Leu Pro Ala Thr Gly Pro Ser Ala Gly Thr Ala
                355                 360                 365

Gly Gln Gln Asp Thr Glu Arg Leu Thr Leu Pro Ala Leu Gln Gln Arg
            370                 375                 380

Leu Ser Leu Phe Pro Gly Thr His Leu Thr Pro Tyr Leu Ser Thr Ser
385                 390                 395                 400

Pro Leu Glu Arg Asp Gly Gly Ala Ala His Ser Pro Leu Leu Gln His
                405                 410                 415

Met Val Leu Leu Glu Gln Pro Pro Ala Gln Ala Pro Leu Val Thr Gly
                420                 425                 430

Leu Gly Ala Leu Pro Leu His Ala Gln Ser Leu Val Gly Ala Asp Arg
            435                 440                 445

Val Ser Pro Ser Ile His Lys Leu Arg Gln His Arg Pro Leu Gly Arg
450                 455                 460

Thr Gln Ser Ala Pro Leu Pro Gln Asn Ala Gln Ala Leu Gln His Leu
465                 470                 475                 480

Val Ile Gln Gln Gln His Gln Gln Phe Leu Glu Lys His Lys Gln Gln
                485                 490                 495

Phe Gln Gln Gln Leu Gln Met Asn Lys Ile Ile Pro Lys Pro Ser
            500                 505                 510

Glu Pro Ala Arg Gln Pro Glu Ser His Pro Glu Glu Thr Glu Glu Glu
            515                 520                 525

Leu Arg Glu His Gln Ala Leu Leu Asp Glu Pro Tyr Leu Asp Arg Leu
            530                 535                 540

Pro Gly Gln Lys Glu Ala His Ala Gln Ala Gly Val Gln Val Lys Gln
545                 550                 555                 560

Glu Pro Ile Glu Ser Asp Glu Glu Ala Glu Pro Pro Arg Glu Val
                565                 570                 575

Glu Pro Gly Gln Arg Gln Pro Ser Glu Gln Glu Leu Leu Phe Arg Gln
            580                 585                 590

Gln Ala Leu Leu Leu Glu Gln Gln Arg Ile His Gln Leu Arg Asn Tyr
                595                 600                 605

Gln Ala Ser Met Glu Ala Ala Gly Ile Pro Val Ser Phe Gly Gly His
            610                 615                 620

Arg Pro Leu Ser Arg Ala Gln Ser Ser Pro Ala Ser Ala Thr Phe Pro
625                 630                 635                 640

Val Ser Val Gln Glu Pro Pro Thr Lys Pro Arg Phe Thr Thr Gly Leu
                645                 650                 655

Val Tyr Asp Thr Leu Met Leu Lys His Gln Cys Thr Cys Gly Ser Ser
                660                 665                 670

Ser Ser His Pro Glu His Ala Gly Arg Ile Gln Ser Ile Trp Ser Arg
            675                 680                 685

Leu Gln Glu Thr Gly Leu Arg Gly Lys Cys Glu Cys Ile Arg Gly Arg
            690                 695                 700

Lys Ala Thr Leu Glu Glu Leu Gln Thr Val His Ser Glu Ala His Thr
705                 710                 715                 720

Leu Leu Tyr Gly Thr Asn Pro Leu Asn Arg Gln Lys Leu Asp Ser Lys
                725                 730                 735
```

```
Lys Leu Leu Gly Ser Leu Ala Ser Val Phe Val Arg Leu Pro Cys Gly
            740                 745                 750

Gly Val Gly Val Asp Ser Asp Thr Ile Trp Asn Glu Val His Ser Ala
        755                 760                 765

Gly Ala Ala Arg Leu Ala Val Gly Cys Val Val Glu Leu Val Phe Lys
    770                 775                 780

Val Ala Thr Gly Glu Leu Lys Asn Gly Phe Ala Val Arg Pro Pro
785                 790                 795                 800

Gly His His Ala Glu Glu Ser Thr Pro Met Gly Phe Cys Tyr Phe Asn
                805                 810                 815

Ser Val Ala Val Ala Ala Lys Leu Leu Gln Gln Arg Leu Ser Val Ser
                820                 825                 830

Lys Ile Leu Ile Val Asp Trp Asp Val His His Gly Asn Gly Thr Gln
                835                 840                 845

Gln Ala Phe Tyr Ser Asp Pro Ser Val Leu Tyr Met Ser Leu His Arg
        850                 855                 860

Tyr Asp Asp Gly Asn Phe Phe Pro Gly Ser Gly Ala Pro Asp Glu Val
865                 870                 875                 880

Gly Thr Gly Pro Gly Val Gly Phe Asn Val Asn Met Ala Phe Thr Gly
                885                 890                 895

Gly Leu Asp Pro Pro Met Gly Asp Ala Glu Tyr Leu Ala Ala Phe Arg
            900                 905                 910

Thr Val Val Met Pro Ile Ala Ser Glu Phe Ala Pro Asp Val Val Leu
            915                 920                 925

Val Ser Ser Gly Phe Asp Ala Val Glu Gly His Pro Thr Pro Leu Gly
        930                 935                 940

Gly Tyr Asn Leu Ser Ala Arg Cys Phe Gly Tyr Leu Thr Lys Gln Leu
945                 950                 955                 960

Met Gly Leu Ala Gly Gly Arg Ile Val Leu Ala Leu Glu Gly Gly His
                965                 970                 975

Asp Leu Thr Ala Ile Cys Asp Ala Ser Glu Ala Cys Val Ser Ala Leu
            980                 985                 990

Leu Gly Asn Glu Leu Asp Pro Leu Pro Glu Lys Val Leu Gln Gln Arg
        995                 1000                1005

Pro Asn Ala Asn Ala Val Arg Ser Met Glu Lys Val Met Glu Ile His
    1010                1015                1020

Ser Lys Tyr Trp Arg Cys Leu Gln Arg Thr Thr Ser Thr Ala Gly Arg
1025                1030                1035                1040

Ser Leu Ile Glu Ala Gln Thr Cys Glu Asn Glu Glu Ala Glu Thr Val
                1045                1050                1055

Thr Ala Met Ala Ser Leu Ser Val Gly Val Lys Pro Ala Glu Lys Arg
            1060                1065                1070

Pro Asp Glu Glu Pro Met Glu Glu Glu Pro Pro Leu
        1075                1080

<210> SEQ ID NO 8
<211> LENGTH: 1122
<212> TYPE: PRT
<213> ORGANISM: Homo sapiens

<400> SEQUENCE: 8

Met Asn Ser Pro Asn Glu Ser Asp Gly Met Ser Gly Arg Glu Pro Ser
 1               5                  10                  15

Leu Glu Ile Leu Pro Arg Thr Ser Leu His Ser Ile Pro Val Thr Val
```

```
                    20                  25                  30
Glu Val Lys Pro Val Leu Pro Arg Ala Met Pro Ser Ser Met Gly Gly
                 35                  40                  45

Gly Gly Gly Gly Ser Pro Ser Pro Val Glu Leu Arg Gly Ala Leu Val
 50                  55                  60

Gly Ser Val Asp Pro Thr Leu Arg Glu Gln Gln Leu Gln Gln Glu Leu
 65                  70                  75                  80

Leu Ala Leu Lys Gln Gln Gln Leu Gln Lys Gln Leu Leu Phe Ala
                 85                  90                  95

Glu Phe Gln Lys Gln His Asp His Leu Thr Arg Gln His Glu Val Gln
                100                 105                 110

Leu Gln Lys His Leu Lys Gln Gln Glu Met Leu Ala Ala Lys Gln
                115                 120                 125

Gln Gln Glu Met Leu Ala Ala Lys Arg Gln Gln Glu Leu Glu Gln Gln
            130                 135                 140

Arg Gln Arg Glu Gln Arg Gln Glu Glu Leu Glu Lys Gln Arg Leu
145                 150                 155                 160

Glu Gln Gln Leu Leu Ile Leu Arg Asn Lys Glu Lys Ser Lys Glu Ser
                165                 170                 175

Ala Ile Ala Ser Thr Glu Val Lys Leu Arg Leu Gln Glu Phe Leu Leu
                180                 185                 190

Ser Lys Ser Lys Glu Pro Thr Pro Gly Gly Leu Asn His Ser Leu Pro
                195                 200                 205

Gln His Pro Lys Cys Trp Gly Ala His His Ala Ser Leu Asp Gln Ser
                210                 215                 220

Ser Pro Pro Gln Ser Gly Pro Pro Gly Thr Pro Pro Ser Tyr Lys Leu
225                 230                 235                 240

Pro Leu Pro Gly Pro Tyr Asp Ser Arg Asp Asp Phe Pro Leu Arg Lys
                245                 250                 255

Thr Ala Ser Glu Pro Asn Leu Lys Val Arg Ser Arg Leu Lys Gln Lys
                260                 265                 270

Val Ala Glu Arg Arg Ser Ser Pro Leu Leu Arg Arg Lys Asp Gly Thr
                275                 280                 285

Val Ile Ser Thr Phe Lys Lys Arg Ala Val Glu Ile Thr Gly Ala Gly
                290                 295                 300

Pro Gly Ala Ser Ser Val Cys Asn Ser Ala Pro Gly Ser Gly Pro Ser
305                 310                 315                 320

Ser Pro Asn Ser Ser His Ser Thr Ile Ala Glu Asn Gly Phe Thr Gly
                325                 330                 335

Ser Val Pro Asn Ile Pro Thr Glu Met Leu Pro Gln His Arg Ala Leu
                340                 345                 350

Pro Leu Asp Ser Ser Pro Asn Gln Phe Ser Leu Tyr Thr Ser Pro Ser
                355                 360                 365

Leu Pro Asn Ile Ser Leu Gly Leu Gln Ala Thr Val Thr Val Thr Asn
                370                 375                 380

Ser His Leu Thr Ala Ser Pro Lys Leu Ser Thr Gln Gln Glu Ala Glu
385                 390                 395                 400

Arg Gln Ala Leu Gln Ser Leu Arg Gln Gly Gly Thr Leu Thr Gly Lys
                405                 410                 415

Phe Met Ser Thr Ser Ser Ile Pro Gly Cys Leu Leu Gly Val Ala Leu
                420                 425                 430

Glu Gly Asp Gly Ser Pro His Gly His Ala Ser Leu Leu Gln His Val
                435                 440                 445
```

```
Leu Leu Leu Glu Gln Ala Arg Gln Gln Ser Thr Leu Ile Ala Val Pro
    450                 455                 460

Leu His Gly Gln Ser Pro Leu Val Thr Gly Glu Arg Val Ala Thr Ser
465                 470                 475                 480

Met Arg Thr Val Gly Lys Leu Pro Arg His Arg Pro Leu Ser Arg Thr
                485                 490                 495

Gln Ser Ser Pro Leu Pro Gln Ser Pro Gln Ala Leu Gln Leu Val
            500                 505                 510

Met Gln Gln Gln His Gln Gln Phe Leu Glu Lys Gln Lys Gln Gln Gln
            515                 520                 525

Leu Gln Leu Gly Lys Ile Leu Thr Lys Thr Gly Glu Leu Pro Arg Gln
    530                 535                 540

Pro Thr Thr His Pro Glu Glu Thr Glu Glu Leu Thr Glu Gln Gln
545                 550                 555                 560

Glu Val Leu Leu Gly Glu Gly Ala Leu Thr Met Pro Arg Glu Gly Ser
                565                 570                 575

Thr Glu Ser Glu Ser Thr Gln Glu Asp Leu Glu Glu Glu Asp Glu Glu
            580                 585                 590

Glu Asp Gly Glu Glu Glu Glu Asp Cys Ile Gln Val Lys Asp Glu Glu
            595                 600                 605

Gly Glu Ser Gly Ala Glu Glu Gly Pro Asp Leu Glu Glu Pro Gly Ala
    610                 615                 620

Gly Tyr Lys Lys Leu Phe Ser Asp Ala Gln Pro Leu Gln Pro Leu Gln
625                 630                 635                 640

Val Tyr Gln Ala Pro Leu Ser Leu Ala Thr Val Pro His Gln Ala Leu
                645                 650                 655

Gly Arg Thr Gln Ser Ser Pro Ala Ala Pro Gly Gly Met Lys Ser Pro
            660                 665                 670

Pro Asp Gln Pro Val Lys His Leu Phe Thr Thr Gly Val Val Tyr Asp
            675                 680                 685

Thr Phe Met Leu Lys His Gln Cys Met Cys Gly Asn Thr His Val His
    690                 695                 700

Pro Glu His Ala Gly Arg Ile Gln Ser Ile Trp Ser Arg Leu Gln Glu
705                 710                 715                 720

Thr Gly Leu Leu Ser Lys Cys Glu Arg Ile Arg Gly Arg Lys Ala Thr
                725                 730                 735

Leu Asp Glu Ile Gln Thr Val His Ser Glu Tyr His Thr Leu Leu Tyr
            740                 745                 750

Gly Thr Ser Pro Leu Asn Arg Gln Lys Leu Asp Ser Lys Lys Leu Leu
            755                 760                 765

Gly Pro Ile Ser Gln Lys Met Tyr Ala Val Leu Pro Cys Gly Gly Ile
    770                 775                 780

Gly Val Asp Ser Asp Thr Val Trp Asn Glu Met His Ser Ser Ser Ala
785                 790                 795                 800

Val Arg Met Ala Val Gly Cys Leu Leu Glu Leu Ala Phe Lys Val Ala
                805                 810                 815

Ala Gly Glu Leu Lys Asn Gly Phe Ala Ile Ile Arg Pro Pro Gly His
            820                 825                 830

His Ala Glu Glu Ser Thr Ala Met Gly Phe Cys Phe Phe Asn Ser Val
            835                 840                 845

Ala Ile Thr Ala Lys Leu Leu Gln Gln Lys Leu Asn Val Gly Lys Val
    850                 855                 860
```

```
Leu Ile Val Asp Trp Asp Ile His His Gly Asn Gly Thr Gln Gln Ala
865                 870                 875                 880

Phe Tyr Asn Asp Pro Ser Val Leu Tyr Ile Ser Leu His Arg Tyr Asp
                885                 890                 895

Asn Gly Asn Phe Phe Pro Gly Ser Gly Ala Pro Glu Glu Val Gly Gly
            900                 905                 910

Gly Pro Gly Val Gly Tyr Asn Val Asn Val Ala Trp Thr Gly Gly Val
        915                 920                 925

Asp Pro Pro Ile Gly Asp Val Glu Tyr Leu Thr Ala Phe Arg Thr Val
    930                 935                 940

Val Met Pro Ile Ala His Glu Phe Ser Pro Asp Val Val Leu Val Ser
945                 950                 955                 960

Ala Gly Phe Asp Ala Val Glu Gly His Leu Ser Pro Leu Gly Gly Tyr
                965                 970                 975

Ser Val Thr Ala Arg Cys Phe Gly His Leu Thr Arg Gln Leu Met Thr
            980                 985                 990

Leu Ala Gly Gly Arg Val Val Leu Ala Leu Glu Gly Gly His Asp Leu
        995                 1000                1005

Thr Ala Ile Cys Asp Ala Ser Glu Ala Cys Val Ser Ala Leu Leu Ser
    1010                1015                1020

Val Glu Leu Gln Pro Leu Asp Glu Ala Val Leu Gln Gln Lys Pro Asn
1025                1030                1035                1040

Ile Asn Ala Val Ala Thr Leu Glu Lys Val Ile Glu Ile Gln Ser Lys
                1045                1050                1055

His Trp Ser Cys Val Gln Lys Phe Ala Ala Gly Leu Gly Arg Ser Leu
            1060                1065                1070

Arg Glu Ala Gln Ala Gly Glu Thr Glu Glu Ala Glu Thr Val Ser Ala
        1075                1080                1085

Met Ala Leu Leu Ser Val Gly Ala Gln Ala Gln Ala Ala Ala Ala
    1090                1095                1100

Arg Glu His Ser Pro Arg Pro Ala Glu Glu Pro Met Glu Gln Glu Pro
1105                1110                1115                1120

Ala Leu

<210> SEQ ID NO 9
<211> LENGTH: 855
<212> TYPE: PRT
<213> ORGANISM: Homo sapiens

<400> SEQUENCE: 9

Met Asp Leu Arg Val Gly Gln Arg Pro Pro Val Glu Pro Pro Pro Glu
1               5                   10                  15

Pro Thr Leu Leu Ala Leu Gln Arg Pro Gln Arg Leu His His His Leu
            20                  25                  30

Phe Leu Ala Gly Leu Gln Gln Gln Arg Ser Val Glu Pro Met Arg Leu
        35                  40                  45

Ser Met Asp Thr Pro Met Pro Glu Leu Gln Val Gly Pro Gln Glu Gln
    50                  55                  60

Glu Leu Arg Gln Leu Leu His Lys Asp Lys Ser Lys Arg Ser Ala Val
65                  70                  75                  80

Ala Ser Ser Val Val Lys Gln Lys Leu Ala Glu Val Ile Leu Lys Lys
                85                  90                  95

Gln Gln Ala Ala Leu Glu Arg Thr Val His Pro Asn Ser Pro Gly Ile
            100                 105                 110
```

```
Pro Tyr Arg Thr Leu Glu Pro Leu Glu Thr Glu Gly Ala Thr Arg Ser
        115                 120                 125

Met Leu Ser Ser Phe Leu Pro Pro Val Pro Ser Leu Pro Ser Asp Pro
    130                 135                 140

Pro Glu His Phe Pro Leu Arg Lys Thr Val Ser Glu Pro Asn Leu Lys
145                 150                 155                 160

Leu Arg Tyr Lys Pro Lys Lys Ser Leu Glu Arg Arg Lys Asn Pro Leu
                165                 170                 175

Leu Arg Lys Glu Ser Ala Pro Pro Ser Leu Arg Arg Arg Pro Ala Glu
            180                 185                 190

Thr Leu Gly Asp Ser Ser Pro Ser Ser Ser Thr Pro Ala Ser Gly
        195                 200                 205

Cys Ser Ser Pro Asn Asp Ser Glu His Gly Pro Asn Pro Ile Leu Gly
210                 215                 220

Asp Ser Asp Arg Arg Thr His Pro Thr Leu Gly Pro Arg Gly Pro Ile
225                 230                 235                 240

Leu Gly Ser Pro His Thr Pro Leu Phe Leu Pro His Gly Leu Glu Pro
                245                 250                 255

Glu Ala Gly Gly Thr Leu Pro Ser Arg Leu Gln Pro Ile Leu Leu Leu
            260                 265                 270

Asp Pro Ser Gly Ser His Ala Pro Leu Leu Thr Val Pro Gly Leu Gly
        275                 280                 285

Pro Leu Pro Phe His Phe Ala Gln Ser Leu Met Thr Thr Glu Arg Leu
    290                 295                 300

Ser Gly Ser Gly Leu His Trp Pro Leu Ser Arg Thr Arg Ser Glu Pro
305                 310                 315                 320

Leu Pro Pro Ser Ala Thr Ala Pro Pro Pro Gly Pro Met Gln Pro
                325                 330                 335

Arg Leu Glu Gln Leu Lys Thr His Val Gln Val Ile Lys Arg Ser Ala
            340                 345                 350

Lys Pro Ser Glu Lys Pro Arg Leu Arg Gln Ile Pro Ser Ala Glu Asp
        355                 360                 365

Leu Glu Thr Asp Gly Gly Pro Gly Gln Val Val Asp Asp Gly Leu
    370                 375                 380

Glu His Arg Glu Leu Gly His Gly Gln Pro Glu Ala Arg Gly Pro Ala
385                 390                 395                 400

Pro Leu Gln Gln His Pro Gln Val Leu Leu Trp Glu Gln Arg Leu
                405                 410                 415

Ala Gly Arg Leu Pro Arg Gly Ser Thr Gly Asp Thr Val Leu Leu Pro
            420                 425                 430

Leu Ala Gln Gly Gly His Arg Pro Leu Ser Arg Ala Gln Ser Ser Pro
        435                 440                 445

Ala Ala Pro Ala Ser Leu Ser Ala Pro Glu Pro Ala Ser Gln Ala Arg
450                 455                 460

Val Leu Ser Ser Ser Glu Thr Pro Ala Arg Thr Leu Pro Phe Thr Thr
465                 470                 475                 480

Gly Leu Ile Tyr Asp Ser Val Met Leu Lys His Gln Cys Ser Cys Gly
                485                 490                 495

Asp Asn Ser Arg His Pro Glu His Ala Gly Arg Ile Gln Ser Ile Trp
            500                 505                 510

Ser Arg Leu Gln Glu Arg Gly Leu Arg Ser Gln Cys Glu Cys Leu Arg
        515                 520                 525

Gly Arg Lys Ala Ser Leu Glu Glu Leu Gln Ser Val His Ser Glu Arg
```

-continued

```
            530                 535                 540
His Val Leu Leu Tyr Gly Thr Asn Pro Leu Ser Arg Leu Lys Leu Asp
545                 550                 555                 560

Asn Gly Lys Leu Ala Gly Leu Leu Ala Gln Arg Met Phe Glu Met Leu
                565                 570                 575

Pro Cys Gly Gly Val Gly Val Asp Thr Asp Thr Ile Trp Asn Glu Leu
                580                 585                 590

His Ser Ser Asn Ala Ala Arg Trp Ala Ala Gly Ser Val Thr Asp Leu
                595                 600                 605

Ala Phe Lys Val Ala Ser Arg Glu Leu Lys Asn Gly Phe Ala Val Val
                610                 615                 620

Arg Pro Pro Gly His His Ala Asp His Ser Thr Ala Met Gly Phe Cys
625                 630                 635                 640

Phe Phe Asn Ser Val Ala Ile Ala Cys Arg Gln Leu Gln Gln Gln Ser
                645                 650                 655

Lys Ala Ser Lys Ala Ser Lys Ile Leu Ile Val Asp Trp Asp Val His
                660                 665                 670

His Gly Asn Gly Thr Gln Gln Thr Phe Tyr Gln Asp Pro Ser Val Leu
                675                 680                 685

Tyr Ile Ser Leu His Arg His Asp Asp Gly Asn Phe Phe Pro Gly Ser
                690                 695                 700

Gly Ala Val Asp Glu Val Gly Ala Gly Ser Gly Glu Gly Phe Asn Val
705                 710                 715                 720

Asn Val Ala Trp Ala Gly Gly Leu Asp Pro Pro Met Gly Asp Pro Glu
                725                 730                 735

Tyr Leu Ala Ala Phe Arg Ile Val Val Met Pro Ile Ala Arg Glu Phe
                740                 745                 750

Ser Pro Asp Leu Val Leu Val Ser Ala Gly Phe Asp Ala Ala Glu Gly
                755                 760                 765

His Pro Ala Pro Leu Gly Gly Tyr His Val Ser Ala Lys Cys Phe Gly
                770                 775                 780

Tyr Met Thr Gln Gln Leu Met Asn Leu Ala Gly Gly Ala Val Val Leu
785                 790                 795                 800

Ala Leu Glu Gly Gly His Asp Leu Thr Ala Ile Cys Asp Ala Ser Glu
                805                 810                 815

Ala Cys Val Ala Ala Leu Leu Gly Asn Arg Val Asp Pro Leu Ser Glu
                820                 825                 830

Glu Gly Trp Lys Gln Lys Pro Gln Pro Gln Cys His Pro Leu Ser Gly
                835                 840                 845

Gly Arg Asp Pro Gly Ala Gln
    850                 855

<210> SEQ ID NO 10
<211> LENGTH: 375
<212> TYPE: PRT
<213> ORGANISM: Aquifex aeolicus

<400> SEQUENCE: 10

Met Lys Lys Val Lys Leu Ile Gly Thr Leu Asp Tyr Gly Lys Tyr Arg
 1               5                  10                  15

Tyr Pro Lys Asn His Pro Leu Lys Ile Pro Arg Val Ser Leu Leu Leu
                20                  25                  30

Arg Phe Lys Asp Ala Met Asn Leu Ile Asp Glu Lys Glu Leu Ile Lys
        35                  40                  45
```

| | | | | | | | | | | | |
|---|---|---|---|---|---|---|---|---|---|---|---|
|Ser|Arg|Pro|Ala|Thr|Lys|Glu|Glu|Leu|Leu|Phe|His|Thr|Glu|Asp|
| |50| | | |55| | | |60| | | | | |

Ser Arg Pro Ala Thr Lys Glu Glu Leu Leu Phe His Thr Glu Asp
    50              55              60

Tyr Ile Asn Thr Leu Met Glu Ala Glu Arg Cys Gln Cys Val Pro Lys
 65            70              75              80

Gly Ala Arg Glu Lys Tyr Asn Ile Gly Gly Tyr Glu Asn Pro Val Ser
            85              90              95

Tyr Ala Met Phe Thr Gly Ser Ser Leu Ala Thr Gly Ser Thr Val Gln
         100             105            110

Ala Ile Glu Glu Phe Leu Lys Gly Asn Val Ala Phe Asn Pro Ala Gly
         115             120            125

Gly Met His His Ala Phe Lys Ser Arg Ala Asn Gly Phe Cys Tyr Ile
    130            135            140

Asn Asn Pro Ala Val Gly Ile Glu Tyr Leu Arg Lys Lys Gly Phe Lys
145            150            155            160

Arg Ile Leu Tyr Ile Asp Leu Asp Ala His His Cys Asp Gly Val Gln
         165             170            175

Glu Ala Phe Tyr Asp Thr Asp Gln Val Phe Val Leu Ser Leu His Gln
         180             185            190

Ser Pro Glu Tyr Ala Phe Pro Phe Glu Lys Gly Phe Leu Glu Glu Ile
    195            200            205

Gly Glu Gly Lys Gly Lys Gly Tyr Asn Leu Asn Ile Pro Leu Pro Lys
210            215            220

Gly Leu Asn Asp Asn Glu Phe Leu Phe Ala Leu Glu Lys Ser Leu Glu
225            230            235            240

Ile Val Lys Glu Val Phe Glu Pro Glu Val Tyr Leu Leu Gln Leu Gly
         245             250            255

Thr Asp Pro Leu Leu Glu Asp Tyr Leu Ser Lys Phe Asn Leu Ser Asn
    260            265            270

Val Ala Phe Leu Lys Ala Phe Asn Ile Val Arg Glu Val Phe Gly Glu
         275             280            285

Gly Val Tyr Leu Gly Gly Gly Gly Tyr His Pro Tyr Ala Leu Ala Arg
    290            295            300

Ala Trp Thr Leu Ile Trp Cys Glu Leu Ser Gly Arg Glu Val Pro Glu
305            310            315            320

Lys Leu Asn Asn Lys Ala Lys Glu Leu Leu Lys Ser Ile Asp Phe Glu
         325             330            335

Glu Phe Asp Asp Glu Val Asp Arg Ser Tyr Met Leu Glu Thr Leu Lys
         340             345            350

Asp Pro Trp Arg Gly Gly Glu Val Arg Lys Glu Val Lys Asp Thr Leu
    355            360            365

Glu Lys Ala Lys Ala Ser Ser
    370            375

```
<210> SEQ ID NO 11
<211> LENGTH: 353
<212> TYPE: DNA
<213> ORGANISM: Homo sapiens

<400> SEQUENCE: 11
ggaattgcct atgacccctt gatgctgaaa caccagtgcg tttgtggcaa ttccaccacc      60
caccctgagc atgctggacg aatacagagt atctggtcac gactgcaaga aactgggctg     120
ctaaataaat gtgaggtaat cccagcgaat tcaaggtcga aaagccagcc tggaggaaat     180
acagcttgtt cattctgaac atcactcact gttgtatggc accaaccccc tggacggaca     240
```

```
gaagctggac cccaggatac tcctaggtct gtataggtga tgactctcaa aagttttttt    300
cctcattacc ttgtggtgga cttggggtaa gtacaggact tggggtaagt aca            353
```

<210> SEQ ID NO 12
<211> LENGTH: 489
<212> TYPE: DNA
<213> ORGANISM: Homo sapiens
<220> FEATURE:
<221> NAME/KEY: CDS
<222> LOCATION: (1)..(489)

<400> SEQUENCE: 12

```
gtg gac agt gac acc att tgg aat gag cta cac tcg tcc ggt gct gca     48
Val Asp Ser Asp Thr Ile Trp Asn Glu Leu His Ser Ser Gly Ala Ala
 1               5                  10                  15 cgc atg gct gtt ggc tgt gtc atc gag ctg gct tcc aaa gtg gcc tca     96
Arg Met Ala Val Gly Cys Val Ile Glu Leu Ala Ser Lys Val Ala Ser
             20                  25                  30 gga gag ctg aag aat ggg ttt gct gtt gtg agg ccc cct ggc cat cac    144
Gly Glu Leu Lys Asn Gly Phe Ala Val Val Arg Pro Pro Gly His His
         35                  40                  45 gct gaa gaa tcc aca gcc atg ggg ttc tgc ttt ttt aat tca gtt gca    192
Ala Glu Glu Ser Thr Ala Met Gly Phe Cys Phe Phe Asn Ser Val Ala
     50                  55                  60 att acc gcc aaa tac ttg aga gac caa cta aat ata agc aag ata ttg    240
Ile Thr Ala Lys Tyr Leu Arg Asp Gln Leu Asn Ile Ser Lys Ile Leu
 65                  70                  75                  80 att gta gat ctg gat gtt cac cat gga aac ggt acc cag cag gcc ttt    288
Ile Val Asp Leu Asp Val His His Gly Asn Gly Thr Gln Gln Ala Phe
                 85                  90                  95 tat gct gac ccc agc atc ctg tac att tca ctc cat cgc tat gat gaa    336
Tyr Ala Asp Pro Ser Ile Leu Tyr Ile Ser Leu His Arg Tyr Asp Glu
            100                 105                 110 ggg aac ttt ttc cct ggc agt gga gcc cca aat gag gtt gga aca ggc    384
Gly Asn Phe Phe Pro Gly Ser Gly Ala Pro Asn Glu Val Gly Thr Gly
        115                 120                 125 ctt gga gaa ggg tac aat ata aat att gcc tgg aca ggt ggc ctt gat    432
Leu Gly Glu Gly Tyr Asn Ile Asn Ile Ala Trp Thr Gly Gly Leu Asp
    130                 135                 140 cct ccc atg gga gat gtt gag tac ctt gaa gca ttc agg ttg gta ctt    480
Pro Pro Met Gly Asp Val Glu Tyr Leu Glu Ala Phe Arg Leu Val Leu
145                 150                 155                 160 ctt tct ctc                                                        489
Leu Ser Leu
```

<210> SEQ ID NO 13
<211> LENGTH: 121
<212> TYPE: DNA
<213> ORGANISM: Homo sapiens

<400> SEQUENCE: 13

```
attttgccgt cactttgtac cctcctagag gaggggtgtg gccttccaat gcatcaaatc    60
cagcagatac taagaccatg tctggatcaa actctttggc cacaggcttc acgatggtcc   120
t                                                                  121
```

<210> SEQ ID NO 14
<211> LENGTH: 529
<212> TYPE: DNA
<213> ORGANISM: Homo sapiens

<400> SEQUENCE: 14

```
gtggacagtg acaccatttg gaatgagcta cactcgtccg gtgctgcacg catggctgtt    60
ggctgtgtca tcgagctggc ttccaaagtg gcctcaggag agctgaaggt gaggtcagaa   120
tgggtttgct gttgtgaggc ccctggcca tcacgctgaa gaatccacag ccatgtaagt   180
acagggggtt ctgctttttt aattcagttg caattaccgc caaatacttg agagaccaac   240
taaatataag caagatattg attgtagatc tggtatgtat aggatgttca ccatggaaac   300
ggtacccagc aggccttta tgctgacccc agcatcctgt acatttcact ccatcgctat   360
gatgaaggga acttttccc tggcagtgga gccccaaatg aggttcggtc aggttggaac   420
aggccttgga gaagggtaca atataaatat tgcctggaca ggtggccttg atcctcccat   480
gggagatgtt gagtaccttg aagcattcag gttggtactt ctttctctc               529
```

<210> SEQ ID NO 15
<211> LENGTH: 362
<212> TYPE: DNA
<213> ORGANISM: Homo sapiens

<400> SEQUENCE: 15

```
aggaccatcg tgaagcctgt ggccaaagag tttgatccag acatggtctt agtatctgct    60
ggatttgatg cattggaagg ccacacccct cctctaggag ggtacaaagt gacggcaaaa   120
tgtaagtata ggttttggtc atttgacgaa gcaattgatg acattggctg atggacgtgt   180
ggtgttggct ctagaaggag gacatgatct cacagccatc tgtgatgcat cagaagcctg   240
tgtaaatgcc cttctaggaa atgaggtaaa aacagctgga gccacttgca aagatattc    300 tccaccaaag cccgaatatg aatgctgtta tttctttaca gaagatcatt gaaattcaaa   360
gt                                                                  362
```

<210> SEQ ID NO 16
<211> LENGTH: 305
<212> TYPE: DNA
<213> ORGANISM: Homo sapiens

<400> SEQUENCE: 16

```
ctactattct tgcagctgga gccacttgca aagatattc tccaccaaag cccgaatatg    60
aatgctgtta tttctttaca gaagatcatt gaaattcaaa gtatgtctag caagtattg   120 gaagtcagta aggatggtgg ctgtgccaag gggctgtgct ctggctggtg ctcagttgca   180
agaggagaca gagaccgttt ctgccctggc ctccctaaca gtggatgtgg aacagcctt   240 tgctcaggaa gacagcaggt atgaacagaa ctgctggtga gcctatggaa gaggagccag   300
ccttg                                                               305
```

<210> SEQ ID NO 17
<211> LENGTH: 340
<212> TYPE: DNA
<213> ORGANISM: Homo sapiens

<400> SEQUENCE: 17

```
aggaccatcg tgaagcctgt ggccaaagag tttgatccag acatggtctt agtatctgct    60
ggatttgatg cattggaagg ccacacccct cctctaggag ggtacaaagt gacggcaaaa   120
tgttttggtc atttgacgaa gcaattgatg acattggctg atggacgtgt ggtgttggct   180
ctagaaggag gacatgatct cacagccatc tgtgatgcat cagaagcctg tgtaaatgcc   240
cttctaggaa atgagctgga gccacttgca aagatattc tccaccaaag cccgaatatg   300
```

-continued

```
aatgctgtta tttctttaca gaagatcatt gaaattcaaa                           340
```

<210> SEQ ID NO 18
<211> LENGTH: 271
<212> TYPE: DNA
<213> ORGANISM: Homo sapiens

<400> SEQUENCE: 18

```
agctggagcc acttgcagaa gatattctcc accaaagccc gaatatgaat gctgttattt    60
ctttacagaa gatcattgaa attcaaagca agtattggaa gtcagtaagg atggtggctg   120
tgccaagggg ctgtgctctg ctggtgctc agttgcaaga ggagacagag accgtttctg    180
ccctggcctc cctaacagtg gatgtggaac agccctttgc tcaggaagac agcagaactg   240
ctggtgagcc tatggaagag gagccagcct t                                   271
```

<210> SEQ ID NO 19
<211> LENGTH: 525
<212> TYPE: DNA
<213> ORGANISM: Homo sapiens
<220> FEATURE:
<221> NAME/KEY: CDS
<222> LOCATION: (1)..(525)

<400> SEQUENCE: 19

```
agg acc atc gtg aag cct gtg gcc aaa gag ttt gat cca gac atg gtc     48
Arg Thr Ile Val Lys Pro Val Ala Lys Glu Phe Asp Pro Asp Met Val
1               5                   10                  15 tta gta tct gct gga ttt gat gca ttg gaa ggc cac acc cct cct cta     96
Leu Val Ser Ala Gly Phe Asp Ala Leu Glu Gly His Thr Pro Pro Leu
            20                  25                  30 gga ggg tac aaa gtg acg gca aaa tgt ttt ggt cat ttg acg aag caa    144
Gly Gly Tyr Lys Val Thr Ala Lys Cys Phe Gly His Leu Thr Lys Gln
        35                  40                  45 ttg atg aca ttg gct gat gga cgt gtg gtg ttg gct cta gaa gga gga    192
Leu Met Thr Leu Ala Asp Gly Arg Val Val Leu Ala Leu Glu Gly Gly
    50                  55                  60 cat gat ctc aca gcc atc tgt gat gca tca gaa gcc tgt gta aat gcc    240
His Asp Leu Thr Ala Ile Cys Asp Ala Ser Glu Ala Cys Val Asn Ala
65                  70                  75                  80 ctt cta gga aat gag ctg gag cca ctt gca gaa gat att ctc cac caa    288
Leu Leu Gly Asn Glu Leu Glu Pro Leu Ala Glu Asp Ile Leu His Gln
                85                  90                  95 agc ccg aat atg aat gct gtt att tct tta cag aag atc att gaa att    336
Ser Pro Asn Met Asn Ala Val Ile Ser Leu Gln Lys Ile Ile Glu Ile
            100                 105                 110 caa agc aag tat tgg aag tca gta agg atg gtg gct gtg cca agg ggc    384
Gln Ser Lys Tyr Trp Lys Ser Val Arg Met Val Ala Val Pro Arg Gly
        115                 120                 125 tgt gct ctg gct ggt gct cag ttg caa gag gag aca gag acc gtt tct    432
Cys Ala Leu Ala Gly Ala Gln Leu Gln Glu Glu Thr Glu Thr Val Ser
    130                 135                 140 gcc ctg gcc tcc cta aca gtg gat gtg gaa cag ccc ttt gct cag gaa    480
Ala Leu Ala Ser Leu Thr Val Asp Val Glu Gln Pro Phe Ala Gln Glu
145                 150                 155                 160 gac agc aga act gct ggt gag cct atg gaa gag gag cca gcc ttg        525
Asp Ser Arg Thr Ala Gly Glu Pro Met Glu Glu Glu Pro Ala Leu
                165                 170                 175
```

<210> SEQ ID NO 20
<211> LENGTH: 120
<212> TYPE: DNA

<213> ORGANISM: Homo sapiens

<400> SEQUENCE: 20

```
attttgccgt cactttgtac cctcctagag gaggggtgtg gccttccaat gcatcaaatc    60
cagcagatac taagaccatg tctggatcaa actctttgcc acaggcttca cgatggtcct   120
```

<210> SEQ ID NO 21
<211> LENGTH: 112
<212> TYPE: PRT
<213> ORGANISM: Homo sapiens

<400> SEQUENCE: 21

```
Thr Ile Val Lys Pro Val Ala Lys Glu Phe Asp Pro Asp Met Val Leu
 1               5                  10                  15
Val Ser Ala Gly Phe Asp Ala Leu Glu Gly His Thr Pro Pro Leu Gly
            20                  25                  30
Gly Tyr Lys Val Thr Ala Lys Cys Phe Gly His Leu Thr Lys Gln Leu
        35                  40                  45
Met Thr Leu Ala Asp Gly Arg Val Val Leu Ala Leu Glu Gly Gly His
    50                  55                  60
Asp Leu Thr Ala Ile Cys Asp Ala Ser Glu Ala Cys Val Asn Ala Leu
65                  70                  75                  80
Leu Gly Asn Glu Leu Glu Pro Leu Ala Glu Asp Ile Leu His Gln Ser
                85                  90                  95
Pro Asn Met Asn Ala Val Ile Ser Leu Gln Lys Ile Ile Glu Ile Gln
            100                 105                 110
```

<210> SEQ ID NO 22
<211> LENGTH: 80
<212> TYPE: PRT
<213> ORGANISM: Homo sapiens

<400> SEQUENCE: 22

```
Leu Glu Pro Leu Ala Glu Asp Ile Leu His Gln Ser Pro Asn Met Asn
 1               5                  10                  15
Ala Val Ile Ser Leu Gln Lys Ile Ile Glu Ile Gln Lys Leu Leu Val
            20                  25                  30
Ser Leu Trp Lys Arg Ser Gln Pro Cys Glu Val Pro Ser Pro Pro Leu
        35                  40                  45
Ile Phe Pro Val Cys Asp Ile Ile Val Tyr Pro Pro Thr Pro Val Pro
    50                  55                  60
Ser Asp Met Ser Cys Leu Leu Pro Gly Trp His Arg Phe Asn Gly Thr
65                  70                  75                  80
```

<210> SEQ ID NO 23
<211> LENGTH: 304
<212> TYPE: DNA
<213> ORGANISM: Homo sapiens

<400> SEQUENCE: 23

```
ggccttggag aagggtacaa tataaatatt gcctggacag gtggccttga tcctcccatg    60
ggagatgttg agtaccttga agcattcagg accatcgtga agcctgtggc aaagagtttg   120
atccagacat ggtcttagta tctgctggat ttgatgcatt ggaaggccac acccctcctc   180
taggagggta caagtgacg gcaaaataaa ctcctgtgct ggaggtacaa cagtttggaa    240
gtatacttgg ggaaagagaa aacacaagat ggaaggaaga tctctctttt cacatcggga   300
gcac                                                               304
```

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 24
ccttgatgct gaaacaccag                                            20

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 25
tcacatttat ttagcagccc a                                          21

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 26
ccttgatgct gaaacaccag                                            20

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 27
ctcacattta tttagcagcc ca                                         22

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 28
agcatgctgg acgaatacag                                            20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 29
ttggtgccat acaacagtga                                            20

<210> SEQ ID NO 30
<211> LENGTH: 20
<212> TYPE: DNA
<213> ORGANISM: Artificial Sequence
<220> FEATURE:

<223> OTHER INFORMATION: Description of Artificial Sequence: Primer

<400> SEQUENCE: 30
ccttgatgct gaaacaccag                                              20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 31
ttggtgccat acaacagtga                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 32
tcactgttgt atggcaccaa                                              20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 33
ccaagtccac cacaaggtaa                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 34
tcactgttgt atggcaccaa                                              20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 35
ccaccacaag gtaatgagga                                              20

<210> SEQ ID NO 36
<211> LENGTH: 77
<212> TYPE: DNA
<213> ORGANISM: Artificial Sequence
<220> FEATURE:
<223> OTHER INFORMATION: Description of Artificial Sequence: Probe

<400> SEQUENCE: 36
gtttcttgca gtcgtgacca gatactctgt attcgtccag catgctcagg gtgggtggtg     60
gaattgccac aaacgca                                                  77

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 37
ggaattgcct atgacccctt ga                                          22

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 38
tgtacttacc ccaagtccac caca                                        24

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 39
ggacagtgac accatttgga                                             20

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 40
agctctcctg aggccactt                                              19

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 41
ggacagtgac accatttgga                                             20

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 42
ctctcctgag gccactttg                                              19

<210> SEQ ID NO 43
<211> LENGTH: 20
<212> TYPE: DNA
<213> ORGANISM: Artificial Sequence
<220> FEATURE:

<223> OTHER INFORMATION: Description of Artificial Sequence: Primer

<400> SEQUENCE: 43
gccttggaga agggtacaat                                               20

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 44
gaaagaagta ccaacctgaa tgc                                           23

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 45
gccttggaga agggtacaat                                               20

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 46
aaagaagtac caacctgaat gc                                            22

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 47
ggacagtgac accatttgga                                               20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 48
tgtggattct tcagcgtgat                                               20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 49
ggacagtgac accatttgga                                               20

```
<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 50
ctcacaacag caaacccatt                                                      20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 51
aatgggtttg ctgttgtgag                                                      20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 52
tctctcaagt atttggcggt                                                      20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 53
aatgggtttg ctgttgtgag                                                      20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 54
gtctctcaag tatttggcgg                                                      20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 55
ttgcaattac cgccaaatac                                                      20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Primer
```

```
<400> SEQUENCE: 56
gaaatgtaca ggatgctggg                                              20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 57
gttgcaatta ccgccaaata                                              20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 58
gaaatgtaca ggatgctggg                                              20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 59
cccagcatcc tgtacatttc                                              20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 60
attgtaccct tctccaaggc                                              20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 61
catcgctatg atgaagggaa                                              20

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 62
ggatcaaggc cacctgtc                                                18

<210> SEQ ID NO 63
<211> LENGTH: 80
```

```
<212> TYPE: DNA
<213> ORGANISM: Artificial Sequence
<220> FEATURE:
<223> OTHER INFORMATION: Description of Artificial Sequence: Probe

<400> SEQUENCE: 63
tgccagggaa aaagttccct tcatcatagc gatggagtga atgtacagg atgctgggt      60 cagcataaaa ggcctgctgg                                                80

<210> SEQ ID NO 64
<211> LENGTH: 79
<212> TYPE: DNA
<213> ORGANISM: Artificial Sequence
<220> FEATURE:
<223> OTHER INFORMATION: Description of Artificial Sequence: Probe

<400> SEQUENCE: 64
gggaaaaagt tcccttcatc atagcgatgg agtgaaatgt acaggatgct ggggtcagca    60
taaaaggcct gctgggtac                                                 79

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 65
gtggacagtg acaccatttg ga                                             22

<210> SEQ ID NO 66
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 66
ggagaaagaa gtaccaacct gaatgctt                                       28

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 67
gtggccaaag agtttgatcc                                                20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 68
ttgccgtcac tttgtaccct                                                20

<210> SEQ ID NO 69
<211> LENGTH: 20
<212> TYPE: DNA
<213> ORGANISM: Artificial Sequence
<220> FEATURE:
```

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 69
gtggccaaag agtttgatcc                                             20

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 70
ttgccgtcac tttgtaccc                                              19

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 71
tggtcatttg acgaagcaat                                             20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 72
agaagggcat ttacacaggc                                             20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 73
tggtcatttg acgaagcaat                                             20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 74
gaagggcatt tacacaggct                                             20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 75
aggagggtac aaagtgacgg                                             20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 76
agggcattta cacaggcttc                                              20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 77
aggagggtac aaagtgacgg                                              20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 78
gggcatttac acaggcttct                                              20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 79
gatgacattg gctgatggac                                              20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 80
agcattcata ttcgggcttt                                              20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 81
tggtcatttg acgaagcaat                                              20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 82
agcattcata ttcgggcttt                                                    20

<210> SEQ ID NO 83
<211> LENGTH: 80
<212> TYPE: DNA
<213> ORGANISM: Artificial Sequence
<220> FEATURE:
<223> OTHER INFORMATION: Description of Artificial Sequence: Probe

<400> SEQUENCE: 83
tcactttgta ccctcctaga ggagggtgt ggccttccaa tgcatcaaat ccagcagata         60
ctaagaccat gtctggatca                                                    80

<210> SEQ ID NO 84
<211> LENGTH: 80
<212> TYPE: DNA
<213> ORGANISM: Artificial Sequence
<220> FEATURE:
<223> OTHER INFORMATION: Description of Artificial Sequence: Probe

<400> SEQUENCE: 84
tcctagagga ggggtgtggc cttccaatgc atcaaatcca gcagatacta agaccatgtc       60
tggatcaaac tctttggcca                                                    80

<210> SEQ ID NO 85
<211> LENGTH: 80
<212> TYPE: DNA
<213> ORGANISM: Artificial Sequence
<220> FEATURE:
<223> OTHER INFORMATION: Description of Artificial Sequence: Probe

<400> SEQUENCE: 85
ggcttctgat gcatcacaga tggctgtgag atcatgtcct ccttctagag ccaacaccac       60
acgtccatca gccaatgtca                                                    80

<210> SEQ ID NO 86
<211> LENGTH: 80
<212> TYPE: DNA
<213> ORGANISM: Artificial Sequence
<220> FEATURE:
<223> OTHER INFORMATION: Description of Artificial Sequence: Probe

<400> SEQUENCE: 86
ggcttctgat gcatcacaga tggctgtgag atcatgtcct ccttctagag ccaacaccac       60
acgtccatca gccaatgtca                                                    80

<210> SEQ ID NO 87
<211> LENGTH: 1069
<212> TYPE: PRT
<213> ORGANISM: Homo sapiens

<400> SEQUENCE: 87

Met His Ser Met Ile Ser Ser Val Asp Val Lys Ser Glu Val Pro Val
  1               5                  10                  15

Gly Leu Glu Pro Ile Ser Pro Leu Asp Leu Arg Thr Asp Leu Arg Met
                 20                  25                  30

Met Met Pro Val Val Asp Pro Val Val Arg Glu Lys Gln Leu Gln Gln
             35                  40                  45

Glu Leu Leu Leu Ile Gln Gln Gln Gln Ile Gln Lys Gln Leu Leu
         50                  55                  60

-continued

```
Ile Ala Glu Phe Gln Lys Gln His Glu Asn Leu Thr Arg Gln His Gln
 65                  70                  75                  80

Ala Gln Leu Gln Glu His Ile Lys Leu Gln Gln Glu Leu Leu Ala Ile
                 85                  90                  95

Lys Gln Gln Gln Glu Leu Leu Glu Lys Glu Gln Lys Leu Glu Gln Gln
            100                 105                 110

Arg Gln Glu Gln Glu Val Glu Arg His Arg Glu Gln Gln Leu Pro
        115                 120                 125

Pro Leu Arg Gly Lys Asp Arg Gly Arg Glu Arg Ala Val Ala Ser Thr
    130                 135                 140

Glu Val Lys Gln Lys Leu Gln Glu Phe Leu Leu Ser Lys Ser Ala Thr
145                 150                 155                 160

Lys Asp Thr Pro Thr Asn Gly Lys Asn His Ser Val Ser Arg His Pro
                165                 170                 175

Lys Leu Trp Tyr Thr Ala Ala His His Thr Ser Leu Asp Gln Ser Ser
            180                 185                 190

Pro Pro Leu Ser Gly Thr Ser Pro Ser Tyr Lys Tyr Thr Leu Pro Gly
        195                 200                 205

Ala Gln Asp Ala Lys Asp Asp Phe Pro Leu Arg Lys Thr Ala Ser Glu
    210                 215                 220

Pro Asn Leu Lys Val Arg Ser Arg Leu Lys Gln Lys Val Ala Glu Arg
225                 230                 235                 240

Arg Ser Ser Pro Leu Leu Arg Arg Lys Asp Gly Asn Val Val Thr Ser
                245                 250                 255

Phe Lys Lys Arg Met Phe Glu Val Thr Glu Ser Ser Val Ser Ser Ser
            260                 265                 270

Ser Pro Gly Ser Gly Pro Ser Pro Asn Asn Gly Pro Thr Gly Ser
        275                 280                 285

Val Thr Glu Asn Glu Thr Ser Val Leu Pro Pro Thr Pro His Ala Glu
    290                 295                 300

Gln Met Val Ser Gln Gln Arg Ile Leu Ile His Glu Asp Ser Met Asn
305                 310                 315                 320

Leu Leu Ser Leu Tyr Thr Ser Pro Ser Leu Pro Asn Ile Thr Leu Gly
                325                 330                 335

Leu Pro Ala Val Pro Ser Gln Leu Asn Ala Ser Asn Ser Leu Lys Glu
            340                 345                 350

Lys Gln Lys Cys Glu Thr Gln Thr Leu Arg Gln Gly Val Pro Leu Pro
        355                 360                 365

Gly Gln Tyr Gly Gly Ser Ile Pro Ala Ser Ser Ser His Pro His Val
    370                 375                 380

Thr Leu Glu Gly Lys Pro Pro Asn Ser Ser His Gln Ala Leu Leu Gln
385                 390                 395                 400

His Leu Leu Leu Lys Glu Gln Met Arg Gln Gln Lys Leu Leu Val Ala
                405                 410                 415

Gly Gly Val Pro Leu His Pro Gln Ser Pro Leu Ala Thr Lys Glu Arg
            420                 425                 430

Ile Ser Pro Gly Ile Arg Gly Thr His Lys Leu Pro Arg His Arg Pro
        435                 440                 445

Leu Asn Arg Thr Gln Ser Ala Pro Leu Pro Gln Ser Thr Leu Ala Gln
    450                 455                 460

Leu Val Ile Gln Gln Gln His Gln Gln Phe Leu Glu Lys Gln Lys Gln
465                 470                 475                 480
```

```
Tyr Gln Gln Gln Ile His Met Asn Lys Leu Leu Ser Lys Ser Ile Glu
                485                 490                 495

Gln Leu Lys Gln Pro Gly Ser His Leu Glu Ala Glu Glu Leu
            500                 505                 510

Gln Gly Asp Gln Ala Met Gln Glu Asp Arg Ala Pro Ser Ser Gly Asn
            515                 520                 525

Ser Thr Arg Ser Asp Ser Ser Ala Cys Val Asp Thr Leu Gly Gln
    530                 535                 540

Val Gly Ala Val Lys Val Lys Glu Glu Pro Val Asp Ser Asp Glu Asp
545                 550                 555                 560

Ala Gln Ile Gln Glu Met Glu Ser Gly Glu Gln Ala Ala Phe Met Gln
                565                 570                 575

Gln Pro Phe Leu Glu Pro Thr His Thr Arg Ala Leu Ser Val Arg Gln
            580                 585                 590

Ala Pro Leu Ala Ala Val Gly Met Asp Gly Leu Glu Lys His Arg Leu
            595                 600                 605

Val Ser Arg Thr His Ser Ser Pro Ala Ala Ser Val Leu Pro His Pro
    610                 615                 620

Ala Met Asp Arg Pro Leu Gln Pro Gly Ser Ala Thr Gly Ile Ala Tyr
625                 630                 635                 640

Asp Pro Leu Met Leu Lys His Gln Cys Val Cys Gly Asn Ser Thr Thr
                645                 650                 655

His Pro Glu His Ala Gly Arg Ile Gln Ser Ile Trp Ser Arg Leu Gln
            660                 665                 670

Glu Thr Gly Leu Leu Asn Lys Cys Glu Arg Ile Gln Gly Arg Lys Ala
    675                 680                 685

Ser Leu Glu Glu Ile Gln Leu Val His Ser Glu His His Ser Leu Leu
690                 695                 700

Tyr Gly Thr Asn Pro Leu Asp Gly Gln Lys Leu Asp Pro Arg Ile Leu
705                 710                 715                 720

Leu Gly Asp Asp Ser Gln Lys Phe Phe Ser Ser Leu Pro Cys Gly Gly
                725                 730                 735

Leu Gly Val Asp Ser Asp Thr Ile Trp Asn Glu Leu His Ser Ser Gly
            740                 745                 750

Ala Ala Arg Met Ala Val Gly Cys Val Ile Glu Leu Ala Ser Lys Val
            755                 760                 765

Ala Ser Gly Glu Leu Lys Asn Gly Phe Ala Val Val Arg Pro Pro Gly
    770                 775                 780

His His Ala Glu Glu Ser Thr Ala Met Gly Phe Cys Phe Phe Asn Ser
785                 790                 795                 800

Val Ala Ile Thr Ala Lys Tyr Leu Arg Asp Gln Leu Asn Ile Ser Lys
                805                 810                 815

Ile Leu Ile Val Asp Leu Asp Val His His Gly Asn Gly Thr Gln Gln
            820                 825                 830

Ala Phe Tyr Ala Asp Pro Ser Ile Leu Tyr Ile Ser Leu His Arg Tyr
            835                 840                 845

Asp Glu Gly Asn Phe Phe Pro Gly Ser Gly Ala Pro Asn Glu Val Gly
    850                 855                 860

Thr Gly Leu Gly Glu Gly Tyr Asn Ile Asn Ile Ala Trp Thr Gly Gly
865                 870                 875                 880

Leu Asp Pro Pro Met Gly Asp Val Glu Tyr Leu Glu Ala Phe Arg Thr
                885                 890                 895

Ile Val Lys Pro Val Ala Lys Glu Phe Asp Pro Asp Met Val Leu Val
```

-continued

```
                 900                 905                 910
Ser Ala Gly Phe Asp Ala Leu Glu Gly His Thr Pro Leu Gly Gly
            915                 920                 925

Tyr Lys Val Thr Ala Lys Cys Phe Gly His Leu Thr Lys Gln Leu Met
        930                 935                 940

Thr Leu Ala Asp Gly Arg Val Leu Ala Leu Glu Gly Gly His Asp
945                 950                 955                 960

Leu Thr Ala Ile Cys Asp Ala Ser Glu Ala Cys Val Asn Ala Leu Leu
                965                 970                 975

Gly Asn Glu Leu Glu Pro Leu Ala Glu Asp Ile Leu His Gln Ser Pro
            980                 985                 990

Asn Met Asn Ala Val Ile Ser Leu Gln Lys Ile Ile Glu Ile Gln Ser
        995                 1000                1005

Lys Tyr Trp Lys Ser Val Arg Met Val Ala Val Pro Arg Gly Cys Ala
    1010                1015                1020

Leu Ala Gly Ala Gln Leu Gln Glu Glu Thr Glu Thr Val Ser Ala Leu
1025                1030                1035                1040

Ala Ser Leu Thr Val Asp Val Glu Gln Pro Phe Ala Gln Glu Asp Ser
                1045                1050                1055

Arg Thr Ala Gly Glu Pro Met Glu Glu Glu Pro Ala Leu
            1060                1065

<210> SEQ ID NO 88
<211> LENGTH: 4467
<212> TYPE: DNA
<213> ORGANISM: Homo sapiens
<220> FEATURE:
<221> NAME/KEY: CDS
<222> LOCATION: (1)..(3207)

<400> SEQUENCE: 88 atg cac agt atg atc agc tca gtg gat gtg aag tca gaa gtt cct gtg       48
Met His Ser Met Ile Ser Ser Val Asp Val Lys Ser Glu Val Pro Val
 1               5                  10                  15 ggc ctg gag ccc atc tca cct tta gac cta agg aca gac ctc agg atg       96
Gly Leu Glu Pro Ile Ser Pro Leu Asp Leu Arg Thr Asp Leu Arg Met
            20                  25                  30 atg atg ccc gtg gtg gac cct gtt gtc cgt gag aag caa ttg cag cag      144
Met Met Pro Val Val Asp Pro Val Val Arg Glu Lys Gln Leu Gln Gln
        35                  40                  45 gaa tta ctt ctt atc cag cag cag caa caa atc cag aag cag ctt ctg      192
Glu Leu Leu Leu Ile Gln Gln Gln Gln Ile Gln Lys Gln Leu Leu
    50                  55                  60 ata gca gag ttt cag aaa cag cat gag aac ttg aca cgg cag cac cag      240
Ile Ala Glu Phe Gln Lys Gln His Glu Asn Leu Thr Arg Gln His Gln
65                  70                  75                  80 gct cag ctt cag gag cat atc aag ttg caa cag gaa ctt cta gcc ata      288
Ala Gln Leu Gln Glu His Ile Lys Leu Gln Gln Glu Leu Leu Ala Ile
                85                  90                  95 aaa cag caa caa gaa ctc cta gaa aag gag cag aaa ctg gag cag cag      336
Lys Gln Gln Gln Glu Leu Leu Glu Lys Glu Gln Lys Leu Glu Gln Gln
            100                 105                 110 agg caa gaa cag gaa gta gag agg cat cgc aga gaa cag cag ctt cct      384
Arg Gln Glu Gln Glu Val Glu Arg His Arg Arg Glu Gln Gln Leu Pro
        115                 120                 125 cct ctc aga ggc aaa gat aga gga cga gaa agg gca gtg gca agt aca      432
Pro Leu Arg Gly Lys Asp Arg Gly Arg Glu Arg Ala Val Ala Ser Thr
    130                 135                 140
```

-continued

| | | |
|---|---|---|
| gaa gta aag cag aag ctt caa gag ttc cta ctg agt aaa tca gca acg<br>Glu Val Lys Gln Lys Leu Gln Glu Phe Leu Leu Ser Lys Ser Ala Thr<br>145                          150                        155                        160 | | 480 |
| aaa gac act cca act aat gga aaa aat cat tcc gtg agc cgc cat ccc<br>Lys Asp Thr Pro Thr Asn Gly Lys Asn His Ser Val Ser Arg His Pro<br>                        165                        170                        175 | | 528 |
| aag ctc tgg tac acg gct gcc cac cac aca tca ttg gat caa agc tct<br>Lys Leu Trp Tyr Thr Ala Ala His His Thr Ser Leu Asp Gln Ser Ser<br>                        180                        185                        190 | | 576 |
| cca ccc ctt agt gga aca tct cca tcc tac aag tac aca tta cca gga<br>Pro Pro Leu Ser Gly Thr Ser Pro Ser Tyr Lys Tyr Thr Leu Pro Gly<br>                   195                        200                        205 | | 624 |
| gca caa gat gca aag gat gat ttc ccc ctt cga aaa act gcc tct gag<br>Ala Gln Asp Ala Lys Asp Asp Phe Pro Leu Arg Lys Thr Ala Ser Glu<br>210                          215                        220 | | 672 |
| ccc aac ttg aag gtg cgg tcc agg tta aaa cag aaa gtg gca gag agg<br>Pro Asn Leu Lys Val Arg Ser Arg Leu Lys Gln Lys Val Ala Glu Arg<br>225                          230                        235                        240 | | 720 |
| aga agc agc ccc tta ctc agg cgg aag gat gga aat gtt gtc act tca<br>Arg Ser Ser Pro Leu Leu Arg Arg Lys Asp Gly Asn Val Val Thr Ser<br>                        245                        250                        255 | | 768 |
| ttc aag aag cga atg ttt gag gtg aca gaa tcc tca gtc agt agc agt<br>Phe Lys Lys Arg Met Phe Glu Val Thr Glu Ser Ser Val Ser Ser Ser<br>                        260                        265                        270 | | 816 |
| tct cca ggc tct ggt ccc agt tca cca aac aat ggg cca act gga agt<br>Ser Pro Gly Ser Gly Pro Ser Ser Pro Asn Asn Gly Pro Thr Gly Ser<br>              275                        280                        285 | | 864 |
| gtt act gaa aat gag act tcg gtt ttg ccc cct acc cct cat gcc gag<br>Val Thr Glu Asn Glu Thr Ser Val Leu Pro Pro Thr Pro His Ala Glu<br>         290                        295                        300 | | 912 |
| caa atg gtt tca cag caa cgc att cta att cat gaa gat tcc atg aac<br>Gln Met Val Ser Gln Gln Arg Ile Leu Ile His Glu Asp Ser Met Asn<br>305                          310                        315                        320 | | 960 |
| ctg cta agt ctt tat acc tct cct tct ttg ccc aac att acc ttg ggg<br>Leu Leu Ser Leu Tyr Thr Ser Pro Ser Leu Pro Asn Ile Thr Leu Gly<br>                        325                        330                        335 | | 1008 |
| ctt ccc gca gtg cca tcc cag ctc aat gct tcg aat tca ctc aaa gaa<br>Leu Pro Ala Val Pro Ser Gln Leu Asn Ala Ser Asn Ser Leu Lys Glu<br>                   340                        345                        350 | | 1056 |
| aag cag aag tgt gag acg cag acg ctt agg caa ggt gtt cct ctg cct<br>Lys Gln Lys Cys Glu Thr Gln Thr Leu Arg Gln Gly Val Pro Leu Pro<br>              355                        360                        365 | | 1104 |
| ggg cag tat gga ggc agc atc ccg gca tct tcc agc cac cct cat gtt<br>Gly Gln Tyr Gly Gly Ser Ile Pro Ala Ser Ser Ser His Pro His Val<br>370                          375                        380 | | 1152 |
| act tta gag gga aag cca ccc aac agc agc cac cag gct ctc ctg cag<br>Thr Leu Glu Gly Lys Pro Pro Asn Ser Ser His Gln Ala Leu Leu Gln<br>385                          390                        395                        400 | | 1200 |
| cat tta tta ttg aaa gaa caa atg cga cag caa aag ctt ctt gta gct<br>His Leu Leu Leu Lys Glu Gln Met Arg Gln Gln Lys Leu Leu Val Ala<br>                        405                        410                        415 | | 1248 |
| ggt gga gtt ccc tta cat cct cag tct ccc ttg gca aca aaa gag aga<br>Gly Gly Val Pro Leu His Pro Gln Ser Pro Leu Ala Thr Lys Glu Arg<br>                   420                        425                        430 | | 1296 |
| att tca cct ggc att aga ggt acc cac aaa ttg ccc cgt cac aga ccc<br>Ile Ser Pro Gly Ile Arg Gly Thr His Lys Leu Pro Arg His Arg Pro<br>              435                        440                        445 | | 1344 |
| ctg aac cga acc cag tct gca cct ttg cct cag agc acg ttg gct cag<br>Leu Asn Arg Thr Gln Ser Ala Pro Leu Pro Gln Ser Thr Leu Ala Gln<br>         450                        455                        460 | | 1392 |

```
ctg gtc att caa cag caa cac cag caa ttc ttg gag aag cag aag caa    1440
Leu Val Ile Gln Gln Gln His Gln Gln Phe Leu Glu Lys Gln Lys Gln
465                 470                 475                 480 tac cag cag cag atc cac atg aac aaa ctg ctt tcg aaa tct att gaa    1488
Tyr Gln Gln Gln Ile His Met Asn Lys Leu Leu Ser Lys Ser Ile Glu
                485                 490                 495 caa ctg aag caa cca ggc agt cac ctt gag gaa gca gag gaa gag ctt    1536
Gln Leu Lys Gln Pro Gly Ser His Leu Glu Glu Ala Glu Glu Glu Leu
            500                 505                 510 cag ggg gac cag gcg atg cag gaa gac aga gcg ccc tct agt ggc aac    1584
Gln Gly Asp Gln Ala Met Gln Glu Asp Arg Ala Pro Ser Ser Gly Asn
        515                 520                 525 agc act agg agc gac agc agt gct tgt gtg gat gac aca ctg gga caa    1632
Ser Thr Arg Ser Asp Ser Ser Ala Cys Val Asp Asp Thr Leu Gly Gln
530                 535                 540 gtt ggg gct gtg aag gtc aag gag gaa cca gtg gac agt gat gaa gat    1680
Val Gly Ala Val Lys Val Lys Glu Glu Pro Val Asp Ser Asp Glu Asp
545                 550                 555                 560 gct cag atc cag gaa atg gaa tct ggg gag cag gct gct ttt atg caa    1728
Ala Gln Ile Gln Glu Met Glu Ser Gly Glu Gln Ala Ala Phe Met Gln
                565                 570                 575 cag cct ttc ctg gaa ccc acg cac aca cgt gcg ctc tct gtg cgc caa    1776
Gln Pro Phe Leu Glu Pro Thr His Thr Arg Ala Leu Ser Val Arg Gln
            580                 585                 590 gct ccg ctg gct gcg gtt ggc atg gat gga tta gag aaa cac cgt ctc    1824
Ala Pro Leu Ala Ala Val Gly Met Asp Gly Leu Glu Lys His Arg Leu
        595                 600                 605 gtc tcc agg act cac tct tcc cct gct gcc tct gtt tta cct cac ccg    1872
Val Ser Arg Thr His Ser Ser Pro Ala Ala Ser Val Leu Pro His Pro
610                 615                 620 gca atg gac cgc ccc ctc cag cct ggc tct gca act gga att gcc tat    1920
Ala Met Asp Arg Pro Leu Gln Pro Gly Ser Ala Thr Gly Ile Ala Tyr
625                 630                 635                 640 gac ccc ttg atg ctg aaa cac cag tgc gtt tgt ggc aat tcc acc acc    1968
Asp Pro Leu Met Leu Lys His Gln Cys Val Cys Gly Asn Ser Thr Thr
                645                 650                 655 cac cct gag cat gct gga cga ata cag agt atc tgg tca cga ctg caa    2016
His Pro Glu His Ala Gly Arg Ile Gln Ser Ile Trp Ser Arg Leu Gln
            660                 665                 670 gaa act ggg ctg cta aat aaa tgt gag cga att caa ggt cga aaa gcc    2064
Glu Thr Gly Leu Leu Asn Lys Cys Glu Arg Ile Gln Gly Arg Lys Ala
        675                 680                 685 agc ctg gag gaa ata cag ctt gtt cat tct gaa cat cac tca ctg ttg    2112
Ser Leu Glu Glu Ile Gln Leu Val His Ser Glu His His Ser Leu Leu
690                 695                 700 tat ggc acc aac ccc ctg gac gga cag aag ctg gac ccc agg ata ctc    2160
Tyr Gly Thr Asn Pro Leu Asp Gly Gln Lys Leu Asp Pro Arg Ile Leu
705                 710                 715                 720 cta ggt gat gac tct caa aag ttt ttt tcc tca tta cct tgt ggt gga    2208
Leu Gly Asp Asp Ser Gln Lys Phe Phe Ser Ser Leu Pro Cys Gly Gly
                725                 730                 735 ctt ggg gtg gac agt gac acc att tgg aat gag cta cac tcg tcc ggt    2256
Leu Gly Val Asp Ser Asp Thr Ile Trp Asn Glu Leu His Ser Ser Gly
            740                 745                 750 gct gca cgc atg gct gtt ggc tgt gtc atc gag ctg gct tcc aaa gtg    2304
Ala Ala Arg Met Ala Val Gly Cys Val Ile Glu Leu Ala Ser Lys Val
        755                 760                 765 gcc tca gga gag ctg aag aat ggg ttt gct gtt gtg agg ccc cct ggc    2352
Ala Ser Gly Glu Leu Lys Asn Gly Phe Ala Val Val Arg Pro Pro Gly
```

-continued

```
              770                 775                 780
cat cac gct gaa gaa tcc aca gcc atg ggg ttc tgc ttt ttt aat tca         2400
His His Ala Glu Glu Ser Thr Ala Met Gly Phe Cys Phe Phe Asn Ser
785                 790                 795                 800 gtt gca att acc gcc aaa tac ttg aga gac caa cta aat ata agc aag         2448
Val Ala Ile Thr Ala Lys Tyr Leu Arg Asp Gln Leu Asn Ile Ser Lys
                    805                 810                 815 ata ttg att gta gat ctg gat gtt cac cat gga aac ggt acc cag cag         2496
Ile Leu Ile Val Asp Leu Asp Val His His Gly Asn Gly Thr Gln Gln
                820                 825                 830 gcc ttt tat gct gac ccc agc atc ctg tac att tca ctc cat cgc tat         2544
Ala Phe Tyr Ala Asp Pro Ser Ile Leu Tyr Ile Ser Leu His Arg Tyr
            835                 840                 845 gat gaa ggg aac ttt ttc cct ggc agt gga gcc cca aat gag gtt gga         2592
Asp Glu Gly Asn Phe Phe Pro Gly Ser Gly Ala Pro Asn Glu Val Gly
850                 855                 860 aca ggc ctt gga gaa ggg tac aat ata aat att gcc tgg aca ggt ggc         2640
Thr Gly Leu Gly Glu Gly Tyr Asn Ile Asn Ile Ala Trp Thr Gly Gly
865                 870                 875                 880 ctt gat cct ccc atg gga gat gtt gag tac ctt gaa gca ttc agg acc         2688
Leu Asp Pro Pro Met Gly Asp Val Glu Tyr Leu Glu Ala Phe Arg Thr
                    885                 890                 895 atc gtg aag cct gtg gcc aaa gag ttt gat cca gac atg gtc tta gta         2736
Ile Val Lys Pro Val Ala Lys Glu Phe Asp Pro Asp Met Val Leu Val
                900                 905                 910 tct gct gga ttt gat gca ttg gaa ggc cac acc cct cct cta gga ggg         2784
Ser Ala Gly Phe Asp Ala Leu Glu Gly His Thr Pro Pro Leu Gly Gly
            915                 920                 925 tac aaa gtg acg gca aaa tgt ttt ggt cat ttg acg aag caa ttg atg         2832
Tyr Lys Val Thr Ala Lys Cys Phe Gly His Leu Thr Lys Gln Leu Met
930                 935                 940 aca ttg gct gat gga cgt gtg gtg ttg gct cta gaa gga gga cat gat         2880
Thr Leu Ala Asp Gly Arg Val Val Leu Ala Leu Glu Gly Gly His Asp
945                 950                 955                 960 ctc aca gcc atc tgt gat gca tca gaa gcc tgt gta aat gcc ctt cta         2928
Leu Thr Ala Ile Cys Asp Ala Ser Glu Ala Cys Val Asn Ala Leu Leu
                    965                 970                 975 gga aat gag ctg gag cca ctt gca gaa gat att ctc cac caa agc ccg         2976
Gly Asn Glu Leu Glu Pro Leu Ala Glu Asp Ile Leu His Gln Ser Pro
                980                 985                 990 aat atg aat gct gtt att tct tta cag aag atc att gaa att caa agc         3024
Asn Met Asn Ala Val Ile Ser Leu Gln Lys Ile Ile Glu Ile Gln Ser
            995                 1000                1005 aag tat tgg aag tca gta agg atg gtg gct gtg cca agg ggc tgt gct         3072
Lys Tyr Trp Lys Ser Val Arg Met Val Ala Val Pro Arg Gly Cys Ala
    1010                1015                1020 ctg gct ggt gct cag ttg caa gag gag aca gag acc gtt tct gcc ctg         3120
Leu Ala Gly Ala Gln Leu Gln Glu Glu Thr Glu Thr Val Ser Ala Leu
1025                1030                1035                1040 gcc tcc cta aca gtg gat gtg gaa cag ccc ttt gct cag gaa gac agc         3168
Ala Ser Leu Thr Val Asp Val Glu Gln Pro Phe Ala Gln Glu Asp Ser
                    1045                1050                1055 aga act gct ggt gag cct atg gaa gag gag cca gcc ttg tgaagtgcca         3217
Arg Thr Ala Gly Glu Pro Met Glu Glu Glu Pro Ala Leu
                1060                1065 agtccccctc tgatatttcc tgtgtgtgac atcattgtgt atccccccac cccagtaccc      3277
tcagacatgt cttgtctgct gcctgggtgg cacagattca atggaacata aacactgggc      3337
acaaaattct gaacagcagc ttcacttgtt ctttggatgg acttgaaagg gcattaaaga      3397
```

-continued

```
ttccttaaac gtaaccgctg tgattctaga gttacagtaa accacgattg gaagaaactg    3457
cttccagcat gctttttaata tgctgggtga cccactccta gacaccaagt ttgaactaga   3517
aacattcagt acagcactag atattgttaa tttcagaagc tatgacagcc agtgaaattt   3577
tgggcaaaac ctgagacata gtcattcctg acattctgat cagcttttttt tggggtaatt  3637 tgttttttcaa acagtcttaa cttgttaca agatttgctt ttagctatga acggatcgta   3697
attccaccca gaatgtaatg tttcttgttt gtttgtttg ttttgttagg gtttttttct    3757
caactttaac acacagttca actgttccta gtaaaagttc aagatggagg aactagcatg   3817
aggctttttt cagtatctcg aagtccaaat gccaaggaa cctcacacac tgtttgtaat    3877
ggtgcaatat tttatatcac tttttttttaa acatccccaa catctttgtg ttctcacaca  3937
caggcaattt gcaatgttgc aattgtgttg gagaatgaag tccccccacc tcccagccac   3997
acacacatcc tttgttctca tgacagtagg tctgagcaaa tgttccacca agcatttttca  4057 gtgtctttga aaagcacgta acttttcaaa ggtggtctta atttgctgca tatctatcaa   4117
ggacttattc actcaccttt cctttttctgc cctctatcaa ttgatttctt cttacctttc  4177
atcattcatt ccttccttta gaaaaactga agattaccca taatctcctc ttattacttg   4237
agggccttga ctatttagtt tatttttgttt actttacagg ttaacacagt tgttttgtct  4297
gattgcattt tattaactgt gaagccgttg aaatgaatat cacttaagca acgttgctaa   4357
atttctatgt gtttgaaatg tgttaatgaa ggcactgctt atttgtagtc accttgaact   4417
gacttaacct agaagctgtg ccttcttgtg aaaaaaaaaa aaaaaaaaaa               4467
```

<210> SEQ ID NO 89
<211> LENGTH: 1011
<212> TYPE: PRT
<213> ORGANISM: Homo sapiens

<400> SEQUENCE: 89

```
Met His Ser Met Ile Ser Ser Val Asp Val Lys Ser Glu Val Pro Val
 1               5                  10                  15

Gly Leu Glu Pro Ile Ser Pro Leu Asp Leu Arg Thr Asp Leu Arg Met
            20                  25                  30

Met Met Pro Val Val Asp Pro Val Val Arg Glu Lys Gln Leu Gln Gln
        35                  40                  45

Glu Leu Leu Leu Ile Gln Gln Gln Gln Ile Gln Lys Gln Leu Leu
    50                  55                  60

Ile Ala Glu Phe Gln Lys Gln His Glu Asn Leu Thr Arg Gln His Gln
65                  70                  75                  80

Ala Gln Leu Gln Glu His Ile Lys Glu Leu Leu Ala Ile Lys Gln Gln
                85                  90                  95

Gln Glu Leu Leu Glu Lys Glu Gln Lys Leu Glu Gln Gln Arg Gln Glu
            100                 105                 110

Gln Glu Val Glu Arg His Arg Arg Glu Gln Gln Leu Pro Pro Leu Arg
        115                 120                 125

Gly Lys Asp Arg Gly Arg Glu Arg Ala Val Ala Ser Thr Glu Val Lys
    130                 135                 140

Gln Lys Leu Gln Glu Phe Leu Leu Ser Lys Ser Ala Thr Lys Asp Thr
145                 150                 155                 160

Pro Thr Asn Gly Lys Asn His Ser Val Ser Arg His Pro Lys Leu Trp
                165                 170                 175

Tyr Thr Ala Ala His His Thr Ser Leu Asp Gln Ser Ser Pro Pro Leu
```

-continued

```
                180                 185                 190
Ser Gly Thr Ser Pro Ser Tyr Lys Tyr Thr Leu Pro Gly Ala Gln Asp
        195                 200                 205

Ala Lys Asp Asp Phe Pro Leu Arg Lys Thr Ala Ser Glu Pro Asn Leu
    210                 215                 220

Lys Val Arg Ser Arg Leu Lys Gln Lys Val Ala Glu Arg Arg Ser Ser
225                 230                 235                 240

Pro Leu Leu Arg Arg Lys Asp Gly Asn Val Val Thr Ser Phe Lys Lys
                245                 250                 255

Arg Met Phe Glu Val Thr Glu Ser Ser Val Ser Ser Ser Ser Pro Gly
            260                 265                 270

Ser Gly Pro Ser Ser Pro Asn Asn Gly Pro Thr Gly Ser Val Thr Glu
        275                 280                 285

Asn Glu Thr Ser Val Leu Pro Pro Thr Pro His Ala Glu Gln Met Val
    290                 295                 300

Ser Gln Gln Arg Ile Leu Ile His Glu Asp Ser Met Asn Leu Leu Ser
305                 310                 315                 320

Leu Tyr Thr Ser Pro Ser Leu Pro Asn Ile Thr Leu Gly Leu Pro Ala
                325                 330                 335

Val Pro Ser Gln Leu Asn Ala Ser Asn Ser Leu Lys Glu Lys Gln Lys
            340                 345                 350

Cys Glu Thr Gln Thr Leu Arg Gln Gly Val Pro Leu Pro Gly Gln Tyr
        355                 360                 365

Gly Gly Ser Ile Pro Ala Ser Ser Ser His Pro His Val Thr Leu Glu
    370                 375                 380

Gly Lys Pro Pro Asn Ser Ser His Gln Ala Leu Leu Gln His Leu Leu
385                 390                 395                 400

Leu Lys Glu Gln Met Arg Gln Gln Lys Leu Leu Val Ala Gly Gly Val
                405                 410                 415

Pro Leu His Pro Gln Ser Pro Leu Ala Thr Lys Glu Arg Ile Ser Pro
            420                 425                 430

Gly Ile Arg Gly Thr His Lys Leu Pro Arg His Arg Pro Leu Asn Arg
        435                 440                 445

Thr Gln Ser Ala Pro Leu Pro Gln Ser Thr Leu Ala Gln Leu Val Ile
    450                 455                 460

Gln Gln Gln His Gln Gln Phe Leu Glu Lys Gln Lys Gln Tyr Gln Gln
465                 470                 475                 480

Gln Ile His Met Asn Lys Leu Leu Ser Lys Ser Ile Glu Gln Leu Lys
                485                 490                 495

Gln Pro Gly Ser His Leu Glu Glu Ala Glu Glu Glu Leu Gln Gly Asp
            500                 505                 510

Gln Ala Met Gln Glu Asp Arg Ala Pro Ser Ser Gly Asn Ser Thr Arg
        515                 520                 525

Ser Asp Ser Ser Ala Cys Val Asp Asp Thr Leu Gly Gln Val Gly Ala
    530                 535                 540

Val Lys Val Lys Glu Glu Pro Val Asp Ser Asp Glu Asp Ala Gln Ile
545                 550                 555                 560

Gln Glu Met Glu Ser Gly Glu Gln Ala Ala Phe Met Gln Gln Pro Phe
                565                 570                 575

Leu Glu Pro Thr His Thr Arg Ala Leu Ser Val Arg Gln Ala Pro Leu
            580                 585                 590

Ala Ala Val Gly Met Asp Gly Leu Glu Lys His Arg Leu Val Ser Arg
        595                 600                 605
```

```
Thr His Ser Ser Pro Ala Ala Ser Val Leu Pro His Pro Ala Met Asp
    610                 615                 620

Arg Pro Leu Gln Pro Gly Ser Ala Thr Gly Ile Ala Tyr Asp Pro Leu
625                 630                 635                 640

Met Leu Lys His Gln Cys Val Cys Gly Asn Ser Thr Thr His Pro Glu
                645                 650                 655

His Ala Gly Arg Ile Gln Ser Ile Trp Ser Arg Leu Gln Glu Thr Gly
            660                 665                 670

Leu Leu Asn Lys Cys Glu Arg Ile Gln Gly Arg Lys Ala Ser Leu Glu
        675                 680                 685

Glu Ile Gln Leu Val His Ser Glu His Ser Leu Leu Tyr Gly Thr
    690                 695                 700

Asn Pro Leu Asp Gly Gln Lys Leu Asp Pro Arg Ile Leu Leu Gly Asp
705                 710                 715                 720

Asp Ser Gln Lys Phe Phe Ser Ser Leu Pro Cys Gly Gly Leu Gly Val
                725                 730                 735

Asp Ser Asp Thr Ile Trp Asn Glu Leu His Ser Ser Gly Ala Ala Arg
            740                 745                 750

Met Ala Val Gly Cys Val Ile Glu Leu Ala Ser Lys Val Ala Ser Gly
        755                 760                 765

Glu Leu Lys Asn Gly Phe Ala Val Val Arg Pro Pro Gly His His Ala
    770                 775                 780

Glu Glu Ser Thr Ala Met Gly Phe Cys Phe Phe Asn Ser Val Ala Ile
785                 790                 795                 800

Thr Ala Lys Tyr Leu Arg Asp Gln Leu Asn Ile Ser Lys Ile Leu Ile
                805                 810                 815

Val Asp Leu Asp Val His His Gly Asn Gly Thr Gln Gln Ala Phe Tyr
            820                 825                 830

Ala Asp Pro Ser Ile Leu Tyr Ile Ser Leu His Arg Tyr Asp Glu Gly
        835                 840                 845

Asn Phe Phe Pro Gly Ser Gly Ala Pro Asn Glu Val Gly Thr Gly Leu
    850                 855                 860

Gly Glu Gly Tyr Asn Ile Asn Ile Ala Trp Thr Gly Gly Leu Asp Pro
865                 870                 875                 880

Pro Met Gly Asp Val Glu Tyr Leu Glu Ala Phe Arg Thr Ile Val Lys
                885                 890                 895

Pro Val Ala Lys Glu Phe Asp Pro Asp Met Val Leu Val Ser Ala Gly
            900                 905                 910

Phe Asp Ala Leu Glu Gly His Thr Pro Pro Leu Gly Gly Tyr Lys Val
        915                 920                 925

Thr Ala Lys Cys Phe Gly His Leu Thr Lys Gln Leu Met Thr Leu Ala
    930                 935                 940

Asp Gly Arg Val Val Leu Ala Leu Glu Gly Gly His Asp Leu Thr Ala
945                 950                 955                 960

Ile Cys Asp Ala Ser Glu Ala Cys Val Asn Ala Leu Leu Gly Asn Glu
                965                 970                 975

Leu Glu Pro Leu Ala Glu Asp Ile Leu His Gln Ser Pro Asn Met Asn
            980                 985                 990

Ala Val Ile Ser Leu Gln Lys Ile Ile Glu Ile Gln Ser Met Ser Leu
        995                 1000                1005

Lys Phe Ser
    1010
```

<210> SEQ ID NO 90
<211> LENGTH: 879
<212> TYPE: PRT
<213> ORGANISM: Homo sapiens

<400> SEQUENCE: 90

Met His Ser Met Ile Ser Ser Val Asp Val Lys Ser Glu Val Pro Val
1               5                   10                  15

Gly Leu Glu Pro Ile Ser Pro Leu Asp Leu Arg Thr Asp Leu Arg Met
            20                  25                  30

Met Met Pro Val Val Asp Pro Val Val Arg Glu Lys Gln Leu Gln Gln
        35                  40                  45

Glu Leu Leu Leu Ile Gln Gln Gln Gln Ile Gln Lys Gln Leu Leu
    50                  55                  60

Ile Ala Glu Phe Gln Lys Gln His Glu Asn Leu Thr Arg Gln His Gln
65                  70                  75                  80

Ala Gln Leu Gln Glu His Ile Lys Glu Leu Ala Ile Lys Gln Gln
                85                  90                  95

Gln Glu Leu Leu Glu Lys Glu Gln Lys Leu Glu Gln Gln Arg Gln Glu
            100                 105                 110

Gln Glu Val Glu Arg His Arg Arg Glu Gln Gln Leu Pro Pro Leu Arg
        115                 120                 125

Gly Lys Asp Arg Gly Arg Glu Arg Ala Val Ala Ser Thr Glu Val Lys
    130                 135                 140

Gln Lys Leu Gln Glu Phe Leu Leu Ser Lys Ser Ala Thr Lys Asp Thr
145                 150                 155                 160

Pro Thr Asn Gly Lys Asn His Ser Val Ser Arg His Pro Lys Leu Trp
                165                 170                 175

Tyr Thr Ala Ala His His Thr Ser Leu Asp Gln Ser Ser Pro Pro Leu
            180                 185                 190

Ser Gly Thr Ser Pro Ser Tyr Lys Tyr Thr Leu Pro Gly Ala Gln Asp
        195                 200                 205

Ala Lys Asp Asp Phe Pro Leu Arg Lys Thr Ala Ser Glu Pro Asn Leu
    210                 215                 220

Lys Val Arg Ser Arg Leu Lys Gln Lys Val Ala Glu Arg Arg Ser Ser
225                 230                 235                 240

Pro Leu Leu Arg Arg Lys Asp Gly Asn Val Val Thr Ser Phe Lys Lys
                245                 250                 255

Arg Met Phe Glu Val Thr Glu Ser Ser Val Ser Ser Ser Pro Gly
            260                 265                 270

Ser Gly Pro Ser Ser Pro Asn Asn Gly Pro Thr Gly Ser Val Thr Glu
        275                 280                 285

Asn Glu Thr Ser Val Leu Pro Pro Thr Pro His Ala Glu Gln Met Val
    290                 295                 300

Ser Gln Gln Arg Ile Leu Ile His Glu Asp Ser Met Asn Leu Leu Ser
305                 310                 315                 320

Leu Tyr Thr Ser Pro Ser Leu Pro Asn Ile Thr Leu Gly Leu Pro Ala
                325                 330                 335

Val Pro Ser Gln Leu Asn Ala Ser Asn Ser Leu Lys Glu Lys Gln Lys
            340                 345                 350

Cys Glu Thr Gln Thr Leu Arg Gln Gly Val Pro Leu Pro Gly Gln Tyr
        355                 360                 365

Gly Gly Ser Ile Pro Ala Ser Ser Ser His Pro His Val Thr Leu Glu
    370                 375                 380

```
Gly Lys Pro Pro Asn Ser Ser His Gln Ala Leu Leu Gln His Leu Leu
385                 390                 395                 400

Leu Lys Glu Gln Met Arg Gln Lys Leu Leu Val Ala Gly Gly Val
            405                 410                 415

Pro Leu His Pro Gln Ser Pro Leu Ala Thr Lys Glu Arg Ile Ser Pro
                420                 425                 430

Gly Ile Arg Gly Thr His Lys Leu Pro Arg His Arg Pro Leu Asn Arg
            435                 440                 445

Thr Gln Ser Ala Pro Leu Pro Gln Ser Thr Leu Ala Gln Leu Val Ile
    450                 455                 460

Gln Gln Gln His Gln Gln Phe Leu Glu Lys Gln Lys Gln Tyr Gln Gln
465                 470                 475                 480

Gln Ile His Met Asn Lys Leu Leu Ser Lys Ser Ile Glu Gln Leu Lys
                485                 490                 495

Gln Pro Gly Ser His Leu Glu Glu Ala Glu Glu Leu Gln Gly Asp
            500                 505                 510

Gln Ala Met Gln Glu Asp Arg Ala Pro Ser Ser Gly Asn Ser Thr Arg
    515                 520                 525

Ser Asp Ser Ser Ala Cys Val Asp Asp Thr Leu Gly Gln Val Gly Ala
530                 535                 540

Val Lys Val Lys Glu Glu Pro Val Asp Ser Asp Glu Asp Ala Gln Ile
545                 550                 555                 560

Gln Glu Met Glu Ser Gly Glu Gln Ala Ala Phe Met Gln Gln Pro Phe
                565                 570                 575

Leu Glu Pro Thr His Thr Arg Ala Leu Ser Val Arg Gln Ala Pro Leu
            580                 585                 590

Ala Ala Val Gly Met Asp Gly Leu Glu Lys His Arg Leu Val Ser Arg
            595                 600                 605

Thr His Ser Ser Pro Ala Ala Ser Val Leu Pro His Pro Ala Met Asp
    610                 615                 620

Arg Pro Leu Gln Pro Gly Ser Ala Thr Gly Ile Ala Tyr Asp Pro Leu
625                 630                 635                 640

Met Leu Lys His Gln Cys Val Cys Gly Asn Ser Thr Thr His Pro Glu
                645                 650                 655

His Ala Gly Arg Ile Gln Ser Ile Trp Ser Arg Leu Gln Glu Thr Gly
            660                 665                 670

Leu Leu Asn Lys Cys Glu Arg Ile Gln Gly Arg Lys Ala Ser Leu Glu
            675                 680                 685

Glu Ile Gln Leu Val His Ser Glu His His Ser Leu Leu Tyr Gly Thr
690                 695                 700

Asn Pro Leu Asp Gly Gln Lys Leu Asp Pro Arg Ile Leu Leu Gly Asp
705                 710                 715                 720

Asp Ser Gln Lys Phe Phe Ser Ser Leu Pro Cys Gly Gly Leu Gly Val
                725                 730                 735

Asp Ser Asp Thr Ile Trp Asn Glu Leu His Ser Ser Gly Ala Ala Arg
            740                 745                 750

Met Ala Val Gly Cys Val Ile Glu Leu Ala Ser Lys Val Ala Ser Gly
            755                 760                 765

Glu Leu Lys Asn Gly Phe Ala Val Val Arg Pro Pro Gly His His Ala
    770                 775                 780

Glu Glu Ser Thr Ala Met Gly Phe Cys Phe Phe Asn Ser Val Ala Ile
785                 790                 795                 800
```

```
Thr Ala Lys Tyr Leu Arg Asp Gln Leu Asn Ile Ser Lys Ile Leu Ile
                805                 810                 815

Val Asp Leu Asp Val His His Gly Asn Gly Thr Gln Gln Ala Phe Tyr
            820                 825                 830

Ala Asp Pro Ser Ile Leu Tyr Ile Ser Leu His Arg Tyr Asp Glu Gly
            835                 840                 845

Asn Phe Phe Pro Gly Ser Gly Ala Pro Asn Glu Val Arg Phe Ile Ser
    850                 855                 860

Leu Glu Pro His Phe Tyr Leu Tyr Leu Ser Gly Asn Cys Ile Ala
865                 870                 875

<210> SEQ ID NO 91
<211> LENGTH: 1122
<212> TYPE: PRT
<213> ORGANISM: Homo sapiens

<400> SEQUENCE: 91

Met Asn Ser Pro Asn Glu Ser Asp Gly Met Ser Gly Arg Glu Pro Ser
 1               5                  10                  15

Leu Glu Ile Leu Pro Arg Thr Ser Leu His Ser Ile Pro Val Thr Val
                20                  25                  30

Glu Val Lys Pro Val Leu Pro Arg Ala Met Pro Ser Ser Met Gly Gly
            35                  40                  45

Gly Gly Gly Gly Ser Pro Ser Pro Val Glu Leu Arg Gly Ala Leu Val
        50                  55                  60

Gly Ser Val Asp Pro Thr Leu Arg Glu Gln Gln Leu Gln Gln Glu Leu
 65                  70                  75                  80

Leu Ala Leu Lys Gln Gln Gln Gln Leu Gln Lys Gln Leu Leu Phe Ala
                85                  90                  95

Glu Phe Gln Lys Gln His Asp His Leu Thr Arg Gln His Glu Val Gln
            100                 105                 110

Leu Gln Lys His Leu Lys Gln Gln Glu Met Leu Ala Ala Lys Gln
        115                 120                 125

Gln Gln Glu Met Leu Ala Ala Lys Arg Gln Gln Glu Leu Glu Gln Gln
130                 135                 140

Arg Gln Arg Glu Gln Gln Arg Gln Glu Glu Leu Glu Lys Gln Arg Leu
145                 150                 155                 160

Glu Gln Gln Leu Leu Ile Leu Arg Asn Lys Glu Lys Ser Lys Glu Ser
                165                 170                 175

Ala Ile Ala Ser Thr Glu Val Lys Leu Arg Leu Gln Glu Phe Leu Leu
            180                 185                 190

Ser Lys Ser Lys Glu Pro Thr Pro Gly Gly Leu Asn His Ser Leu Pro
        195                 200                 205

Gln His Pro Lys Cys Trp Gly Ala His His Ala Ser Leu Asp Gln Ser
    210                 215                 220

Ser Pro Pro Gln Ser Gly Pro Pro Gly Thr Pro Ser Tyr Lys Leu
225                 230                 235                 240

Pro Leu Pro Gly Pro Tyr Asp Ser Arg Asp Asp Phe Pro Leu Arg Lys
                245                 250                 255

Thr Ala Ser Glu Pro Asn Leu Lys Val Arg Ser Arg Leu Lys Gln Lys
            260                 265                 270

Val Ala Glu Arg Arg Ser Ser Pro Leu Leu Arg Arg Lys Asp Gly Thr
        275                 280                 285

Val Ile Ser Thr Phe Lys Lys Arg Ala Val Glu Ile Thr Gly Ala Gly
    290                 295                 300
```

-continued

```
Pro Gly Ala Ser Ser Val Cys Asn Ser Ala Pro Gly Ser Gly Pro Ser
305                 310                 315                 320

Ser Pro Asn Ser Ser His Ser Thr Ile Ala Glu Asn Gly Phe Thr Gly
            325                 330                 335

Ser Val Pro Asn Ile Pro Thr Glu Met Leu Pro Gln His Arg Ala Leu
            340                 345                 350

Pro Leu Asp Ser Ser Pro Asn Gln Phe Ser Leu Tyr Thr Ser Pro Ser
            355                 360                 365

Leu Pro Asn Ile Ser Leu Gly Leu Gln Ala Thr Val Thr Val Thr Asn
370                 375                 380

Ser His Leu Thr Ala Ser Pro Lys Leu Ser Thr Gln Glu Ala Glu
385                 390                 395                 400

Arg Gln Ala Leu Gln Ser Leu Arg Gln Gly Gly Thr Leu Thr Gly Lys
                405                 410                 415

Phe Met Ser Thr Ser Ser Ile Pro Gly Cys Leu Leu Gly Val Ala Leu
                420                 425                 430

Glu Gly Asp Gly Ser Pro His Gly His Ala Ser Leu Leu Gln His Val
                435                 440                 445

Leu Leu Leu Glu Gln Ala Arg Gln Gln Ser Thr Leu Ile Ala Val Pro
450                 455                 460

Leu His Gly Gln Ser Pro Leu Val Thr Gly Glu Arg Val Ala Thr Ser
465                 470                 475                 480

Met Arg Thr Val Gly Lys Leu Pro Arg His Arg Pro Leu Ser Arg Thr
                485                 490                 495

Gln Ser Ser Pro Leu Pro Gln Ser Pro Gln Ala Leu Gln Gln Leu Val
                500                 505                 510

Met Gln Gln His Gln Gln Phe Leu Glu Lys Gln Lys Gln Gln Gln
            515                 520                 525

Leu Gln Leu Gly Lys Ile Leu Thr Lys Thr Gly Glu Leu Pro Arg Gln
530                 535                 540

Pro Thr Thr His Pro Glu Glu Thr Glu Glu Leu Thr Glu Gln Gln
545                 550                 555                 560

Glu Val Leu Leu Gly Glu Gly Ala Leu Thr Met Pro Arg Glu Gly Ser
                565                 570                 575

Thr Glu Ser Glu Ser Thr Gln Glu Asp Leu Glu Glu Asp Glu Glu
            580                 585                 590

Glu Asp Gly Glu Glu Glu Glu Asp Cys Ile Gln Val Lys Asp Glu Glu
            595                 600                 605

Gly Glu Ser Gly Ala Glu Gly Pro Asp Leu Glu Glu Pro Gly Ala
            610                 615                 620

Gly Tyr Lys Lys Leu Phe Ser Asp Ala Gln Pro Leu Gln Pro Leu Gln
625                 630                 635                 640

Val Tyr Gln Ala Pro Leu Ser Leu Ala Thr Val Pro His Gln Ala Leu
                645                 650                 655

Gly Arg Thr Gln Ser Ser Pro Ala Ala Pro Gly Gly Met Lys Ser Pro
                660                 665                 670

Pro Asp Gln Pro Val Lys His Leu Phe Thr Thr Gly Val Val Tyr Asp
            675                 680                 685

Thr Phe Met Leu Lys His Gln Cys Met Cys Gly Asn Thr His Val His
            690                 695                 700

Pro Glu His Ala Gly Arg Ile Gln Ser Ile Trp Ser Arg Leu Gln Glu
705                 710                 715                 720
```

-continued

```
Thr Gly Leu Leu Ser Lys Cys Glu Arg Ile Arg Gly Arg Lys Ala Thr
            725                 730                 735

Leu Asp Glu Ile Gln Thr Val His Ser Glu Tyr His Thr Leu Leu Tyr
            740                 745                 750

Gly Thr Ser Pro Leu Asn Arg Gln Lys Leu Asp Ser Lys Lys Leu Leu
            755                 760                 765

Gly Pro Ile Ser Gln Lys Met Tyr Ala Val Leu Pro Cys Gly Gly Ile
            770                 775                 780

Gly Val Asp Ser Asp Thr Val Trp Asn Glu Met His Ser Ser Ser Ala
785                 790                 795                 800

Val Arg Met Ala Val Gly Cys Leu Leu Glu Leu Ala Phe Lys Val Ala
                805                 810                 815

Ala Gly Glu Leu Lys Asn Gly Phe Ala Ile Arg Pro Pro Gly His
                820                 825                 830

His Ala Glu Glu Ser Thr Ala Met Gly Phe Cys Phe Phe Asn Ser Val
                835                 840                 845

Ala Ile Thr Ala Lys Leu Leu Gln Gln Lys Leu Asn Val Gly Lys Val
                850                 855                 860

Leu Ile Val Asp Trp Asp Ile His His Gly Asn Gly Thr Gln Gln Ala
865                 870                 875                 880

Phe Tyr Asn Asp Pro Ser Val Leu Tyr Ile Ser Leu His Arg Tyr Asp
                885                 890                 895

Asn Gly Asn Phe Phe Pro Gly Ser Gly Ala Pro Glu Glu Val Gly Gly
                900                 905                 910

Gly Pro Gly Val Gly Tyr Asn Val Asn Val Ala Trp Thr Gly Gly Val
                915                 920                 925

Asp Pro Pro Ile Gly Asp Val Glu Tyr Leu Thr Ala Phe Arg Thr Val
                930                 935                 940

Val Met Pro Ile Ala His Glu Phe Ser Pro Asp Val Val Leu Val Ser
945                 950                 955                 960

Ala Gly Phe Asp Ala Val Glu Gly His Leu Ser Pro Leu Gly Gly Tyr
                965                 970                 975

Ser Val Thr Ala Arg Cys Phe Gly His Leu Thr Arg Gln Leu Met Thr
                980                 985                 990

Leu Ala Gly Gly Arg Val Val Leu Ala Leu Glu Gly Gly His Asp Leu
                995                1000                1005

Thr Ala Ile Cys Asp Ala Ser Glu Ala Cys Val Ser Ala Leu Leu Ser
            1010                1015                1020

Val Glu Leu Gln Pro Leu Asp Glu Ala Val Leu Gln Gln Lys Pro Asn
1025                1030                1035                1040

Ile Asn Ala Val Ala Thr Leu Glu Lys Val Ile Glu Ile Gln Ser Lys
                1045                1050                1055

His Trp Ser Cys Val Gln Lys Phe Ala Ala Gly Leu Gly Arg Ser Leu
                1060                1065                1070

Arg Glu Ala Gln Ala Gly Glu Thr Glu Glu Ala Glu Thr Val Ser Ala
                1075                1080                1085

Met Ala Leu Leu Ser Val Gly Ala Glu Gln Ala Gln Ala Ala Ala
                1090                1095                1100

Arg Glu His Ser Pro Arg Pro Ala Glu Glu Pro Met Glu Gln Glu Pro
1105                1110                1115                1120

Ala Leu
```

<210> SEQ ID NO 92

<211> LENGTH: 282
<212> TYPE: DNA
<213> ORGANISM: Homo sapiens

<400> SEQUENCE: 92

```
ggaaatgagc tggagccact tgcagaagat attctccacc aaagcccgaa tatgaatgct    60
gttatttctt tacagaagat cattgaaatt caaagcaagt attggaagtc agtaaggatg   120
gtggctgtgc caagggggctg tgctctggct ggtgctcagt tgcaagagga gacagagacc   180
gtttctgccc tggcctccct aacagtggat gtggaacagc cctttgctca ggaagacagc   240
agaactgctg gtgagcctat ggaagaggag ccagccttgt ga                      282
```

<210> SEQ ID NO 93
<211> LENGTH: 780
<212> TYPE: PRT
<213> ORGANISM: Homo sapiens

<400> SEQUENCE: 93

```
Ala Glu Asn Glu Thr Ser Val Leu Pro Pro Thr Pro His Ala Glu Gln
 1               5                  10                  15
Met Val Ser Gln Gln Arg Ile Leu Ile His Glu Asp Ser Met Asn Leu
            20                  25                  30
Leu Ser Leu Tyr Thr Ser Pro Ser Leu Pro Asn Ile Thr Leu Gly Leu
        35                  40                  45
Pro Ala Val Pro Ser Gln Leu Asn Ala Ser Asn Ser Leu Lys Glu Lys
    50                  55                  60
Gln Lys Cys Glu Thr Gln Thr Leu Arg Gln Gly Val Pro Leu Pro Gly
65                  70                  75                  80
Gln Tyr Gly Gly Ser Ile Pro Ala Ser Ser Ser His Pro His Val Thr
                85                  90                  95
Leu Glu Gly Lys Pro Pro Asn Ser Ser His Gln Ala Leu Leu Gln His
            100                 105                 110
Leu Leu Leu Lys Glu Gln Met Arg Gln Gln Lys Leu Leu Val Ala Gly
        115                 120                 125
Gly Val Pro Leu His Pro Gln Ser Pro Leu Ala Thr Lys Glu Arg Ile
    130                 135                 140
Ser Pro Gly Ile Arg Gly Thr His Lys Leu Pro Arg His Arg Pro Leu
145                 150                 155                 160
Asn Arg Thr Gln Ser Ala Pro Leu Pro Gln Ser Thr Leu Ala Gln Leu
                165                 170                 175
Val Ile Gln Gln Gln His Gln Gln Phe Leu Glu Lys Gln Lys Gln Tyr
            180                 185                 190
Gln Gln Gln Ile His Met Asn Lys Leu Leu Ser Lys Ser Ile Glu Gln
        195                 200                 205
Leu Lys Gln Pro Gly Ser His Leu Glu Glu Ala Glu Glu Glu Leu Gln
    210                 215                 220
Gly Asp Gln Ala Met Gln Glu Asp Arg Ala Pro Ser Ser Gly Asn Ser
225                 230                 235                 240
Thr Arg Ser Asp Ser Ser Ala Cys Val Asp Asp Thr Leu Gly Gln Val
                245                 250                 255
Gly Ala Val Lys Val Lys Glu Glu Pro Val Asp Ser Asp Glu Asp Ala
            260                 265                 270
Gln Ile Gln Glu Met Glu Ser Gly Glu Gln Ala Ala Phe Met Gln Gln
        275                 280                 285
Pro Phe Leu Glu Pro Thr His Thr Arg Ala Leu Ser Val Arg Gln Ala
```

```
            290                 295                 300
Pro Leu Ala Ala Val Gly Met Asp Gly Leu Glu Lys His Arg Leu Val
305                 310                 315                 320

Ser Arg Thr His Ser Ser Pro Ala Ala Ser Val Leu Pro His Pro Ala
                325                 330                 335

Met Asp Arg Pro Leu Gln Pro Gly Ser Ala Thr Gly Ile Ala Tyr Asp
            340                 345                 350

Pro Leu Met Leu Lys His Gln Cys Val Cys Gly Asn Ser Thr Thr His
                355                 360                 365

Pro Glu His Ala Gly Arg Ile Gln Ser Ile Trp Ser Arg Leu Gln Glu
370                 375                 380

Thr Gly Leu Leu Asn Lys Cys Glu Arg Ile Gln Gly Arg Lys Ala Ser
385                 390                 395                 400

Leu Glu Glu Ile Gln Leu Val His Ser Glu His His Ser Leu Leu Tyr
                405                 410                 415

Gly Thr Asn Pro Leu Asp Gly Gln Lys Leu Asp Pro Arg Ile Leu Leu
            420                 425                 430

Gly Asp Asp Ser Gln Lys Phe Phe Ser Ser Leu Pro Cys Gly Gly Leu
            435                 440                 445

Gly Val Asp Ser Asp Thr Ile Trp Asn Glu Leu His Ser Ser Gly Ala
        450                 455                 460

Ala Arg Met Ala Val Gly Cys Val Ile Glu Leu Ala Ser Lys Val Ala
465                 470                 475                 480

Ser Gly Glu Leu Lys Asn Gly Phe Ala Val Arg Pro Pro Gly His
                485                 490                 495

His Ala Glu Glu Ser Thr Ala Met Gly Phe Cys Phe Phe Asn Ser Val
            500                 505                 510

Ala Ile Thr Ala Lys Tyr Leu Arg Asp Gln Leu Asn Ile Ser Lys Ile
        515                 520                 525

Leu Ile Val Asp Leu Asp Val His His Gly Asn Gly Thr Gln Gln Ala
        530                 535                 540

Phe Tyr Ala Asp Pro Ser Ile Leu Tyr Ile Ser Leu His Arg Tyr Asp
545                 550                 555                 560

Glu Gly Asn Phe Phe Pro Gly Ser Gly Ala Pro Asn Glu Val Gly Thr
                565                 570                 575

Gly Leu Gly Glu Gly Tyr Asn Ile Asn Ile Ala Trp Thr Gly Gly Leu
            580                 585                 590

Asp Pro Pro Met Gly Asp Val Glu Tyr Leu Glu Ala Phe Arg Thr Ile
            595                 600                 605

Val Lys Pro Val Ala Lys Glu Phe Asp Pro Asp Met Val Leu Val Ser
        610                 615                 620

Ala Gly Phe Asp Ala Leu Glu Gly His Thr Pro Pro Leu Gly Gly Tyr
625                 630                 635                 640

Lys Val Thr Ala Lys Cys Phe Gly His Leu Thr Lys Gln Leu Met Thr
                645                 650                 655

Leu Ala Asp Gly Arg Val Val Leu Ala Leu Glu Gly Gly His Asp Leu
            660                 665                 670

Thr Ala Ile Cys Asp Ala Ser Glu Ala Cys Val Asn Ala Leu Leu Gly
        675                 680                 685

Asn Glu Leu Glu Pro Leu Ala Glu Asp Ile Leu His Gln Ser Pro Asn
        690                 695                 700

Met Asn Ala Val Ile Ser Leu Gln Lys Ile Ile Glu Ile Gln Ser Lys
705                 710                 715                 720
```

```
Tyr Trp Lys Ser Val Arg Met Val Ala Val Pro Arg Gly Cys Ala Leu
            725                 730                 735

Ala Gly Ala Gln Leu Gln Glu Glu Thr Glu Thr Val Ser Ala Leu Ala
            740                 745                 750

Ser Leu Thr Val Asp Val Gln Pro Phe Ala Gln Glu Asp Ser Arg
            755                 760                 765

Thr Ala Gly Glu Pro Met Glu Glu Pro Ala Leu
            770                 775                 780

<210> SEQ ID NO 94
<211> LENGTH: 3650
<212> TYPE: DNA
<213> ORGANISM: Homo sapiens
<220> FEATURE:
<221> NAME/KEY: CDS
<222> LOCATION: (1)..(2340)

<400> SEQUENCE: 94 gct gaa aat gag act tcg gtt ttg ccc cct acc cct cat gcc gag caa      48
Ala Glu Asn Glu Thr Ser Val Leu Pro Pro Thr Pro His Ala Glu Gln
  1               5                  10                  15 atg gtt tca cag caa cgc att cta att cat gaa gat tcc atg aac ctg      96
Met Val Ser Gln Gln Arg Ile Leu Ile His Glu Asp Ser Met Asn Leu
             20                  25                  30 cta agt ctt tat acc tct cct tct ttg ccc aac att acc ttg ggg ctt     144
Leu Ser Leu Tyr Thr Ser Pro Ser Leu Pro Asn Ile Thr Leu Gly Leu
         35                  40                  45 ccc gca gtg cca tcc cag ctc aat gct tcg aat tca ctc aaa gaa aag     192
Pro Ala Val Pro Ser Gln Leu Asn Ala Ser Asn Ser Leu Lys Glu Lys
     50                  55                  60 cag aag tgt gag acg cag acg ctt agg caa ggt gtt cct ctg cct ggg     240
Gln Lys Cys Glu Thr Gln Thr Leu Arg Gln Gly Val Pro Leu Pro Gly
 65                  70                  75                  80 cag tat gga ggc agc atc ccg gca tct tcc agc cac cct cat gtt act     288
Gln Tyr Gly Gly Ser Ile Pro Ala Ser Ser Ser His Pro His Val Thr
                 85                  90                  95 tta gag gga aag cca ccc aac agc agc cac cag gct ctc ctg cag cat     336
Leu Glu Gly Lys Pro Pro Asn Ser Ser His Gln Ala Leu Leu Gln His
            100                 105                 110 tta tta ttg aaa gaa caa atg cga cag caa aag ctt ctt gta gct ggt     384
Leu Leu Leu Lys Glu Gln Met Arg Gln Gln Lys Leu Leu Val Ala Gly
        115                 120                 125 gga gtt ccc tta cat cct cag tct ccc ttg gca aca aaa gag aga att     432
Gly Val Pro Leu His Pro Gln Ser Pro Leu Ala Thr Lys Glu Arg Ile
    130                 135                 140 tca cct ggc att aga ggt acc cac aaa ttg ccc cgt cac aga ccc ctg     480
Ser Pro Gly Ile Arg Gly Thr His Lys Leu Pro Arg His Arg Pro Leu
145                 150                 155                 160 aac cga acc cag tct gca cct ttg cct cag agc acg ttg gct cag ctg     528
Asn Arg Thr Gln Ser Ala Pro Leu Pro Gln Ser Thr Leu Ala Gln Leu
                165                 170                 175 gtc att caa cag caa cac cag caa ttc ttg gag aag cag aag caa tac     576
Val Ile Gln Gln Gln His Gln Gln Phe Leu Glu Lys Gln Lys Gln Tyr
            180                 185                 190 cag cag cag atc cac atg aac aaa ctg ctt tcg aaa tct att gaa caa     624
Gln Gln Gln Ile His Met Asn Lys Leu Leu Ser Lys Ser Ile Glu Gln
        195                 200                 205 ctg aag caa cca ggc agt cac ctt gag gaa gca gag gaa gag ctt cag     672
Leu Lys Gln Pro Gly Ser His Leu Glu Glu Ala Glu Glu Glu Leu Gln
    210                 215                 220
```

-continued

| | |
|---|---|
| ggg gac cag gcg atg cag gaa gac aga gcg ccc tct agt ggc aac agc<br>Gly Asp Gln Ala Met Gln Glu Asp Arg Ala Pro Ser Ser Gly Asn Ser<br>225                         230                     235                   240 | 720 |
| act agg agc gac agc agt gct tgt gtg gat gac aca ctg gga caa gtt<br>Thr Arg Ser Asp Ser Ser Ala Cys Val Asp Asp Thr Leu Gly Gln Val<br>                     245                   250                     255 | 768 |
| ggg gct gtg aag gtc aag gag gaa cca gtg gac agt gat gaa gat gct<br>Gly Ala Val Lys Val Lys Glu Glu Pro Val Asp Ser Asp Glu Asp Ala<br>       260                   265                   270 | 816 |
| cag atc cag gaa atg gaa tct ggg gag cag gct gct ttt atg caa cag<br>Gln Ile Gln Glu Met Glu Ser Gly Glu Gln Ala Ala Phe Met Gln Gln<br>275                     280                     285 | 864 |
| cct ttc ctg gaa ccc acg cac aca cgt gcg ctc tct gtg cgc caa gct<br>Pro Phe Leu Glu Pro Thr His Thr Arg Ala Leu Ser Val Arg Gln Ala<br>              290                   295                   300 | 912 |
| ccg ctg gct gcg gtt ggc atg gat gga tta gag aaa cac cgt ctc gtc<br>Pro Leu Ala Ala Val Gly Met Asp Gly Leu Glu Lys His Arg Leu Val<br>305                     310                   315                  320 | 960 |
| tcc agg act cac tct tcc cct gct gcc tct gtt tta cct cac ccg gca<br>Ser Arg Thr His Ser Ser Pro Ala Ala Ser Val Leu Pro His Pro Ala<br>                     325                   330                   335 | 1008 |
| atg gac cgc ccc ctc cag cct ggc tct gca act gga att gcc tat gac<br>Met Asp Arg Pro Leu Gln Pro Gly Ser Ala Thr Gly Ile Ala Tyr Asp<br>              340                   345                   350 | 1056 |
| ccc ttg atg ctg aaa cac cag tgc gtt tgt ggc aat tcc acc acc cac<br>Pro Leu Met Leu Lys His Gln Cys Val Cys Gly Asn Ser Thr Thr His<br>       355                   360                   365 | 1104 |
| cct gag cat gct gga cga ata cag agt atc tgg tca cga ctg caa gaa<br>Pro Glu His Ala Gly Arg Ile Gln Ser Ile Trp Ser Arg Leu Gln Glu<br>370                     375                     380 | 1152 |
| act ggg ctg cta aat aaa tgt gag cga att caa ggt cga aaa gcc agc<br>Thr Gly Leu Leu Asn Lys Cys Glu Arg Ile Gln Gly Arg Lys Ala Ser<br>385                     390                     395                  400 | 1200 |
| ctg gag gaa ata cag ctt gtt cat tct gaa cat cac tca ctg ttg tat<br>Leu Glu Glu Ile Gln Leu Val His Ser Glu His His Ser Leu Leu Tyr<br>                     405                   410                   415 | 1248 |
| ggc acc aac ccc ctg gac gga cag aag ctg gac ccc agg ata ctc cta<br>Gly Thr Asn Pro Leu Asp Gly Gln Lys Leu Asp Pro Arg Ile Leu Leu<br>              420                   425                   430 | 1296 |
| ggt gat gac tct caa aag ttt ttt tcc tca tta cct tgt ggt gga ctt<br>Gly Asp Asp Ser Gln Lys Phe Phe Ser Ser Leu Pro Cys Gly Gly Leu<br>             435                   440                   445 | 1344 |
| ggg gtg gac agt gac acc att tgg aat gag cta cac tcg tcc ggt gct<br>Gly Val Asp Ser Asp Thr Ile Trp Asn Glu Leu His Ser Ser Gly Ala<br>450                     455                     460 | 1392 |
| gca cgc atg gct gtt ggc tgt gtc atc gag ctg gct tcc aaa gtg gcc<br>Ala Arg Met Ala Val Gly Cys Val Ile Glu Leu Ala Ser Lys Val Ala<br>465                     470                   475                  480 | 1440 |
| tca gga gag ctg aag aat ggg ttt gct gtt gtg agg ccc cct ggc cat<br>Ser Gly Glu Leu Lys Asn Gly Phe Ala Val Val Arg Pro Pro Gly His<br>                     485                   490                   495 | 1488 |
| cac gct gaa gaa tcc aca gcc atg ggg ttc tgc ttt ttt aat tca gtt<br>His Ala Glu Glu Ser Thr Ala Met Gly Phe Cys Phe Phe Asn Ser Val<br>              500                   505                   510 | 1536 |
| gca att acc gcc aaa tac ttg aga gac caa cta aat ata agc aag ata<br>Ala Ile Thr Ala Lys Tyr Leu Arg Asp Gln Leu Asn Ile Ser Lys Ile<br>       515                   520                   525 | 1584 |
| ttg att gta gat ctg gat gtt cac cat gga aac ggt acc cag cag gcc<br>Leu Ile Val Asp Leu Asp Val His His Gly Asn Gly Thr Gln Gln Ala | 1632 |

```
                   530                 535                 540
ttt tat gct gac ccc agc atc ctg tac att tca ctc cat cgc tat gat    1680
Phe Tyr Ala Asp Pro Ser Ile Leu Tyr Ile Ser Leu His Arg Tyr Asp
545                 550                 555                 560 gaa ggg aac ttt ttc cct ggc agt gga gcc cca aat gag gtt gga aca    1728
Glu Gly Asn Phe Phe Pro Gly Ser Gly Ala Pro Asn Glu Val Gly Thr
                565                 570                 575 ggc ctt gga gaa ggg tac aat ata aat att gcc tgg aca ggt ggc ctt    1776
Gly Leu Gly Glu Gly Tyr Asn Ile Asn Ile Ala Trp Thr Gly Gly Leu
            580                 585                 590 gat cct ccc atg gga gat gtt gag tac ctt gaa gca ttc agg acc atc    1824
Asp Pro Pro Met Gly Asp Val Glu Tyr Leu Glu Ala Phe Arg Thr Ile
        595                 600                 605 gtg aag cct gtg gcc aaa gag ttt gat cca gac atg gtc tta gta tct    1872
Val Lys Pro Val Ala Lys Glu Phe Asp Pro Asp Met Val Leu Val Ser
    610                 615                 620 gct gga ttt gat gca ttg gaa ggc cac acc cct cct cta gga ggg tac    1920
Ala Gly Phe Asp Ala Leu Glu Gly His Thr Pro Pro Leu Gly Gly Tyr
625                 630                 635                 640 aaa gtg acg gca aaa tgt ttt ggt cat ttg acg aag caa ttg atg aca    1968
Lys Val Thr Ala Lys Cys Phe Gly His Leu Thr Lys Gln Leu Met Thr
                645                 650                 655 ttg gct gat gga cgt gtg gtg ttg gct cta gaa gga gga cat gat ctc    2016
Leu Ala Asp Gly Arg Val Val Leu Ala Leu Glu Gly Gly His Asp Leu
            660                 665                 670 aca gcc atc tgt gat gca tca gaa gcc tgt gta aat gcc ctt cta gga    2064
Thr Ala Ile Cys Asp Ala Ser Glu Ala Cys Val Asn Ala Leu Leu Gly
        675                 680                 685 aat gag ctg gag cca ctt gca gaa gat att ctc cac caa agc ccg aat    2112
Asn Glu Leu Glu Pro Leu Ala Glu Asp Ile Leu His Gln Ser Pro Asn
    690                 695                 700 atg aat gct gtt att tct tta cag aag atc att gaa att caa agc aag    2160
Met Asn Ala Val Ile Ser Leu Gln Lys Ile Ile Glu Ile Gln Ser Lys
705                 710                 715                 720 tat tgg aag tca gta agg atg gtg gct gtg cca agg ggc tgt gct ctg    2208
Tyr Trp Lys Ser Val Arg Met Val Ala Val Pro Arg Gly Cys Ala Leu
                725                 730                 735 gct ggt gct cag ttg caa gag gag aca gag acc gtt tct gcc ctg gcc    2256
Ala Gly Ala Gln Leu Gln Glu Glu Thr Glu Thr Val Ser Ala Leu Ala
            740                 745                 750 tcc cta aca gtg gat gtg gaa cag ccc ttt gct cag gaa gac agc aga    2304
Ser Leu Thr Val Asp Val Glu Gln Pro Phe Ala Gln Glu Asp Ser Arg
        755                 760                 765 act gct ggt gag cct atg gaa gag gag cca gcc ttg tgaagtgcca         2350
Thr Ala Gly Glu Pro Met Glu Glu Glu Pro Ala Leu
    770                 775                 780 agtcccctc  tgatatttcc  tgtgtgtgac  atcattgtgt  atccccccac  cccagtaccc    2410
tcagacatgt  cttgtctgct  gcctgggtgg  cacagattca  atggaacata  aacactgggc    2470
acaaaattct  gaacagcagc  ttcacttgtt  ctttggatgg  acttgaaagg  gcattaaaga    2530
ttccttaaac  gtaaccgctg  tgattctaga  gttacagtaa  accacgattg  gaagaaactg    2590
cttccagcat  gctttttaata tgctgggtga  cccactccta  gacaccaagt  ttgaactaga    2650
aacattcagt  acagcactag  atattgttaa  tttcagaagc  tatgacagcc  agtgaaattt    2710
tgggcaaaac  ctgagacata  gtcattcctg  acattctgat  cagcttttt   tggggtaatt    2770 tgttttcaa   acagtcttaa  cttgttaca   agatttgctt  ttagctatga  acggatcgta    2830
attccaccca  gaatgtaatg  tttcttgttt  gtttgttttg  ttttgttagg  gttttttct     2890
```

```
caactttaac acacagttca actgttccta gtaaaagttc aagatggagg aactagcatg      2950 aggcttttt  cagtatctcg aagtccaaat gccaaggaa  cctcacacac tgtttgtaat      3010
ggtgcaatat tttatatcac ttttttttaa acatccccaa catctttgtg ttctcacaca      3070
caggcaattt gcaatgttgc aattgtgttg gagaatgaag tcccccccacc tcccagccac     3130 acacacatcc tttgttctca tgacagtagg tctgagcaaa tgttccacca agcattttca     3190
gtgtctttga aaagcacgta acttttcaaa ggtggtctta atttgctgca tatctatcaa     3250
ggacttattc actcaccttt cctttctgc  cctctatcaa ttgatttctt cttaccttc      3310 atcattcatt ccttcctta  gaaaaactga agattaccca taatctcctc ttattacttg     3370
agggccttga ctatttagtt tattttgttt actttacagg ttaacacagt tgttttgtct     3430
gattgcattt tattaactgt gaagccgttg aaatgaatat cacttaagca acgttgctaa     3490
atttctatgt gtttgaaatg tgttaatgaa ggcactgctt atttgtagtc accttgaact     3550 gacttaaccct agaagctgtg ccttcttgtg aaaaaaaaaa aaaaaaaaaa aaaaaaaaa     3610 aaaaaaaaaa aaaaaaaaaa aaaaaaaaa  aaaaaaaaa                            3650

<210> SEQ ID NO 95
<211> LENGTH: 495
<212> TYPE: PRT
<213> ORGANISM: Homo sapiens

<400> SEQUENCE: 95

Met His Ser Met Ile Ser Ser Val Asp Val Lys Ser Glu Val Pro Val
 1               5                  10                  15

Gly Leu Glu Pro Ile Ser Pro Leu Asp Leu Arg Thr Asp Leu Arg Met
            20                  25                  30

Met Met Pro Val Val Asp Pro Val Val Arg Glu Lys Gln Leu Gln Gln
        35                  40                  45

Glu Leu Leu Leu Ile Gln Gln Gln Gln Ile Gln Lys Gln Leu Leu
    50                  55                  60

Ile Ala Glu Phe Gln Lys Gln His Glu Asn Leu Thr Arg Gln His Gln
65                  70                  75                  80

Ala Gln Leu Gln Glu His Ile Lys Leu Gln Gln Glu Leu Leu Ala Ile
                85                  90                  95

Lys Gln Gln Gln Glu Leu Leu Glu Lys Glu Gln Lys Leu Glu Gln Gln
            100                 105                 110

Arg Gln Glu Gln Glu Val Glu Arg His Arg Glu Gln Gln Leu Pro
        115                 120                 125

Pro Leu Arg Gly Lys Asp Arg Gly Arg Glu Arg Ala Val Ala Ser Thr
    130                 135                 140

Glu Val Lys Gln Lys Leu Gln Glu Phe Leu Leu Ser Lys Ser Ala Thr
145                 150                 155                 160

Lys Asp Thr Pro Thr Asn Gly Lys Asn His Ser Val Ser Arg His Pro
                165                 170                 175

Lys Leu Trp Tyr Thr Ala Ala His His Thr Ser Leu Asp Gln Ser Ser
            180                 185                 190

Pro Pro Leu Ser Gly Thr Ser Pro Ser Tyr Lys Tyr Thr Leu Pro Gly
        195                 200                 205

Ala Gln Asp Ala Lys Asp Asp Phe Pro Leu Arg Lys Thr Ala Ser Glu
    210                 215                 220

Pro Asn Leu Lys Val Arg Ser Arg Leu Lys Gln Lys Val Ala Glu Arg
225                 230                 235                 240
```

```
Arg Ser Ser Pro Leu Leu Arg Arg Lys Asp Gly Asn Val Val Thr Ser
                245                 250                 255

Phe Lys Lys Arg Met Phe Glu Val Thr Glu Ser Ser Val Ser Ser Ser
                260                 265                 270

Ser Pro Gly Ser Gly Pro Ser Ser Pro Asn Asn Gly Pro Thr Gly Ser
                275                 280                 285

Val Thr Glu Asn Glu Thr Ser Val Leu Pro Pro Thr Pro His Ala Glu
            290                 295                 300

Gln Met Val Ser Gln Gln Arg Ile Leu Ile His Glu Asp Ser Met Asn
305                 310                 315                 320

Leu Leu Ser Leu Tyr Thr Ser Pro Ser Leu Pro Asn Ile Thr Leu Gly
                325                 330                 335

Leu Pro Ala Val Pro Ser Gln Leu Ala Ser Asn Ser Leu Lys Glu
                340                 345                 350

Lys Gln Lys Cys Glu Thr Gln Thr Leu Arg Gln Gly Val Pro Leu Pro
                355                 360                 365

Gly Gln Tyr Gly Gly Ser Ile Pro Ala Ser Ser Ser His Pro His Val
            370                 375                 380

Thr Leu Glu Gly Lys Pro Pro Asn Ser Ser His Gln Ala Leu Leu Gln
385                 390                 395                 400

His Leu Leu Leu Lys Glu Gln Met Arg Gln Gln Lys Leu Leu Val Ala
                405                 410                 415

Gly Gly Val Pro Leu His Pro Gln Ser Pro Leu Ala Thr Lys Glu Arg
                420                 425                 430

Ile Ser Pro Gly Ile Arg Gly Thr His Lys Leu Pro Arg His Arg Pro
                435                 440                 445

Leu Asn Arg Thr Gln Ser Ala Pro Leu Pro Gln Ser Thr Leu Ala Gln
                450                 455                 460

Leu Val Ile Gln Gln Gln His Gln Gln Phe Leu Glu Lys Gln Lys Gln
465                 470                 475                 480

Tyr Gln Gln Gln Ile His Met Asn Lys Glu Leu Pro Met Thr Pro
                485                 490                 495

<210> SEQ ID NO 96
<211> LENGTH: 3391
<212> TYPE: DNA
<213> ORGANISM: Homo sapiens
<220> FEATURE:
<221> NAME/KEY: CDS
<222> LOCATION: (307)..(1791)

<400> SEQUENCE: 96
ccacgcgtcc gtaggagaag ggcaccggct ggagccactt gcaggactga gggttttgc      60 aacaaaaccc tagcagcctg aagaactcta agccaggttt aattggtttc ttttctcgt     120 gggtagactt aataatttc tacgtattct gacaaagaaa taaccccgaa gcacgttcct     180
atttcccacc tgcttgtagt ttccgggata acctaaactc cagagagcta tagcatccac     240
tctgtccttt ctgctttgca cacagatggg gtggctggac gagagcagct cttggctcag     300 caaaga atg cac agt atg atc agc tca gtg gat gtg aag tca gaa gtt         348
       Met His Ser Met Ile Ser Ser Val Asp Val Lys Ser Glu Val
         1               5                  10 cct gtg ggc ctg gag ccc atc tca cct tta gac cta agg aca gac ctc         396
Pro Val Gly Leu Glu Pro Ile Ser Pro Leu Asp Leu Arg Thr Asp Leu
 15                  20                  25                  30 agg atg atg atg ccc gtg gtg gac cct gtt gtc cgt gag aag caa ttg         444
```

```
                Arg Met Met Met Pro Val Val Asp Pro Val Val Arg Glu Lys Gln Leu
                                35                  40                  45 cag cag gaa tta ctt ctt atc cag cag cag caa caa atc cag aag cag              492
Gln Gln Glu Leu Leu Leu Ile Gln Gln Gln Gln Gln Ile Gln Lys Gln
            50                  55                  60 ctt ctg ata gca gag ttt cag aaa cag cat gag aac ttg aca cgg cag              540
Leu Leu Ile Ala Glu Phe Gln Lys Gln His Glu Asn Leu Thr Arg Gln
        65                  70                  75 cac cag gct cag ctt cag gag cat atc aag ttg caa cag gaa ctt cta              588
His Gln Ala Gln Leu Gln Glu His Ile Lys Leu Gln Gln Glu Leu Leu
    80                  85                  90 gcc ata aaa cag caa caa gaa ctc cta gaa aag gag cag aaa ctg gag              636
Ala Ile Lys Gln Gln Gln Glu Leu Leu Glu Lys Glu Gln Lys Leu Glu
95                  100                 105                 110 cag cag agg caa gaa cag gaa gta gag agg cat cgc aga gaa cag cag              684
Gln Gln Arg Gln Glu Gln Glu Val Glu Arg His Arg Arg Glu Gln Gln
                115                 120                 125 ctt cct cct ctc aga ggc aaa gat aga gga cga gaa agg gca gtg gca              732
Leu Pro Pro Leu Arg Gly Lys Asp Arg Gly Arg Glu Arg Ala Val Ala
            130                 135                 140 agt aca gaa gta aag cag aag ctt caa gag ttc cta ctg agt aaa tca              780
Ser Thr Glu Val Lys Gln Lys Leu Gln Glu Phe Leu Leu Ser Lys Ser
        145                 150                 155 gca acg aaa gac act cca act aat gga aaa aat cat tcc gtg agc cgc              828
Ala Thr Lys Asp Thr Pro Thr Asn Gly Lys Asn His Ser Val Ser Arg
    160                 165                 170 cat ccc aag ctc tgg tac acg gct gcc cac cac aca tca ttg gat caa              876
His Pro Lys Leu Trp Tyr Thr Ala Ala His His Thr Ser Leu Asp Gln
175                 180                 185                 190 agc tct cca ccc ctt agt gga aca tct cca tcc tac aag tac aca tta              924
Ser Ser Pro Pro Leu Ser Gly Thr Ser Pro Ser Tyr Lys Tyr Thr Leu
                195                 200                 205 cca gga gca caa gat gca aag gat gat ttc ccc ctt cga aaa act gcc              972
Pro Gly Ala Gln Asp Ala Lys Asp Asp Phe Pro Leu Arg Lys Thr Ala
            210                 215                 220 tct gag ccc aac ttg aag gtg cgg tcc agg tta aaa cag aaa gtg gca             1020
Ser Glu Pro Asn Leu Lys Val Arg Ser Arg Leu Lys Gln Lys Val Ala
        225                 230                 235 gag agg aga agc agc ccc tta ctc agg cgg aag gat gga aat gtt gtc             1068
Glu Arg Arg Ser Ser Pro Leu Leu Arg Arg Lys Asp Gly Asn Val Val
    240                 245                 250 act tca ttc aag aag cga atg ttt gag gtg aca gaa tcc tca gtc agt             1116
Thr Ser Phe Lys Lys Arg Met Phe Glu Val Thr Glu Ser Ser Val Ser
255                 260                 265                 270 agc agt tct cca ggc tct ggt ccc agt tca cca aac aat ggg cca act             1164
Ser Ser Ser Pro Gly Ser Gly Pro Ser Ser Pro Asn Asn Gly Pro Thr
                275                 280                 285 gga agt gtt act gaa aat gag act tcg gtt ttg ccc cct acc cct cat             1212
Gly Ser Val Thr Glu Asn Glu Thr Ser Val Leu Pro Pro Thr Pro His
            290                 295                 300 gcc gag caa atg gtt tca cag caa cgc att cta att cat gaa gat tcc             1260
Ala Glu Gln Met Val Ser Gln Gln Arg Ile Leu Ile His Glu Asp Ser
        305                 310                 315 atg aac ctg cta agt ctt tat acc tct cct tct ttg ccc aac att acc             1308
Met Asn Leu Leu Ser Leu Tyr Thr Ser Pro Ser Leu Pro Asn Ile Thr
    320                 325                 330 ttg ggg ctt ccc gca gtg cca tcc cag ctc aat gct tcg aat tca ctc             1356
Leu Gly Leu Pro Ala Val Pro Ser Gln Leu Asn Ala Ser Asn Ser Leu
335                 340                 345                 350
```

|  |  |  |  |  |  |  |  |  |  |  |  |  |  |  |  |
|---|---|---|---|---|---|---|---|---|---|---|---|---|---|---|---|
| aaa | gaa | aag | cag | aag | tgt | gag | acg | cag | acg | ctt | agg | caa | ggt | gtt | cct | 1404 |
| Lys | Glu | Lys | Gln | Lys | Cys | Glu | Thr | Gln | Thr | Leu | Arg | Gln | Gly | Val | Pro |
|  |  |  |  | 355 |  |  |  | 360 |  |  |  |  | 365 |  |  |

```
aaa gaa aag cag aag tgt gag acg cag acg ctt agg caa ggt gtt cct    1404
Lys Glu Lys Gln Lys Cys Glu Thr Gln Thr Leu Arg Gln Gly Val Pro
                355                 360                 365 ctg cct ggg cag tat gga ggc agc atc ccg gca tct tcc agc cac cct    1452
Leu Pro Gly Gln Tyr Gly Gly Ser Ile Pro Ala Ser Ser Ser His Pro
    370                 375                 380 cat gtt act tta gag gga aag cca ccc aac agc agc cac cag gct ctc    1500
His Val Thr Leu Glu Gly Lys Pro Pro Asn Ser Ser His Gln Ala Leu
385                 390                 395 ctg cag cat tta tta ttg aaa gaa caa atg cga cag caa aag ctt ctt    1548
Leu Gln His Leu Leu Leu Lys Glu Gln Met Arg Gln Gln Lys Leu Leu
    400                 405                 410 gta gct ggt gga gtt ccc tta cat cct cag tct ccc ttg gca aca aaa    1596
Val Ala Gly Gly Val Pro Leu His Pro Gln Ser Pro Leu Ala Thr Lys
415                 420                 425                 430 gag aga att tca cct ggc att aga ggt acc cac aaa ttg ccc cgt cac    1644
Glu Arg Ile Ser Pro Gly Ile Arg Gly Thr His Lys Leu Pro Arg His
                435                 440                 445 aga ccc ctg aac cga acc cag tct gca cct ttg cct cag agc acg ttg    1692
Arg Pro Leu Asn Arg Thr Gln Ser Ala Pro Leu Pro Gln Ser Thr Leu
            450                 455                 460 gct cag ctg gtc att caa cag caa cac cag caa ttc ttg gag aag cag    1740
Ala Gln Leu Val Ile Gln Gln Gln His Gln Gln Phe Leu Glu Lys Gln
        465                 470                 475 aag caa tac cag cag cag atc cac atg aac aaa gaa ttg cct atg acc    1788
Lys Gln Tyr Gln Gln Gln Ile His Met Asn Lys Glu Leu Pro Met Thr
    480                 485                 490 cct tgatgctgaa acaccagtgc gtttgtggca attccaccac ccaccctgag         1841
Pro
495 catgctggac gaatacagag tatctggtca cgactgcaag aaactgggct gctaaataaa   1901 tgtgagcgaa ttcaaggtcg aaaagccagc ctggaggaaa tacagcttgt tcattctgaa   1961 catcactcac tgttgtatgg caccaacccc ctggacggac agaagctgga ccccaggata   2021 ctcctaggtg atgactctca aaagtttttt tcctcattac cttgtggtgg acttggggtg   2081 gacagtgaca ccatttggaa tgagctacac tcgtccggtg ctgcacgcat ggctgttggc   2141 tgtgtcatcg agctggcttc caaagtggcc tcaggagagc tgaaggtgag gtccgggttg   2201 cattaagtgt gggaaatcca gagaagaaac tgaaacagag atgttgttat gtgggaattg   2261 cggggagtgt ggcgtggtaa taaaggaag ggcagaagga agagggtaga gatggccact    2321 aaggtgtgat aataactcat ctgtaggcag ggagcagctc atcctgctct cagggccttc   2381 ttctgcctga gaacactctg cagtcagggc ccaccggtgt gcatgtaaga gcacagagat   2441 aataagcaaa gctatggttc aggttaaaaa tacctttagt atatacatgt ctgtcatgcc   2501 atcctgagat tctcttttga ggcaattta aaaatatgat tactgagaag tgtgtataag    2561 ctcagaatac cacccagaga gagggaggca gagaaaggta ataccagac gggaaggatt    2621 gggaggagga aggaaattgt tgattagaag ggtaatgatc cagagtgtgt ttttccatga   2681 aagaacttaa aaaatgagct atgctttatt gttcttttct ttttatggtc tcttcttttc   2741 tacatcgtat gaaaagaaca atgtccaaac cccagcgttt cccagtctaa acaatttata   2801 aaagctagag acctgacaga cgttgacatt ttatttggta ttttaacagt gctatttaaa   2861 ggtacgccat gtgcgtcttg aatgcagtta ccccaataaa ctttgttggt gctaacacgg   2921 ccttttaatg cactagttca cacacttcat gacgcaatct gggtcgtgat tgattcggta   2981 ttttttagcaa ttgcggggct tagggaaata tattatgacc aataacatat gcactgtgag   3041
```

```
tttgtgaaa ccaagataaa ataattagga ttacttttct ttatgtctag tgaatttta      3101 ttcaattaca tgggactctt ccagttgtga ttaaaaatgt ggagtaggaa tgtgcacttc      3161
acaatgcaac gtttgtccaa gaagtcttta ctcttaactc tttaaagagt cagagcctac      3221
ggaaatataa ttttgatagg gtgagctcta tttaaaaagt agatgtgcct gtatatattt      3281
gacataagta gtattaggac attgctcatc tcaggggata tatggggtca ttaatgtggt      3341
gcttactctt cagtctttac ctttgaaaat gagcaaaaaa aaaaaaaaaa                3391

<210> SEQ ID NO 97
<211> LENGTH: 3186
<212> TYPE: DNA
<213> ORGANISM: Homo sapiens
<220> FEATURE:
<221> NAME/KEY: CDS
<222> LOCATION: (151)..(3183)

<400> SEQUENCE: 97
ggggaagaga ggcacagaca cagataggag aagggcaccg gctggagcca cttgcaggac       60
tgagggtttt tgcaacaaaa ccctagcagc ctgaagaact ctaagccaga tggggtggct      120
ggacgagagc agctcttggc tcagcaaaga atg cac agt atg atc agc tca gtg      174
                                   Met His Ser Met Ile Ser Ser Val
                                    1               5 gat gtg aag tca gaa gtt cct gtg ggc ctg gag ccc atc tca cct tta      222
Asp Val Lys Ser Glu Val Pro Val Gly Leu Glu Pro Ile Ser Pro Leu
         10                  15                  20 gac cta agg aca gac ctc agg atg atg atg ccc gtg gtg gac cct gtt      270
Asp Leu Arg Thr Asp Leu Arg Met Met Met Pro Val Val Asp Pro Val
 25                  30                  35                  40 gtc cgt gag aag caa ttg cag cag gaa tta ctt ctt atc cag cag cag      318
Val Arg Glu Lys Gln Leu Gln Gln Glu Leu Leu Leu Ile Gln Gln Gln
                 45                  50                  55 caa caa atc cag aag cag ctt ctg ata gca gag ttt cag aaa cag cat      366
Gln Gln Ile Gln Lys Gln Leu Leu Ile Ala Glu Phe Gln Lys Gln His
             60                  65                  70 gag aac ttg aca cgg cag cac cag gct cag ctt cag gag cat atc aag      414
Glu Asn Leu Thr Arg Gln His Gln Ala Gln Leu Gln Glu His Ile Lys
         75                  80                  85 gaa ctt cta gcc ata aaa cag caa caa gaa ctc cta gaa aag gag cag      462
Glu Leu Leu Ala Ile Lys Gln Gln Gln Glu Leu Leu Glu Lys Glu Gln
     90                  95                 100 aaa ctg gag cag cag agg caa gaa cag gaa gta gag agg cat cgc aga      510
Lys Leu Glu Gln Gln Arg Gln Glu Gln Glu Val Glu Arg His Arg Arg
105                 110                 115                 120 gaa cag cag ctt cct cct ctc aga ggc aaa gat aga gga cga gaa agg      558
Glu Gln Gln Leu Pro Pro Leu Arg Gly Lys Asp Arg Gly Arg Glu Arg
                125                 130                 135 gca gtg gca agt aca gaa gta aag cag aag ctt caa gag ttc cta ctg      606
Ala Val Ala Ser Thr Glu Val Lys Gln Lys Leu Gln Glu Phe Leu Leu
            140                 145                 150 agt aaa tca gca acg aaa gac act cca act aat gga aaa aat cat tcc      654
Ser Lys Ser Ala Thr Lys Asp Thr Pro Thr Asn Gly Lys Asn His Ser
        155                 160                 165 gtg agc cgc cat ccc aag ctc tgg tac acg gct gcc cac cac aca tca      702
Val Ser Arg His Pro Lys Leu Trp Tyr Thr Ala Ala His His Thr Ser
    170                 175                 180 ttg gat caa agc tct cca ccc ctt agt gga aca tct cca tcc tac aag      750
Leu Asp Gln Ser Ser Pro Pro Leu Ser Gly Thr Ser Pro Ser Tyr Lys
185                 190                 195                 200
```

-continued

| | |
|---|---|
| tac aca tta cca gga gca caa gat gca aag gat gat ttc ccc ctt cga<br>Tyr Thr Leu Pro Gly Ala Gln Asp Ala Lys Asp Asp Phe Pro Leu Arg<br>                   205                 210                 215 | 798 |
| aaa act gcc tct gag ccc aac ttg aag gtg cgg tcc agg tta aaa cag<br>Lys Thr Ala Ser Glu Pro Asn Leu Lys Val Arg Ser Arg Leu Lys Gln<br>           220                 225                 230 | 846 |
| aaa gtg gca gag agg aga agc agc ccc tta ctc agg cgg aag gat gga<br>Lys Val Ala Glu Arg Arg Ser Ser Pro Leu Leu Arg Arg Lys Asp Gly<br>               235                 240                 245 | 894 |
| aat gtt gtc act tca ttc aag aag cga atg ttt gag gtg aca gaa tcc<br>Asn Val Val Thr Ser Phe Lys Lys Arg Met Phe Glu Val Thr Glu Ser<br>           250                 255                 260 | 942 |
| tca gtc agt agc agt tct cca ggc tct ggt ccc agt tca cca aac aat<br>Ser Val Ser Ser Ser Ser Pro Gly Ser Gly Pro Ser Ser Pro Asn Asn<br>265                 270                 275                 280 | 990 |
| ggg cca act gga agt gtt act gaa aat gag act tcg gtt ttg ccc cct<br>Gly Pro Thr Gly Ser Val Thr Glu Asn Glu Thr Ser Val Leu Pro Pro<br>               285                 290                 295 | 1038 |
| acc cct cat gcc gag caa atg gtt tca cag caa cgc att cta att cat<br>Thr Pro His Ala Glu Gln Met Val Ser Gln Gln Arg Ile Leu Ile His<br>           300                 305                 310 | 1086 |
| gaa gat tcc atg aac ctg cta agt ctt tat acc tct cct tct ttg ccc<br>Glu Asp Ser Met Asn Leu Leu Ser Leu Tyr Thr Ser Pro Ser Leu Pro<br>               315                 320                 325 | 1134 |
| aac att acc ttg ggg ctt ccc gca gtg cca tcc cag ctc aat gct tcg<br>Asn Ile Thr Leu Gly Leu Pro Ala Val Pro Ser Gln Leu Asn Ala Ser<br>           330                 335                 340 | 1182 |
| aat tca ctc aaa gaa aag cag aag tgt gag acg cag acg ctt agg caa<br>Asn Ser Leu Lys Glu Lys Gln Lys Cys Glu Thr Gln Thr Leu Arg Gln<br>345                 350                 355                 360 | 1230 |
| ggt gtt cct ctg cct ggg cag tat gga ggc agc atc ccg gca tct tcc<br>Gly Val Pro Leu Pro Gly Gln Tyr Gly Gly Ser Ile Pro Ala Ser Ser<br>               365                 370                 375 | 1278 |
| agc cac cct cat gtt act tta gag gga aag cca ccc aac agc agc cac<br>Ser His Pro His Val Thr Leu Glu Gly Lys Pro Pro Asn Ser Ser His<br>           380                 385                 390 | 1326 |
| cag gct ctc ctg cag cat tta tta ttg aaa gaa caa atg cga cag caa<br>Gln Ala Leu Leu Gln His Leu Leu Leu Lys Glu Gln Met Arg Gln Gln<br>               395                 400                 405 | 1374 |
| aag ctt ctt gta gct ggt gga gtt ccc tta cat cct cag tct ccc ttg<br>Lys Leu Leu Val Ala Gly Gly Val Pro Leu His Pro Gln Ser Pro Leu<br>           410                 415                 420 | 1422 |
| gca aca aaa gag aga att tca cct ggc att aga ggt acc cac aaa ttg<br>Ala Thr Lys Glu Arg Ile Ser Pro Gly Ile Arg Gly Thr His Lys Leu<br>425                 430                 435                 440 | 1470 |
| ccc cgt cac aga ccc ctg aac cga acc cag tct gca cct ttg cct cag<br>Pro Arg His Arg Pro Leu Asn Arg Thr Gln Ser Ala Pro Leu Pro Gln<br>               445                 450                 455 | 1518 |
| agc acg ttg gct cag ctg gtc att caa cag caa cac cag caa ttc ttg<br>Ser Thr Leu Ala Gln Leu Val Ile Gln Gln Gln His Gln Gln Phe Leu<br>           460                 465                 470 | 1566 |
| gag aag cag aag caa tac cag cag cag atc cac atg aac aaa ctg ctt<br>Glu Lys Gln Lys Gln Tyr Gln Gln Gln Ile His Met Asn Lys Leu Leu<br>               475                 480                 485 | 1614 |
| tcg aaa tct att gaa caa ctg aag caa cca ggc agt cac ctt gag gaa<br>Ser Lys Ser Ile Glu Gln Leu Lys Gln Pro Gly Ser His Leu Glu Glu<br>           490                 495                 500 | 1662 |
| gca gag gaa gag ctt cag ggg gac cag gcg atg cag gaa gac aga gcg<br>Ala Glu Glu Glu Leu Gln Gly Asp Gln Ala Met Gln Glu Asp Arg Ala | 1710 |

```
                505                 510                 515                 520
ccc tct agt ggc aac agc act agg agc gac agc agt gct tgt gtg gat         1758
Pro Ser Ser Gly Asn Ser Thr Arg Ser Asp Ser Ser Ala Cys Val Asp
                525                 530                 535 gac aca ctg gga caa gtt ggg gct gtg aag gtc aag gag gaa cca gtg         1806
Asp Thr Leu Gly Gln Val Gly Ala Val Lys Val Lys Glu Glu Pro Val
                540                 545                 550 gac agt gat gaa gat gct cag atc cag gaa atg gaa tct ggg gag cag         1854
Asp Ser Asp Glu Asp Ala Gln Ile Gln Glu Met Glu Ser Gly Glu Gln
                555                 560                 565 gct gct ttt atg caa cag cct ttc ctg gaa ccc acg cac aca cgt gcg         1902
Ala Ala Phe Met Gln Gln Pro Phe Leu Glu Pro Thr His Thr Arg Ala
                570                 575                 580 ctc tct gtg cgc caa gct ccg ctg gct gcg gtt ggc atg gat gga tta         1950
Leu Ser Val Arg Gln Ala Pro Leu Ala Ala Val Gly Met Asp Gly Leu
585                 590                 595                 600 gag aaa cac cgt ctc gtc tcc agg act cac tct tcc cct gct gcc tct         1998
Glu Lys His Arg Leu Val Ser Arg Thr His Ser Ser Pro Ala Ala Ser
                605                 610                 615 gtt tta cct cac cca gca atg gac cgc ccc ctc cag cct ggc tct gca         2046
Val Leu Pro His Pro Ala Met Asp Arg Pro Leu Gln Pro Gly Ser Ala
                620                 625                 630 act gga att gcc tat gac ccc ttg atg ctg aaa cac cag tgc gtt tgt         2094
Thr Gly Ile Ala Tyr Asp Pro Leu Met Leu Lys His Gln Cys Val Cys
                635                 640                 645 ggc aat tcc acc acc cac cct gag cat gct gga cga ata cag agt atc         2142
Gly Asn Ser Thr Thr His Pro Glu His Ala Gly Arg Ile Gln Ser Ile
                650                 655                 660 tgg tca cga ctg caa gaa act ggg ctg cta aat aaa tgt gag cga att         2190
Trp Ser Arg Leu Gln Glu Thr Gly Leu Leu Asn Lys Cys Glu Arg Ile
665                 670                 675                 680 caa ggt cga aaa gcc agc ctg gag gaa ata cag ctt gtt cat tct gaa         2238
Gln Gly Arg Lys Ala Ser Leu Glu Glu Ile Gln Leu Val His Ser Glu
                685                 690                 695 cat cac tca ctg ttg tat ggc acc aac ccc ctg gac gga cag aag ctg         2286
His His Ser Leu Leu Tyr Gly Thr Asn Pro Leu Asp Gly Gln Lys Leu
                700                 705                 710 gac ccc agg ata ctc cta ggt gat gac tct caa aag ttt ttt tcc tca         2334
Asp Pro Arg Ile Leu Leu Gly Asp Asp Ser Gln Lys Phe Phe Ser Ser
                715                 720                 725 tta cct tgt ggt gga ctt ggg gtg gac agt gac acc att tgg aat gag         2382
Leu Pro Cys Gly Gly Leu Gly Val Asp Ser Asp Thr Ile Trp Asn Glu
                730                 735                 740 cta cac tcg tcc ggt gct gca cgc atg gct gtt ggc tgt gtc atc gag         2430
Leu His Ser Ser Gly Ala Ala Arg Met Ala Val Gly Cys Val Ile Glu
745                 750                 755                 760 ctg gct tcc aaa gtg gcc tca gga gag ctg aag aat ggg ttt gct gtt         2478
Leu Ala Ser Lys Val Ala Ser Gly Glu Leu Lys Asn Gly Phe Ala Val
                765                 770                 775 gtg agg ccc cct ggc cat cac gct gaa gaa tcc aca gcc atg ggg ttc         2526
Val Arg Pro Pro Gly His His Ala Glu Glu Ser Thr Ala Met Gly Phe
                780                 785                 790 tgc ttt ttt aat tca gtt gca att acc gcc aaa tac ttg aga gac caa         2574
Cys Phe Phe Asn Ser Val Ala Ile Thr Ala Lys Tyr Leu Arg Asp Gln
                795                 800                 805 cta aat ata agc aag ata ttg att gta gat ctg gat gtt cac cat gga         2622
Leu Asn Ile Ser Lys Ile Leu Ile Val Asp Leu Asp Val His His Gly
                810                 815                 820 aac ggt acc cag cag gcc ttt tat gct gac ccc agc atc ctg tac att         2670
```

```
Asn Gly Thr Gln Gln Ala Phe Tyr Ala Asp Pro Ser Ile Leu Tyr Ile
825                 830                 835                 840 tca ctc cat cgc tat gat gaa ggg aac ttt ttc cct ggc agt gga gcc      2718
Ser Leu His Arg Tyr Asp Glu Gly Asn Phe Phe Pro Gly Ser Gly Ala
                845                 850                 855 cca aat gag gtt gga aca ggc ctt gga gaa ggg tac aat ata aat att      2766
Pro Asn Glu Val Gly Thr Gly Leu Gly Glu Gly Tyr Asn Ile Asn Ile
            860                 865                 870 gcc tgg aca ggt ggc ctt gat cct ccc atg gga gat gtt gag tac ctt      2814
Ala Trp Thr Gly Gly Leu Asp Pro Pro Met Gly Asp Val Glu Tyr Leu
        875                 880                 885 gaa gca ttc agg acc atc gtg aag cct gtg gcc aaa gag ttt gat cca      2862
Glu Ala Phe Arg Thr Ile Val Lys Pro Val Ala Lys Glu Phe Asp Pro
    890                 895                 900 gac atg gtc tta gta tct gct gga ttt gat gca ttg gaa ggc cac acc      2910
Asp Met Val Leu Val Ser Ala Gly Phe Asp Ala Leu Glu Gly His Thr
905                 910                 915                 920 cct cct cta gga ggg tac aaa gtg acg gca aaa tgt ttt ggt cat ttg      2958
Pro Pro Leu Gly Gly Tyr Lys Val Thr Ala Lys Cys Phe Gly His Leu
                925                 930                 935 acg aag caa ttg atg aca ttg gct gat gga cgt gtg gtg ttg gct cta      3006
Thr Lys Gln Leu Met Thr Leu Ala Asp Gly Arg Val Val Leu Ala Leu
            940                 945                 950 gaa gga gga cat gat ctc aca gcc atc tgt gat gca tca gaa gcc tgt      3054
Glu Gly Gly His Asp Leu Thr Ala Ile Cys Asp Ala Ser Glu Ala Cys
        955                 960                 965 gta aat gcc ctt cta gga aat gag ctg gag cca ctt gca gaa gat att      3102
Val Asn Ala Leu Leu Gly Asn Glu Leu Glu Pro Leu Ala Glu Asp Ile
    970                 975                 980 ctc cac caa agc ccg aat atg aat gct gtt att tct tta cag aag atc      3150
Leu His Gln Ser Pro Asn Met Asn Ala Val Ile Ser Leu Gln Lys Ile
985                 990                 995                 1000 att gaa att caa agt atg tct tta aag ttc tct taa                      3186
Ile Glu Ile Gln Ser Met Ser Leu Lys Phe Ser
                1005                1010

<210> SEQ ID NO 98
<211> LENGTH: 2790
<212> TYPE: DNA
<213> ORGANISM: Homo sapiens
<220> FEATURE:
<221> NAME/KEY: CDS
<222> LOCATION: (151)..(2787)

<400> SEQUENCE: 98
ggggaagaga ggcacagaca cagataggag aagggcaccg gctggagcca cttgcaggac      60
tgagggtttt tgcaacaaaa ccctagcagc ctgaagaact ctaagccaga tggggtggct     120
ggacgagagc agctcttggc tcagcaaaga atg cac agt atg atc agc tca gtg     174
                                  Met His Ser Met Ile Ser Ser Val
                                  1               5 gat gtg aag tca gaa gtt cct gtg ggc ctg gag ccc atc tca cct tta      222
Asp Val Lys Ser Glu Val Pro Val Gly Leu Glu Pro Ile Ser Pro Leu
    10                  15                  20 gac cta agg aca gac ctc agg atg atg atg ccc gtg gtg gac cct gtt      270
Asp Leu Arg Thr Asp Leu Arg Met Met Met Pro Val Val Asp Pro Val
25                  30                  35                  40 gtc cgt gag aag caa ttg cag cag gaa tta ctt ctt atc cag cag cag      318
Val Arg Glu Lys Gln Leu Gln Gln Glu Leu Leu Leu Ile Gln Gln Gln
                45                  50                  55 caa caa atc cag aag cag ctt ctg ata gca gag ttt cag aaa cag cat      366
```

```
                Gln Gln Ile Gln Lys Gln Leu Leu Ile Ala Glu Phe Gln Lys Gln His
                                60                  65                  70 gag aac ttg aca cgg cag cac cag gct cag ctt cag gag cat atc aag             414
Glu Asn Leu Thr Arg Gln His Gln Ala Gln Leu Gln Glu His Ile Lys
            75                  80                  85 gaa ctt cta gcc ata aaa cag caa caa gaa ctc cta gaa aag gag cag             462
Glu Leu Leu Ala Ile Lys Gln Gln Gln Glu Leu Leu Glu Lys Glu Gln
        90                  95                  100 aaa ctg gag cag cag agg caa gaa cag gaa gta gag agg cat cgc aga             510
Lys Leu Glu Gln Gln Arg Gln Glu Gln Glu Val Glu Arg His Arg Arg
105                 110                 115                 120 gaa cag cag ctt cct cct ctc aga ggc aaa gat aga gga cga gaa agg             558
Glu Gln Gln Leu Pro Pro Leu Arg Gly Lys Asp Arg Gly Arg Glu Arg
                125                 130                 135 gca gtg gca agt aca gaa gta aag cag aag ctt caa gag ttc cta ctg             606
Ala Val Ala Ser Thr Glu Val Lys Gln Lys Leu Gln Glu Phe Leu Leu
            140                 145                 150 agt aaa tca gca acg aaa gac act cca act aat gga aaa aat cat tcc             654
Ser Lys Ser Ala Thr Lys Asp Thr Pro Thr Asn Gly Lys Asn His Ser
        155                 160                 165 gtg agc cgc cat ccc aag ctc tgg tac acg gct gcc cac cac aca tca             702
Val Ser Arg His Pro Lys Leu Trp Tyr Thr Ala Ala His His Thr Ser
170                 175                 180 ttg gat caa agc tct cca ccc ctt agt gga aca tct cca tcc tac aag             750
Leu Asp Gln Ser Ser Pro Pro Leu Ser Gly Thr Ser Pro Ser Tyr Lys
185                 190                 195                 200 tac aca tta cca gga gca caa gat gca aag gat gat ttc ccc ctt cga             798
Tyr Thr Leu Pro Gly Ala Gln Asp Ala Lys Asp Asp Phe Pro Leu Arg
                205                 210                 215 aaa act gcc tct gag ccc aac ttg aag gtg cgg tcc agg tta aaa cag             846
Lys Thr Ala Ser Glu Pro Asn Leu Lys Val Arg Ser Arg Leu Lys Gln
            220                 225                 230 aaa gtg gca gag agg aga agc agc ccc tta ctc agg cgg aag gat gga             894
Lys Val Ala Glu Arg Arg Ser Ser Pro Leu Leu Arg Arg Lys Asp Gly
        235                 240                 245 aat gtt gtc act tca ttc aag aag cga atg ttt gag gtg aca gaa tcc             942
Asn Val Val Thr Ser Phe Lys Lys Arg Met Phe Glu Val Thr Glu Ser
250                 255                 260 tca gtc agt agc agt tct cca ggc tct ggt ccc agt tca cca aac aat             990
Ser Val Ser Ser Ser Ser Pro Gly Ser Gly Pro Ser Ser Pro Asn Asn
265                 270                 275                 280 ggg cca act gga agt gtt act gaa aat gag act tcg gtt ttg ccc cct            1038
Gly Pro Thr Gly Ser Val Thr Glu Asn Glu Thr Ser Val Leu Pro Pro
                285                 290                 295 acc cct cat gcc gag caa atg gtt tca cag caa cgc att cta att cat            1086
Thr Pro His Ala Glu Gln Met Val Ser Gln Gln Arg Ile Leu Ile His
            300                 305                 310 gaa gat tcc atg aac ctg cta agt ctt tat acc tct cct tct ttg ccc            1134
Glu Asp Ser Met Asn Leu Leu Ser Leu Tyr Thr Ser Pro Ser Leu Pro
        315                 320                 325 aac att acc ttg ggg ctt ccc gca gtg cca tcc cag ctc aat gct tcg            1182
Asn Ile Thr Leu Gly Leu Pro Ala Val Pro Ser Gln Leu Asn Ala Ser
330                 335                 340 aat tca ctc aaa gaa aag cag aag tgt gag acg cag acg ctt agg caa            1230
Asn Ser Leu Lys Glu Lys Gln Lys Cys Glu Thr Gln Thr Leu Arg Gln
345                 350                 355                 360 ggt gtt cct ctg cct ggg cag tat gga ggc agc atc ccg gca tct tcc            1278
Gly Val Pro Leu Pro Gly Gln Tyr Gly Gly Ser Ile Pro Ala Ser Ser
                365                 370                 375
```

-continued

| | | |
|---|---|---|
| agc cac cct cat gtt act tta gag gga aag cca ccc aac agc agc cac<br>Ser His Pro His Val Thr Leu Glu Gly Lys Pro Pro Asn Ser Ser His<br>           380                       385                          390 | 1326 |
| cag gct ctc ctg cag cat tta tta ttg aaa gaa caa atg cga cag caa<br>Gln Ala Leu Leu Gln His Leu Leu Leu Lys Glu Gln Met Arg Gln Gln<br>        395                        400                          405 | 1374 |
| aag ctt ctt gta gct ggt gga gtt ccc tta cat cct cag tct ccc ttg<br>Lys Leu Leu Val Ala Gly Gly Val Pro Leu His Pro Gln Ser Pro Leu<br>410                          415                        420 | 1422 |
| gca aca aaa gag aga att tca cct ggc att aga ggt acc cac aaa ttg<br>Ala Thr Lys Glu Arg Ile Ser Pro Gly Ile Arg Gly Thr His Lys Leu<br>425                          430                        435                        440 | 1470 |
| ccc cgt cac aga ccc ctg aac cga acc cag tct gca cct ttg cct cag<br>Pro Arg His Arg Pro Leu Asn Arg Thr Gln Ser Ala Pro Leu Pro Gln<br>                        445                        450                        455 | 1518 |
| agc acg ttg gct cag ctg gtc att caa cag caa cac cag caa ttc ttg<br>Ser Thr Leu Ala Gln Leu Val Ile Gln Gln Gln His Gln Gln Phe Leu<br>                460                        465                        470 | 1566 |
| gag aag cag aag caa tac cag cag cag atc cac atg aac aaa ctg ctt<br>Glu Lys Gln Lys Gln Tyr Gln Gln Gln Ile His Met Asn Lys Leu Leu<br>        475                        480                          485 | 1614 |
| tcg aaa tct att gaa caa ctg aag caa cca ggc agt cac ctt gag gaa<br>Ser Lys Ser Ile Glu Gln Leu Lys Gln Pro Gly Ser His Leu Glu Glu<br>490                          495                        500 | 1662 |
| gca gag gaa gag ctt cag ggg gac cag gcg atg cag gaa gac aga gcg<br>Ala Glu Glu Glu Leu Gln Gly Asp Gln Ala Met Gln Glu Asp Arg Ala<br>505                          510                        515                        520 | 1710 |
| ccc tct agt ggc aac agc act agg agc gac agc agt gct tgt gtg gat<br>Pro Ser Ser Gly Asn Ser Thr Arg Ser Asp Ser Ser Ala Cys Val Asp<br>                            525                        530                        535 | 1758 |
| gac aca ctg gga caa gtt ggg gct gtg aag gtc aag gag gaa cca gtg<br>Asp Thr Leu Gly Gln Val Gly Ala Val Lys Val Lys Glu Glu Pro Val<br>                540                        545                        550 | 1806 |
| gac agt gat gaa gat gct cag atc cag gaa atg gaa tct ggg gag cag<br>Asp Ser Asp Glu Asp Ala Gln Ile Gln Glu Met Glu Ser Gly Glu Gln<br>        555                        560                          565 | 1854 |
| gct gct ttt atg caa cag cct ttc ctg gaa ccc acg cac aca cgt gcg<br>Ala Ala Phe Met Gln Gln Pro Phe Leu Glu Pro Thr His Thr Arg Ala<br>570                          575                        580 | 1902 |
| ctc tct gtg cgc caa gct ccg ctg gct gcg gtt ggc atg gat gga tta<br>Leu Ser Val Arg Gln Ala Pro Leu Ala Ala Val Gly Met Asp Gly Leu<br>585                          590                        595                        600 | 1950 |
| gag aaa cac cgt ctc gtc tcc agg act cac tct tcc cct gct gcc tct<br>Glu Lys His Arg Leu Val Ser Arg Thr His Ser Ser Pro Ala Ala Ser<br>                            605                        610                        615 | 1998 |
| gtt tta cct cac cca gca atg gac cgc ccc ctc cag cct ggc tct gca<br>Val Leu Pro His Pro Ala Met Asp Arg Pro Leu Gln Pro Gly Ser Ala<br>                620                        625                        630 | 2046 |
| act gga att gcc tat gac ccc ttg atg ctg aaa cac cag tgc gtt tgt<br>Thr Gly Ile Ala Tyr Asp Pro Leu Met Leu Lys His Gln Cys Val Cys<br>        635                        640                          645 | 2094 |
| ggc aat tcc acc acc cac cct gag cat gct gga cga ata cag agt atc<br>Gly Asn Ser Thr Thr His Pro Glu His Ala Gly Arg Ile Gln Ser Ile<br>650                          655                        660 | 2142 |
| tgg tca cga ctg caa gaa act ggg ctg cta aat aaa tgt gag cga att<br>Trp Ser Arg Leu Gln Glu Thr Gly Leu Leu Asn Lys Cys Glu Arg Ile<br>665                          670                        675                        680 | 2190 |
| caa ggt cga aaa gcc agc ctg gag gaa ata cag ctt gtt cat tct gaa<br>Gln Gly Arg Lys Ala Ser Leu Glu Glu Ile Gln Leu Val His Ser Glu<br>                        685                        690                        695 | 2238 |

| | | | | | | | | | | | | | | |
|---|---|---|---|---|---|---|---|---|---|---|---|---|---|---|
| cat | cac | tca | ctg | ttg | tat | ggc | acc | aac | ccc | ctg | gac | gga | cag | aag | ctg | 2286 |
| His | His | Ser | Leu | Leu | Tyr | Gly | Thr | Asn | Pro | Leu | Asp | Gly | Gln | Lys | Leu |
| | | 700 | | | | | 705 | | | | 710 | | | | |

| gac | ccc | agg | ata | ctc | cta | ggt | gat | gac | tct | caa | aag | ttt | ttt | tcc | tca | 2334 |
| Asp | Pro | Arg | Ile | Leu | Leu | Gly | Asp | Asp | Ser | Gln | Lys | Phe | Phe | Ser | Ser |
| 715 | | | | | 720 | | | | | 725 | | | | | |

| tta | cct | tgt | ggt | gga | ctt | ggg | gtg | gac | agt | gac | acc | att | tgg | aat | gag | 2382 |
| Leu | Pro | Cys | Gly | Gly | Leu | Gly | Val | Asp | Ser | Asp | Thr | Ile | Trp | Asn | Glu |
| | 730 | | | | | 735 | | | | | 740 | | | | |

| cta | cac | tcg | tcc | ggt | gct | gca | cgc | atg | gct | gtt | ggc | tgt | gtc | atc | gag | 2430 |
| Leu | His | Ser | Ser | Gly | Ala | Ala | Arg | Met | Ala | Val | Gly | Cys | Val | Ile | Glu |
| 745 | | | | 750 | | | | | 755 | | | | | 760 | |

| ctg | gct | tcc | aaa | gtg | gcc | tca | gga | gag | ctg | aag | aat | ggg | ttt | gct | gtt | 2478 |
| Leu | Ala | Ser | Lys | Val | Ala | Ser | Gly | Glu | Leu | Lys | Asn | Gly | Phe | Ala | Val |
| | | | 765 | | | | | 770 | | | | | 775 | | |

| gtg | agg | ccc | cct | ggc | cat | cac | gct | gaa | gaa | tcc | aca | gcc | atg | ggg | ttc | 2526 |
| Val | Arg | Pro | Pro | Gly | His | His | Ala | Glu | Glu | Ser | Thr | Ala | Met | Gly | Phe |
| | | | 780 | | | | | 785 | | | | | 790 | | |

| tgc | ttt | ttt | aat | tca | gtt | gca | att | acc | gcc | aaa | tac | ttg | aga | gac | caa | 2574 |
| Cys | Phe | Phe | Asn | Ser | Val | Ala | Ile | Thr | Ala | Lys | Tyr | Leu | Arg | Asp | Gln |
| | | 795 | | | | | 800 | | | | | 805 | | | |

| cta | aat | ata | agc | aag | ata | ttg | att | gta | gat | ctg | gat | gtt | cac | cat | gga | 2622 |
| Leu | Asn | Ile | Ser | Lys | Ile | Leu | Ile | Val | Asp | Leu | Asp | Val | His | His | Gly |
| 810 | | | | | 815 | | | | | 820 | | | | | |

| aac | ggt | acc | cag | cag | gcc | ttt | tat | gct | gac | ccc | agc | atc | ctg | tac | att | 2670 |
| Asn | Gly | Thr | Gln | Gln | Ala | Phe | Tyr | Ala | Asp | Pro | Ser | Ile | Leu | Tyr | Ile |
| 825 | | | | 830 | | | | | 835 | | | | | 840 | |

| tca | ctc | cat | cgc | tat | gat | gaa | ggg | aac | ttt | ttc | cct | ggc | agt | gga | gcc | 2718 |
| Ser | Leu | His | Arg | Tyr | Asp | Glu | Gly | Asn | Phe | Phe | Pro | Gly | Ser | Gly | Ala |
| | | | 845 | | | | | 850 | | | | | 855 | | |

| cca | aat | gag | gtt | cgg | ttt | att | tct | tta | gag | ccc | cac | ttt | tat | ttg | tat | 2766 |
| Pro | Asn | Glu | Val | Arg | Phe | Ile | Ser | Leu | Glu | Pro | His | Phe | Tyr | Leu | Tyr |
| | | 860 | | | | | 865 | | | | | 870 | | | |

| ctt | tca | ggt | aat | tgc | att | gca | tga | | | | | | | | | 2790 |
| Leu | Ser | Gly | Asn | Cys | Ile | Ala |
| | | 875 | | | | | |

<210> SEQ ID NO 99
<211> LENGTH: 590
<212> TYPE: PRT
<213> ORGANISM: Homo sapiens

<400> SEQUENCE: 99

Met His Ser Met Ile Ser Ser Val Asp Val Lys Ser Glu Val Pro Val
1               5                   10                  15

Gly Leu Glu Pro Ile Ser Pro Leu Asp Leu Arg Thr Asp Leu Arg Met
            20                  25                  30

Met Met Pro Val Val Asp Pro Val Val Arg Glu Lys Gln Leu Gln Gln
        35                  40                  45

Glu Leu Leu Leu Ile Gln Gln Gln Gln Ile Gln Lys Gln Leu Leu
    50                  55                  60

Ile Ala Glu Phe Gln Lys Gln His Glu Asn Leu Thr Arg Gln His Gln
65                  70                  75                  80

Ala Gln Leu Gln Glu His Ile Lys Glu Leu Leu Ala Ile Lys Gln Gln
                85                  90                  95

Gln Glu Leu Leu Glu Lys Glu Gln Lys Leu Glu Gln Gln Arg Gln Glu
            100                 105                 110

Gln Glu Val Glu Arg His Arg Arg Glu Gln Gln Leu Pro Pro Leu Arg

-continued

```
            115                 120                 125
Gly Lys Asp Arg Gly Arg Glu Arg Ala Val Ala Ser Thr Glu Val Lys
    130                 135                 140
Gln Lys Leu Gln Glu Phe Leu Leu Ser Lys Ser Ala Thr Lys Asp Thr
145                 150                 155                 160
Pro Thr Asn Gly Lys Asn His Ser Val Ser Arg His Pro Lys Leu Trp
                165                 170                 175
Tyr Thr Ala Ala His His Thr Ser Leu Asp Gln Ser Ser Pro Pro Leu
                180                 185                 190
Ser Gly Thr Ser Pro Ser Tyr Lys Tyr Thr Leu Pro Gly Ala Gln Asp
        195                 200                 205
Ala Lys Asp Asp Phe Pro Leu Arg Lys Thr Ala Ser Glu Pro Asn Leu
    210                 215                 220
Lys Val Arg Ser Arg Leu Lys Gln Lys Val Ala Glu Arg Arg Ser Ser
225                 230                 235                 240
Pro Leu Leu Arg Arg Lys Asp Gly Asn Val Val Thr Ser Phe Lys Lys
                245                 250                 255
Arg Met Phe Glu Val Thr Glu Ser Ser Val Ser Ser Ser Ser Pro Gly
                260                 265                 270
Ser Gly Pro Ser Ser Pro Asn Asn Gly Pro Thr Gly Ser Val Thr Glu
        275                 280                 285
Asn Glu Thr Ser Val Leu Pro Pro Thr Pro His Ala Glu Gln Met Val
    290                 295                 300
Ser Gln Gln Arg Ile Leu Ile His Glu Asp Ser Met Asn Leu Leu Ser
305                 310                 315                 320
Leu Tyr Thr Ser Pro Ser Leu Pro Asn Ile Thr Leu Gly Leu Pro Ala
                325                 330                 335
Val Pro Ser Gln Leu Asn Ala Ser Asn Ser Leu Lys Glu Lys Gln Lys
                340                 345                 350
Cys Glu Thr Gln Thr Leu Arg Gln Gly Val Pro Leu Pro Gly Gln Tyr
        355                 360                 365
Gly Gly Ser Ile Pro Ala Ser Ser Ser His Pro His Val Thr Leu Glu
    370                 375                 380
Gly Lys Pro Pro Asn Ser Ser His Gln Ala Leu Leu Gln His Leu Leu
385                 390                 395                 400
Leu Lys Glu Gln Met Arg Gln Gln Lys Leu Leu Val Ala Gly Gly Val
                405                 410                 415
Pro Leu His Pro Gln Ser Pro Leu Ala Thr Lys Glu Arg Ile Ser Pro
                420                 425                 430
Gly Ile Arg Gly Thr His Lys Leu Pro Arg His Arg Pro Leu Asn Arg
        435                 440                 445
Thr Gln Ser Ala Pro Leu Pro Gln Ser Thr Leu Ala Gln Leu Val Ile
    450                 455                 460
Gln Gln Gln His Gln Gln Phe Leu Glu Lys Gln Lys Gln Tyr Gln Gln
465                 470                 475                 480
Gln Ile His Met Asn Lys Leu Leu Ser Lys Ser Ile Glu Gln Leu Lys
                485                 490                 495
Gln Pro Gly Ser His Leu Glu Glu Ala Glu Glu Glu Leu Gln Gly Asp
                500                 505                 510
Gln Ala Met Gln Glu Asp Arg Ala Pro Ser Ser Gly Asn Ser Thr Arg
        515                 520                 525
Ser Asp Ser Ser Ala Cys Val Asp Asp Thr Leu Gly Gln Val Gly Ala
530                 535                 540
```

```
Val Lys Val Lys Glu Glu Pro Val Asp Ser Asp Glu Asp Ala Gln Ile
545                 550                 555                 560

Gln Glu Met Glu Ser Gly Glu Gln Ala Ala Phe Met Gln Gln Val Ile
            565                 570                 575

Gly Lys Asp Leu Ala Pro Gly Phe Val Ile Lys Val Ile Ile
            580                 585                 590

<210> SEQ ID NO 100
<211> LENGTH: 4238
<212> TYPE: DNA
<213> ORGANISM: Homo sapiens
<220> FEATURE:
<221> NAME/KEY: CDS
<222> LOCATION: (151)..(1920)

<400> SEQUENCE: 100
ggggaagaga ggcacagaca cagataggag aagggcaccg gctggagcca cttgcaggac      60
tgagggtttt tgcaacaaaa ccctagcagc ctgaagaact ctaagccaga tggggtggct     120
ggacgagagc agctcttggc tcagcaaaga atg cac agt atg atc agc tca gtg     174
                                  Met His Ser Met Ile Ser Ser Val
                                    1               5 gat gtg aag tca gaa gtt cct gtg ggc ctg gag ccc atc tca cct tta     222
Asp Val Lys Ser Glu Val Pro Val Gly Leu Glu Pro Ile Ser Pro Leu
 10                  15                  20 gac cta agg aca gac ctc agg atg atg atg ccc gtg gtg gac cct gtt     270
Asp Leu Arg Thr Asp Leu Arg Met Met Met Pro Val Val Asp Pro Val
 25                  30                  35                  40 gtc cgt gag aag caa ttg cag cag gaa tta ctt ctt atc cag cag cag     318
Val Arg Glu Lys Gln Leu Gln Gln Glu Leu Leu Leu Ile Gln Gln Gln
                 45                  50                  55 caa caa atc cag aag cag ctt ctg ata gca gag ttt cag aaa cag cat     366
Gln Gln Ile Gln Lys Gln Leu Leu Ile Ala Glu Phe Gln Lys Gln His
             60                  65                  70 gag aac ttg aca cgg cag cac cag gct cag ctt cag gag cat atc aag     414
Glu Asn Leu Thr Arg Gln His Gln Ala Gln Leu Gln Glu His Ile Lys
         75                  80                  85 gaa ctt cta gcc ata aaa cag caa caa gaa ctc cta gaa aag gag cag     462
Glu Leu Leu Ala Ile Lys Gln Gln Gln Glu Leu Leu Glu Lys Glu Gln
     90                  95                 100 aaa ctg gag cag cag agg caa gaa cag gaa gta gag agg cat cgc aga     510
Lys Leu Glu Gln Gln Arg Gln Glu Gln Glu Val Glu Arg His Arg Arg
105                 110                 115                 120 gaa cag cag ctt cct cct ctc aga ggc aaa gat aga gga cga gaa agg     558
Glu Gln Gln Leu Pro Pro Leu Arg Gly Lys Asp Arg Gly Arg Glu Arg
                125                 130                 135 gca gtg gca agt aca gaa gta aag cag aag ctt caa gag ttc cta ctg     606
Ala Val Ala Ser Thr Glu Val Lys Gln Lys Leu Gln Glu Phe Leu Leu
            140                 145                 150 agt aaa tca gca acg aaa gac act cca act aat gga aaa aat cat tcc     654
Ser Lys Ser Ala Thr Lys Asp Thr Pro Thr Asn Gly Lys Asn His Ser
        155                 160                 165 gtg agc cgc cat ccc aag ctc tgg tac acg gct gcc cac cac aca tca     702
Val Ser Arg His Pro Lys Leu Trp Tyr Thr Ala Ala His His Thr Ser
    170                 175                 180 ttg gat caa agc tct cca ccc ctt agt gga aca tct cca tcc tac aag     750
Leu Asp Gln Ser Ser Pro Pro Leu Ser Gly Thr Ser Pro Ser Tyr Lys
185                 190                 195                 200 tac aca tta cca gga gca caa gat gca aag gat gat ttc ccc ctt cga     798
Tyr Thr Leu Pro Gly Ala Gln Asp Ala Lys Asp Asp Phe Pro Leu Arg
```

-continued

```
                 205                 210                 215
aaa act gcc tct gag ccc aac ttg aag gtg cgg tcc agg tta aaa cag       846
Lys Thr Ala Ser Glu Pro Asn Leu Lys Val Arg Ser Arg Leu Lys Gln
            220                 225                 230 aaa gtg gca gag agg aga agc agc ccc tta ctc agg cgg aag gat gga       894
Lys Val Ala Glu Arg Arg Ser Ser Pro Leu Leu Arg Arg Lys Asp Gly
            235                 240                 245 aat gtt gtc act tca ttc aag aag cga atg ttt gag gtg aca gaa tcc       942
Asn Val Val Thr Ser Phe Lys Lys Arg Met Phe Glu Val Thr Glu Ser
        250                 255                 260 tca gtc agt agc agt tct cca ggc tct ggt ccc agt tca cca aac aat       990
Ser Val Ser Ser Ser Ser Pro Gly Ser Gly Pro Ser Ser Pro Asn Asn
265                 270                 275                 280 ggg cca act gga agt gtt act gaa aat gag act tcg gtt ttg ccc cct      1038
Gly Pro Thr Gly Ser Val Thr Glu Asn Glu Thr Ser Val Leu Pro Pro
                285                 290                 295 acc cct cat gcc gag caa atg gtt tca cag caa cgc att cta att cat      1086
Thr Pro His Ala Glu Gln Met Val Ser Gln Gln Arg Ile Leu Ile His
            300                 305                 310 gaa gat tcc atg aac ctg cta agt ctt tat acc tct cct tct ttg ccc      1134
Glu Asp Ser Met Asn Leu Leu Ser Leu Tyr Thr Ser Pro Ser Leu Pro
            315                 320                 325 aac att acc ttg ggg ctt ccc gca gtg cca tcc cag ctc aat gct tcg      1182
Asn Ile Thr Leu Gly Leu Pro Ala Val Pro Ser Gln Leu Asn Ala Ser
        330                 335                 340 aat tca ctc aaa gaa aag cag aag tgt gag acg cag acg ctt agg caa      1230
Asn Ser Leu Lys Glu Lys Gln Lys Cys Glu Thr Gln Thr Leu Arg Gln
345                 350                 355                 360 ggt gtt cct ctg cct ggg cag tat gga ggc agc atc ccg gca tct tcc      1278
Gly Val Pro Leu Pro Gly Gln Tyr Gly Gly Ser Ile Pro Ala Ser Ser
                365                 370                 375 agc cac cct cat gtt act tta gag gga aag cca ccc aac agc agc cac      1326
Ser His Pro His Val Thr Leu Glu Gly Lys Pro Pro Asn Ser Ser His
            380                 385                 390 cag gct ctc ctg cag cat tta tta ttg aaa gaa caa atg cga cag caa      1374
Gln Ala Leu Leu Gln His Leu Leu Leu Lys Glu Gln Met Arg Gln Gln
            395                 400                 405 aag ctt ctt gta gct ggt gga gtt ccc tta cat cct cag tct ccc ttg      1422
Lys Leu Leu Val Ala Gly Gly Val Pro Leu His Pro Gln Ser Pro Leu
        410                 415                 420 gca aca aaa gag aga att tca cct ggc att aga ggt acc cac aaa ttg      1470
Ala Thr Lys Glu Arg Ile Ser Pro Gly Ile Arg Gly Thr His Lys Leu
425                 430                 435                 440 ccc cgt cac aga ccc ctg aac cga acc cag tct gca cct ttg cct cag      1518
Pro Arg His Arg Pro Leu Asn Arg Thr Gln Ser Ala Pro Leu Pro Gln
                445                 450                 455 agc acg ttg gct cag ctg gtc att caa cag caa cac cag caa ttc ttg      1566
Ser Thr Leu Ala Gln Leu Val Ile Gln Gln Gln His Gln Gln Phe Leu
            460                 465                 470 gag aag cag aag caa tac cag cag cag atc cac atg aac aaa ctg ctt      1614
Glu Lys Gln Lys Gln Tyr Gln Gln Gln Ile His Met Asn Lys Leu Leu
            475                 480                 485 tcg aaa tct att gaa caa ctg aag caa cca ggc agt cac ctt gag gaa      1662
Ser Lys Ser Ile Glu Gln Leu Lys Gln Pro Gly Ser His Leu Glu Glu
        490                 495                 500 gca gag gaa gag ctt cag ggg gac cag gcg atg cag gaa gac aga gcg      1710
Ala Glu Glu Glu Leu Gln Gly Asp Gln Ala Met Gln Glu Asp Arg Ala
505                 510                 515                 520 ccc tct agt ggc aac agc act agg agc gac agc agt gct tgt gtg gat      1758
Pro Ser Ser Gly Asn Ser Thr Arg Ser Asp Ser Ser Ala Cys Val Asp
```

```
Pro Ser Ser Gly Asn Ser Thr Arg Ser Asp Ser Ser Ala Cys Val Asp
            525                 530                 535 gac aca ctg gga caa gtt ggg gct gtg aag gtc aag gag gaa cca gtg     1806
Asp Thr Leu Gly Gln Val Gly Ala Val Lys Val Lys Glu Glu Pro Val
            540                 545                 550 gac agt gat gaa gat gct cag atc cag gaa atg gaa tct ggg gag cag     1854
Asp Ser Asp Glu Asp Ala Gln Ile Gln Glu Met Glu Ser Gly Glu Gln
            555                 560                 565 gct gct ttt atg caa cag gta ata ggc aaa gat tta gct cca gga ttt     1902
Ala Ala Phe Met Gln Gln Val Ile Gly Lys Asp Leu Ala Pro Gly Phe
            570                 575                 580 gta att aaa gtc att atc tgaacatgaa atgcattgca ggtttggtaa            1950
Val Ile Lys Val Ile Ile
585             590 atggatatga tttcctatca gtttatattt ctctatgatt tgagttcagt gtttaaggat   2010
tctacctaat gcagatatat gtatatatct atatagaggt ctttctatat actgatctct   2070
atatagatat caatgtttca ttgaaaatcc actggtaagg aaatacctgt tatactaaaa   2130
ttatgataca taatatctga gcagttaata ggctttaaat ttatcccaaa gcctgctaca   2190
ccaattactt ctaaagaaaa caaattcact gttattttga gtttatgtgt tgagatcagt   2250
gactgctgga tagtctccca gtctgatcaa tgaagcattc gattagtttt tgattttttg   2310
caacatctag aatttaattt tcacatcact gtacataatg tatcatacta tagtcttgaa   2370
cactgttaaa ggtagtctgc cccttccttc ctctctcttt tttagttaa gtagaaatgt    2430 tctggtcacc atgccagtag tcctaggtta ttgtgtaggt tgcaattgaa catattagga   2490
atacaggtgg ttttaaatat atagatgcaa attgcagcac tactttaaat attagattat   2550
gtctcacata gcactgctca tttctacttt attttgtgta atttgatgac actgtctatc   2610
aaaaaagagc aaatgaagca gatgcaaatg ttagtgagaa gtaatgtgca gcattatggt   2670
ccaatcagat acaatattgt gtctacaatt gcaaaaaaca cagtaacagg atgaatatta   2730
tctgatatca agtcaaaatc agtttgaaaa gaaggtgtat catattttat attgtcacta   2790
gaatctctta agtataattc cataatgaca tgggcatata ccgtaacatt ctggcaaata   2850
acaattagaa aagataggtt taacaaaaaa atttacttgt atataatgca ccttcaggag   2910
gactatgtcc tttgatgcta taaaatacaa acaactttga aggcaacaga agacactgtt   2970
tattcaagtc agttctttgt caggttcctg ctgttctcct acagaaaagt gattctgtga   3030
gggtgaacag gaaatgcctt gtggaaacag gaagtccaag tgattcatgt actgaggaat   3090
gtaggaaaaa aaatctgagg atagtgcttt actctttctg tttttaaagg gcactctatg   3150
aattgattta ttgtctaaga aaataacacc acaagtaggg aaattgttac ggaagctttt   3210
cactggaaca tttccttcat attcccttt gatatgttta ccttgtttta taggtttact    3270
tttgttaagc tagttaaagg ttcgttgtat taagacccct ttaatatgga taatccaaat   3330
tgacctagaa tctttgtgag gttttttcta ttaaaatatt tatatttcta aatccgaggt   3390
atttcaaggt gtagtatcct atttcaaagg agatatagca gttttgccaa atgtagacat   3450
tgttcaactg tatgttattg gcacgtgttg tttacatttt gctgtgacat ttaaaaatat   3510
ttcttttaaa atgttactgc taaagataca ttatcctttt ttaaaaagtc tccattcaaa   3570
ttaaattaac ataactagaa gttagaaagt ttaaaagttt tccacataat gaaagtcctt   3630
ctgataattt gacaaatagc tataatagga acactcccta tcaccaacat attttggtta   3690
gtatattcct tcatattaaa atgactttt gtcagttgtt ttgcattaaa aatatggcat    3750
```

-continued

```
gcctaagata aaattgtata ttttttccat ctcataaata ttcatttct tcaaagtctt    3810 ttttcaatct cataaaaaag ggatagtgca tcttttaaaa tacattttat ttggggagga    3870
acatgtggct gagcagactt ttgtataata ttacttcaaa gatatgtaat cacaaacaaa    3930
aaaaactatt ttttataatg tcatttgaga gagtttcatc agtacagttg gtggacgtta    3990
attgtttgaa tttgatagtc tttgaattta atcaagaaac tacctggaac cagtgaaaag    4050
gaaagctgga cttaaataat cttagaatta attgataaat gtctctttta aaatctactg    4110
tatttattat aatttacacc cttgaaggtg atctcttgtt ttgtgttgta aatatattgt    4170
ttgtatgttt cccttcttgc cttctgttat aagtctcttc ctttctcaaa taaagttttt    4230
tttaaaag                                                             4238
```

<210> SEQ ID NO 101
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101

```
gtttcttgca gtcgtgacca gatactctga ttcgtccagc atgctcaggg tgggtgggtg    60
gaattgccac aaacgca                                                   77
```

<210> SEQ ID NO 102
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102

```
tgccagggaa aaagttccct tcatcatagc gatggagtga atgtacagg atgctgggt      60 cagcataaaa ggcctgctgg                                                80
```

<210> SEQ ID NO 103
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103

```
tgatccagac atggtcttag tatctgctgg atttgatgca ttggaaggcc acaccctcc     60 tctaggaggg tacaaagtga                                                80
```

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 104

```
gtgacaccat ttggaatgag ctac                                           24
```

<210> SEQ ID NO 105
<211> LENGTH: 20
<212> TYPE: DNA

```
<213> ORGANISM: Artificial Sequence
<220> FEATURE:
<223> OTHER INFORMATION: Description of Artificial Sequence: Primer

<400> SEQUENCE: 105
ttggaagcca gctcgatgac                                              20

<210> SEQ ID NO 106
<211> LENGTH: 3209
<212> TYPE: DNA
<213> ORGANISM: Artificial Sequence
<220> FEATURE:
<223> OTHER INFORMATION: Description of Artificial Sequence: Consensus
      sequence
<220> FEATURE:
<221> NAME/KEY: modified_base
<222> LOCATION: (2013)
<223> OTHER INFORMATION: Unknown consensus marker
<220> FEATURE:
<221> NAME/KEY: modified_base
<222> LOCATION: (2731)
<223> OTHER INFORMATION: Unknown consensus marker
<220> FEATURE:
<221> NAME/KEY: modified_base
<222> LOCATION: (2733)
<223> OTHER INFORMATION: Unknown consensus marker
<220> FEATURE:
<221> NAME/KEY: modified_base
<222> LOCATION: (2735)
<223> OTHER INFORMATION: Unknown consensus marker
<220> FEATURE:
<221> NAME/KEY: modified_base
<222> LOCATION: (2737)
<223> OTHER INFORMATION: Unknown consensus marker
<220> FEATURE:
<221> NAME/KEY: modified_base
<222> LOCATION: (2740)..(2741)
<223> OTHER INFORMATION: Unknown consensus marker
<220> FEATURE:
<221> NAME/KEY: modified_base
<222> LOCATION: (2749)..(2752)
<223> OTHER INFORMATION: Unknown consensus marker
<220> FEATURE:
<221> NAME/KEY: modified_base
<222> LOCATION: (2755)..(2756)
<223> OTHER INFORMATION: Unknown consensus marker
<220> FEATURE:
<221> NAME/KEY: modified_base
<222> LOCATION: (2761)
<223> OTHER INFORMATION: Unknown consensus marker
<220> FEATURE:
<221> NAME/KEY: modified_base
<222> LOCATION: (2763)
<223> OTHER INFORMATION: Unknown consensus marker
<220> FEATURE:
<221> NAME/KEY: modified_base
<222> LOCATION: (2768)
<223> OTHER INFORMATION: Unknown consensus marker
<220> FEATURE:
<221> NAME/KEY: modified_base
<222> LOCATION: (2771)
<223> OTHER INFORMATION: Unknown consensus marker
<220> FEATURE:
<221> NAME/KEY: modified_base
<222> LOCATION: (2773)..(2777)
<223> OTHER INFORMATION: Unknown consensus marker
<220> FEATURE:
<221> NAME/KEY: modified_base
<222> LOCATION: (2779)
<223> OTHER INFORMATION: Unknown consensus marker
<220> FEATURE:
<221> NAME/KEY: modified_base
<222> LOCATION: (2782)
<223> OTHER INFORMATION: Unknown consensus marker
<220> FEATURE:
<221> NAME/KEY: modified_base
<222> LOCATION: (2786)..(2787)
```

```
<223> OTHER INFORMATION: Unknown consensus marker
<220> FEATURE:
<221> NAME/KEY: modified_base
<222> LOCATION: (2790)
<223> OTHER INFORMATION: Unknown consensus marker
<220> FEATURE:
<221> NAME/KEY: modified_base
<222> LOCATION: (2792)..(2796)
<223> OTHER INFORMATION: Unknown consensus marker
<220> FEATURE:
<221> NAME/KEY: modified_base
<222> LOCATION: (2799)..(2800)
<223> OTHER INFORMATION: Unknown consensus marker
<220> FEATURE:
<221> NAME/KEY: modified_base
<222> LOCATION: (2802)..(2807)
<223> OTHER INFORMATION: Unknown consensus marker
<220> FEATURE:
<221> NAME/KEY: modified_base
<222> LOCATION: (2809)..(2811)
<223> OTHER INFORMATION: Unknown consensus marker
<220> FEATURE:
<221> NAME/KEY: modified_base
<222> LOCATION: (2813)..(2815)
<223> OTHER INFORMATION: Unknown consensus marker
<220> FEATURE:
<221> NAME/KEY: modified_base
<222> LOCATION: (2817)..(2820)
<223> OTHER INFORMATION: Unknown consensus marker
<220> FEATURE:
<221> NAME/KEY: modified_base
<222> LOCATION: (2822)..(2826)
<223> OTHER INFORMATION: Unknown consensus marker
<220> FEATURE:
<221> NAME/KEY: modified_base
<222> LOCATION: (2828)..(2831)
<223> OTHER INFORMATION: Unknown consensus marker
<220> FEATURE:
<221> NAME/KEY: modified_base
<222> LOCATION: (2835)..(2836)
<223> OTHER INFORMATION: Unknown consensus marker
<220> FEATURE:
<221> NAME/KEY: modified_base
<222> LOCATION: (2838)
<223> OTHER INFORMATION: Unknown consensus marker
<220> FEATURE:
<221> NAME/KEY: modified_base
<222> LOCATION: (2840)
<223> OTHER INFORMATION: Unknown consensus marker
<220> FEATURE:
<221> NAME/KEY: modified_base
<222> LOCATION: (2842)..(2847)
<223> OTHER INFORMATION: Unknown consensus marker
<220> FEATURE:
<221> NAME/KEY: modified_base
<222> LOCATION: (2849)..(2850)
<223> OTHER INFORMATION: Unknown consensus marker
<220> FEATURE:
<221> NAME/KEY: modified_base
<222> LOCATION: (2852)
<223> OTHER INFORMATION: Unknown consensus marker
<220> FEATURE:
<221> NAME/KEY: modified_base
<222> LOCATION: (2854)..(2855)
<223> OTHER INFORMATION: Unknown consensus marker
<220> FEATURE:
<221> NAME/KEY: modified_base
<222> LOCATION: (2857)
<223> OTHER INFORMATION: Unknown consensus marker
<220> FEATURE:
<221> NAME/KEY: modified_base
<222> LOCATION: (2860)..(2863)
<223> OTHER INFORMATION: Unknown consensus marker
<220> FEATURE:
<221> NAME/KEY: modified_base
<222> LOCATION: (2865)
<223> OTHER INFORMATION: Unknown consensus marker
<220> FEATURE:
<221> NAME/KEY: modified_base
```

-continued

```
<222> LOCATION: (2867)..(2871)
<223> OTHER INFORMATION: Unknown consensus marker
<220> FEATURE:
<221> NAME/KEY: modified_base
<222> LOCATION: (2874)
<223> OTHER INFORMATION: Unknown consensus marker
<220> FEATURE:
<221> NAME/KEY: modified_base
<222> LOCATION: (2877)
<223> OTHER INFORMATION: Unknown consensus marker
<220> FEATURE:
<221> NAME/KEY: modified_base
<222> LOCATION: (2879)
<223> OTHER INFORMATION: Unknown consensus marker
<220> FEATURE:
<221> NAME/KEY: modified_base
<222> LOCATION: (2882)..(2885)
<223> OTHER INFORMATION: Unknown consensus marker
<220> FEATURE:
<221> NAME/KEY: modified_base
<222> LOCATION: (2887)..(2888)
<223> OTHER INFORMATION: Unknown consensus marker
<220> FEATURE:
<221> NAME/KEY: modified_base
<222> LOCATION: (2890)..(2894)
<223> OTHER INFORMATION: Unknown consensus marker
<220> FEATURE:
<221> NAME/KEY: modified_base
<222> LOCATION: (2896)
<223> OTHER INFORMATION: Unknown consensus marker
<220> FEATURE:
<221> NAME/KEY: modified_base
<222> LOCATION: (2898)..(2899)
<223> OTHER INFORMATION: Unknown consensus marker
<220> FEATURE:
<221> NAME/KEY: modified_base
<222> LOCATION: (2901)..(2905)
<223> OTHER INFORMATION: Unknown consensus marker
<220> FEATURE:
<221> NAME/KEY: modified_base
<222> LOCATION: (2907)..(2908)
<223> OTHER INFORMATION: Unknown consensus marker
<220> FEATURE:
<221> NAME/KEY: modified_base
<222> LOCATION: (2911)
<223> OTHER INFORMATION: Unknown consensus marker
<220> FEATURE:
<221> NAME/KEY: modified_base
<222> LOCATION: (2914)
<223> OTHER INFORMATION: Unknown consensus marker
<220> FEATURE:
<221> NAME/KEY: modified_base
<222> LOCATION: (2917)
<223> OTHER INFORMATION: Unknown consensus marker
<220> FEATURE:
<221> NAME/KEY: modified_base
<222> LOCATION: (2920)
<223> OTHER INFORMATION: Unknown consensus marker
<220> FEATURE:
<221> NAME/KEY: modified_base
<222> LOCATION: (2923)
<223> OTHER INFORMATION: Unknown consensus marker
<220> FEATURE:
<221> NAME/KEY: modified_base
<222> LOCATION: (2925)..(2928)
<223> OTHER INFORMATION: Unknown consensus marker
<220> FEATURE:
<221> NAME/KEY: modified_base
<222> LOCATION: (2931)..(2932)
<223> OTHER INFORMATION: Unknown consensus marker
<220> FEATURE:
<221> NAME/KEY: modified_base
<222> LOCATION: (2935)..(2938)
<223> OTHER INFORMATION: Unknown consensus marker
<220> FEATURE:
<221> NAME/KEY: modified_base
<222> LOCATION: (2943)..(2946)
<223> OTHER INFORMATION: Unknown consensus marker
<220> FEATURE:
```

```
-continued

<221> NAME/KEY: modified_base
<222> LOCATION: (2948)..(2949)
<223> OTHER INFORMATION: Unknown consensus marker
<220> FEATURE:
<221> NAME/KEY: modified_base
<222> LOCATION: (2951)..(2954)
<223> OTHER INFORMATION: Unknown consensus marker
<220> FEATURE:
<221> NAME/KEY: modified_base
<222> LOCATION: (2957)..(2958)
<223> OTHER INFORMATION: Unknown consensus marker
<220> FEATURE:
<221> NAME/KEY: modified_base
<222> LOCATION: (2960)
<223> OTHER INFORMATION: Unknown consensus marker
<220> FEATURE:
<221> NAME/KEY: modified_base
<222> LOCATION: (2962)
<223> OTHER INFORMATION: Unknown consensus marker
<220> FEATURE:
<221> NAME/KEY: modified_base
<222> LOCATION: (2964)
<223> OTHER INFORMATION: Unknown consensus marker
<220> FEATURE:
<221> NAME/KEY: modified_base
<222> LOCATION: (2967)
<223> OTHER INFORMATION: Unknown consensus marker
<220> FEATURE:
<221> NAME/KEY: modified_base
<222> LOCATION: (2969)
<223> OTHER INFORMATION: Unknown consensus marker
<220> FEATURE:
<221> NAME/KEY: modified_base
<222> LOCATION: (2972)..(2976)
<223> OTHER INFORMATION: Unknown consensus marker
<220> FEATURE:
<221> NAME/KEY: modified_base
<222> LOCATION: (2979)
<223> OTHER INFORMATION: Unknown consensus marker
<220> FEATURE:
<221> NAME/KEY: modified_base
<222> LOCATION: (2981)
<223> OTHER INFORMATION: Unknown consensus marker
<220> FEATURE:
<221> NAME/KEY: modified_base
<222> LOCATION: (2985)
<223> OTHER INFORMATION: Unknown consensus marker
<220> FEATURE:
<221> NAME/KEY: modified_base
<222> LOCATION: (2987)..(2989)
<223> OTHER INFORMATION: Unknown consensus marker
<220> FEATURE:
<221> NAME/KEY: modified_base
<222> LOCATION: (2992)..(2994)
<223> OTHER INFORMATION: Unknown consensus marker
<220> FEATURE:
<221> NAME/KEY: modified_base
<222> LOCATION: (2999)..(3000)
<223> OTHER INFORMATION: Unknown consensus marker
<220> FEATURE:
<221> NAME/KEY: modified_base
<222> LOCATION: (3002)
<223> OTHER INFORMATION: Unknown consensus marker
<220> FEATURE:
<221> NAME/KEY: modified_base
<222> LOCATION: (3004)..(3006)
<223> OTHER INFORMATION: Unknown consensus marker
<220> FEATURE:
<221> NAME/KEY: modified_base
<222> LOCATION: (3008)..(3010)
<223> OTHER INFORMATION: Unknown consensus marker
<220> FEATURE:
<221> NAME/KEY: modified_base
<222> LOCATION: (3012)..(3014)
<223> OTHER INFORMATION: Unknown consensus marker
<220> FEATURE:
<221> NAME/KEY: modified_base
<222> LOCATION: (3017)
<223> OTHER INFORMATION: Unknown consensus marker
```

```
<220> FEATURE:
<221> NAME/KEY: modified_base
<222> LOCATION: (3019)..(3020)
<223> OTHER INFORMATION: Unknown consensus marker
<220> FEATURE:
<221> NAME/KEY: modified_base
<222> LOCATION: (3024)
<223> OTHER INFORMATION: Unknown consensus marker
<220> FEATURE:
<221> NAME/KEY: modified_base
<222> LOCATION: (3026)..(3028)
<223> OTHER INFORMATION: Unknown consensus marker
<220> FEATURE:
<221> NAME/KEY: modified_base
<222> LOCATION: (3030)..(3031)
<223> OTHER INFORMATION: Unknown consensus marker
<220> FEATURE:
<221> NAME/KEY: modified_base
<222> LOCATION: (3041)
<223> OTHER INFORMATION: Unknown consensus marker
<220> FEATURE:
<221> NAME/KEY: modified_base
<222> LOCATION: (3043)..(3044)
<223> OTHER INFORMATION: Unknown consensus marker
<220> FEATURE:
<221> NAME/KEY: modified_base
<222> LOCATION: (3046)
<223> OTHER INFORMATION: Unknown consensus marker
<220> FEATURE:
<221> NAME/KEY: modified_base
<222> LOCATION: (3050)..(3053)
<223> OTHER INFORMATION: Unknown consensus marker
<220> FEATURE:
<221> NAME/KEY: modified_base
<222> LOCATION: (3055)..(3058)
<223> OTHER INFORMATION: Unknown consensus marker
<220> FEATURE:
<221> NAME/KEY: modified_base
<222> LOCATION: (3062)..(3067)
<223> OTHER INFORMATION: Unknown consensus marker
<220> FEATURE:
<221> NAME/KEY: modified_base
<222> LOCATION: (3069)..(3070)
<223> OTHER INFORMATION: Unknown consensus marker
<220> FEATURE:
<221> NAME/KEY: modified_base
<222> LOCATION: (3073)
<223> OTHER INFORMATION: Unknown consensus marker
<220> FEATURE:
<221> NAME/KEY: modified_base
<222> LOCATION: (3075)
<223> OTHER INFORMATION: Unknown consensus marker
<220> FEATURE:
<221> NAME/KEY: modified_base
<222> LOCATION: (3079)..(3080)
<223> OTHER INFORMATION: Unknown consensus marker
<220> FEATURE:
<221> NAME/KEY: modified_base
<222> LOCATION: (3082)..(3088)
<223> OTHER INFORMATION: Unknown consensus marker
<220> FEATURE:
<221> NAME/KEY: modified_base
<222> LOCATION: (3090)..(3092)
<223> OTHER INFORMATION: Unknown consensus marker
<220> FEATURE:
<221> NAME/KEY: modified_base
<222> LOCATION: (3095)
<223> OTHER INFORMATION: Unknown consensus marker
<220> FEATURE:
<221> NAME/KEY: modified_base
<222> LOCATION: (3097)..(3101)
<223> OTHER INFORMATION: Unknown consensus marker
<220> FEATURE:
<221> NAME/KEY: modified_base
<222> LOCATION: (3103)..(3104)
<223> OTHER INFORMATION: Unknown consensus marker
<220> FEATURE:
<221> NAME/KEY: modified_base
<222> LOCATION: (3106)
```

```
<223> OTHER INFORMATION: Unknown consensus marker
<220> FEATURE:
<221> NAME/KEY: modified_base
<222> LOCATION: (3108)..(3109)
<223> OTHER INFORMATION: Unknown consensus marker
<220> FEATURE:
<221> NAME/KEY: modified_base
<222> LOCATION: (3112)..(3116)
<223> OTHER INFORMATION: Unknown consensus marker
<220> FEATURE:
<221> NAME/KEY: modified_base
<222> LOCATION: (3122)..(3125)
<223> OTHER INFORMATION: Unknown consensus marker
<220> FEATURE:
<221> NAME/KEY: modified_base
<222> LOCATION: (3128)..(3130)
<223> OTHER INFORMATION: Unknown consensus marker
<220> FEATURE:
<221> NAME/KEY: modified_base
<222> LOCATION: (3132)..(3133)
<223> OTHER INFORMATION: Unknown consensus marker
<220> FEATURE:
<221> NAME/KEY: modified_base
<222> LOCATION: (3136)..(3137)
<223> OTHER INFORMATION: Unknown consensus marker
<220> FEATURE:
<221> NAME/KEY: modified_base
<222> LOCATION: (3141)..(3144)
<223> OTHER INFORMATION: Unknown consensus marker
<220> FEATURE:
<221> NAME/KEY: modified_base
<222> LOCATION: (3148)..(3149)
<223> OTHER INFORMATION: Unknown consensus marker
<220> FEATURE:
<221> NAME/KEY: modified_base
<222> LOCATION: (3152)
<223> OTHER INFORMATION: Unknown consensus marker
<220> FEATURE:
<221> NAME/KEY: modified_base
<222> LOCATION: (3154)..(3155)
<223> OTHER INFORMATION: Unknown consensus marker
<220> FEATURE:
<221> NAME/KEY: modified_base
<222> LOCATION: (3157)..(3158)
<223> OTHER INFORMATION: Unknown consensus marker
<220> FEATURE:
<221> NAME/KEY: modified_base
<222> LOCATION: (3160)..(3165)
<223> OTHER INFORMATION: Unknown consensus marker
<220> FEATURE:
<221> NAME/KEY: modified_base
<222> LOCATION: (3168)
<223> OTHER INFORMATION: Unknown consensus marker
<220> FEATURE:
<221> NAME/KEY: modified_base
<222> LOCATION: (3170)
<223> OTHER INFORMATION: Unknown consensus marker
<220> FEATURE:
<221> NAME/KEY: modified_base
<222> LOCATION: (3173)..(3174)
<223> OTHER INFORMATION: Unknown consensus marker
<220> FEATURE:
<221> NAME/KEY: modified_base
<222> LOCATION: (3178)..(3208)
<223> OTHER INFORMATION: Unknown consensus marker

<400> SEQUENCE: 106
```

| | | | | | |
|---|---|---|---|---|---|
| ggggaagaga | ggcacagaca | cagataggag | aagggcaccg | gctggagcca | cttgcaggac | 60 |
| tgagggtttt | tgcaacaaaa | ccctagcagc | ctgaagaact | ctaagccaga | tggggtggct | 120 |
| ggacgagagc | agctcttggc | tcagcaaaga | atgcacagta | tgatcagctc | agtggatgtg | 180 |
| aagtcagaag | ttcctgtggg | cctggagccc | atctcacctt | tagacctaag | gacagacctc | 240 |
| aggatgatga | tgcccgtggt | ggaccctgtt | gtccgtgaga | agcaattgca | gcaggaatta | 300 |
| cttcttatcc | agcagcagca | acaaatccag | aagcagcttc | tgatagcaga | gtttcagaaa | 360 |

-continued

```
cagcatgaga acttgacacg gcagcaccag gctcagcttc aggagcatat caaggaactt    420
ctagccataa aacagcaaca agaactccta gaaaaggagc agaaactgga gcagcagagg    480
caagaacagg aagtagagag gcatcgcaga gaacagcagc ttcctcctct cagaggcaaa    540
gatagaggac gagaaagggc agtggcaagt acagaagtaa agcagaagct tcaagagttc    600
ctactgagta aatcagcaac gaaagacact ccaactaatg gaaaaaatca ttccgtgagc    660
cgccatccca agctctggta cacggctgcc caccacacat cattggatca aagctctcca    720 cccccttagtg gaacatctcc atcctacaag tacacattac caggagcaca agatgcaaag    780
gatgatttcc cccttcgaaa aactgcctct gagcccaact tgaaggtgcg gtccaggtta    840
aaacagaaag tggcagagag gagaagcagc cccttactca ggcggaagga tggaaatgtt    900
gtcacttcat tcaagaagcg aatgtttgag gtgacagaat cctcagtcag tagcagttct    960
ccaggctctg gtcccagttc accaaacaat gggccaactg gaagtgttac tgaaaatgag   1020
acttcggttt tgcccctac ccctcatgcc gagcaaatgg tttcacagca acgcattcta   1080
attcatgaag attccatgaa cctgctaagt ctttatacct ctccttcttt gcccaacatt   1140
accttggggc ttcccgcagt gccatcccag ctcaatgctt cgaattcact caaagaaaag   1200
cagaagtgtg agacgcagac gcttaggcaa ggtgttcctc tgcctgggca gtatggaggc   1260
agcatcccgg catcttccag ccaccctcat gttactttag agggaaagcc acccaacagc   1320
agccaccagg ctctcctgca gcatttatta ttgaaagaac aaatgcgaca gcaaaagctt   1380
cttgtagctg gtggagttcc cttacatcct cagtctccct tggcaacaaa agagagaatt   1440
tcacctggca ttagaggtac ccacaaattg ccccgtcaca gacccctgaa ccgaacccag   1500
tctgcacctt tgcctcagag cacgttggct cagctggtca ttcaacagca acaccagcaa   1560
ttcttggaga agcagaagca ataccagcag cagatccaca tgaacaaact gctttcgaaa   1620
tctattgaac aactgaagca accaggcagt caccttgagg aagcagagga agagcttcag   1680
ggggaccagg cgatgcagga agacagagcg ccctctagtg gcaacagcac taggagcgac   1740
agcagtgctt gtgtggatga cactgggaa caagttgggg ctgtgaaggt caaggaggaa   1800
ccagtggaca gtgatgaaga tgctcagatc caggaaatgg aatctgggga gcaggctgct   1860
tttatgcaac agccttttcct ggaacccacg cacacacgtg cgctctctgt gcgccaagct   1920
ccgctggctg cggttggcat ggatggatta gagaaacacc gtctcgtctc caggactcac   1980
tcttcccctg ctgcctctgt tttacctcac ccngcaatgg accgcccct ccagcctggc   2040 tctgcaactg gaattgccta tgaccccttg atgctgaaac accagtgcgt ttgtggcaat   2100
tccaccaccc accctgagca tgctggacga atacagagta tctggtcacg actgcaagaa   2160
actgggctgc taaataaatg tgagcgaatt caaggtcgaa aagccagcct ggaggaaata   2220
cagcttgttc attctgaaca tcactcactg ttgtatggca ccaacccct ggacggacag   2280 aagctggacc ccaggatact cctaggtgat gactctcaaa agttttttc ctcattacct   2340 tgtggtggac ttggggtgga cagtgacacc atttggaatg agctacactc gtccggtgct   2400
gcacgcatgg ctgttggctg tgtcatcgag ctggcttcca aagtggcctc aggagagctg   2460
aagaatgggt ttgctgttgt gaggcccct ggccatcacg ctgaagaatc cacagccatg   2520
gggttctgct ttttttaattc agttgcaatt accgccaaat acttgagaga ccaactaaat   2580
ataagcaaga tattgattgt agatctggat gttcaccatg gaaacggtac ccagcaggcc   2640
ttttatgctg acccccagcat cctgtacatt tcactccatc gctatgatga agggaacttt   2700
```

-continued

| | |
|---|---|
| ttccctggca gtggagcccc aaatgaggtt ngnanantcn nttgagaann nnacnntata | 2760 |
| nanattgnct ngnnnnntng cnttgnnccn cnnnnnggnn annnnnngnn ncnnnannnn | 2820 |
| tnnnnnannn ncgtnnancn tnnnnnnann gngnntnatn nnnanannnn nttngtntnt | 2880 |
| gnnnnanntn nnnnantnna nnnnnanncc nctnctntan gangnnnnaa nntgnnnnca | 2940 |
| aannnntnng nnnnttnnan gnancantng annnnnttng ntgangnnng tnnnntgtnn | 3000 |
| gntnnngnnn gnnnacntnn tctnannncn ntctgtgatg nannanaagn nnntnnnnat | 3060 |
| gnnnnnntnn ganangagnn gnnnnnnntn nnagnannnn ntnncnanna annnnngaat | 3120 |
| annnntgnnn tnnttnnttt nnnnaagnnc antnnanntn nnnnnatntn ttnnaagnnn | 3180 |
| nnnnnnnnnn nnnnnnnnnn nnnnnnnng | 3209 |

```
<210> SEQ ID NO 107
<211> LENGTH: 1141
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MOD_RES
<222> LOCATION: (2)
<223> OTHER INFORMATION: Unknown consensus marker
<220> FEATURE:
<221> NAME/KEY: MOD_RES
<222> LOCATION: (4)..(7)
<223> OTHER INFORMATION: Unknown consensus marker
<220> FEATURE:
<221> NAME/KEY: MOD_RES
<222> LOCATION: (15)..(16)
<223> OTHER INFORMATION: Unknown consensus marker
<220> FEATURE:
<221> NAME/KEY: MOD_RES
<222> LOCATION: (21)..(24)
<223> OTHER INFORMATION: Unknown consensus marker
<220> FEATURE:
<221> NAME/KEY: MOD_RES
<222> LOCATION: (26)..(27)
<223> OTHER INFORMATION: Unknown consensus marker
<220> FEATURE:
<221> NAME/KEY: MOD_RES
<222> LOCATION: (29)..(30)
<223> OTHER INFORMATION: Unknown consensus marker
<220> FEATURE:
<221> NAME/KEY: MOD_RES
<222> LOCATION: (35)..(37)
<223> OTHER INFORMATION: Unknown consensus marker
<220> FEATURE:
<221> NAME/KEY: MOD_RES
<222> LOCATION: (40)..(41)
<223> OTHER INFORMATION: Unknown consensus marker
<220> FEATURE:
<221> NAME/KEY: MOD_RES
<222> LOCATION: (43)..(46)
<223> OTHER INFORMATION: Unknown consensus marker
<220> FEATURE:
<221> NAME/KEY: MOD_RES
<222> LOCATION: (49)..(62)
<223> OTHER INFORMATION: Unknown consensus marker
<220> FEATURE:
<221> NAME/KEY: MOD_RES
<222> LOCATION: (66)..(67)
<223> OTHER INFORMATION: Unknown consensus marker
<220> FEATURE:
<221> NAME/KEY: MOD_RES
<222> LOCATION: (70)
<223> OTHER INFORMATION: Unknown consensus marker
<220> FEATURE:
<221> NAME/KEY: MOD_RES
<222> LOCATION: (74)
<223> OTHER INFORMATION: Unknown consensus marker
<220> FEATURE:
```

```
<221> NAME/KEY: MOD_RES
<222> LOCATION: (82)
<223> OTHER INFORMATION: Unknown consensus marker
<220> FEATURE:
<221> NAME/KEY: MOD_RES
<222> LOCATION: (84)
<223> OTHER INFORMATION: Unknown consensus marker
<220> FEATURE:
<221> NAME/KEY: MOD_RES
<222> LOCATION: (86)
<223> OTHER INFORMATION: Unknown consensus marker
<220> FEATURE:
<221> NAME/KEY: MOD_RES
<222> LOCATION: (95)
<223> OTHER INFORMATION: Unknown consensus marker
<220> FEATURE:
<221> NAME/KEY: MOD_RES
<222> LOCATION: (104)
<223> OTHER INFORMATION: Unknown consensus marker
<220> FEATURE:
<221> NAME/KEY: MOD_RES
<222> LOCATION: (110)..(111)
<223> OTHER INFORMATION: Unknown consensus marker
<220> FEATURE:
<221> NAME/KEY: MOD_RES
<222> LOCATION: (114)..(115)
<223> OTHER INFORMATION: Unknown consensus marker
<220> FEATURE:
<221> NAME/KEY: MOD_RES
<222> LOCATION: (119)
<223> OTHER INFORMATION: Unknown consensus marker
<220> FEATURE:
<221> NAME/KEY: MOD_RES
<222> LOCATION: (126)
<223> OTHER INFORMATION: Unknown consensus marker
<220> FEATURE:
<221> NAME/KEY: MOD_RES
<222> LOCATION: (128)
<223> OTHER INFORMATION: Unknown consensus marker
<220> FEATURE:
<221> NAME/KEY: MOD_RES
<222> LOCATION: (134)..(138)
<223> OTHER INFORMATION: Unknown consensus marker
<220> FEATURE:
<221> NAME/KEY: MOD_RES
<222> LOCATION: (143)..(144)
<223> OTHER INFORMATION: Unknown consensus marker
<220> FEATURE:
<221> NAME/KEY: MOD_RES
<222> LOCATION: (147)..(148)
<223> OTHER INFORMATION: Unknown consensus marker
<220> FEATURE:
<221> NAME/KEY: MOD_RES
<222> LOCATION: (158)..(160)
<223> OTHER INFORMATION: Unknown consensus marker
<220> FEATURE:
<221> NAME/KEY: MOD_RES
<222> LOCATION: (163)
<223> OTHER INFORMATION: Unknown consensus marker
<220> FEATURE:
<221> NAME/KEY: MOD_RES
<222> LOCATION: (165)..(166)
<223> OTHER INFORMATION: Unknown consensus marker
<220> FEATURE:
<221> NAME/KEY: MOD_RES
<222> LOCATION: (169)
<223> OTHER INFORMATION: Unknown consensus marker
<220> FEATURE:
<221> NAME/KEY: MOD_RES
<222> LOCATION: (173)
<223> OTHER INFORMATION: Unknown consensus marker
<220> FEATURE:
<221> NAME/KEY: MOD_RES
<222> LOCATION: (176)
<223> OTHER INFORMATION: Unknown consensus marker
<220> FEATURE:
<221> NAME/KEY: MOD_RES
<222> LOCATION: (185)
<223> OTHER INFORMATION: Unknown consensus marker
```

```
<220> FEATURE:
<221> NAME/KEY: MOD_RES
<222> LOCATION: (193)
<223> OTHER INFORMATION: Unknown consensus marker
<220> FEATURE:
<221> NAME/KEY: MOD_RES
<222> LOCATION: (195)..(202)
<223> OTHER INFORMATION: Unknown consensus marker
<220> FEATURE:
<221> NAME/KEY: MOD_RES
<222> LOCATION: (205)
<223> OTHER INFORMATION: Unknown consensus marker
<220> FEATURE:
<221> NAME/KEY: MOD_RES
<222> LOCATION: (208)
<223> OTHER INFORMATION: Unknown consensus marker
<220> FEATURE:
<221> NAME/KEY: MOD_RES
<222> LOCATION: (210)..(212)
<223> OTHER INFORMATION: Unknown consensus marker
<220> FEATURE:
<221> NAME/KEY: MOD_RES
<222> LOCATION: (215)
<223> OTHER INFORMATION: Unknown consensus marker
<220> FEATURE:
<221> NAME/KEY: MOD_RES
<222> LOCATION: (218)..(221)
<223> OTHER INFORMATION: Unknown consensus marker
<220> FEATURE:
<221> NAME/KEY: MOD_RES
<222> LOCATION: (223)
<223> OTHER INFORMATION: Unknown consensus marker
<220> FEATURE:
<221> NAME/KEY: MOD_RES
<222> LOCATION: (232)
<223> OTHER INFORMATION: Unknown consensus marker
<220> FEATURE:
<221> NAME/KEY: MOD_RES
<222> LOCATION: (238)..(240)
<223> OTHER INFORMATION: Unknown consensus marker
<220> FEATURE:
<221> NAME/KEY: MOD_RES
<222> LOCATION: (243)..(245)
<223> OTHER INFORMATION: Unknown consensus marker
<220> FEATURE:
<221> NAME/KEY: MOD_RES
<222> LOCATION: (247)
<223> OTHER INFORMATION: Unknown consensus marker
<220> FEATURE:
<221> NAME/KEY: MOD_RES
<222> LOCATION: (249)..(250)
<223> OTHER INFORMATION: Unknown consensus marker
<220> FEATURE:
<221> NAME/KEY: MOD_RES
<222> LOCATION: (292)
<223> OTHER INFORMATION: Unknown consensus marker
<220> FEATURE:
<221> NAME/KEY: MOD_RES
<222> LOCATION: (296)..(297)
<223> OTHER INFORMATION: Unknown consensus marker
<220> FEATURE:
<221> NAME/KEY: MOD_RES
<222> LOCATION: (301)..(302)
<223> OTHER INFORMATION: Unknown consensus marker
<220> FEATURE:
<221> NAME/KEY: MOD_RES
<222> LOCATION: (311)..(312)
<223> OTHER INFORMATION: Unknown consensus marker
<220> FEATURE:
<221> NAME/KEY: MOD_RES
<222> LOCATION: (314)..(316)
<223> OTHER INFORMATION: Unknown consensus marker
<220> FEATURE:
<221> NAME/KEY: MOD_RES
<222> LOCATION: (329)..(335)
<223> OTHER INFORMATION: Unknown consensus marker
<220> FEATURE:
<221> NAME/KEY: MOD_RES
<222> LOCATION: (338)..(343)
```

```
<223> OTHER INFORMATION: Unknown consensus marker
<220> FEATURE:
<221> NAME/KEY: MOD_RES
<222> LOCATION: (345)..(348)
<223> OTHER INFORMATION: Unknown consensus marker
<220> FEATURE:
<221> NAME/KEY: MOD_RES
<222> LOCATION: (350)..(356)
<223> OTHER INFORMATION: Unknown consensus marker
<220> FEATURE:
<221> NAME/KEY: MOD_RES
<222> LOCATION: (358)..(370)
<223> OTHER INFORMATION: Unknown consensus marker
<220> FEATURE:
<221> NAME/KEY: MOD_RES
<222> LOCATION: (372)..(393)
<223> OTHER INFORMATION: Unknown consensus marker
<220> FEATURE:
<221> NAME/KEY: MOD_RES
<222> LOCATION: (395)..(396)
<223> OTHER INFORMATION: Unknown consensus marker
<220> FEATURE:
<221> NAME/KEY: MOD_RES
<222> LOCATION: (404)..(405)
<223> OTHER INFORMATION: Unknown consensus marker
<220> FEATURE:
<221> NAME/KEY: MOD_RES
<222> LOCATION: (407)..(411)
<223> OTHER INFORMATION: Unknown consensus marker
<220> FEATURE:
<221> NAME/KEY: MOD_RES
<222> LOCATION: (413)
<223> OTHER INFORMATION: Unknown consensus marker
<220> FEATURE:
<221> NAME/KEY: MOD_RES
<222> LOCATION: (415)..(417)
<223> OTHER INFORMATION: Unknown consensus marker
<220> FEATURE:
<221> NAME/KEY: MOD_RES
<222> LOCATION: (419)
<223> OTHER INFORMATION: Unknown consensus marker
<220> FEATURE:
<221> NAME/KEY: MOD_RES
<222> LOCATION: (421)..(445)
<223> OTHER INFORMATION: Unknown consensus marker
<220> FEATURE:
<221> NAME/KEY: MOD_RES
<222> LOCATION: (447)..(448)
<223> OTHER INFORMATION: Unknown consensus marker
<220> FEATURE:
<221> NAME/KEY: MOD_RES
<222> LOCATION: (456)
<223> OTHER INFORMATION: Unknown consensus marker
<220> FEATURE:
<221> NAME/KEY: MOD_RES
<222> LOCATION: (459)..(461)
<223> OTHER INFORMATION: Unknown consensus marker
<220> FEATURE:
<221> NAME/KEY: MOD_RES
<222> LOCATION: (463)..(464)
<223> OTHER INFORMATION: Unknown consensus marker
<220> FEATURE:
<221> NAME/KEY: MOD_RES
<222> LOCATION: (469)
<223> OTHER INFORMATION: Unknown consensus marker
<220> FEATURE:
<221> NAME/KEY: MOD_RES
<222> LOCATION: (476)
<223> OTHER INFORMATION: Unknown consensus marker
<220> FEATURE:
<221> NAME/KEY: MOD_RES
<222> LOCATION: (481)..(483)
<223> OTHER INFORMATION: Unknown consensus marker
<220> FEATURE:
<221> NAME/KEY: MOD_RES
<222> LOCATION: (488)..(489)
<223> OTHER INFORMATION: Unknown consensus marker
<220> FEATURE:
<221> NAME/KEY: MOD_RES
```

```
<222> LOCATION: (492)..(494)
<223> OTHER INFORMATION: Unknown consensus marker
<220> FEATURE:
<221> NAME/KEY: MOD_RES
<222> LOCATION: (497)..(498)
<223> OTHER INFORMATION: Unknown consensus marker
<220> FEATURE:
<221> NAME/KEY: MOD_RES
<222> LOCATION: (503)
<223> OTHER INFORMATION: Unknown consensus marker
<220> FEATURE:
<221> NAME/KEY: MOD_RES
<222> LOCATION: (513)..(514)
<223> OTHER INFORMATION: Unknown consensus marker
<220> FEATURE:
<221> NAME/KEY: MOD_RES
<222> LOCATION: (516)
<223> OTHER INFORMATION: Unknown consensus marker
<220> FEATURE:
<221> NAME/KEY: MOD_RES
<222> LOCATION: (518)..(519)
<223> OTHER INFORMATION: Unknown consensus marker
<220> FEATURE:
<221> NAME/KEY: MOD_RES
<222> LOCATION: (533)
<223> OTHER INFORMATION: Unknown consensus marker
<220> FEATURE:
<221> NAME/KEY: MOD_RES
<222> LOCATION: (543)
<223> OTHER INFORMATION: Unknown consensus marker
<220> FEATURE:
<221> NAME/KEY: MOD_RES
<222> LOCATION: (545)
<223> OTHER INFORMATION: Unknown consensus marker
<220> FEATURE:
<221> NAME/KEY: MOD_RES
<222> LOCATION: (547)
<223> OTHER INFORMATION: Unknown consensus marker
<220> FEATURE:
<221> NAME/KEY: MOD_RES
<222> LOCATION: (549)..(552)
<223> OTHER INFORMATION: Unknown consensus marker
<220> FEATURE:
<221> NAME/KEY: MOD_RES
<222> LOCATION: (554)..(555)
<223> OTHER INFORMATION: Unknown consensus marker
<220> FEATURE:
<221> NAME/KEY: MOD_RES
<222> LOCATION: (559)
<223> OTHER INFORMATION: Unknown consensus marker
<220> FEATURE:
<221> NAME/KEY: MOD_RES
<222> LOCATION: (562)
<223> OTHER INFORMATION: Unknown consensus marker
<220> FEATURE:
<221> NAME/KEY: MOD_RES
<222> LOCATION: (565)
<223> OTHER INFORMATION: Unknown consensus marker
<220> FEATURE:
<221> NAME/KEY: MOD_RES
<222> LOCATION: (570)..(572)
<223> OTHER INFORMATION: Unknown consensus marker
<220> FEATURE:
<221> NAME/KEY: MOD_RES
<222> LOCATION: (574)..(598)
<223> OTHER INFORMATION: Unknown consensus marker
<220> FEATURE:
<221> NAME/KEY: MOD_RES
<222> LOCATION: (600)..(608)
<223> OTHER INFORMATION: Unknown consensus marker
<220> FEATURE:
<221> NAME/KEY: MOD_RES
<222> LOCATION: (611)
<223> OTHER INFORMATION: Unknown consensus marker
<220> FEATURE:
<221> NAME/KEY: MOD_RES
<222> LOCATION: (619)..(622)
<223> OTHER INFORMATION: Unknown consensus marker
<220> FEATURE:
```

```
<221> NAME/KEY: MOD_RES
<222> LOCATION: (624)..(657)
<223> OTHER INFORMATION: Unknown consensus marker
<220> FEATURE:
<221> NAME/KEY: MOD_RES
<222> LOCATION: (659)
<223> OTHER INFORMATION: Unknown consensus marker
<220> FEATURE:
<221> NAME/KEY: MOD_RES
<222> LOCATION: (661)..(664)
<223> OTHER INFORMATION: Unknown consensus marker
<220> FEATURE:
<221> NAME/KEY: MOD_RES
<222> LOCATION: (666)
<223> OTHER INFORMATION: Unknown consensus marker
<220> FEATURE:
<221> NAME/KEY: MOD_RES
<222> LOCATION: (668)..(671)
<223> OTHER INFORMATION: Unknown consensus marker
<220> FEATURE:
<221> NAME/KEY: MOD_RES
<222> LOCATION: (673)..(674)
<223> OTHER INFORMATION: Unknown consensus marker
<220> FEATURE:
<221> NAME/KEY: MOD_RES
<222> LOCATION: (676)
<223> OTHER INFORMATION: Unknown consensus marker
<220> FEATURE:
<221> NAME/KEY: MOD_RES
<222> LOCATION: (678)..(679)
<223> OTHER INFORMATION: Unknown consensus marker
<220> FEATURE:
<221> NAME/KEY: MOD_RES
<222> LOCATION: (685)..(692)
<223> OTHER INFORMATION: Unknown consensus marker
<220> FEATURE:
<221> NAME/KEY: MOD_RES
<222> LOCATION: (694)
<223> OTHER INFORMATION: Unknown consensus marker
<220> FEATURE:
<221> NAME/KEY: MOD_RES
<222> LOCATION: (696)..(701)
<223> OTHER INFORMATION: Unknown consensus marker
<220> FEATURE:
<221> NAME/KEY: MOD_RES
<222> LOCATION: (705)
<223> OTHER INFORMATION: Unknown consensus marker
<220> FEATURE:
<221> NAME/KEY: MOD_RES
<222> LOCATION: (708)..(709)
<223> OTHER INFORMATION: Unknown consensus marker
<220> FEATURE:
<221> NAME/KEY: MOD_RES
<222> LOCATION: (716)
<223> OTHER INFORMATION: Unknown consensus marker
<220> FEATURE:
<221> NAME/KEY: MOD_RES
<222> LOCATION: (719)
<223> OTHER INFORMATION: Unknown consensus marker
<220> FEATURE:
<221> NAME/KEY: MOD_RES
<222> LOCATION: (721)..(722)
<223> OTHER INFORMATION: Unknown consensus marker
<220> FEATURE:
<221> NAME/KEY: MOD_RES
<222> LOCATION: (743)..(744)
<223> OTHER INFORMATION: Unknown consensus marker
<220> FEATURE:
<221> NAME/KEY: MOD_RES
<222> LOCATION: (748)
<223> OTHER INFORMATION: Unknown consensus marker
<220> FEATURE:
<221> NAME/KEY: MOD_RES
<222> LOCATION: (750)
<223> OTHER INFORMATION: Unknown consensus marker
<220> FEATURE:
<221> NAME/KEY: MOD_RES
<222> LOCATION: (761)
<223> OTHER INFORMATION: Unknown consensus marker
```

```
<220> FEATURE:
<221> NAME/KEY: MOD_RES
<222> LOCATION: (766)
<223> OTHER INFORMATION: Unknown consensus marker
<220> FEATURE:
<221> NAME/KEY: MOD_RES
<222> LOCATION: (774)
<223> OTHER INFORMATION: Unknown consensus marker
<220> FEATURE:
<221> NAME/KEY: MOD_RES
<222> LOCATION: (777)..(778)
<223> OTHER INFORMATION: Unknown consensus marker
<220> FEATURE:
<221> NAME/KEY: MOD_RES
<222> LOCATION: (783)
<223> OTHER INFORMATION: Unknown consensus marker
<220> FEATURE:
<221> NAME/KEY: MOD_RES
<222> LOCATION: (785)
<223> OTHER INFORMATION: Unknown consensus marker
<220> FEATURE:
<221> NAME/KEY: MOD_RES
<222> LOCATION: (789)..(794)
<223> OTHER INFORMATION: Unknown consensus marker
<220> FEATURE:
<221> NAME/KEY: MOD_RES
<222> LOCATION: (796)..(797)
<223> OTHER INFORMATION: Unknown consensus marker
<220> FEATURE:
<221> NAME/KEY: MOD_RES
<222> LOCATION: (818)
<223> OTHER INFORMATION: Unknown consensus marker
<220> FEATURE:
<221> NAME/KEY: MOD_RES
<222> LOCATION: (831)..(832)
<223> OTHER INFORMATION: Unknown consensus marker
<220> FEATURE:
<221> NAME/KEY: MOD_RES
<222> LOCATION: (836)
<223> OTHER INFORMATION: Unknown consensus marker
<220> FEATURE:
<221> NAME/KEY: MOD_RES
<222> LOCATION: (858)
<223> OTHER INFORMATION: Unknown consensus marker
<220> FEATURE:
<221> NAME/KEY: MOD_RES
<222> LOCATION: (870)
<223> OTHER INFORMATION: Unknown consensus marker
<220> FEATURE:
<221> NAME/KEY: MOD_RES
<222> LOCATION: (873)
<223> OTHER INFORMATION: Unknown consensus marker
<220> FEATURE:
<221> NAME/KEY: MOD_RES
<222> LOCATION: (875)..(877)
<223> OTHER INFORMATION: Unknown consensus marker
<220> FEATURE:
<221> NAME/KEY: MOD_RES
<222> LOCATION: (879)
<223> OTHER INFORMATION: Unknown consensus marker
<220> FEATURE:
<221> NAME/KEY: MOD_RES
<222> LOCATION: (881)
<223> OTHER INFORMATION: Unknown consensus marker
<220> FEATURE:
<221> NAME/KEY: MOD_RES
<222> LOCATION: (888)
<223> OTHER INFORMATION: Unknown consensus marker
<220> FEATURE:
<221> NAME/KEY: MOD_RES
<222> LOCATION: (902)
<223> OTHER INFORMATION: Unknown consensus marker
<220> FEATURE:
<221> NAME/KEY: MOD_RES
<222> LOCATION: (916)
<223> OTHER INFORMATION: Unknown consensus marker
<220> FEATURE:
<221> NAME/KEY: MOD_RES
<222> LOCATION: (927)
```

```
<223> OTHER INFORMATION: Unknown consensus marker
<220> FEATURE:
<221> NAME/KEY: MOD_RES
<222> LOCATION: (930)..(946)
<223> OTHER INFORMATION: Unknown consensus marker
<220> FEATURE:
<221> NAME/KEY: MOD_RES
<222> LOCATION: (948)
<223> OTHER INFORMATION: Unknown consensus marker
<220> FEATURE:
<221> NAME/KEY: MOD_RES
<222> LOCATION: (954)
<223> OTHER INFORMATION: Unknown consensus marker
<220> FEATURE:
<221> NAME/KEY: MOD_RES
<222> LOCATION: (958)
<223> OTHER INFORMATION: Unknown consensus marker
<220> FEATURE:
<221> NAME/KEY: MOD_RES
<222> LOCATION: (965)
<223> OTHER INFORMATION: Unknown consensus marker
<220> FEATURE:
<221> NAME/KEY: MOD_RES
<222> LOCATION: (969)
<223> OTHER INFORMATION: Unknown consensus marker
<220> FEATURE:
<221> NAME/KEY: MOD_RES
<222> LOCATION: (972)
<223> OTHER INFORMATION: Unknown consensus marker
<220> FEATURE:
<221> NAME/KEY: MOD_RES
<222> LOCATION: (989)..(990)
<223> OTHER INFORMATION: Unknown consensus marker
<220> FEATURE:
<221> NAME/KEY: MOD_RES
<222> LOCATION: (996)
<223> OTHER INFORMATION: Unknown consensus marker
<220> FEATURE:
<221> NAME/KEY: MOD_RES
<222> LOCATION: (1011)
<223> OTHER INFORMATION: Unknown consensus marker
<220> FEATURE:
<221> NAME/KEY: MOD_RES
<222> LOCATION: (1014)
<223> OTHER INFORMATION: Unknown consensus marker
<220> FEATURE:
<221> NAME/KEY: MOD_RES
<222> LOCATION: (1039)
<223> OTHER INFORMATION: Unknown consensus marker
<220> FEATURE:
<221> NAME/KEY: MOD_RES
<222> LOCATION: (1043)..(1044)
<223> OTHER INFORMATION: Unknown consensus marker
<220> FEATURE:
<221> NAME/KEY: MOD_RES
<222> LOCATION: (1047)
<223> OTHER INFORMATION: Unknown consensus marker
<220> FEATURE:
<221> NAME/KEY: MOD_RES
<222> LOCATION: (1050)
<223> OTHER INFORMATION: Unknown consensus marker
<220> FEATURE:
<221> NAME/KEY: MOD_RES
<222> LOCATION: (1052)
<223> OTHER INFORMATION: Unknown consensus marker
<220> FEATURE:
<221> NAME/KEY: MOD_RES
<222> LOCATION: (1055)
<223> OTHER INFORMATION: Unknown consensus marker
<220> FEATURE:
<221> NAME/KEY: MOD_RES
<222> LOCATION: (1057)
<223> OTHER INFORMATION: Unknown consensus marker
<220> FEATURE:
<221> NAME/KEY: MOD_RES
<222> LOCATION: (1060)
<223> OTHER INFORMATION: Unknown consensus marker
<220> FEATURE:
<221> NAME/KEY: MOD_RES
```

```
<222> LOCATION: (1064)
<223> OTHER INFORMATION: Unknown consensus marker
<220> FEATURE:
<221> NAME/KEY: MOD_RES
<222> LOCATION: (1067)
<223> OTHER INFORMATION: Unknown consensus marker
<220> FEATURE:
<221> NAME/KEY: MOD_RES
<222> LOCATION: (1073)
<223> OTHER INFORMATION: Unknown consensus marker
<220> FEATURE:
<221> NAME/KEY: MOD_RES
<222> LOCATION: (1075)..(1087)
<223> OTHER INFORMATION: Unknown consensus marker
<220> FEATURE:
<221> NAME/KEY: MOD_RES
<222> LOCATION: (1089)
<223> OTHER INFORMATION: Unknown consensus marker
<220> FEATURE:
<221> NAME/KEY: MOD_RES
<222> LOCATION: (1092)
<223> OTHER INFORMATION: Unknown consensus marker
<220> FEATURE:
<221> NAME/KEY: MOD_RES
<222> LOCATION: (1095)..(1099)
<223> OTHER INFORMATION: Unknown consensus marker
<220> FEATURE:
<221> NAME/KEY: MOD_RES
<222> LOCATION: (1102)
<223> OTHER INFORMATION: Unknown consensus marker
<220> FEATURE:
<221> NAME/KEY: MOD_RES
<222> LOCATION: (1110)
<223> OTHER INFORMATION: Unknown consensus marker
<220> FEATURE:
<221> NAME/KEY: MOD_RES
<222> LOCATION: (1113)..(1128)
<223> OTHER INFORMATION: Unknown consensus marker
<220> FEATURE:
<221> NAME/KEY: MOD_RES
<222> LOCATION: (1130)..(1132)
<223> OTHER INFORMATION: Unknown consensus marker
<220> FEATURE:
<221> NAME/KEY: MOD_RES
<222> LOCATION: (1137)
<223> OTHER INFORMATION: Unknown consensus marker
<220> FEATURE:
<221> NAME/KEY: MOD_RES
<222> LOCATION: (1140)
<223> OTHER INFORMATION: Unknown consensus marker

<400> SEQUENCE: 107

Met Xaa Ser Xaa Xaa Xaa Xaa Asp Gly Leu Ser Gly Arg Asp Xaa Xaa
  1               5                  10                  15

Leu Glu Ile Leu Xaa Xaa Xaa Xaa Met Xaa Xaa Met Xaa Xaa Ser Val
             20                  25                  30

Asp Val Xaa Xaa Xaa Val Pro Xaa Xaa Leu Xaa Xaa Xaa Xaa Gly Gly
         35                  40                  45

Xaa Xaa Xaa Xaa Xaa Xaa Xaa Xaa Xaa Xaa Xaa Xaa Xaa Xaa Leu Val
     50                  55                  60

Gly Xaa Xaa Asp Pro Xaa Val Arg Glu Xaa Gln Leu Gln Gln Glu Leu
 65                  70                  75                  80

Leu Xaa Ile Xaa Gln Xaa Gln Gln Ile Gln Lys Gln Leu Leu Xaa Ala
             85                  90                  95

Glu Phe Gln Lys Gln His Glu Xaa Leu Thr Arg Gln His Xaa Xaa Gln
            100                 105                 110

Leu Xaa Xaa His Ile Lys Xaa Gln Gln Glu Leu Leu Ala Xaa Lys Xaa
        115                 120                 125

Gln Gln Glu Leu Leu Xaa Xaa Xaa Xaa Xaa Gln Glu Leu Glu Xaa Xaa
    130                 135                 140
```

```
Arg Gln Xaa Xaa Gln Gln Arg Gln Glu Glu Val Glu Arg Xaa Xaa Xaa
145                 150                 155                 160

Glu Gln Xaa Leu Xaa Xaa Leu Arg Xaa Lys Asp Arg Xaa Arg Glu Xaa
                165                 170                 175

Ala Val Ala Ser Thr Glu Val Lys Xaa Lys Leu Gln Glu Phe Leu Leu
            180                 185                 190

Xaa Lys Xaa Xaa Xaa Xaa Xaa Xaa Xaa Asn Gly Xaa Asn His Xaa
        195                 200                 205

Val Xaa Xaa Xaa Pro Lys Xaa Trp Tyr Xaa Xaa Xaa Xaa His Xaa Ser
    210                 215                 220

Leu Asp Gln Ser Ser Pro Pro Xaa Ser Gly Pro Gly Xaa Xaa Xaa
225                 230                 235                 240

Ser Tyr Xaa Xaa Xaa Leu Xaa Gly Xaa Xaa Asp Ala Lys Asp Asp Phe
                245                 250                 255

Pro Leu Arg Lys Thr Ala Ser Glu Pro Asn Leu Lys Val Arg Ser Arg
            260                 265                 270

Leu Lys Gln Lys Val Ala Glu Arg Arg Ser Ser Pro Leu Leu Arg Arg
        275                 280                 285

Lys Asp Gly Xaa Val Val Thr Xaa Xaa Lys Lys Arg Xaa Xaa Glu Val
    290                 295                 300

Thr Gly Ala Gly Pro Gly Xaa Xaa Ser Xaa Xaa Xaa Ser Ser Pro Gly
305                 310                 315                 320

Ser Gly Pro Ser Ser Pro Asn Asn Xaa Xaa Xaa Xaa Xaa Xaa Xaa Glu
                325                 330                 335

Asn Xaa Xaa Xaa Xaa Xaa Xaa Pro Xaa Xaa Xaa Xaa Glu Xaa Xaa Xaa
        340                 345                 350

Xaa Xaa Xaa Xaa Ile Xaa Xaa Xaa Xaa Xaa Xaa Xaa Xaa Xaa Xaa Xaa
    355                 360                 365

Xaa Xaa Thr Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Ser Xaa Xaa Lys Leu Ser Thr
385                 390                 395                 400

Gln Gln Glu Xaa Xaa Lys Xaa Xaa Xaa Xaa Leu Xaa Gln Xaa Xaa
                405                 410                 415

Xaa Leu Xaa Gly Xaa Xaa Xaa Xaa Xaa Xaa Xaa Xaa Xaa Xaa Xaa Xaa
        420                 425                 430

Xaa Xaa Xaa Xaa Xaa Xaa Xaa Xaa Xaa Xaa Xaa Xaa His Xaa Xaa
    435                 440                 445

Leu Leu Gln His Leu Leu Xaa Glu Gln Xaa Xaa Xaa Gln Xaa Xaa
450                 455                 460

Leu Val Thr Gly Xaa Gly Gly Val Pro Leu His Xaa Gln Ser Pro Leu
465                 470                 475                 480

Xaa Xaa Xaa Glu Arg Ile Ser Xaa Xaa Ile Arg Xaa Xaa Xaa Lys Leu
            485                 490                 495

Xaa Xaa His Arg Pro Leu Xaa Arg Thr Gln Ser Ala Pro Leu Pro Gln
            500                 505                 510

Xaa Xaa Gln Xaa Leu Xaa Xaa Leu Val Ile Gln Gln His Gln Gln
        515                 520                 525

Phe Leu Glu Lys Xaa Lys Gln Gln Tyr Gln Gln Gln Ile Xaa Met
                530                 535                 540

Xaa Lys Xaa Leu Xaa Xaa Xaa Xaa Glu Xaa Xaa Lys Gln Pro Xaa Ser
545                 550                 555                 560
```

-continued

```
His Xaa Glu Glu Xaa Glu Glu Leu Xaa Xaa Xaa Gln Xaa Xaa Xaa
            565                 570

-continued

```
                           980                 985                 990
Gly Gly Tyr Xaa Val Thr Ala Lys Cys Phe Gly His Leu Thr Lys Gln
              995                1000                1005
Leu Met Xaa Leu Ala Xaa Gly Arg Val Val Leu Ala Leu Glu Gly Gly
       1010                1015                1020
His Asp Leu Thr Ala Ile Cys Asp Ala Ser Glu Ala Cys Val Xaa Ala
1025                1030                1035                1040
Leu Leu Xaa Xaa Glu Leu Xaa Pro Leu Xaa Glu Xaa Ile Leu Xaa Gln
                   1045                1050                1055
Xaa Pro Asn Xaa Asn Ala Val Xaa Ser Leu Xaa Lys Ile Ile Glu Ile
              1060                1065                1070
Xaa Ser Xaa Xaa Xaa Xaa Xaa Xaa Xaa Xaa Xaa Xaa Xaa Xaa Xaa Gly
       1075                1080                1085
Xaa Ser Leu Xaa Glu Ala Xaa Xaa Xaa Xaa Glu Glu Xaa Glu Thr
       1090                1095                1100
Val Ser Ala Met Ala Xaa Leu Ser Xaa Xaa Xaa Xaa Xaa Xaa Xaa Xaa
1105                1110                1115                1120
Xaa Xaa Xaa Xaa Xaa Xaa Xaa Xaa Arg Xaa Xaa Xaa Glu Pro Met Glu
              1125                1130                1135
Xaa Glu Pro Xaa Leu
         1140

<210> SEQ ID NO 108
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide fragment

<400> SEQUENCE: 108

Arg His Arg Lys
  1

<210> SEQ ID NO 109
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 109

Lys Cys Glu Arg Ile Gln Gly Arg Lys Ala Ser Leu Glu Glu
  1               5                  10

<210> SEQ ID NO 110
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 110

Gln Cys Val Cys Gly Asn Ser Thr Thr His Pro Glu His Ala
  1               5                  10

<210> SEQ ID NO 111
<211> LENGTH: 14
<212> TYPE: PRT
<213> ORGANISM: Artificial Sequence
```

```
<220> FEATURE:
<223> OTHER INFORMATION: Description of Artificial Sequence: Synthetic
      peptide motif

<400> SEQUENCE: 111

Glu Arg Ile Gln Gly Arg Lys Ala Ser Leu Glu Glu Ile Gln
  1               5                  10

<210> SEQ ID NO 112
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 112

Cys Gly Asn Ser Thr Thr His Pro Glu His Ala Gly Arg Ile
  1               5                  10

<210> SEQ ID NO 113
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 113

Gln Gly Arg Lys Ala Ser Leu Glu Glu Ile Gln Leu Val His
  1               5                  10

<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 114

His Gln Cys Val Cys Gly Asn Ser Thr Thr His Pro Glu His Ala Gly
  1               5                  10                  15

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 115

Ser Leu Pro Cys Gly Gly Leu Gly Val Ser Thr
  1               5                  10

<210> SEQ ID NO 116
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 116

Leu Leu Gly Asp Asp Ser Gln Lys Phe Phe Ser Ser Leu
  1               5                  10
```

<210> SEQ ID NO 117
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 117

Leu Arg Asp Gln Leu Asn Ile Ser Lys Ile Leu Ile Val Asp
 1               5                  10

<210> SEQ ID NO 118
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 118

Asp Val His His Gly Asn Gly Thr Gln Gln Ala Phe Tyr Ala
 1               5                  10

<210> SEQ ID NO 119
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 119

Val His His Gly Asn Gly Thr Gln Gln Ala Phe Tyr Ala Asp Pro Ser
 1               5                  10                  15

<210> SEQ ID NO 120
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 120

Ala Pro Asn Glu Val Gly Thr Gly Leu Gly Glu Gly Tyr Asn Ile Asn
 1               5                  10                  15

<210> SEQ ID NO 121
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 121

Asn Glu Val Gly Thr Gly Leu Gly Glu Gly Tyr Asn Ile Asn Ile Ala
 1               5                  10                  15

<210> SEQ ID NO 122
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide motif -continued

```
<400> SEQUENCE: 122

Asn Ser Val Ala Ile Thr Ala Lys Tyr Leu Arg Asp Gln
 1               5                  10

<210> SEQ ID NO 123
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 123

Thr Lys Gln Leu Met Thr Leu Ala Asp Gly Arg Val Val Leu
 1               5                  10

<210> SEQ ID NO 124
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 124

Gln Glu Asp Ser Arg Thr Ala Gly Glu Pro Met Glu Glu Glu
 1               5                  10

<210> SEQ ID NO 125
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 125

Val Ala Val Pro Arg Gly Cys Ala Leu Ala Gly Ala Gln Leu Gln Glu
 1               5                  10                  15

<210> SEQ ID NO 126
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 126

Gly Gly Tyr Lys Val Thr Ala Lys Cys Phe Gly His Leu
 1               5                  10

<210> SEQ ID NO 127
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 127

Ser Lys Tyr Trp Lys Ser Val Arg Met Val Ala Val Pro
 1               5                  10
```